US006525203B1

(12) United States Patent
Tino

(10) Patent No.: US 6,525,203 B1
(45) Date of Patent: Feb. 25, 2003

(54) HETEROCYCLIC AROMATIC COMPOUNDS USEFUL AS GROWTH HORMONE SECRETAGOGUES

(75) Inventor: Joseph A. Tino, Lawenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 24 days.

(21) Appl. No.: 09/662,448

(22) Filed: Sep. 14, 2000

Related U.S. Application Data

(63) Continuation-in-part of application No. 09/506,749, filed on Feb. 18, 2000.
(60) Provisional application No. 60/154,919, filed on Sep. 21, 1999, and provisional application No. 60/124,131, filed on Mar. 12, 1999.

(51) Int. Cl.[7] ........................ C07D 401/12; A01K 31/11
(52) U.S. Cl. ........................ 548/125; 514/367; 514/375; 548/180; 548/217; 548/309.7
(58) Field of Search ............................ 548/309.7, 180, 548/217; 514/307, 375, 387

(56) References Cited

U.S. PATENT DOCUMENTS

| | | | |
|---|---|---|---|
| 3,239,345 | A | 3/1966 | Hodge et al. |
| 4,036,979 | A | 7/1977 | Asato |
| 4,411,890 | A | 10/1983 | Momany |
| 5,206,235 | A | 4/1993 | Fisher et al. |
| 5,283,241 | A | 2/1994 | Bochis et al. |
| 5,284,841 | A | 2/1994 | Chu et al. |
| 5,310,737 | A | 5/1994 | Fisher et al. |
| 5,317,017 | A | 5/1994 | Ok et al. |
| 5,374,721 | A | 12/1994 | Schoen et al. |
| 5,430,144 | A | 7/1995 | Schoen et al. |
| 5,430,150 | A | 7/1995 | Trova et al. |
| 5,434,261 | A | 7/1995 | Schoen et al. |
| 5,438,136 | A | 8/1995 | Devita et al. |
| 5,536,716 | A | 7/1996 | Chen et al. |
| 5,545,735 | A | 8/1996 | Bochis et al. |
| 5,578,593 | A | 11/1996 | Chen et al. |
| 5,583,130 | A | 12/1996 | Bochis et al. |
| 5,606,054 | A | 2/1997 | Fisher et al. |
| 5,622,973 | A | 4/1997 | Morriello et al. |
| 5,652,235 | A | 7/1997 | Chen et al. |
| 5,663,171 | A | 9/1997 | Chen et al. |
| 5,672,596 | A | 9/1997 | Wyvratt et al. |
| 5,726,307 | A | 3/1998 | Schoen et al. |

FOREIGN PATENT DOCUMENTS

| | | |
|---|---|---|
| WO | WO 93/14072 | 7/1993 |
| WO | WO94/19367 | 9/1994 |
| WO | WO95/16675 | 6/1995 |
| WO | WO96/05195 | 2/1996 |
| WO | WO96/22997 | 8/1996 |
| WO | WO97/24369 | 7/1997 |
| WO | WO98/58948 | 12/1998 |
| WO | WO 99/64401 | 12/1999 |

OTHER PUBLICATIONS

Maekawa, Pesticides Environ Qual Saf suppl (2975) 3 478–53.*

J.S. Morley, et al. "Antibacterial Activity and Uptake into *Escherichia coli* of Backbone–modified Analogues of Small Peptides"; Journal of General Microbiology (1983), 129. pp.3701–3708.

Smissman et al. "Synthesis of Inhibitors of Bacterial Cell Wall Biogenesis. Analogs of D–Alanyl–D–alanine", Journal of Medicinal Chemistry (1976) 19, pp. 165–167.

Maekawa et al., Synthesis and Biological Activities of Benzimidazole Derivatives; Agric. Biol. Chem. 1977 41 (5), pp. 811–818.

Nargund et al., "Growth Hormone Secretagogues" In: Ann. Reports Med. Chem. Edited by James A. Bristol, Academic Press, 1997, vol. 32, pp. 221–230.

* cited by examiner

*Primary Examiner*—Robert Gerstl
(74) *Attorney, Agent, or Firm*—Ronald S. Hermenau

(57) ABSTRACT

Heterocyclic aromatic compounds are provided which are useful in stimulating endogenous production or release of growth hormone and in treating obesity, osteoporosis (improving bone density) and in improving muscle mass and muscle strength.

The heterocyclic aromatic compounds have the structure

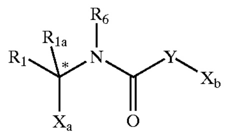

including pharmaceutically acceptable salts thereof and all stereoisomers thereof, wherein $X_a$ is heteroaryl, preferably,

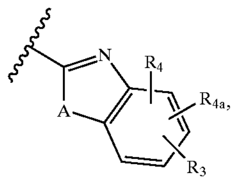

,
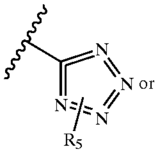
or
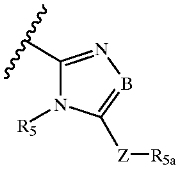

and $R_1$, $R_{1a}$, $R_6$, Y, $X_b$, A, B, Z, $R_3$, $R_4$, $R_{4a}$, $R_5$ and $R_{5a}$ are as defined herein.

19 Claims, No Drawings

HETEROCYCLIC AROMATIC COMPOUNDS USEFUL AS GROWTH HORMONE SECRETAGOGUES

This application is a continuation in part of U.S. application Ser. No. 09/506,749 filed Feb. 18, 2000, which claims priority from provisional U.S. Application Serial No. 60/154,919 filed Sep. 21, 1999 and from provisional U.S. Application Serial No. 60/124,131 filed Mar. 12, 1999. The entirety of each of these applications is incorporated herein by reference.

FIELD OF THE INVENTION

The present invention relates to novel heterocyclic aromatic compounds which stimulate endogenous production and/or release of growth hormone, and to methods for treating obesity, improving bone density (to treat osteoporosis) and stimulating increase in muscle mass and muscle strength employing such compounds.

BACKGROUND OF THE INVENTION

The pituitary gland secretes growth hormone which stimulates growth in body tissue capable of growing and affects metabolic processes by increasing rate of protein synthesis and decreasing rate of carbohydrate synthesis in cells. Growth hormone also increases mobilization of free fatty acids and use of free fatty acids for energy.

The prior art is replete with patents/applications which disclose compounds which are useful as growth hormone secretagogues.

The following patents/applications, disclose benzofused lactams which are disclosed as being useful in promoting release of growth hormone:

U.S. Patent Nos. 5,206,235; 5,283,741; 5,284,841; 5,310,737; 5,317,017; 5,374,721; 5,430,144; 5,434,261; 5,438,136; 5,545,735; 5,583,130; 5,606,054; 5,672,596 and 5,726,307; WO 96-05195 and WO 95-16675.

The following patents/applications, disclose diverse chemotypes as being useful in promoting release of growth hormone:

U.S. Pat. Nos. 5,536,716; 5,578,593; 5,622,973; 5,652,235; 5,663,171; WO 94-19367; WO 96-22997; WO 97-24369 and WO 98-58948.

SUMMARY OF THE INVENTION

In accordance with the present invention, novel heterocyclic aromatic compounds are provided which are growth hormone secretagogues and have the structure

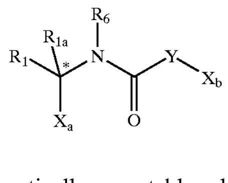

including pharmaceutically acceptable salts thereof, prodrug esters thereof, and all stereoisomers thereof, wherein $R_1$ is alkyl, aryl, alkenyl, alkynyl, arylalkyl, cycloalkyl, cycloalkylalkyl, alkoxyalkyl, arylalkyloxyalkyl, aryloxyalkyl, heteroaryl, cycloalkylalkoxyalkyl, heteroarylalkyl, cycloheteroalkyl or cycloheteroalkylalkyl (where the above groups are defined below) and these groups may be optionally substituted by 1,2 or 3-substituents selected from halogen, —$OR_8$, —OC(O)$R_8$, alkyl, phenyl, phenoxy, halophenyl, —$CF_3$, —$OCF_3$, —$N(R_{8a})C(O)(R_8)$, or —$N(R_8)(R_{8a})$;

$R_{1a}$ is H, alkyl, or cycloalkyl;

$X_a$ is heteroaryl, which preferably include

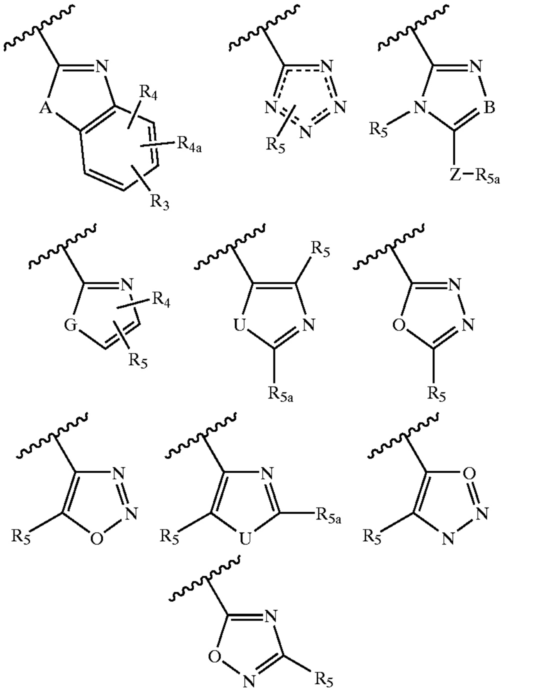

A is oxygen, sulfur, —NH—, —N—$R_5$, or —NC(O)—$R_2$;

B is —$CR_{5b}$ or —N—;

Z is a bond or —S—;

G is oxygen or sulfur;

U is oxygen, sulfur, —NH—, or —N—$R_{5b}$;

$R_2$ is alkyl, aryl, alkenyl, alkynyl, arylalkyl, cycloalkyl, cycloalkylalkyl, alkoxyalkyl, aryloxyalkyl, heteroaryl, or heteroarylalkyl (where the above groups are defined below) and these groups may optionally be substituted by 1,2 or 3-substituents selected from halogen, —$OR_{8b}$, —OC(O)$R_{8b}$, alkyl, phenyl, phenoxy, halophenyl, —$CF_3$, —$OCF_3$, —$N(R_{8c})C(O)(R_{8b})$, or —$N(R_{8c})(R_{8b})$;

$R_3$ is H, halogen, alkyl, aryl, alkenyl, alkynyl, alkaryl, alkoxy, aryloxy or J1, and where alkyl, aryl, alkenyl, alkynyl, arylalkyl, alkoxy, or aryloxy may be optionally substituted with 1 to 3 J1;

$R_4$ and $R_{4a}$ are the same or different and are independently H, halogen, —$CF_3$, alkyl, or aryl;

$R_5$ is H, alkyl, aryl, alkenyl, arylalkenyl, alkynyl, arylalkyl, arylalkynyl, cycloalkylalkyl, alkoxyalkyl, aryloxyalkyl, arylalkyloxyalkyl, heteroaryl, cycloalkylalkoxyalkyl, —$SO_2T_1$, —$SO_2N(T_{1a})T_1$, or heteroarylalkyl, and where alkyl, aryl, alkenyl, arylalkenyl, alkynyl, arylalkyl, arylalkynyl, cycloalkylalkyl, alkoxyalkyl, aryloxyalkyl, arylalkyloxyalkyl, heteroaryl, heteroaryloxyalkyl, cycloalkylalkoxyalkyl, or heteroarylalkyl may be independently optionally substituted with 1 to 3 J1;

$R_{5a}$ and $R_{5b}$ are the same or different and are independently H, alkyl, aryl, alkenyl, arylalkenyl, alkynyl, arylalkyl, arylalkynyl, cycloalkylalkyl, alkoxyalkyl, aryloxyalkyl, arylalkyloxyalkyl, heteroaryl, cycloalkylalkoxyalkyl, heteroarylalkyl, or J1, and where alkyl, aryl, alkenyl, arylalkenyl, alkynyl, arylalkyl, arylalkynyl, cycloalkylalkyl, alkoxyalkyl, aryloxyalkyl, arylalkyloxyalkyl, heteroaryl, heteroaryloxyalkyl, cycloalkylalkoxyalkyl, or heteroarylalkyl may be independently optionally substituted with 1 to 3 J1;

Y is

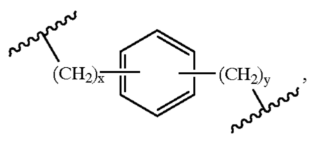

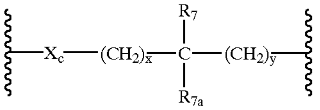

or

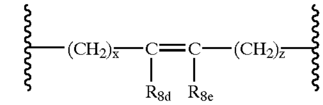

where x and y are independently 0 to 3 and z is 1 to 3;

$X_c$ is a bond, —N—$R_{6a}$ or —O—;

$R_7$ and $R_{7a}$ are the same or different and are independently H, alkyl, —$CF_3$, phenyl, aryl, arylalkyl, and cycloalkyl; or one or both of $R_7$ and $R_{7a}$ can be independently joined to one or both of $R_9$ and $R_{10}$ groups (of $X_b$) to form an alkylene bridge of 1 to 5 carbon atoms; or $R_7$ and $R_{7a}$ are joined together to form a ring of from 3–7 carbon atoms;

$R_6$, $R_{6a}$, $R_{6b}$, $R_{6c}$, $R_8$, $R_{8a}$, $R_{8b}$, $R_{8c}$, $R_{8d}$, $R_{8e}$, $R_{8f}$, $R_{8g}$, $R_{8h}$, $R_{8i}$, $R_{8k}$, $R_{8l}$, and $R_{8m}$ are the same or different and are independently H, alkyl, cycloalkyl, alkenyl or aryl;

$R_{8j}$ is H, alkyl, aryl, hydroxy or —$OC(O)R_{8k}$;

$X_b$ is

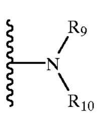

or

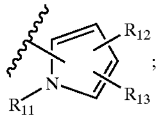

;

$R_9$ and $R_{10}$ are the same or different and are independently selected from H, alkyl, and substituted alkyl where the substituents may be 1 to 3 hydroxys, 1 to 3 $C_1$–$C_{10}$-alkanoyloxy; 1 to 3 $C_{1-6}$ alkoxy, phenyl, phenoxy, $C_1$–$C_6$-alkoxycarbonyl; or $R_9$ and $R_{10}$ can together form —$(CH_2)_tX_d(CH_2)_u$— where $X_d$ is $C(R_{8h})(R_{8j})$, —O— or —$N(R_{6b})$, t and u are independently 1–3;

$R_{11}$ is H, $C_1$–$C_6$alkyl, —$CF_3$, arylalkyl, or aryl, and with the alkyl and aryl groups being optionally substituted with 1 to 3 hydroxy, 1 to 3 $C_{1-10}$alkanoyloxy, 1 to 3 $C_{1-6}$ alkoxy, phenyl, phenoxy or $C_{1-6}$alkoxycarbonyl;

$R_{12}$ and $R_{13}$ are independently H, $C_1$–$C_6$alkyl, —$CF_3$, aryl, or halogen, and with the alkyl and aryl groups being optionally substituted with 1 to 3 hydroxy, 1 to 3 $C_1$–$C_{10}$-alkanoyloxy, 1 to 3 $C_{1-6}$ alkoxy, or $C_1$–$C_6$ alkoxycarbonyl;

J1 is nitro, —$(CH_2)vN(T_{1a})C(O)T_1$, —$(CH_2)_vCN$, —$(CH_2)_vN(T_{1a})C(O)OT_1$, —$(CH_2)_vN(T_{1a})C(O)N(T_{1b})T_1$, —$(CH_2)_vN(T_{1a})SO_2T_1$, —$(CH_2)_vC(O)N(T_{1a})T_1$, —$(CH_2)_vC(O)OT_1$, —$(CH_2)_vOC(O)OT_1$, —$(CH_2)_vOC(O)T_1$, —$(CH_2)_vOC(O)N(T_{1a})T_1$, —$(CH_2)_vN(T_{1a})SO_2N(T_{1b})T_1$, —$(CH_2)_vOT_1$, —$(CH_2)_vSO_2T_1$, —$(CH_2)vSO_2N(T_{1a})T_1$, —$(CH_2)vC(O)T_1$, —$(CH_2)vCH(OH)T_1$, cycloheteroalkyl, or heteroaryl as defined below, with v being 0–5;

$T_1$, $T_{1a}$ and $T_{1b}$ are the same or different and are independently H, alkyl, alkenyl, alkynyl, lower alkythioalkyl, alkoxyalkyl, aryl, arylalkyl, heteroaryl, heteroarylalkyl, cycloheteroalkyl, or cycloalkyl, each of which may be optionally substituted with 1, 2 or 3 of the following groups, halogen, hydroxyl, —$NR_{8f}C(O)NR_{8g}R_{8i}$, —$C(O)NR_{8f}R_{8g}$, —$NR_{8f}C(O)R_{8g}$, —CN, —$N(R_{8f})SO_2R_{14}$, —$OC(O)R_{8f}$, —$SO_2NR_{8f}R_{8g}$, —$SOR_{14}$, —$SO_2R_{14}$, alkoxy, —COOH, cycloheteroalkyl, or —$C(O)OR_{14}$; or $T_1$ and $T_{1a}$ or $T_1$ and $T_{1b}$ can together form —$(CH_2)_wX_e(CH_2)_z$— where $X_e$ is —$C(R_{8m})(R_{8l})$, —O—, —S—, —SO—, —$SO_2$—, —$NC(O)OR_{14a}$, —$NC(O)NR_{14a}R_{14b}$, —$NC(O)R_{14a}$ or —$N(R_{6c})$ where w and z are each independently 1–3; with the proviso that $T_1$ can not be hydrogen when it is connected to carbonyl or sulfur, as in —$C(O)T_1$ or —$SO_2T_1$;

$R_{14}$, $R_{14a}$, and $R_{14b}$ are independently $C_1$–$C_6$alkyl, heteroaryl, or aryl, each optionally substituted with —$(CH_2)_sOH$, with s being 0–5;

with the proviso that where $X_a$ is

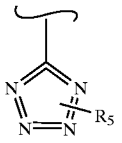

(1) where one or both of $R_7$ and $R_{7a}$, and one or both of $R_9$ and $R_{10}$ form an alkylene bridge, then where $R_5$ is —$(CH_2)C(O)N(T_{1a})T_1$, then at least one of $T_{1a}$ and T≠H; or (2) where $R_1$ is arylalkyl and $R_{1a}$ is H and $R_5$ is —$(CH_2)C(O)N(T_{1a})T_1$, then $T_{1a}$ or $T_1$ is other than

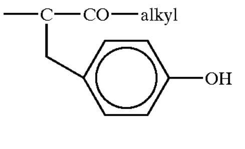

or

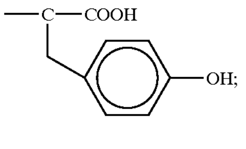

or (3) where $R_1$ and $R_7$ are each 2-naphthyl-$CH_2$—, then $R^5$≠phenethyl.

The compounds of the instant invention all have at least one asymmetric center as noted by the asterisk in structural formula I. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in formula I, the more active and thus more preferred configuration is R as determined by the R/S rules when $R_{1a}$ is H. Isomers may be separated by conventional methods, for example, chromatographic or fractional crystallization.

The pharmaceutically acceptable salts of the compounds of formulae I of the invention include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as phosphate, mandelate, chloride, bromide, iodide, tartrate, acetate, methanesulfonate, maleate, succinate, glutarate, and salts of naturally occurring amino acids such as arginine, lysine, alanine and the like, and prodrug esters thereof.

In addition, in accordance with the present invention, a method for increasing levels of endogenous growth hormone or increasing the endogenous production or release of growth hormone is provided wherein a compound of formula I as defined hereinbefore is administered in a therapeutically effective amount.

Furthermore, in accordance with the present invention, a method is provided for preventing or treating osteoporosis (improving bone density and/or strength), or treating obesity, or increasing muscle mass and/or muscle strength, or maintenance of muscle strength and function in elderly humans, or reversal or prevention of fraility in elderly humans, wherein a compound of formula I as defined hereinbefore is administered in a therapeutically effective amount.

DETAILED DESCRIPTION OF THE INVENTION

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 6 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 3 substituents including alkyl, aryl, alkenyl, alkynyl, hydroxy, arylalkyl, cycloalkyl, cycloalkylalkyl, alkoxy, arylalkyloxy, alkanoyl, amino, haloaryl, $CF_3$, $OCF_3$, aryloxy, heteroaryl, cycloalkylalkoxyalkyl, or cycloheteroalkyl.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 7 carbons, forming the ring and which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

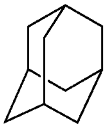,
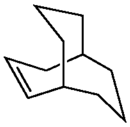,
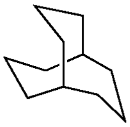,

-continued

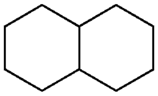, any of which groups may be optionally substituted with 1 to 3 substituents as defined above for alkyl.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or cycloheteroalkyl rings) and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, fluorenyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or preferably any of the aryl substituents as set out above.

Preferred aryl groups include phenyl, biphenyl or naphthyl.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxyl", "alkoxyl", "aryloxyl" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl, aryl, arylalkyl, heteroaryl, heteroarylalkyl, cycloheteroalkyl, cycloheteroalkylalkyl and/or cycloalkyl.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include alkanoyl, alkenoyl, aroyl, aralkanoyl, heteroaroyl, cycloalkanoyl, and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 2 to 6 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio or any of the substituents for alkyl as set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the substituents for alkyl as set out herein.

The term "alkylene" as employed herein alone or as part of another group refers to alkyl groups as defined above having single bonds for attachment to other groups at two different carbon atoms and may optionally be substituted as defined above for "alkyl".

The terms "alkenylene" and "alkynylene" as employed herein alone or as part of another group refer to alkenyl groups as defined above and alkynyl groups as defined above, respectively, having single bonds for attachment at two different carbon atoms.

Examples of $(CH_2)_x$, $(CH_2)_y$, $(CH_2)_w$, $(CH_2)_v$, $(CH_2)_s$, $(CH_2)_t$, $(CH_2)_u$ or $(CH_2)_z$ groups (which may include alkylene, alkenylene or alkynylene groups as defined herein, and may optionally include 1, 2, or 3 substituents which may be any of the alkyl substituents set out herein), are as follows:

$-(CH_2)_2-$ , $-(CH_2)_3-$ , $-(CH_2)_4-$ ,

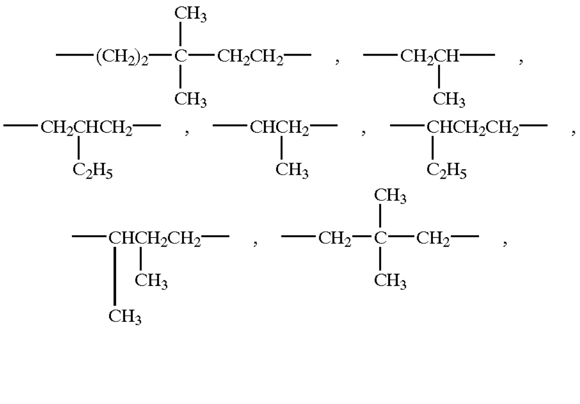

-continued

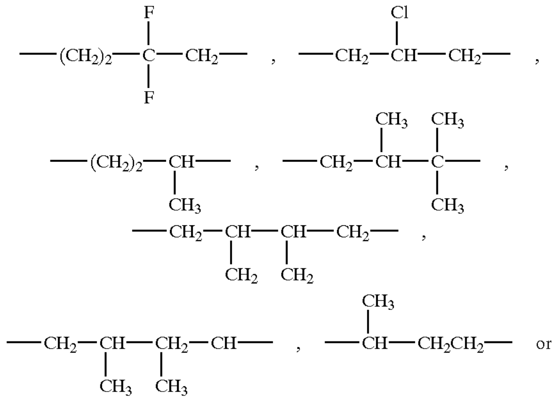

or $-(CH_2)_3-CF_3$.

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "heterocyclic", "heterocyclo" or "heterocycle" as employed herein alone or as part of another group refers to "heteroaryl" groups or "cycloheteroalkyl" groups.

The term "cycloheteroalkyl" as used herein alone or as part of another group refers to a 4-, 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

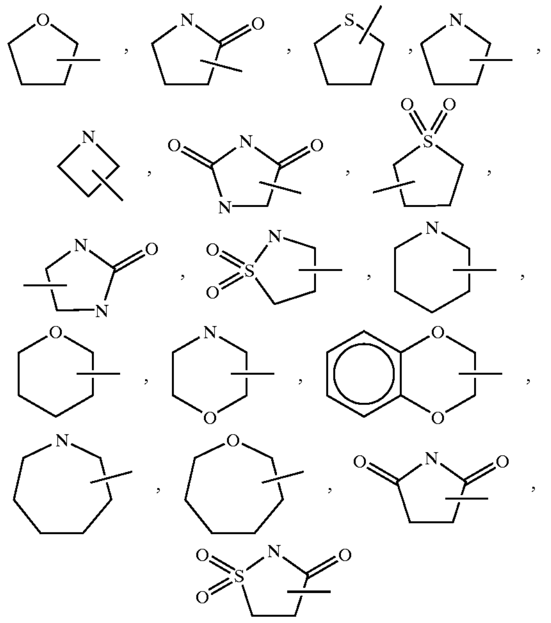

and the like. The above groups may include 1 to 4 substituents such as alkyl, halo, oxo and/or any of of the aryl substituents set out herein. In addition, any of the above rings can be fused to a cycloalkyl, aryl, heteroaryl or cycloheteroalkyl ring.

The term "heteroaryl" or "heterocyclicaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides, such as

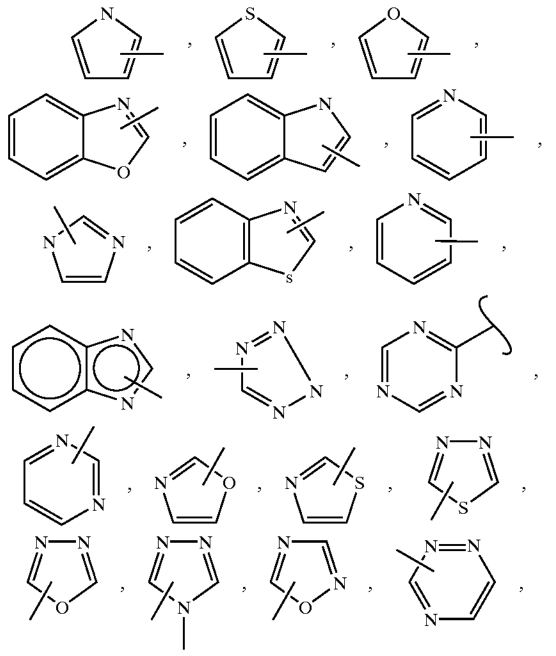

and the like.

The heteroaryl groups may optionally include 1 to 4 substituents such as any of the aryl substituents set out herein. In addition, any of the above rings can be fused to a cycloalkyl, aryl, heteroaryl or cycloheteroalkyl ring.

The term "prodrug esters" of the formula I compounds includes esters of hydroxyls and phenols, such as acetate, benzoate, pivolate, stearoylate, isobutyrate, and the like as known in the art.

General Synthetic Schemes

The compounds of the present invention may be prepared according to the following general synthetic schemes, as well as relevant published literature procedures that are used by the one skilled in the art. Exemplary reagents and procedures for these reactions appear hereinafter and in the working Examples. Unless otherwise specified, the various substituents of the compounds are defined in the same manner as the formula I compound of the invention.

In the following reactions, amide bond forming (peptide coupling) reactions are conducted under standard peptide coupling procedures know in the art. Optimally, the reaction is conducted in a solvent such as dimethylformamide (DMF) at 0° C. to room temperature using 1-ethyl-3-(3-dimethylamino-propyl)carbodiimide (EDAC) or (WSC)), 1-hydroxybenzo-triazole hydrate (HOBt) or 1-hydroxy-7-azabenzotriazole (HOAt) and a base, for example 4-dimethlaminopyridine (DMAP) or Hunig's base.

Unnatural protected amino acids can be purchased or prepared by standard methods known in the art. Chiral preparations include Meyers, A. G. et al., *J. Am. Chem. Soc.,* 119, 656–673 (1997). O-Alkylated serine derivatives can be formed from serine by known methods, Maligres, P. E. et al., *Tetrahedron,* 53, 10983–10992 (1997).

The cyclizations to benzimidazoles or benzoxazoles in Schemes 1, 1a, and 1b can be carried out under standard conditions known in the art. Suitable cyclization procedures are described in Nestor, Jr., J. J., *J. Med. Chem.,* 27, 320–5 (1984) and are optimally heating (60–90° C.) in an acidic solvent, such as acetic acid. Benzothiazoles can be prepared as in Spitulnik, M. J., *Synthesis,* 730 (1976), and by other methods known in the art.

Protection and deprotection in the Schemes below may be carried out by procedures generally known in the art. See, for example, T. W. Greene, Protecting Groups in Organic Synthesis, Second Edition, 1991. PG in the Schemes below denotes a nitrogen protecting group, optimally BOC. The BOC group can be removed under acidic conditions, optimally HCl or trifluoroacetic acid.

Reduction of nitro groups in Schemes 1c and 1d can be carried out by methods know in the art. Optimally the reduction can be carried out with $H_2$ in the presence of a catalyst (palladium or platinum).

The arylation reaction covered in Scheme 2 can be performed under the known Suzuki coupling conditions in the literature, or other conditions using the metals zinc or tin known in the art. If the Rx is a chloro, the coupling can be performed as disclosed in Indolese, A. F., *Tet. Lett.,* 38, 3513–3516 (1997) or Shen, W. *Tet. Lett.,* 38, 5575–5578 (1997) using a nickel catalyst.

The tetrazole forming reaction found in Scheme 3 can be carried out under standard conditions known in the art. Suitable procedures are described in Duncia et al. *J. Org. Chem.,* 56, 2395 (1991).

The triazole forming reaction found in Scheme 4 can be carried out under standard conditions known in the art. Suitable procedures are described in Sung, K et al. *Heterocyc. Chem.,* 29, 1101 (1992), Shukla, J. S. et al. *Indian J Chem,* 30B, 332 (1991), and Wilson, M. W. et al. *Molecular Diversity,* 3, 95 (1998).

Other heterocycles can be prepared by methods known to those skilled in the art and by methods found in A. Katritzky, Comprehensive Heterocyclic Chemistry, Volume 1 and Volume 2, Elseveir. Oxazoles can be formed following methods found in Hamada, Y. et al. *Tet. Lett.,* 23, 235–6 (1982). Oxazoles can also be prepared as in Zhang, X. et al. *J. Heterocyclic Chem.,* 34, 1061–4 (1997), and references cited therein. Thiazoles can be prepared following the procedures in Bredenkamp, M. W. et al., *Synth. Commun.,* 2235–2249 (1990) or Aguilar, E., *Tet. Lett.,* 2473–2476 (1994). Oxadiazoles can be prepared as in Borg, S. et al. *J. Org. Chem.,* 60, 3112–3120 (1995).

The transformation of alcohols 69 to azido 70 and 75 to 76 (Schemes 5 and 5a) can be performed by methods known in the art. A single pot procedure described in Thompson, A. S. et al. *J Org Chem.,* 58, 886 (1993), is the optimal transformation.

The imidazoles prepared as shown in Scheme 5 and 5a can be carried out following the procedures given in Chadwick, D. J. et al. *J. Chem. Soc. Perkin Trans. I,* 481 (1984) and Iddon, B., *Heterocycles,* 23, 117 (1985).

The tetrazole forming reaction shown in Scheme 6 can be carried out on solid phase resin.

The solid balls in the schemes and examples below are used to designate a solid phase resin, for example

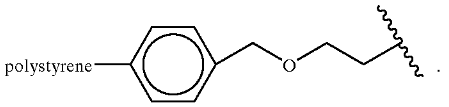

The resin may be a Merrifield type resin.

Intermediates 28 and 42 can be further transformed as shown previously in Schemes 3. Alternatively, intermediates 28 and 42 can be treated with an acid linked to a resin, such as Merrifield or Rink, to give resin bound amides, which can be cleaved to give compounds VI and IX. The carbamate resin linker depicted in Scheme 6 is only one possible candidate (Hernandez, A. et al. *J. Org. Chem.,* 62, 3153 (1997)).

Compounds in all Schemes except 1b with a terminal —NH—$R_9$ moiety can be transformed by methods known in the art, such as reductive amination or alkylation, to compounds of the form

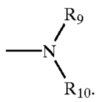

Scheme 1

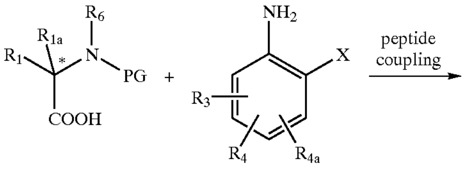

1 2

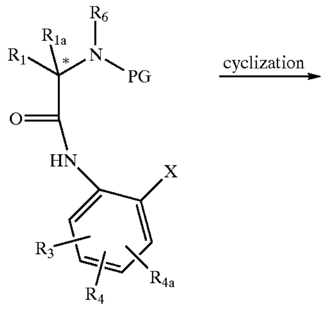

3

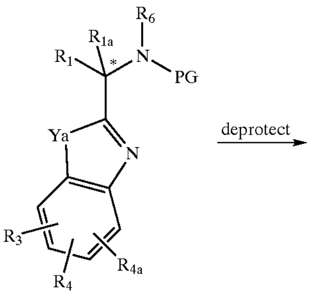

4

-continued

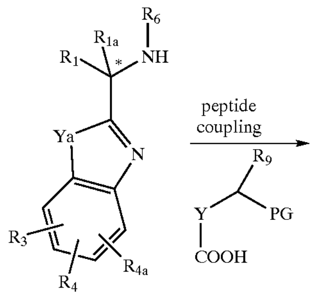

5 6

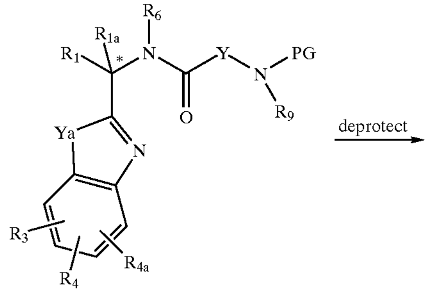

7

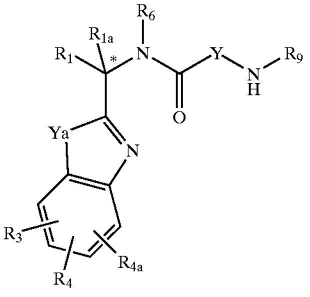

II

5

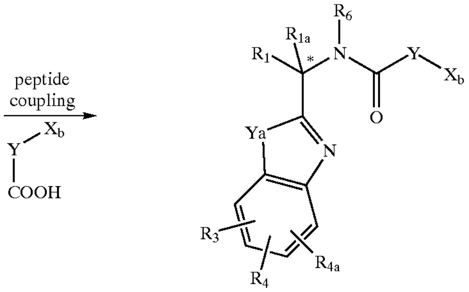

6a IIA

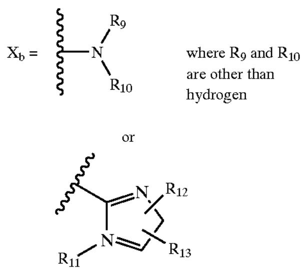

X = O, SH, $NH_2$
Ya = O, S, NH
PG = protecting group

Scheme 1a
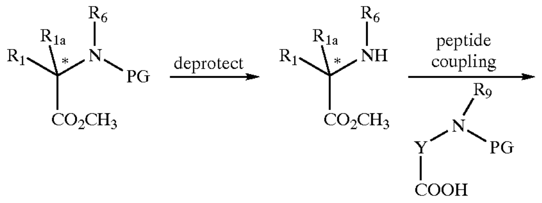
9 10 6
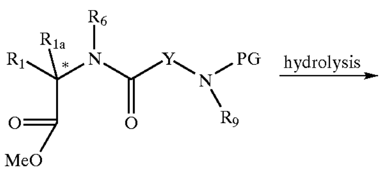
11
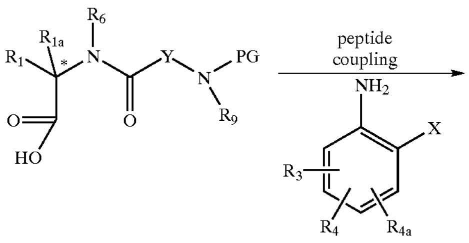
12 2
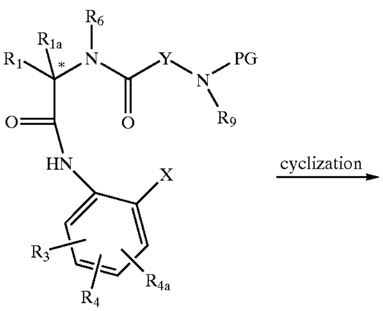
3
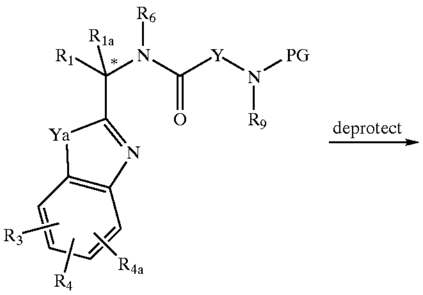
7
-continued
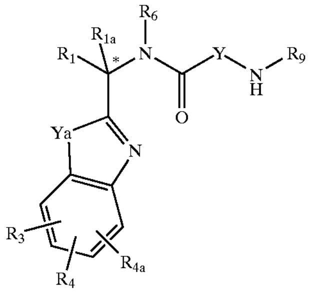
II
X = O, SH, $NH_2$
Ya = O, S, NH
Scheme 1b
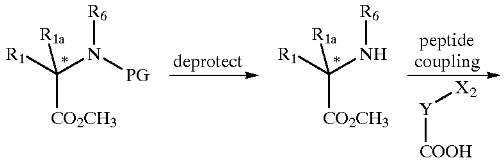
9 10 6a
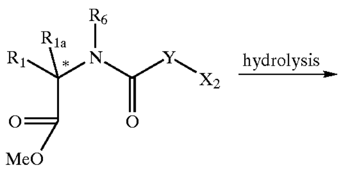
11a
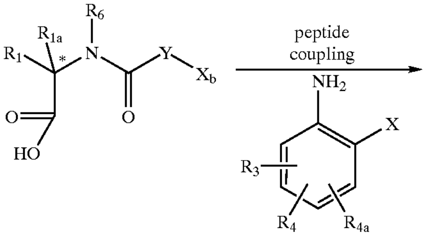
12a 2
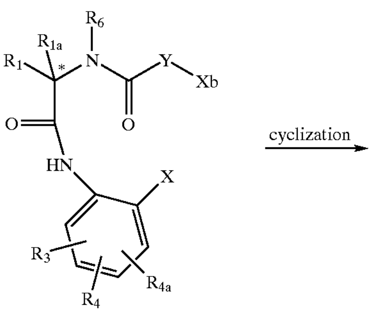
3a -continued
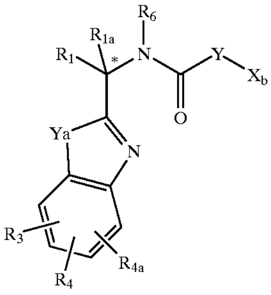
IIa
X = O, SH, $NH_2$
Ya = O, S, NH
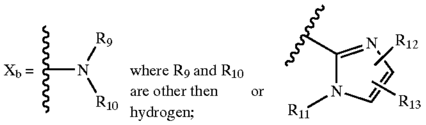
Scheme 1c
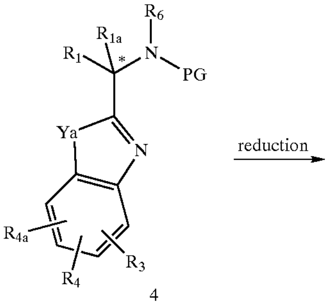
4
where $R_3$ is nitro ($NO_2$)
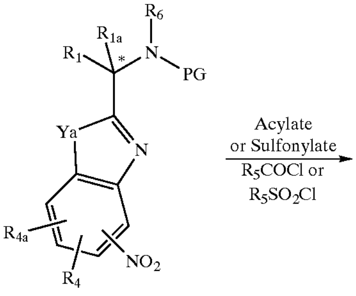
13
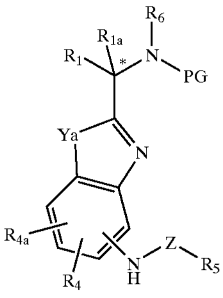
14
14
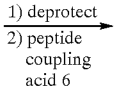
-continued
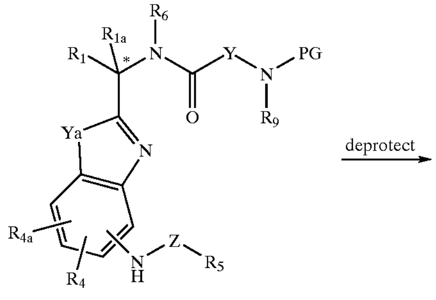
15
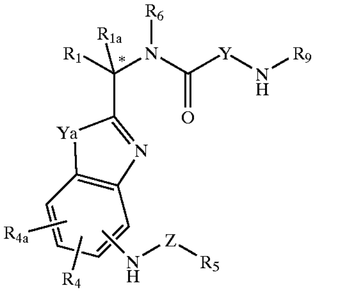
III
14
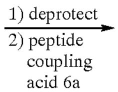
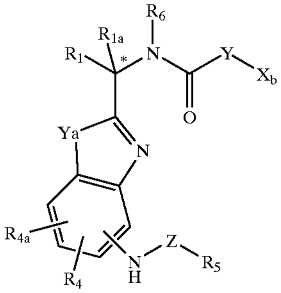
IIIa
X = O, S, NH
Ya = —CO, —$SO_2$.
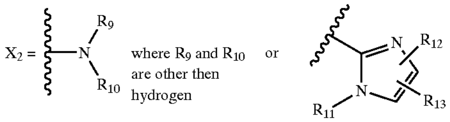
Scheme 1d
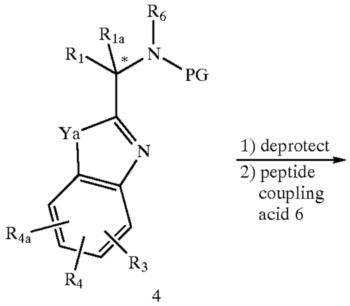
4
where $R_3$ is nitro ($NO_2$)

-continued
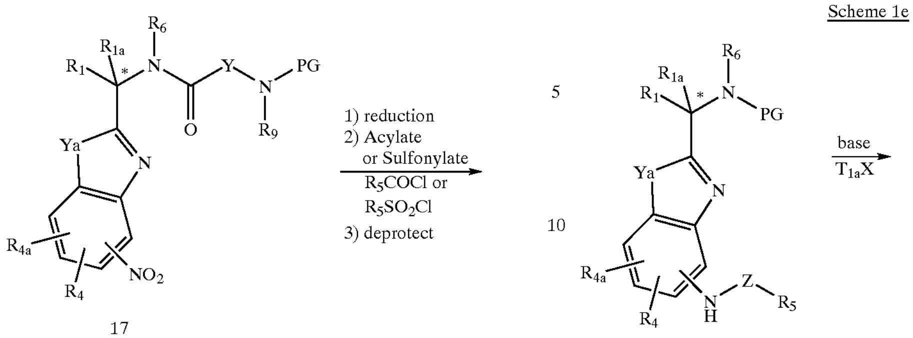
17
14 Ya = O, S, NH
Z = —CO, —$SO_2$.
Scheme 1e
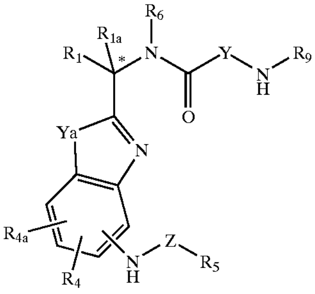
IV
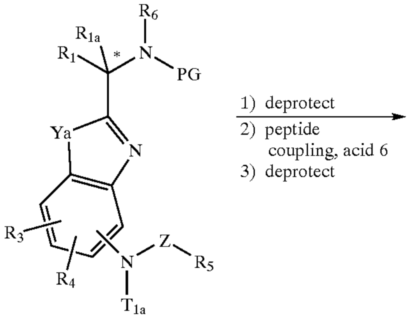
19
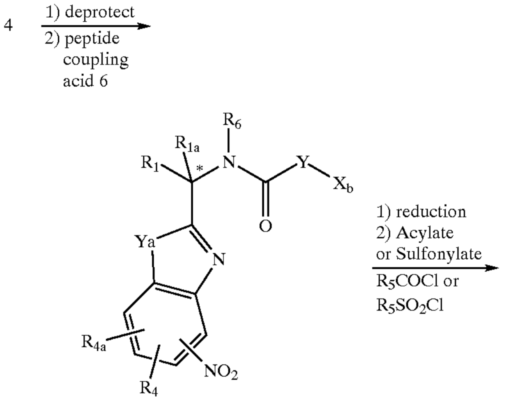
17a
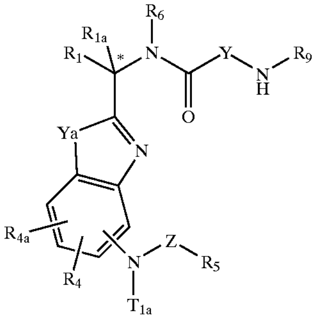
V
Z = —CO, —$SO_2$.
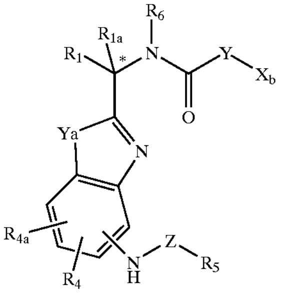
18a
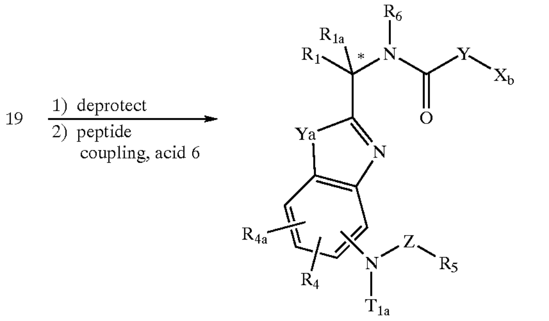
VA
where Rx is nitro ($NO_2$)
X = O, S, NH
Ya = —$CO_2$, —$SO_2$.
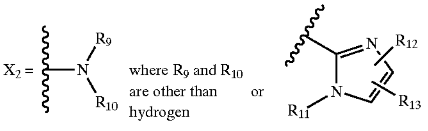
Ya = O, S, NH
Z = —CO, —$SO_2$.
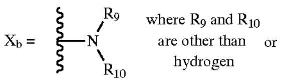
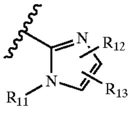

Scheme 2
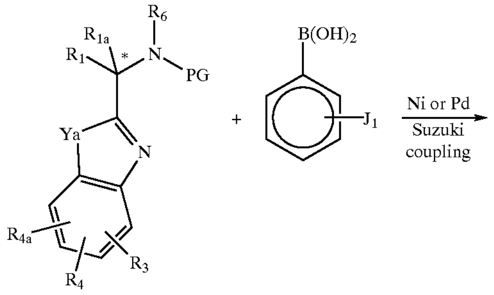
21
where $R_3$ is halo (Cl, Br, I)
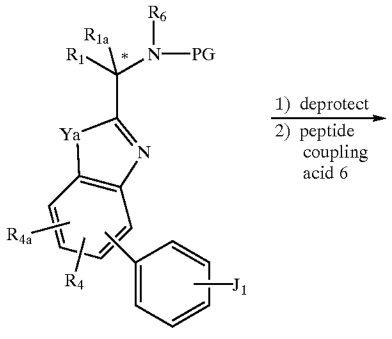
22
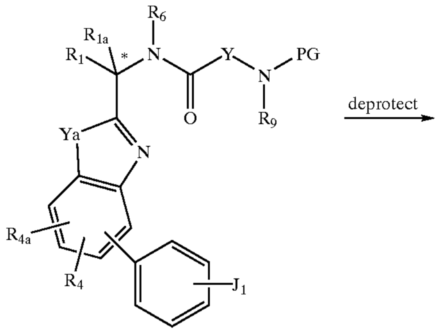
23
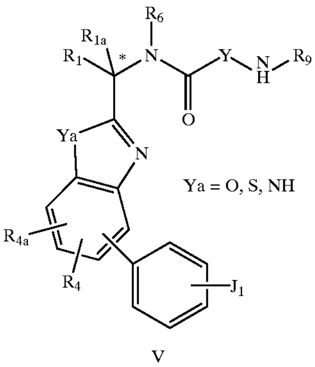
Ya = O, S, NH
V
-continued
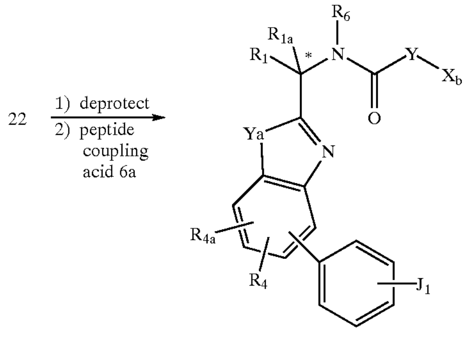
VA
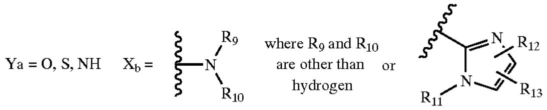
Scheme 3: Tetrazole
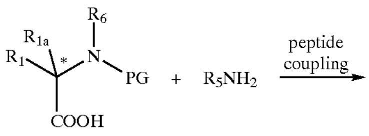
1
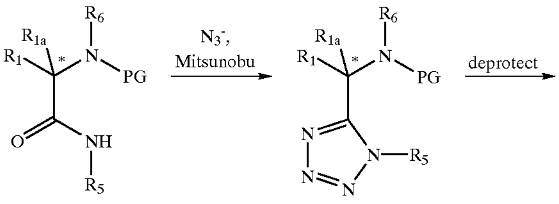
26
27
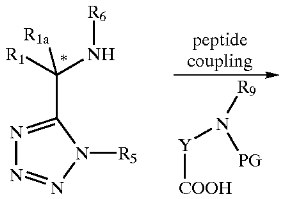
28
6
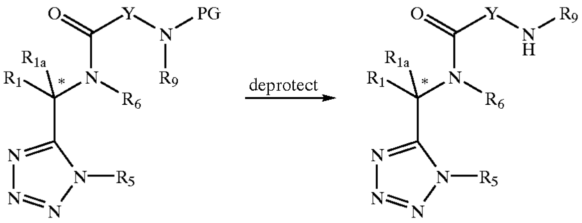
29
VI
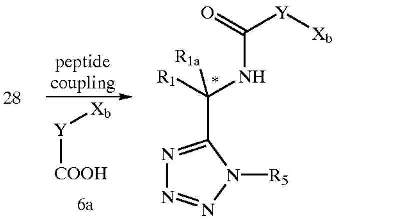
6a
VIA -continued
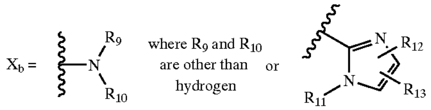
Scheme 3a: Tetrazole
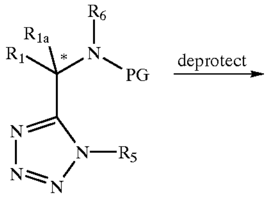
27
where $R_5$ is a protecting group PGx
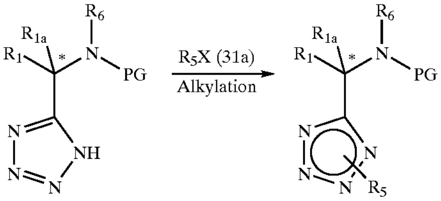
31
32
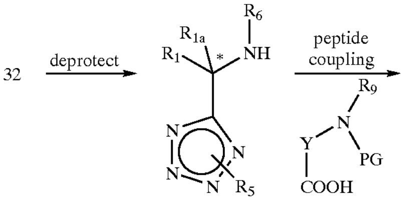
33
6
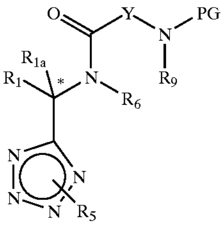
34
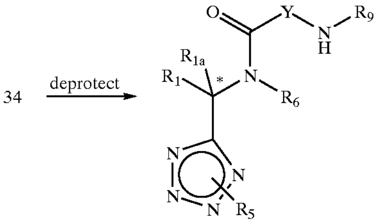
VII
-continued
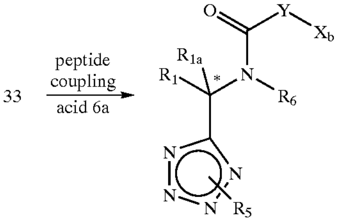
VIIA
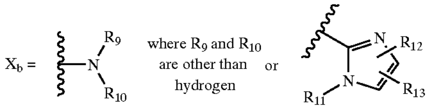
Scheme 3b
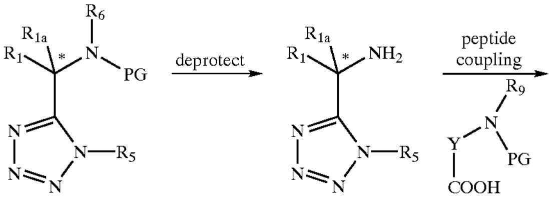
27
(where $R_5$ is a protecting group PGx)
36
6
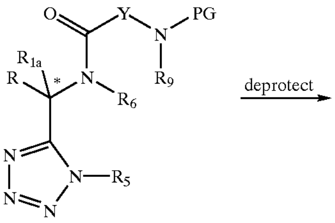
37
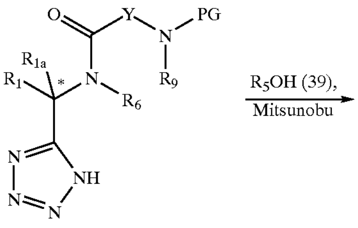
38
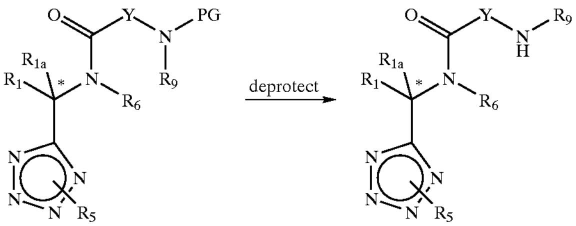
34
VIII -continued
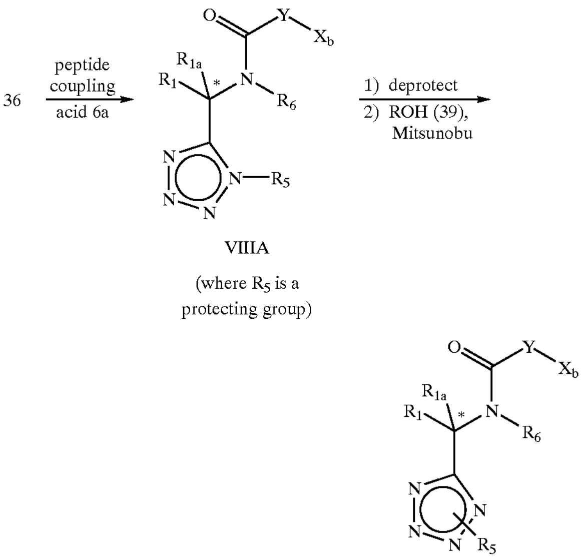
36
VIIIA
(where $R_5$ is a protecting group)
34a
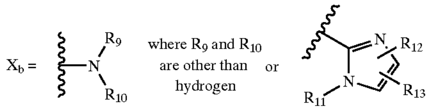
Scheme 3c
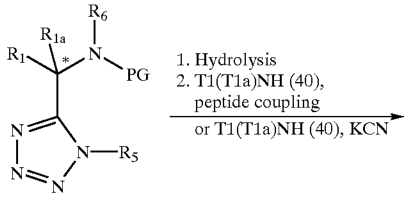
27
Where $R_5$ = —$CH_2(CH_2)nCO_2R_x$
n = 0–4, Rx = alkyl, alkaryl, alkenyl
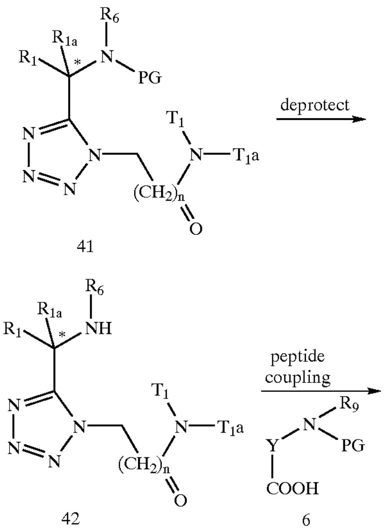
41
42 6
-continued
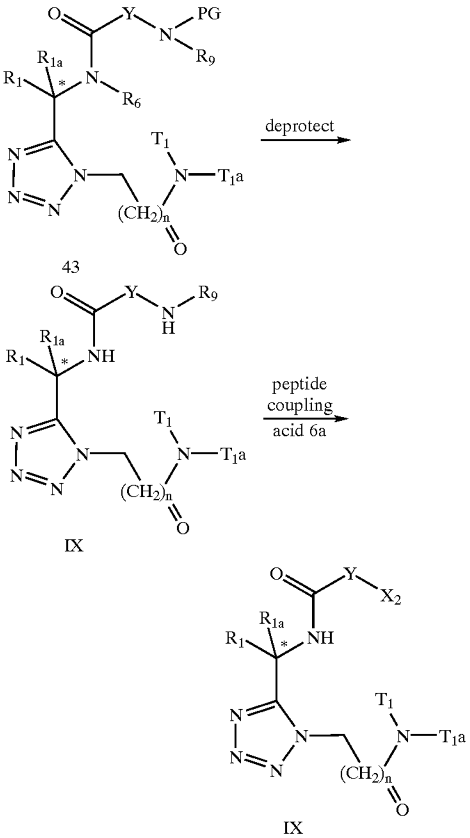
43
IX
IX
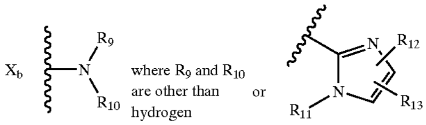
Scheme 3d
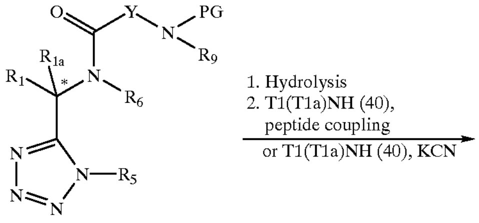
29
Where $R_5$ = —$CH_2(CH_2)nCO_2R_x$
n = 0–4
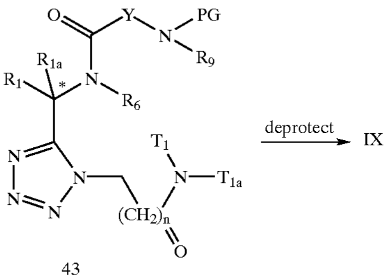
43

-continued
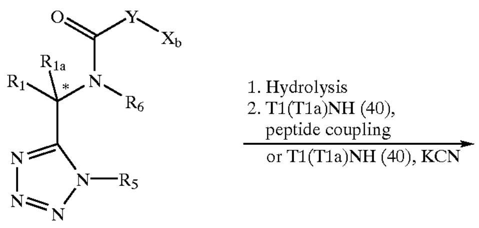
29a
Where $R_5$ = $-CH_2(CH_2)nCO_2R_x$
n = 0–4
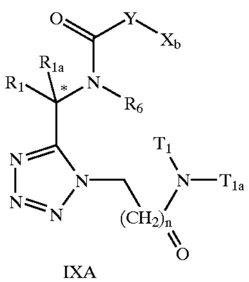
IXA
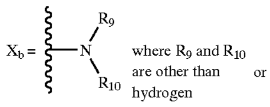
or
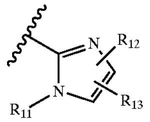
Scheme 3e
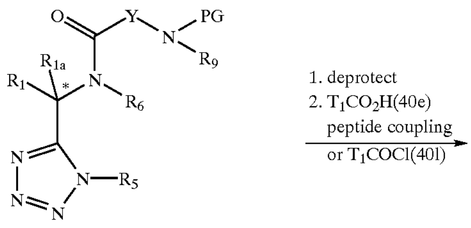
29
Where $R_5$ = $-CH_2(CH_2)n-N(T_{1a})-PG_x$
n = 0–4, $PG_x$ = a protecting group
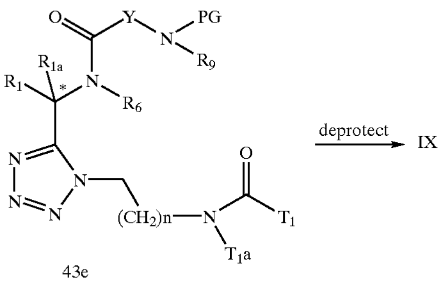
43e
-continued
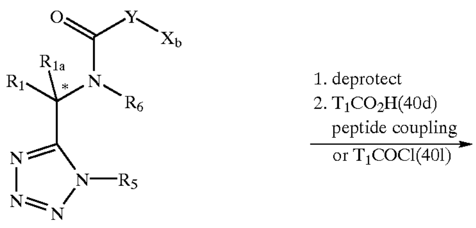
29a
Where $R_5$ = $-CH_2(CH_2)n-N(T_{1a})-PG_x$
n = 0–4, $PG_x$ = a protecting group
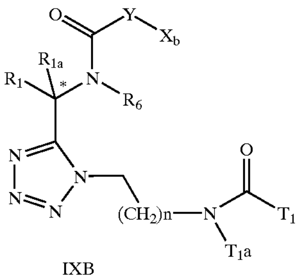
IXB
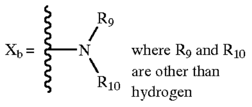
or
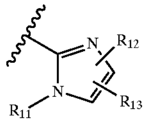
Scheme 3f
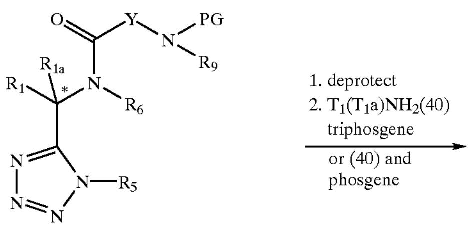
29
Where $R_5$ = $-CH_2(CH_2)n-N(T_{1a})-PG_x$
n = 0–4, $PG_x$ = a protecting group
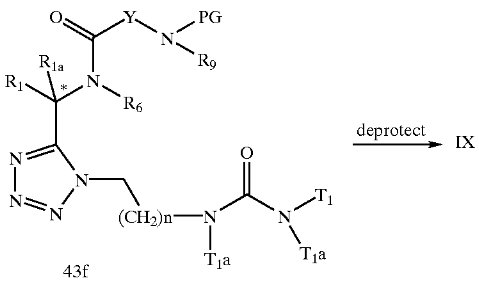
43f -continued
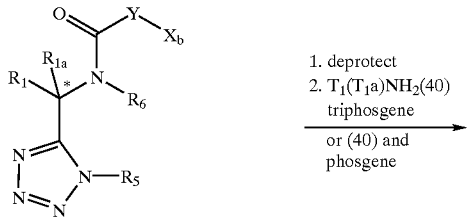
29a
Where $R_5$ = —$CH_2(CH_2)n$—$N(T_{1a})$-$PG_x$
n = 0–4, $PG_x$ = a protecting group
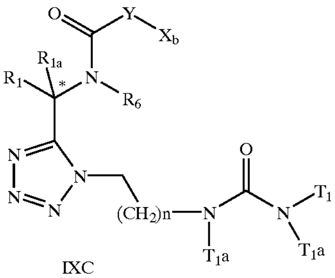
IXC
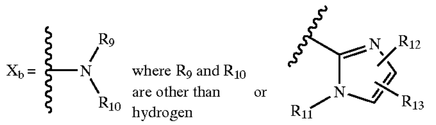
Scheme 3g
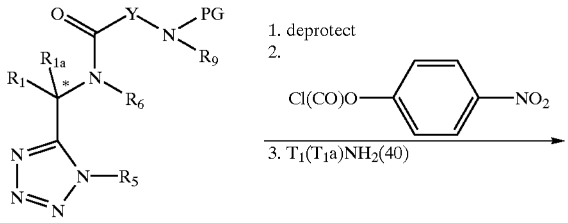
29
Where $R_5$ = —$CH_2(CH_2)n$—O—$PG_x$
n = 0–4, $PG_x$ = a protecting group
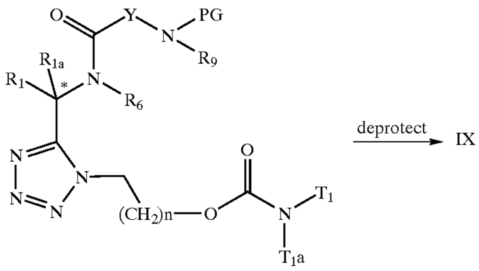
43g
-continued
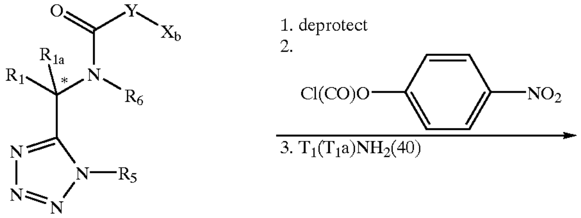
29a
Where $R_5$ = —$CH_2(CH_2)n$—O—$PG_x$
n = 0–4, $PG_x$ = a protecting group
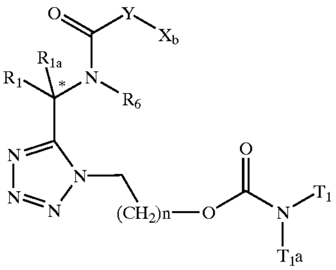
IXD
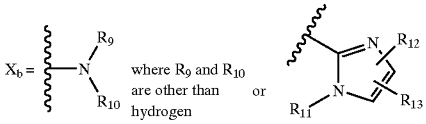
Scheme 3h
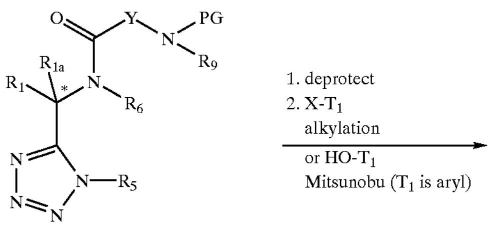
29
Where $R_5$ = —$CH_2(CH_2)n$—O—$PG_x$
n = 0–4, $PG_x$ = a protecting group
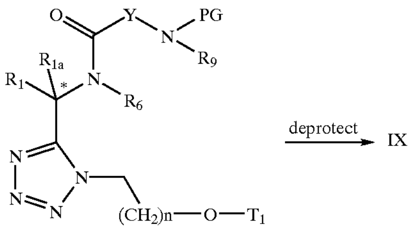
43h -continued
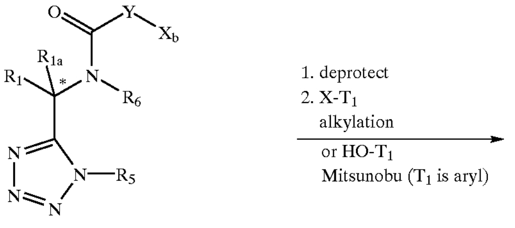
29a
Where $R_5$ = $—CH_2(CH_2)n—O—PG_x$
n = 0–4, $PG_x$ = a protecting group
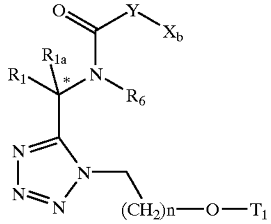
IXE
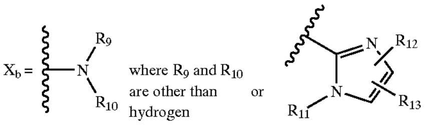
Scheme 4
Triazoles
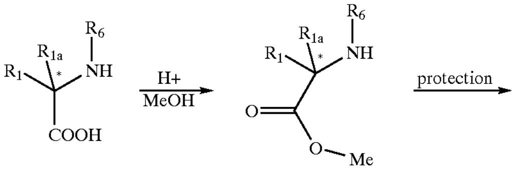
45 46
45 can be any natural or unnatural α-amino acid
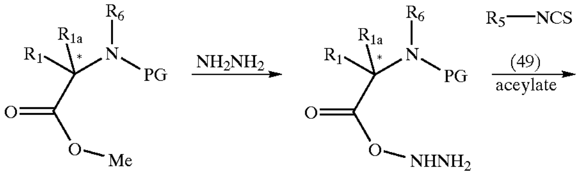
47 48
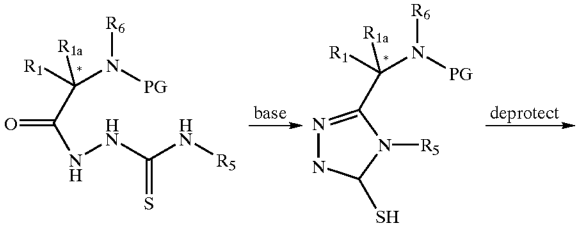
50 51
-continued
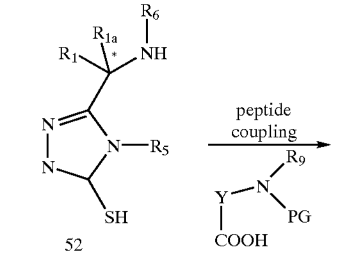
52 6
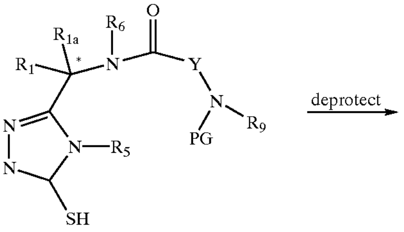
53
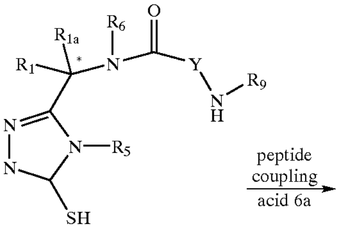
X
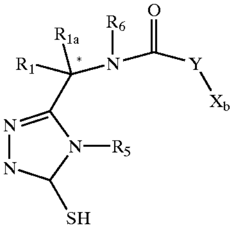
XA
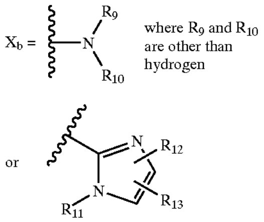
Scheme 4a
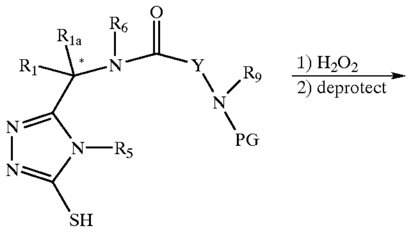
53

-continued
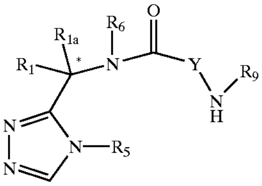
XI
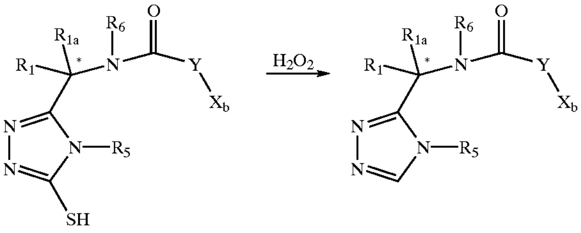
53a XIA
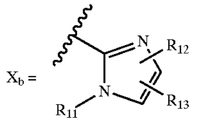
Scheme 4b
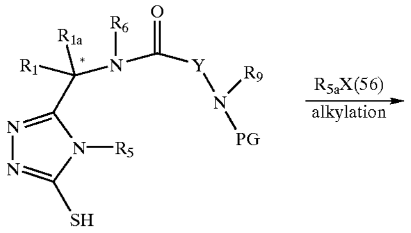
53
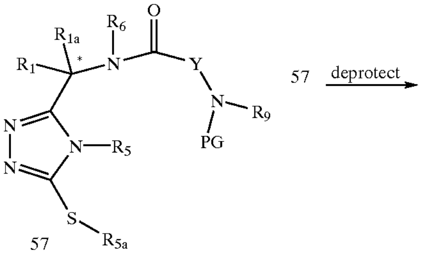
57
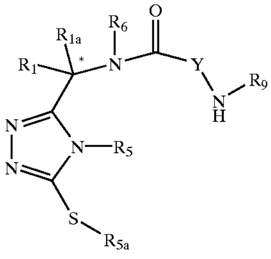
XII
-continued
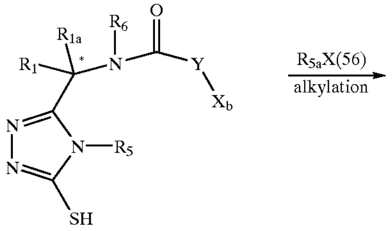
53a
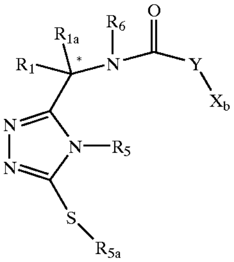
XIIA
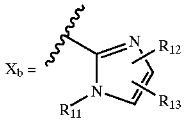
Scheme 4c
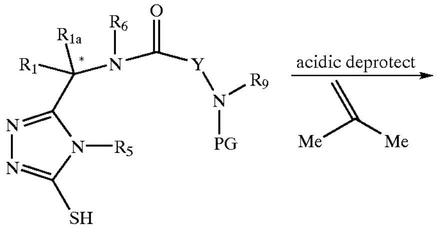
53
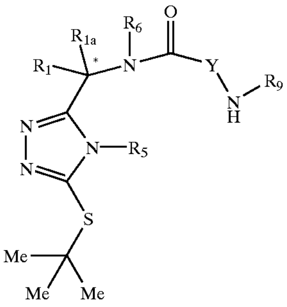
XIII
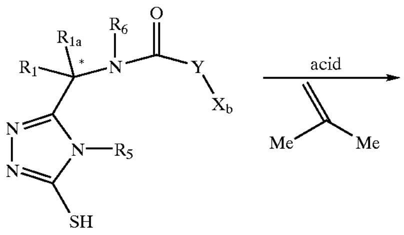
53a -continued
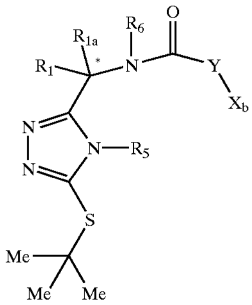
XIIIA
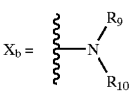
where $R_9$ and $R_{10}$ are other than hydrogen
or
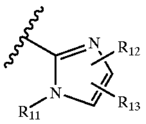
Scheme 4d
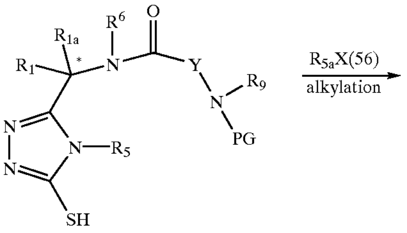
53
$R_5$ is —$(CH_2)nCO_2Me$
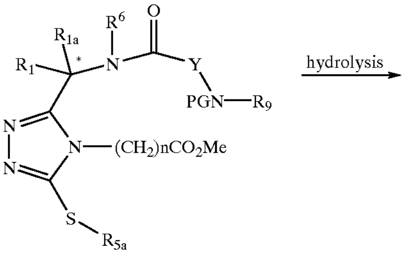
61
60
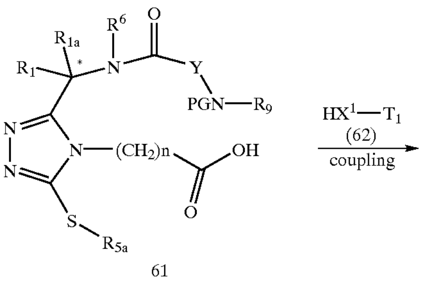
61
-continued
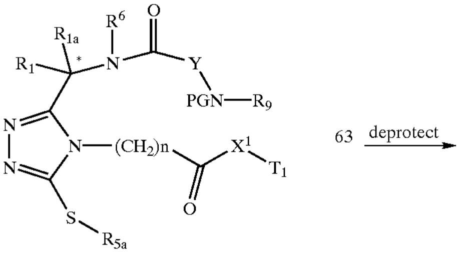
63
$X^1$ is NH, O
$T_1$ is not H
63
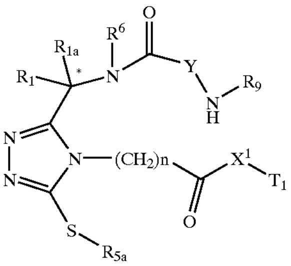
XIV
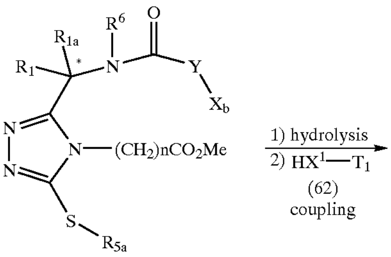
60a
example:
$R_5$ is —$(CH_2)nCO_2Me$,
$X^1$ is NH, O
$T_1$ is not H
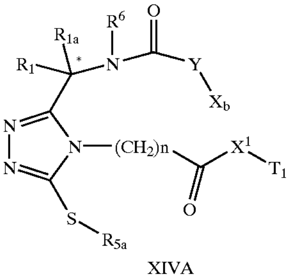
XIVA
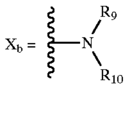
where $R_9$ and $R_{10}$ are other than hydrogen
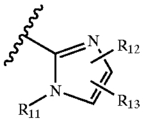

Scheme 5: Imidazoles
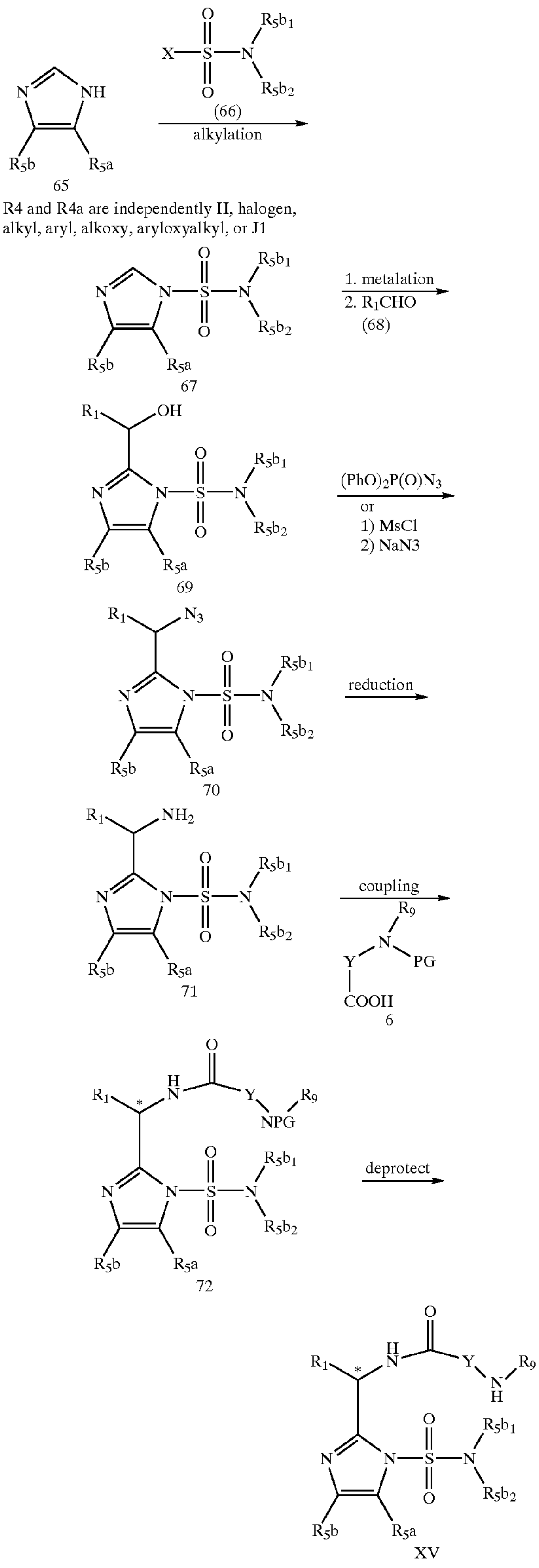
65
R4 and R4a are independently H, halogen, alkyl, aryl, alkoxy, aryloxyalkyl, or J1
67
69
70
71
72
XV
-continued
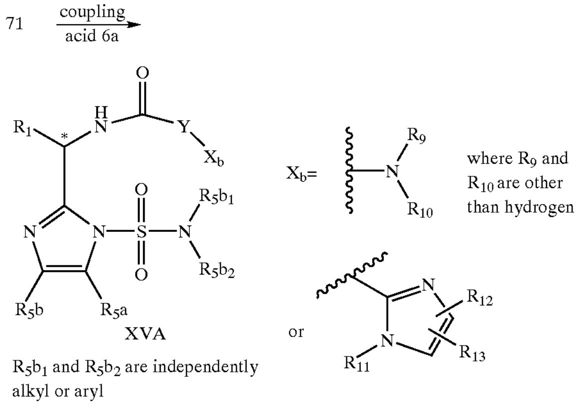
XVA
$R_5b_1$ and $R_5b_2$ are independently alkyl or aryl
Scheme 5a
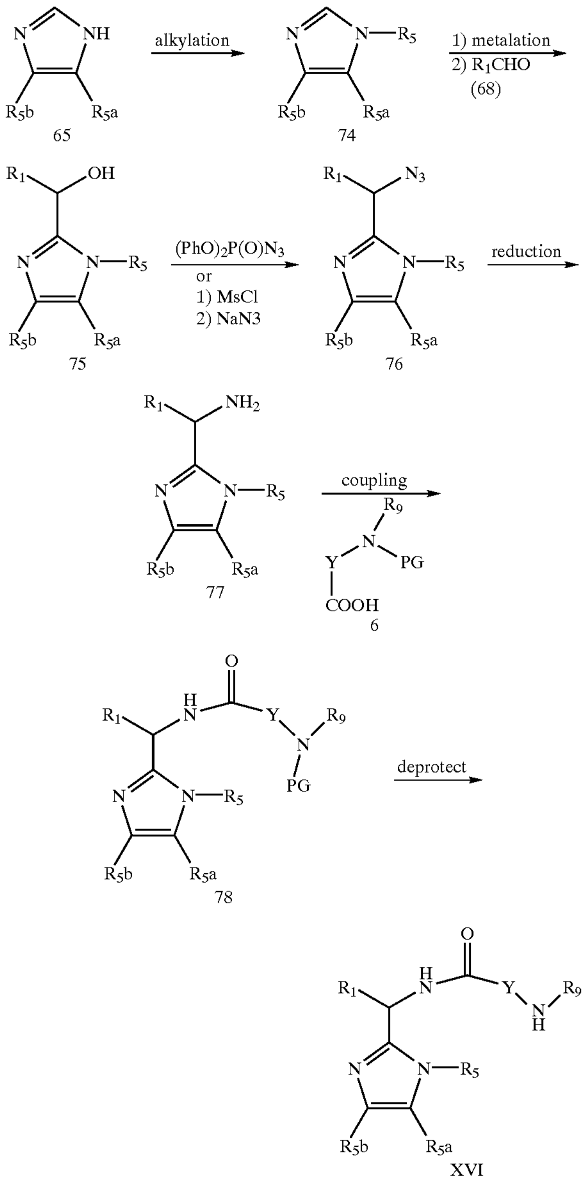
65
74
75
76
77
78
XVI -continued

77

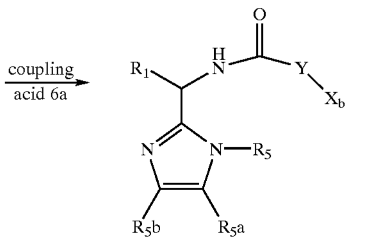

XVIA $X_b$ =

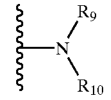

where $R_9$ and $R_{10}$ are other than hydrogen or

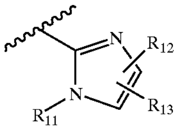

Scheme 6

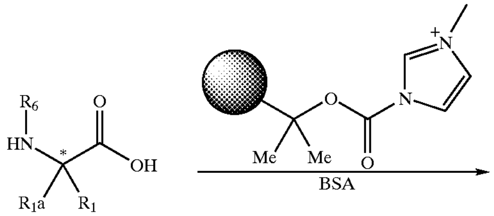

79

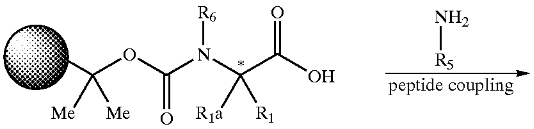

80

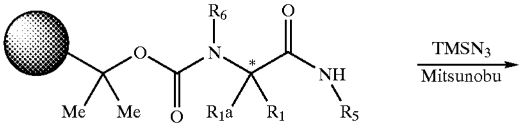

81

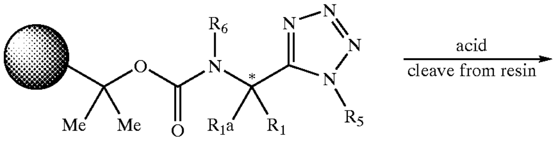

82

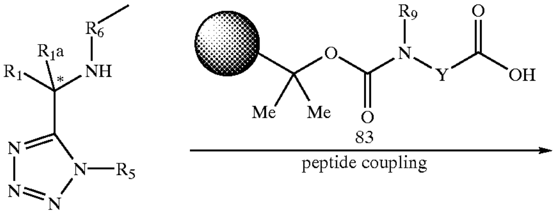

28

83

-continued

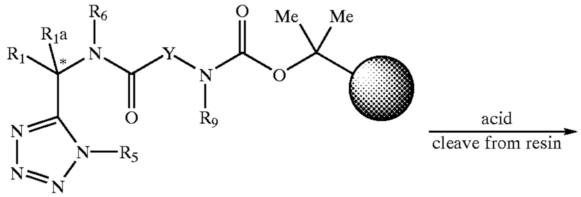

84

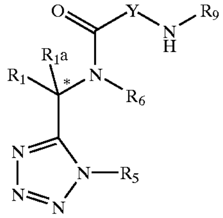

VI

Alternatively, when $R_5$ is $—CH_2(CH_2)nCO_2R_x$

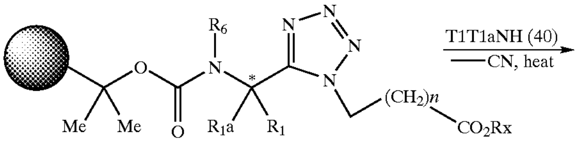

82a

Rx is alkyl, alkaryl, alkenyl,
n is from 0–4

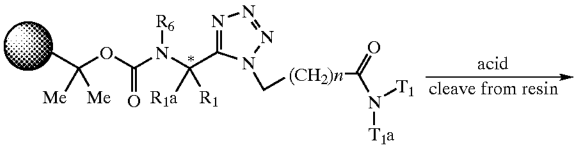

85

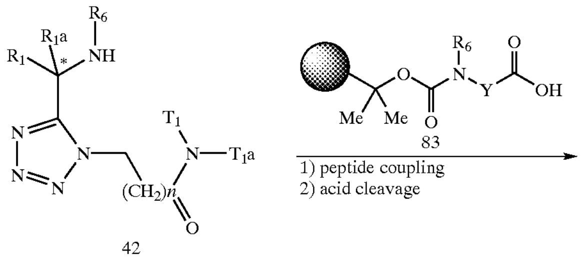

42

83

IX
as in Scheme 3c

The conditions described here for carrying out each step in the general synthetic schemes are conventional and capable of wide variation. They are presented for illustrative purpose only and are not intended as a restriction on the scope of invention.

Final compounds can be easily purified by recrystallization, silica gel chromatography, or reverse phase prep HPLC. In the cases where reverse phase prep HPLC is used, a mixture of solvent A (10% MeOH/90% $H_2O$/0.2% TFA) and solvent B (90% MeOH/10% $H_2O$/0.2% TFA) are used.

Preferred compounds of formula I of the invention include compounds of the structure wherein Xa is as indicated:

IA

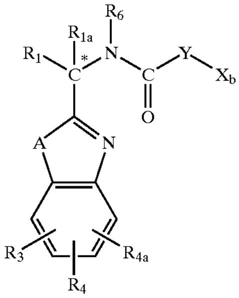

IB

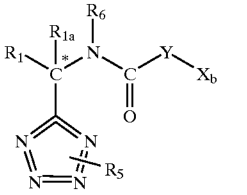

IC

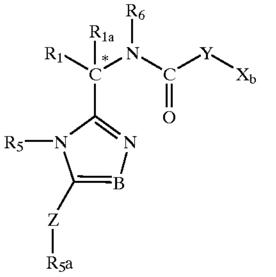

Preferred are compounds of the present invention of the structure I wherein $R_1$ is arylalkyl,arylalkyloxyalkyl, aryloxyalkyl, cycloheteroalkylalkyl, heteroarylalkyl, for example

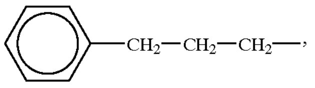

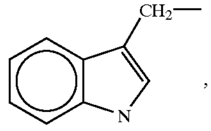

,

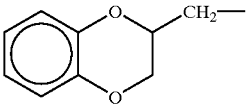

and

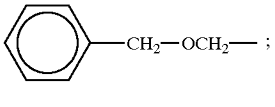

$R_{1a}$ is H or alkyl;

and (1) $X_a$ is

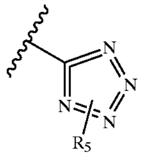

where $R_5$ is alkyl, alkenyl or heteroaryloxy-alkyl, each substituted with J1, and J1 is $-(CH_2)_vOC(O)N(T_{1a})(T_1)$, $-(CH_2)_vCN$, or heteroaryl; or (2) $X_a$ is

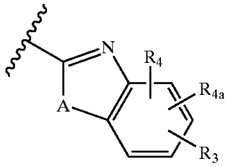

where A is NH, $R_4$ and $R_{4a}$ are H and $R_3$ is J1; or (3) $X_a$ is

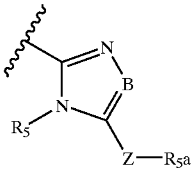

where B is —N—; Z is a bond or —S—; $R_{5a}$ is H, or alkyl or arylalkyl each substituted with 1 to 3 J1; $R_5$ is alkyl optionally substituted with J1;

$R_6$ is H;

Y is

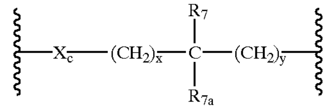

where x and y are 0, $X_c$ is a bond, and $R_7$ and $R_{7a}$ are independently alkyl;

$X_b$ is

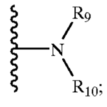

$R_{8j}$ is hydroxy or $-OC(O)R_{8k}$ where $R_{8k}$ is alkyl or aryl;

$R_9$ and $R_{10}$ are independently H and substituted alkyl where the substituents may be 1 or 2 hydroxyls;

J1 is $-(CH_2)_vCN$, $-(CH_2)_vN(T_{1a})SO_2T_1$, $-(CH_2)_vC(O)N(T_{1a})T_1$, $-(CH_2)_vN(T_{1a})C(O)T_1$, $-(CH_2)_vOC(O)N(T_{1a})T_1$, $-(CH_2)_vN(T_{1a})C(O)N(T_{1b})T_1$, or heteroaryl, with v being 0–4;

$T_1$, $T_{1a}$ and $T_{1b}$ are independently alkyl, lower alkythioalkyl, alkoxyalkyl, aryl, arylalkyl, heteroarylalkyl, cycloheteroalkyl, or cycloalkyl, each of which may be optionally substituted with $-OC(O)R_{8f}$, $-C(O)NR_8R_{8a}$, $-(CH_2)_sOH$, with s being 0–2, $-SO_2NR_8R_{8a}$, $-SO_2R_{14}$, or alkoxy; or $T_1$ and $T_{1a}$ or $T_1$ and $T_{1b}$ can together form $-(CH_2)_wX_e(CH_2)_z-$ where $X_e$ is $C(R_{8m})(R_8l)$;

$R_{14}$ is $C_1$–$C_6$alkyl optionally substituted with $-(CH_2)_vOH$, with v being 0–2;

Preferred compounds of the invention include the following:

Chiral
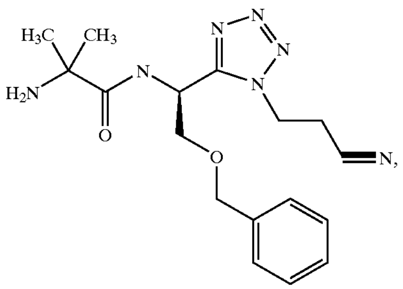
Chiral
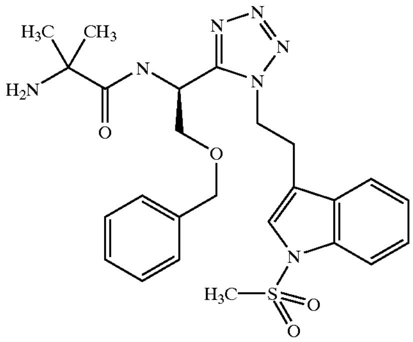
,
Chiral
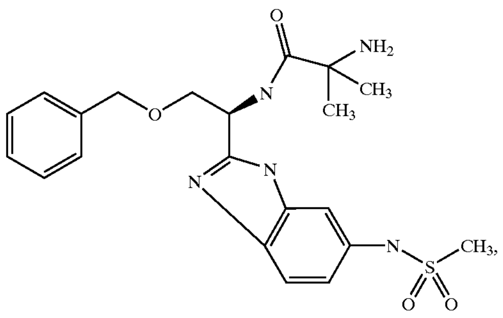
Chiral
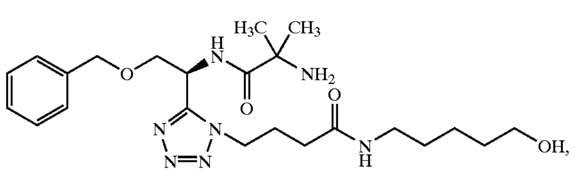
Chiral
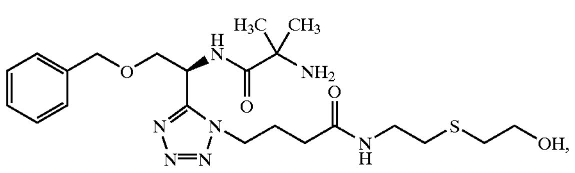
Chiral
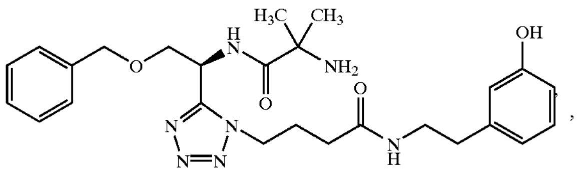
Chiral
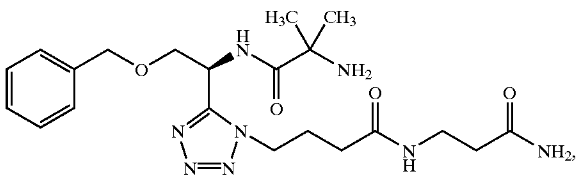
Chiral
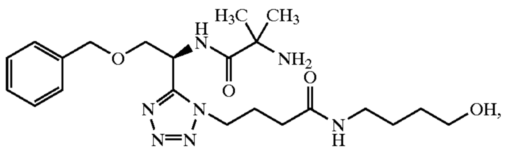
Chiral
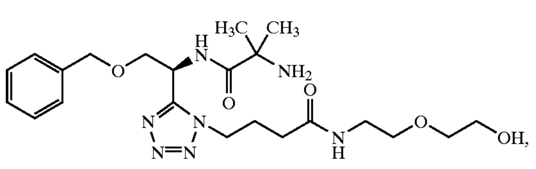
Chiral
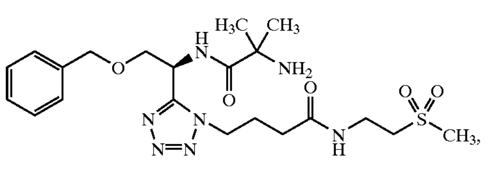

-continued
Chiral
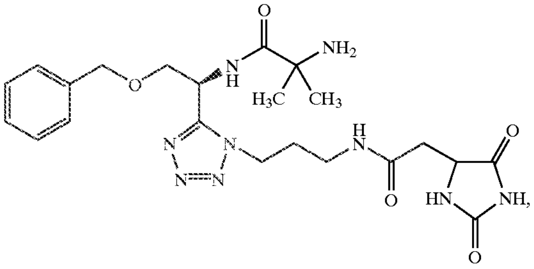
Chiral
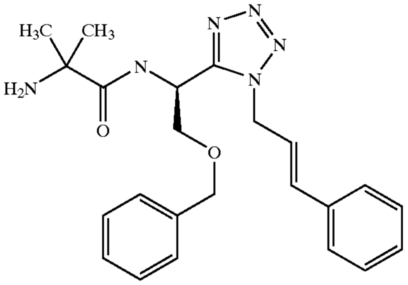
,
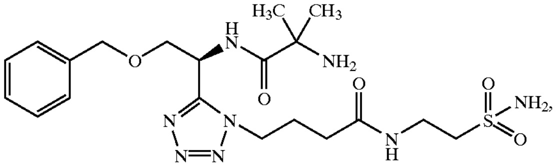
Chiral
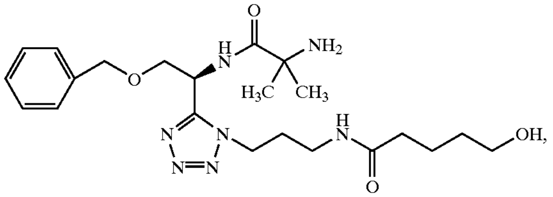
Chiral
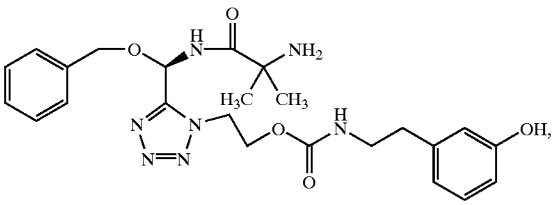
Chiral
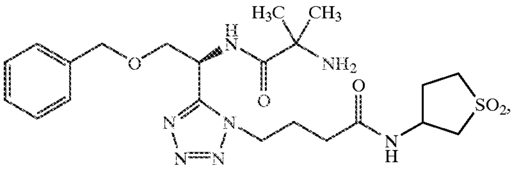
Chiral
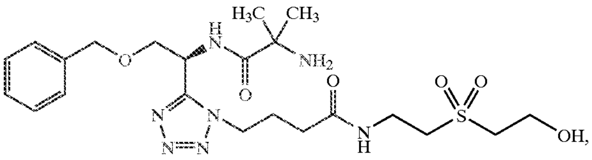
Chiral
Chiral
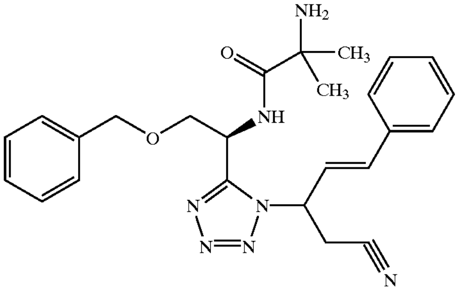
,
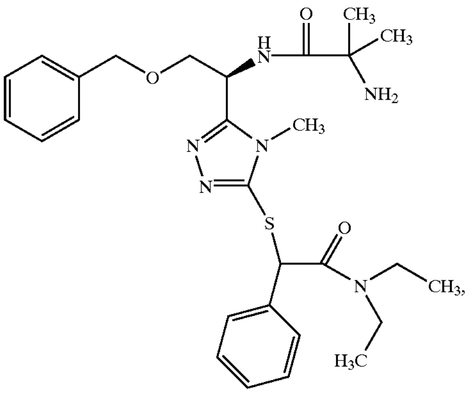

-continued
Chiral
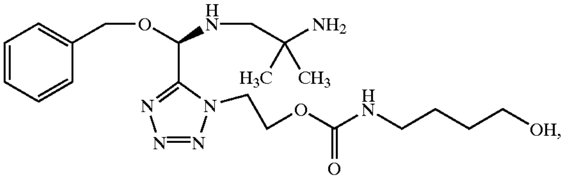
Chiral
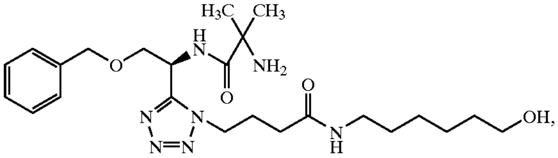
Chiral
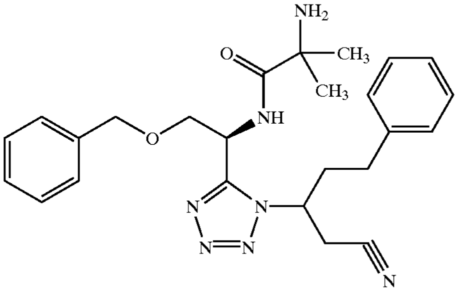
,
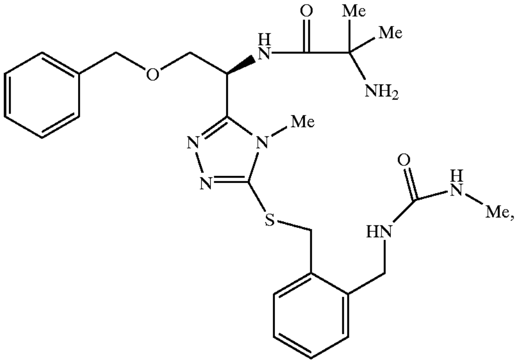
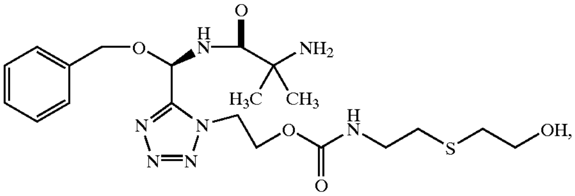
Chiral
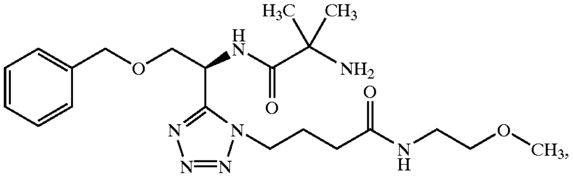
Chiral
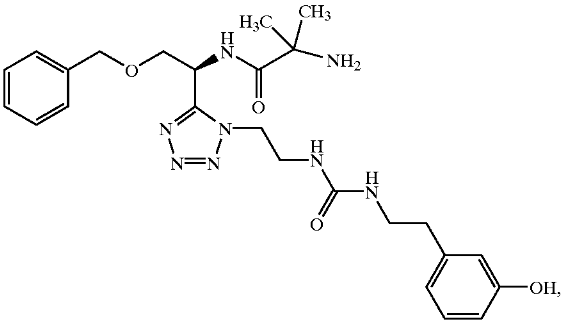
Chiral
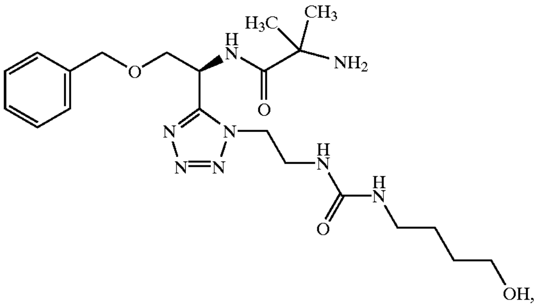
Chiral
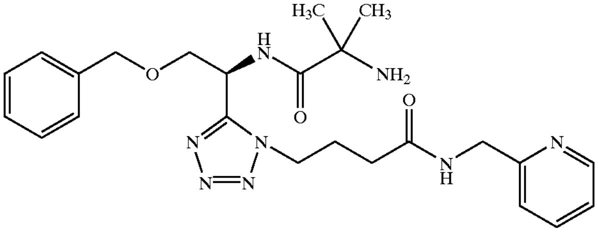
,
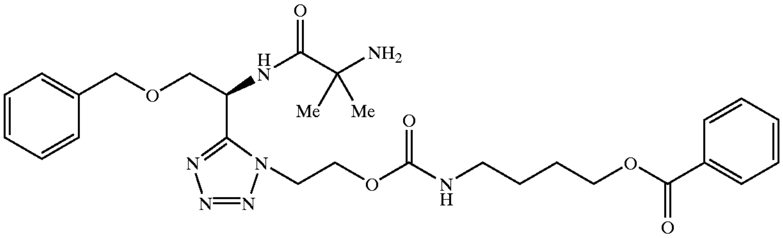
, -continued
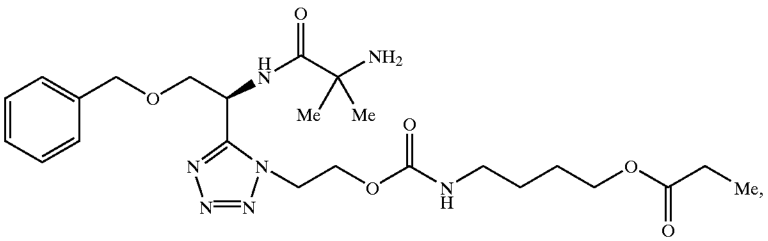
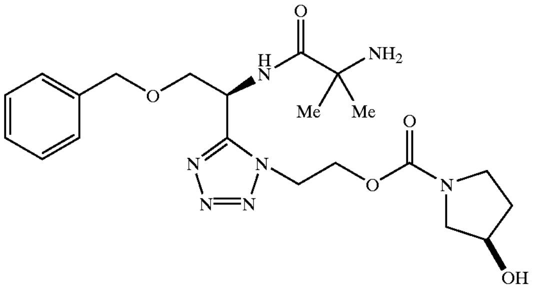
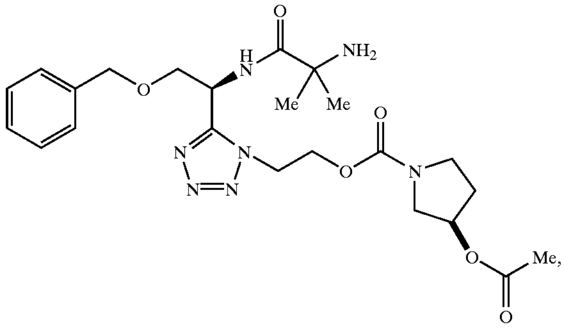
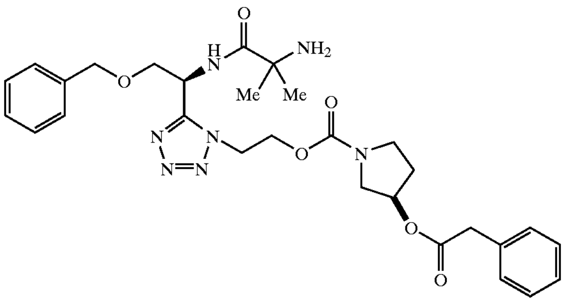
,
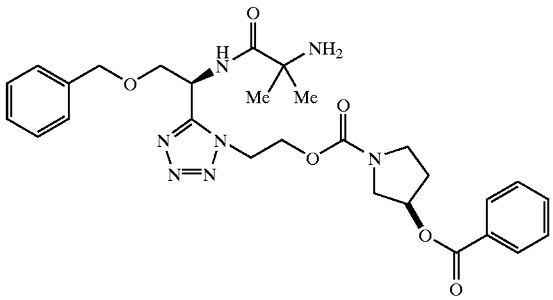
,
Chiral
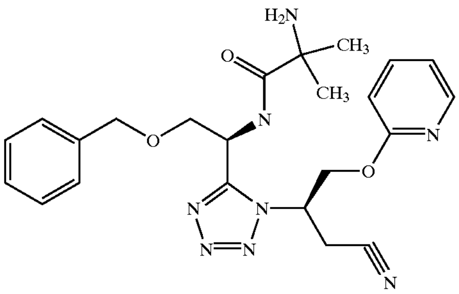
,
Chiral
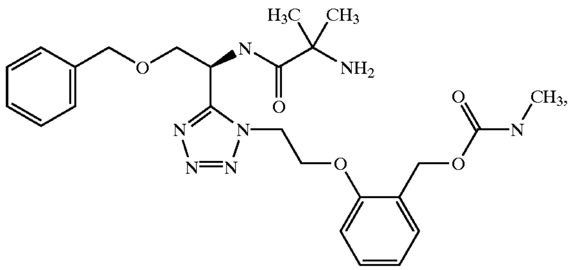
Chiral
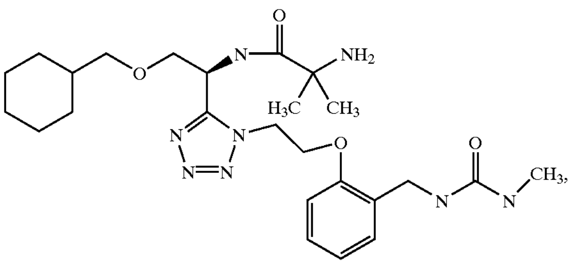
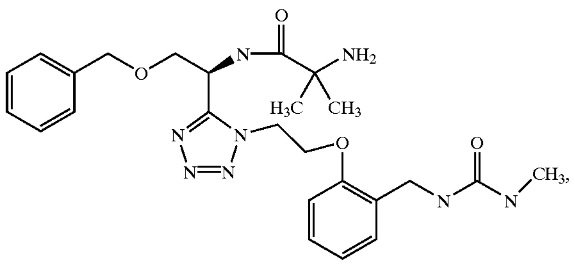

-continued
Chiral
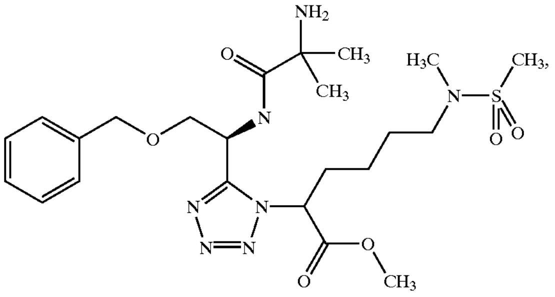
Chiral
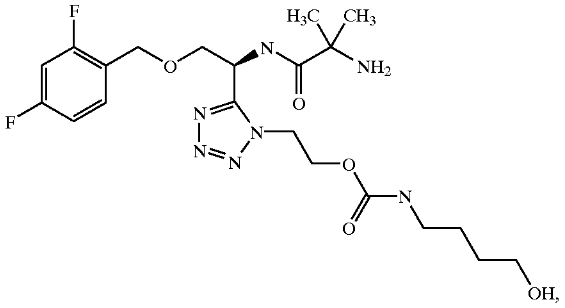
Chiral
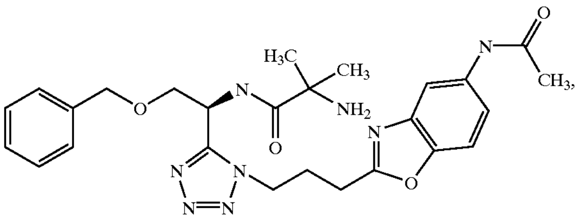
Chiral
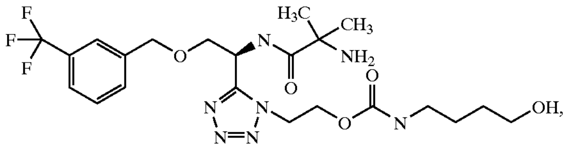
Chiral
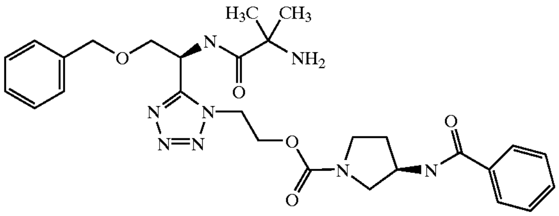
,
Chiral
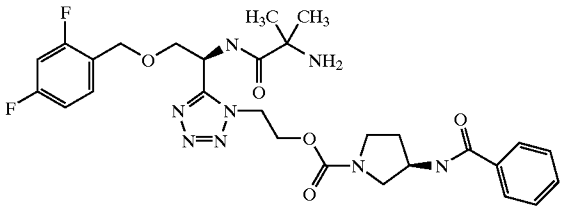
,
Chiral
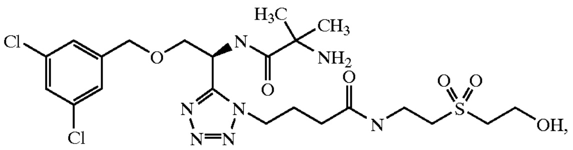
Chiral
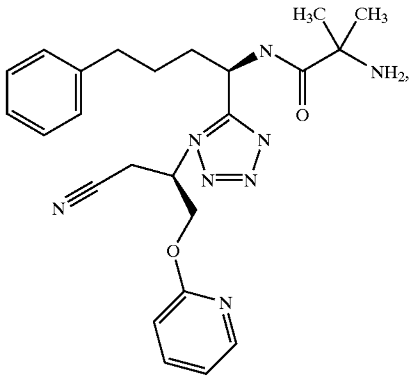
Chiral
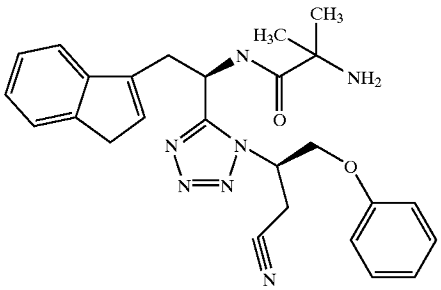
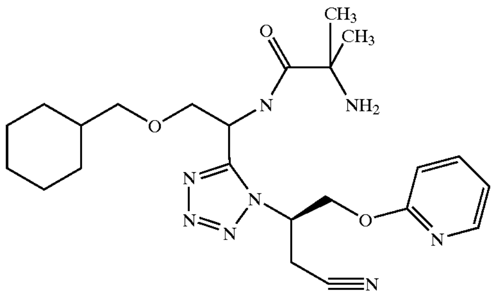
, -continued
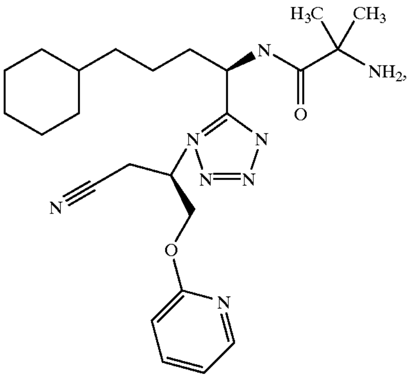
Chiral
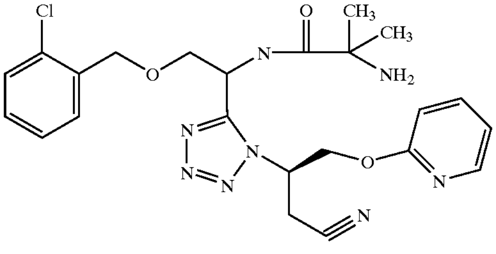
,
Chiral
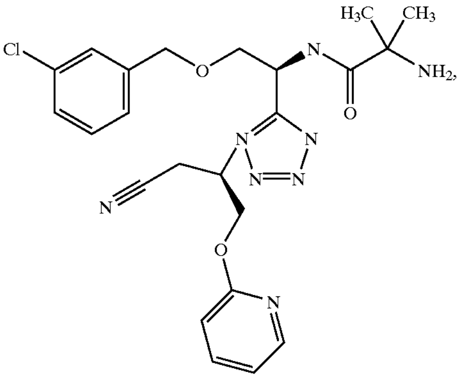
Chiral
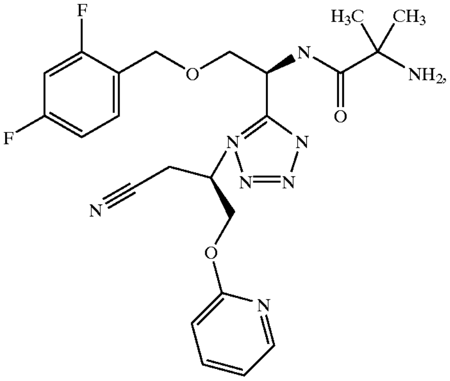
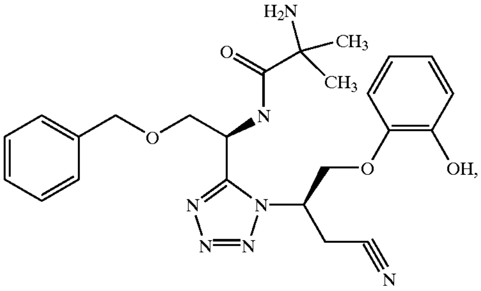
Chiral
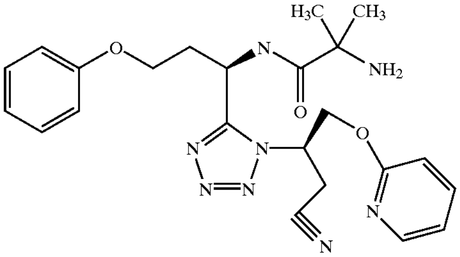
,
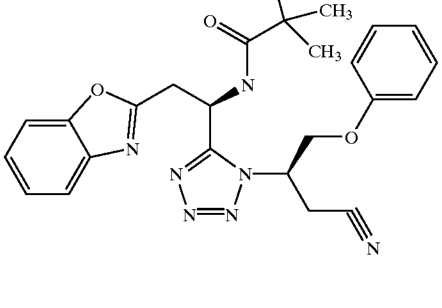
.

More preferred compounds of the invention include the following:
Chiral
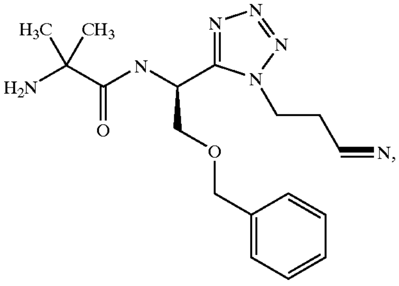
,
Chiral
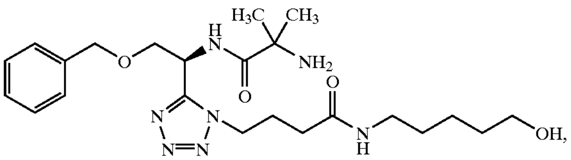
,
Chiral
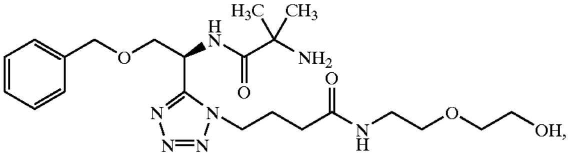
,
Chiral
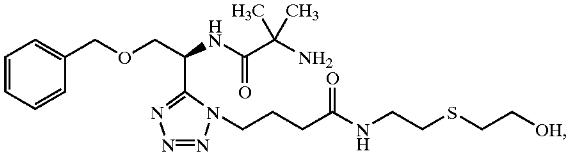
,
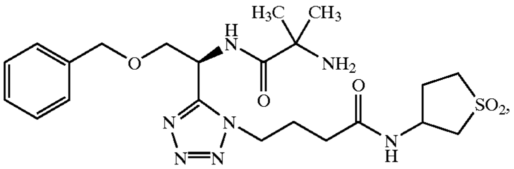
,
Chiral
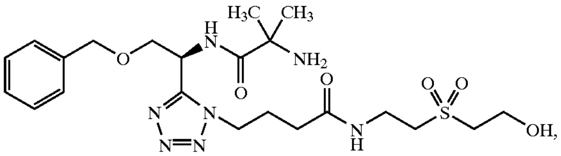
,
Chiral
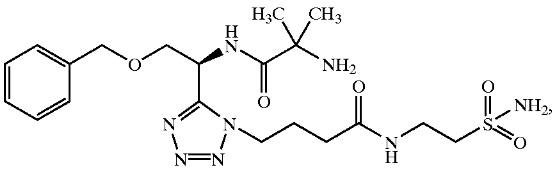
,
Chiral
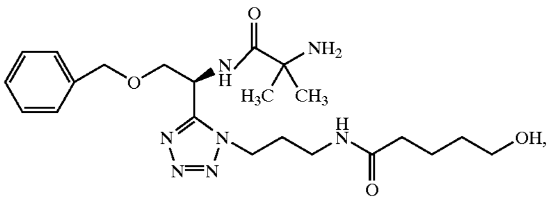
,
Chiral
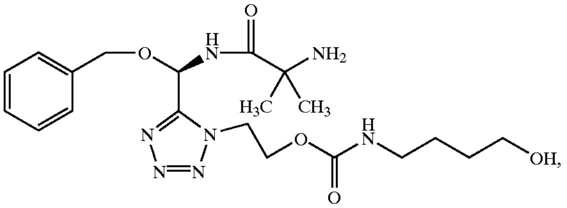
,
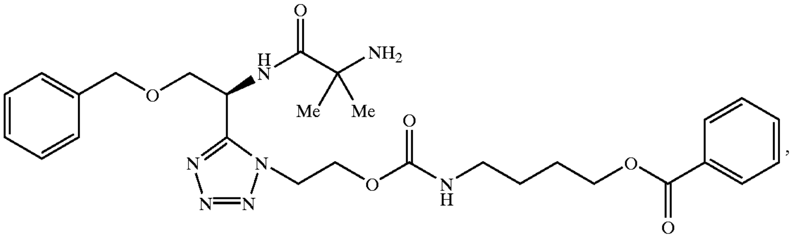
, -continued
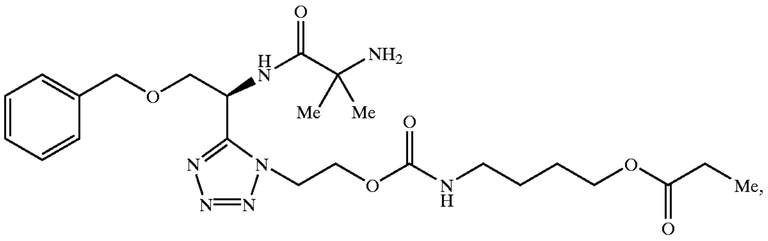
,
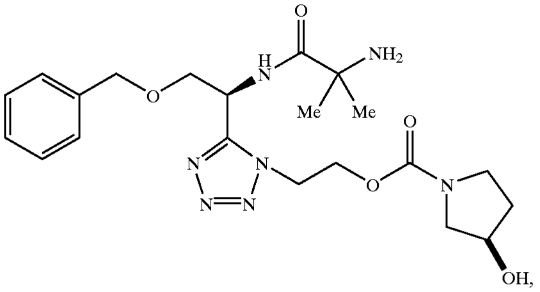
,
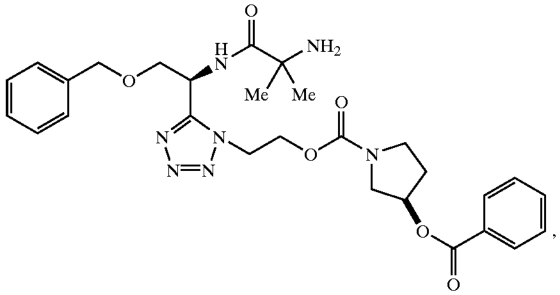
,
Chiral
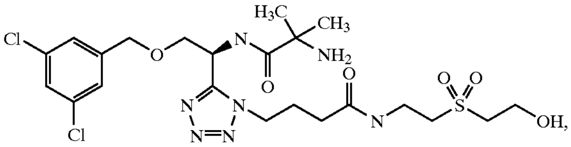
,
Chiral
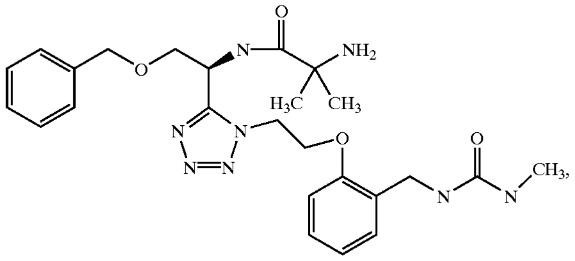
,
Chiral
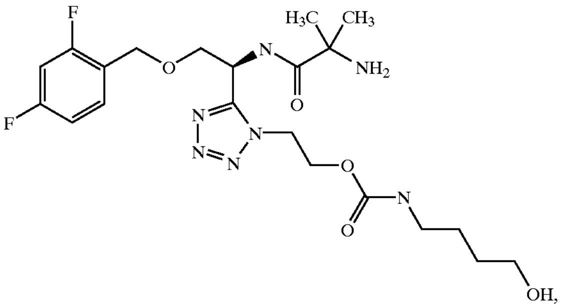
,
Chiral
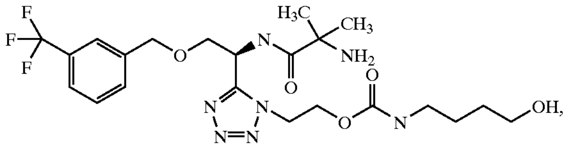
,
Chiral
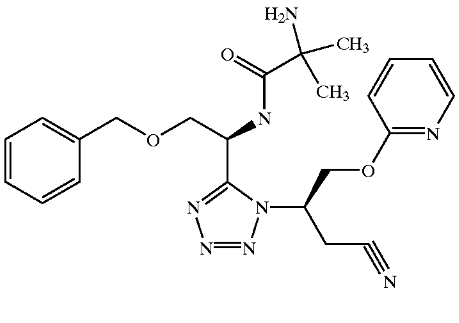
,
Chiral
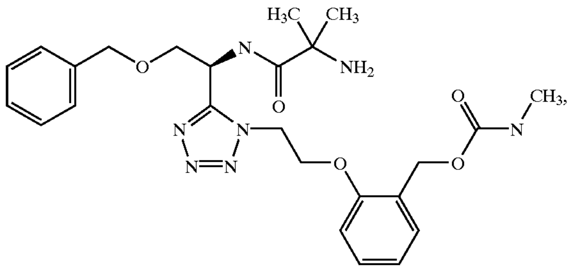
, -continued Chiral

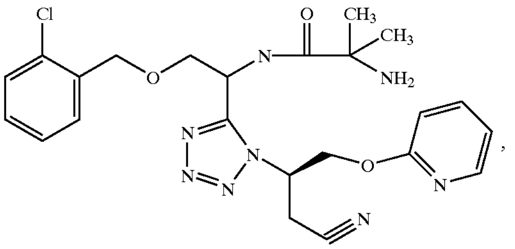

Chiral

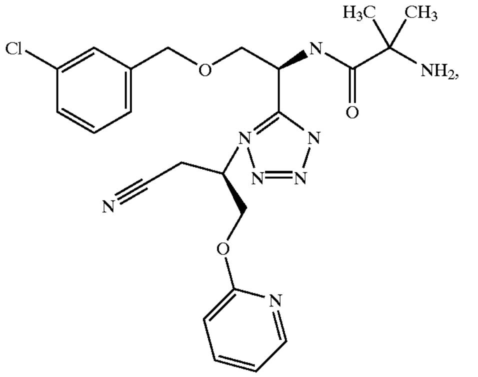

Chiral

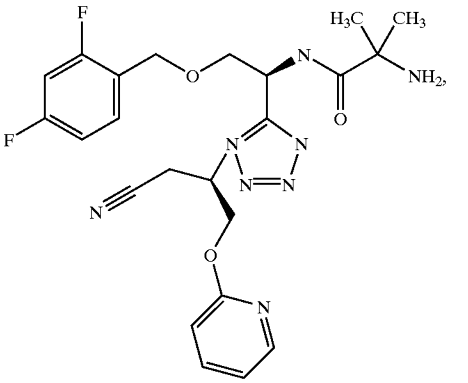

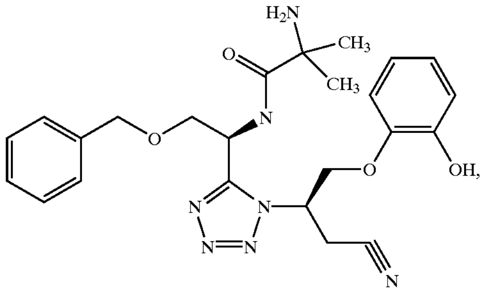

Chiral

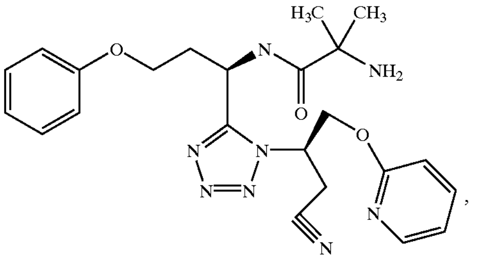

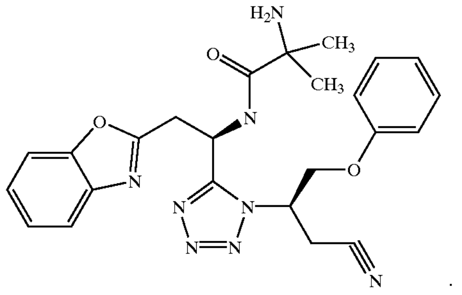

The growth hormone releasing compounds of formula I can be administered to animals, including man, to release growth hormone in vivo. For example, the compounds can be administered to commercially important animals such as swine, cattle, sheep and the like to accelerate and increase their rate and extent of growth, and to increase milk production in such animals.

The present invention includes within its scope pharmaceutical compositions comprising, as an active ingredient, at least one of the compounds of formula I in association with a pharmaceutical carrier or diluent. Optionally, the active ingredient of the pharmaceutical compositions can comprise a growth promoting agent in addition to at least one of the compounds of formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed compounds of formula I of the invention is in combination with other growth hormone secretagogues such as GHRP-6, GHRP-1 as described in U.S. Pat. No. 4,411,890; and publications WO 89/07110 and WO 89/07111 and B-HT920 or growth hormone releasing factor and its analogs or growth hormone and its analogs or somatomedins including IGF-1 and IGF-2. A still further use of the disclosed compounds of formula I of the invention is in combination with parathyroid hormone or a bisphosphonate, such as MK-217 (alendronate), in the treatment of osteoporosis.

A still further use of the disclosed compounds of formula I is in combination with estrogen, testosterone, a selective estrogen receptor modulator, such as tamoxifen or raloxifene, or a selective androgen receptor modulator, such as disclosed in Edwards, J. P. et al., *Bio. Med. Chem. Let.,* 9, 1003–1008 (1999) and Hamann, L. G. et al., *J. Med. Chem.,* 42, 210–212 (1999), for the treatment of aspects of Metabolic Syndrome, maintenance of muscle strength and function in elderly humans, reversal or prevention of fraility in elderly humans, stimulation and increase in muscle mass and muscle strength, attenuation of protein catabolic response after a major operation or trauma; reducing cachexia and protein loss due to chronic illness such as cancer or AIDS; improvement in muscle mobility, and maintenance of skin thickness.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; maintenance of muscle strength and function in elderly humans, reversal or prevention of fraility in elderly humans, prevention of catabolic side effects of glucocorticoids, treatment of osteoporosis, stimulation and increase in muscle mass and muscle strength, stimulation of the immune system, acceleration of wound healing, acceleration of bone fracture repair, treatment of renal failure or insufficiency resulting in growth retardation, treatment of physiological short stature, including growth hormone deficient children, treatment of short stature associated with chronic illness, treatment of obesity and growth retardation associated with obesity, treating growth retardation associated with Prader-Willis syndrome and Turner's syndrome; accelerating the recovery and reducing hospitalization of burn patients; treatment of intrauterine growth retardation, skeletal dysplasia, hypercortisolism and Cushings syndrome; induction of pulsatile growth hormone release; replacement of growth hormone in stressed patients; treatment of osteochondrodysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation or trauma; reducing cachexia and protein loss due to chronic illness such as cancer or AIDS; treatment of hyperinsulinemia including nesidioblastosis; adjuvant treatment for ovulation induction; to stimulate thymic development and prevent the age-related decline of thymic function; treatment of immunosuppressed patients; improvement in muscle mobility, maintenance of skin thickness, metabolic homeostasis, renal homeostasis in the frail elderly; stimulation of osteoblasts, bone remodeling, and cartilage growth; stimulation of the immune system in companion animals and treatment of disorders of aging in companion animals; growth promotant in livestock; and stimulation of wool growth in sheep.

In addition, the conditions, diseases, and maladies collectively referenced to as "Syndrome X" or Metabolic Syndrome as detailed in Johannsson *J. Clin. Endocrinol. Metab.,* 82, 727–34 (1997), may be treated employing the compounds of the invention.

The compounds of the present invention are agents that are growth hormone secretagogues and can be administered to various mammalian species, such as monkeys, dogs, cats, rats, humans, etc., in need of treatment. These agents can be administered systemically, such as orally or parenterally.

The compounds of the invention can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), anti-oxidants (ascorbic acid or sodium bisulfite) or the like. Oral dosage forms are preferred, although parenteral intranasal or aerosol forms are quite satisfactory as well.

The dose administered must be carefully adjusted according to the age, weight, and condition of the patient, as well as the route of administration, dosage form and regimen, and the desired result. In general, the dosage forms described above may be administered in amounts from about 0.0001 to about 100 mg/kg or body weight or in an amount within the range from about 1 to about 1000 mg per day, preferably, from about 5 to about 500 mg per day in single or divided doses of one to four times daily.

The following Examples represent preferred embodiments of the invention. All temperatures are in ° C. unless indicated otherwise.

General Experimental

The term HPLCa refers to a Shimadzu high performance liquid chromatograph (HPLC) using a 4 minute gradient of from 0–100% solvent B [MeOH:$H_2O$:0.2% $H_3PO_4$] with a 1 min. hold, an ultra violet (UV) detector set at 220 nM, and using a column (4.6x50 mm) packed with YMC C18 5 micron resin. The term HPLCb refers to a Shimadzu HPLC using a 4 minute gradient of from 0–100% solvent B [MeOH:$H_2O$:0.1% TFA], with a 1 min. hold, an ultra violet (UV) detector set at 220 nM, and using a column (4.6x50 mm) packed with YMC C18 5 micron resin. A mixture of solvent A (10% MeOH/90% $H_2O$/0.2% TFA) and solvent B (90% MeOH/10%$H_2O$/0.2% TFA) are used for preparative reverse phase HPLC in an automated Shimadzu system. The preparative columns are packed with YMC ODS C18 5 micron resin.

EXAMPLE 1

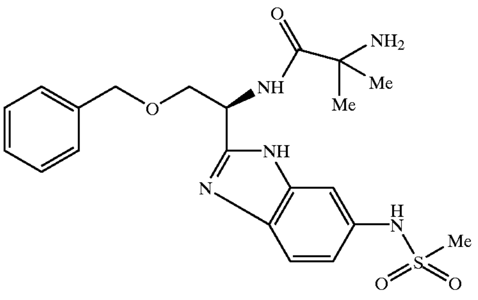

A

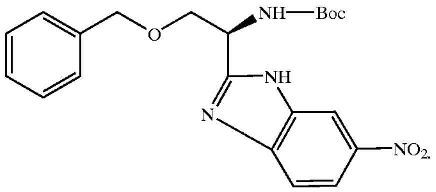

To a 0° C. solution of the carboxylic acid

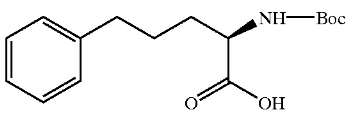

(5.0 g, 16.9 mmol, Sigma), dianiline

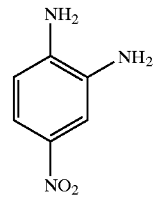

(2.3 g, 15 mmol, Aldrich), and 1-hydroxy-zazabenzotriazole (HOAt) (2.5 g, 18 mmol) in DMF (48 ml) under nitrogen was added 1-(3-dimethylaminopropyl)-3-ethylcarbodiimide (EDAC or EDCI) (3.25 g, 17 mmol) then diisopropylethyl amine (2.95 ml, 17 mmol). The reaction mixture was allowed to slowly warm to room temperature overnight. After 18 hrs, the reaction was diluted with ethyl acetate. The organic layer was extracted with dilute aqueous sodium bicarbonate, water, brine, dried over sodium sulfate, and concentrated in vacuo to give

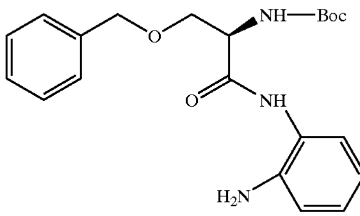

as a red colored oil (5.47 g), containing starting dianiline, (referred to here as crude compound). The above crude compound was used in the subsequent reaction without further purification. HPLCb rt=3.19 min.

A portion of the above crude compound (1.25 g,≦2.9 mmol) was dissolved in acetic acid (45 mL) and heated at 69° C. for 4.5 h. After stirring at room temperature overnight, the volatiles were removed in vacuo to give crude title compound in the form of a red colored oil, which may be used without further purification. Alternatively, the red colored oil was dissolved in ethyl acetate and the organic layers were extracted three times with 1 N aqueous hydrogen chloride, water, brine, dried over sodium sulfate, and concentrated in vacuo to give pure title compound (0.92 g) as a dark colored oily foam. HPLCa rt=3.99 min.

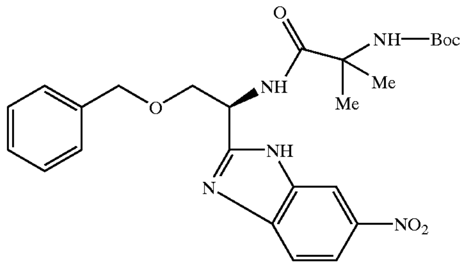

Crude Part A compound (≦450 mg, ≦1.04 mmol)) was treated with a solution of hydrogen chloride in dioxane (6 ml, 4N) and after 45 min. a brown solid had fallen from solution. The volatiles were evaporated in vacuo after 2 h. to give a dark colored solid. The residue was triturated three times with hot ethyl acetate to give impure (crude) compound

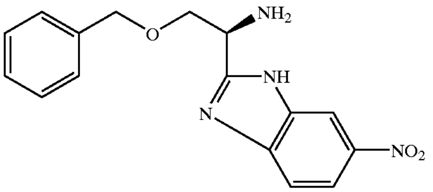

as a brown colored solid (338 mg). The crude compound was used without further purification in the next reaction. HPLCa rt=2.93 min.

To a 0° C. solution of Boc-methylalanine carboxylic acid (256 mg, 1.26 mmol, Aldrich), and the above crude compound (338 mg, ≦0.97 mmol), and HOAt (207 mg, 1.52 mmol) in DMF (5 ml) under nitrogen was added EDAC (245 mg, 1.28 mmol) then diisopropylethyl amine (0.39 ml, 2.25 mmol). The reaction mixture was allowed to slowly warm to room temperature overnight. After 18 h., the reaction was diluted with ethyl acetate. The organic layer was extracted with dilute aqueous sodium bicarbonate, 1N hydrogen chloride, water, brine, dried over sodium sulfate, and concentrated in vacuo to give a dark colored oil (564 mg). The crude residue was combined with material from another reaction (0.10 mmol) and was purified by flash chromatography ($SiO_2$, 40 g), eluting with 3.5% methanol/dichloromethane to give title compound as an orange colored oil (305 mg). HPLCb rt=4.20 min; LC/MS (electrospray, +ions) m/z 498 (M+H).

C.

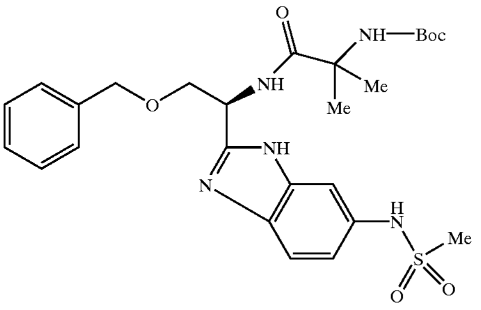

A solution of Part B compound (100 mg, 0.2 mmol) in methanol (2 ml) containing 10% palladium on carbon (15 mg) was purged with hydrogen and stirred under a hydrogen atmosphere (balloon) for 2 h. The reaction mixture was filtered through a Nylon frit, washing well with methanol, and the solvents evaporated to give amine compound

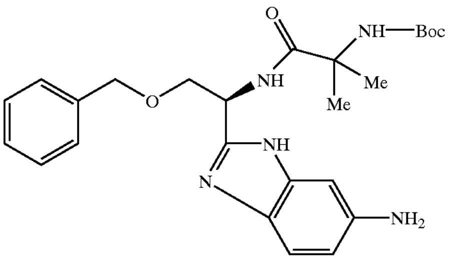

as an orange colored foam (82 mg, 88% crude recovery), ~80% pure by HPLCa rt=3.0 min. The amine material was used without further purification in the next reaction. LC/MS (electrospray, +ions) m/z 468 (M+H).

To a solution of crude amine (82 mg, 0.18 mmol) and triethylamine (35 μl, 0.25 mmol) in dichloromethane (1.8 ml) under nitrogen was added methanesulfonyl chloride (18 μl, 0.23 mmol). After 2 h., the reaction was diluted with ethyl acetate and the organic layer was extracted with water, brine, dried over sodium sulfate, and concentrated in vacuo. The crude residue was purified by flash chromatography ($SiO_2$, 10 g), eluting with 5.25% methanol/dichloromethane to give title compound as an orange colored solid (30.7 mg). HPLCa rt=3.37 min.

D.

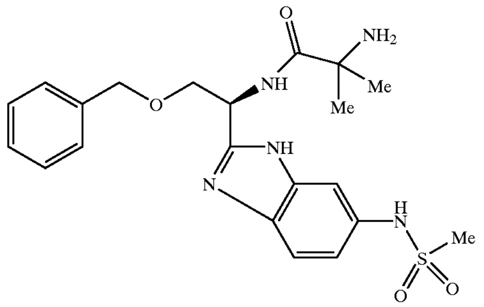

To neat Part C compound (31 mg, 56.8 μmol) was added hydrogen chloride (0.8 ml, 4N in dioxane) and the mixture stirred for 2.5 h. The volatiles were removed in vacuo and co-evaporated twice with dichloromethane to give a tan colored solid. The crude residue was combined with material from another reaction (39.8 μmol) and neutralized by dissolving in 9% methanol/dichloromethane containing ammonium hydroxide. The resulting suspension was purified by flash chromatography ($SiO_2$, 5 g), eluting with 9% methanol/dichloromethane containing 0.9% ammonium hydroxide to give a glassy solid (35 mg). The residue was dissolved in methanol (2.5 ml) and treated with trifluoroacetic acid (4.5 μl). After 15 min, the volatiles were removed in vacuo to give the title compound (43 mg) as a tan colored solid. HPLCb rt=2.43 min. MS (electrospray, +ions) m/z 446 (M+H).

EXAMPLE 2

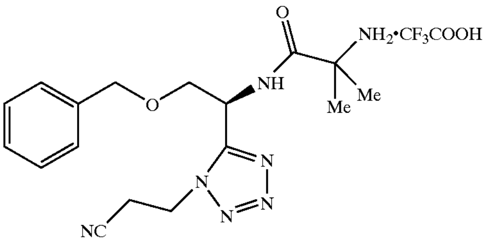

A.

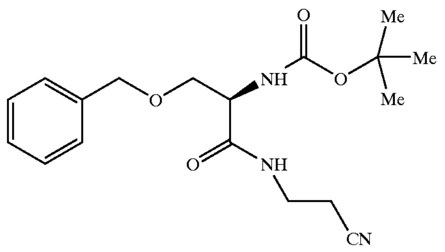

N-Methyl morpholine (1.08 mL, 9.83 mmol) and isobutyl chloroformate (1.27 mL, 9.80 mmol) were added to a solution of N-Boc-O-benzyl serine (2.91 g, 9.84 mmol, Sigma) in THF (14.0 mL), cooled at −18° C. After stirring the mixture for 0.5 h. at −18° C., a −14° C. solution of 3-aminopropionitrile (0.73 mL, 9.89 mmol) and N-methyl morpholine (1.08 mL, 9.83 mmol) in THF (6.0 mL) was added and the resulting mixture was allowed to warm up to −6° C. over a period of 5.25 h. The mixture was filtered and the solution was evaporated near to dryness. The residue was taken up in EtOAc (70 mL) and washed with 5% $NaHCO_3$ (2×60 mL), water (60 mL) and brine (60 mL). The organic solution was dried ($Na_2SO_4$), evaporated and chromatographed($SiO_2$ 230–400 mesh, 1/1 hexanes/EtOAc) to afford title compound (3.33 g, 97% yield): LC/MS (electrospray, +ions) m/z 348 (M+H).

B.

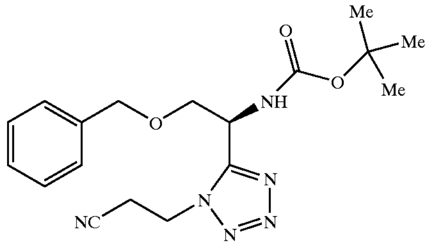

Diethylazodicarboxylate (1.51 mL, 9.59 mmol) and azidotrimethylsilane (1.27 mL, 9.57 mmol) were added to a solution of Part A compound (3.33 g, 9.60 mmol), triphenylphosphine (2.52 g, 9.61 mmol) and diisopropylethyl amine (0.42 mL, 2.41 mmol) in THF (30 mL), previously cooled at 0° C. The mixture was stirred at room temperature (rt) overnight and then cooled at 0° C. Another equivalent each of triphenylphosphine (2.52 g), diethylazodicarboxylate (1.51 mL) and azidotrimethylsilane (1.27 mL) was added and stirring was continued for an additional 28 h at rt. The reaction mixture was cooled at 0° C. and mixed with an aqueous solution of ammonium cerium (IV) nitrate (2.63 g/100 mL). The aqueous mixture was extracted with $CH_2Cl_2$ (3×150 mL) and the combined organic phase was dried ($Na_2SO_4$), evaporated and chromatographed ($SiO_2$ 230–400 mesh, 1/1 hexanes/EtOAc) to give the tetrazole (3.5 g, contaminated with 1,2-dicarbethoxyhydrazine) and Part A compound (1.47 g contaminated with triphenylphosphine oxide). The contaminated tetrazole was dissolved in $CHCl_3$ and ether was added to precipitate title compound (2.08 g) as a colorless solid: MS (electrospray, +ions) m/z 373 (M+H).

C.

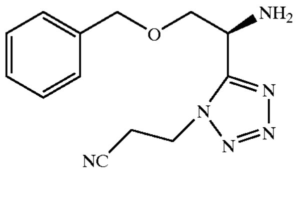

To a solution of Part B compound (354 mg, 0.95 mmol) in $CH_2Cl_2$ (2.0 mL) was added a 4M HCl/dioxane solution (3.0 mL) and the combined solution was allowed to stand for 1.25 h. The solvents were removed at reduce pressure and the residue was taken up in i-PrOH (1.5 mL). Brine (25.0 mL) was added and the pH of the aqueous solution was adjusted to 10 by addition of 1M $K_2CO_3$. The aqueous solution was extracted with $CH_2Cl_2$ (3×40 mL) and the combined organic layer was dried ($Na_2SO_4$) and evaporated to provide title amine compound (258 mg) as a colorless oil. This material was used without further purification in the subsequent reaction: $^1$H NMR δ ($CDCl_3$,ppm) 7.31 (m, 5H), 4.80 (m, 2H), 4.54 (m, 3H), 3.88 (m, 2H), 2.99 (m, 2H), 1.82 (broad s, 2H).

D.

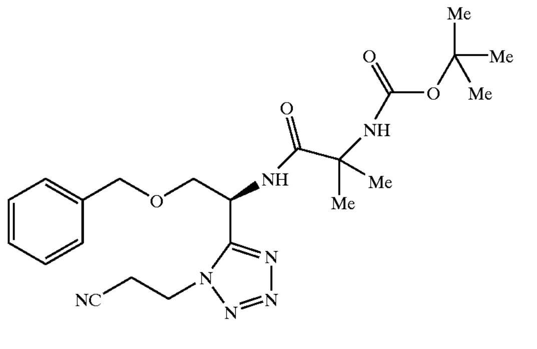

N-Boc-methyl alanine

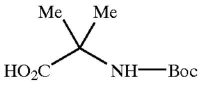

(285 mg, 1.40 mmol, Sigma), EDAC (272 mg, 1.42 mmol), HOAt (190 mg, 1.40 mmol), 1,2-dichloroethane (1,2-DCE) (1.6 mL) and DMF (250 μL) were mixed at 0° C. and stirred for 15 min. The resulting cloudy solution was transferred, via syringe, to a 0° C. solution of the crude Part C amine compound (258 mg, 0.95 mmol) in 1,2-DCE (1.4 mL) and the mixture was stirred for 20 h at rt. The reaction mixture was diluted with EtOAc (75 mL) and washed with saturated $NaHCO_3$ (2x40 mL), water (40 mL) and brine (40 mL). The organic layer was dried ($Na_2SO_4$), evaporated and chromatographed ($SiO_2$ 230–400 mesh, 1/1 hexanes/EtOAc) to provide title compound (338.5 mg) as a colorless oil: $^1$H NMR δ ($CDCl_3$,ppm) 7.36 (m, 6H), 5.55 (m, 1H), 5.13 (broad s, 1H), 4.72 (t, J=6.6 Hz, 2H), 4.51 (2d, J=12 Hz, 2H), 4.02 (dd, J=9.2, 5.8 Hz, 1H), 3.86 (t, J=8.3 Hz, 1H), 2.98 (m, 2H), 1.44 (s, 3H), 1.41 (s, 3H), 1.32 (s, 9H).

E.

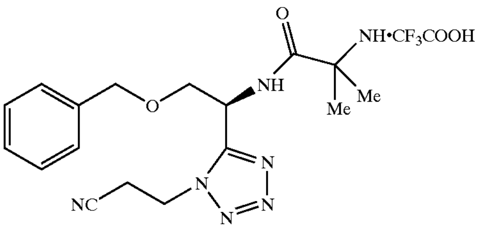

Part D compound (181 mg, 0.40 mmol) was treated with 15% TFA (4.0 mL) for 2.2 h and evaporated in vacuo and the residual TFA was coevaporated with $CH_2Cl_2$ (5x6 mL). The oily crude residue was dissolved in $CH_2Cl_2$/MeOH (several drops) and ether was added to precipitate the title compound (157 mg) as a white solid: LC/MS (electrospray, +ions) m/z 358 (M+H).

EXAMPLE 3

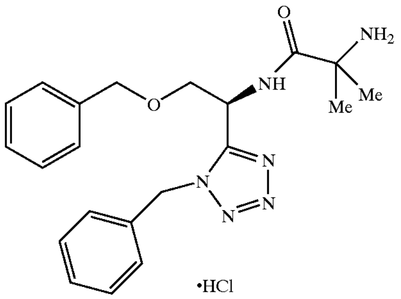

•HCl

A.

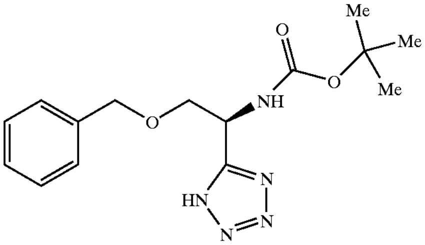

Diethylazodicarboxylate (1.51 mL, 9.59 mmol) and azidotrimethylsilane (1.27 mL, 9.57 mmol) were added to a solution of Example 2 Part A compound

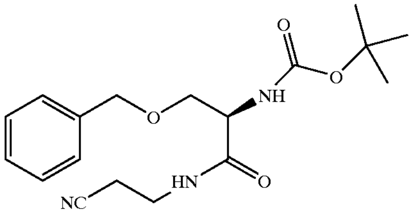

(3.33 g, 9.60 mmol), triphenylphosphine (2.52 g, 9.61 mmol) and diisopropylethyl amine (0.42 mL, 2.41 mmol) in THF (30 mL), previously cooled at 0° C. The mixture was stirred at rt. overnight and then cooled at 0° C. Another equivalent each of triphenylphosphine (2.52 g), diethylazodicarboxylate (1.51 mL) and azidotrimethylsilane (1.27 mL) was added and stirring was continued for an additional 28 h at rt. The reaction mixture was cooled at 0° C. and mixed with an aqueous solution of ammonium cerium (IV) nitrate (2.63 g/100 mL). The aqueous mixture was extracted with $CH_2Cl_2$ (3x150 mL) and the combined organic phase was dried ($Na_2SO_4$), evaporated and chromatographed ($SiO_2$ 230–400 mesh, 1/1 Hex/EtOAc) to give crude Example 2 Part B compound (3.5 g). The contaminated residue containing Example 2 Part B compound was dissolved in $CHCl_3$, Example 2 Part B compound (2.08 g) precipitated by addition of ether, and the filtrate concentrated. The resulting residue containing more Example 2 Part B compound was dissolved in THF (12 mL) and 1M NaOH and additional volumes of THF were added until disappearence of Example 2 Part B compound, monitoring by TLC (1/1 hexanes/EtOAc). The final reaction mixture was diluted with brine (70 mL), and washed with ether (60 mL) and $CHCl_3$ (2x50 mL). The aqueous layer pH was adjusted to 3, by addition of 1M $H_3PO_4$, and the solution was extracted with EtOAc (3x60 mL). The combined organic phase was washed with phosphate buffer (2x40 mL, pH 3) and brine (40 mL), dried ($Na_2SO_4$) and evaporated to afford the the title compound (571 mg): LC/MS (electrospray, +ions) m/z 320 (M+H).

B.

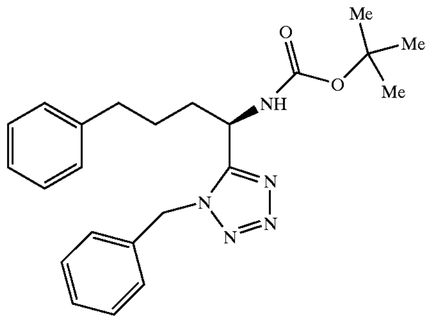

Benzyl bromide (54 μL, 0.45 mmol) was added to a stirred suspension of the Part A compound (115 mg, 0.36 mmol) and cesium carbonate (258 mg, 0.79 mmol) in $CH_3CN$ (1.0 mL), and the mixture was stirred for 18 h. at rt. The reaction mixture was diluted with $CH_2Cl_2$ (20 mL) and washed with water (8 mL). The aqueous phase was back extracted with $CH_2Cl_2$ twice and the combined organic phase was dried ($Na_2SO_4$), evaporated and chromatographed ($SiO_2$ 230–400 mesh, 3/1 hexanes/EtOAc) to give the title compound as a mixture of N-1/N-2 tetrazole isomers (122 mg): LC/MS (electrospray, +ions) m/z 410 (M+H).

C.

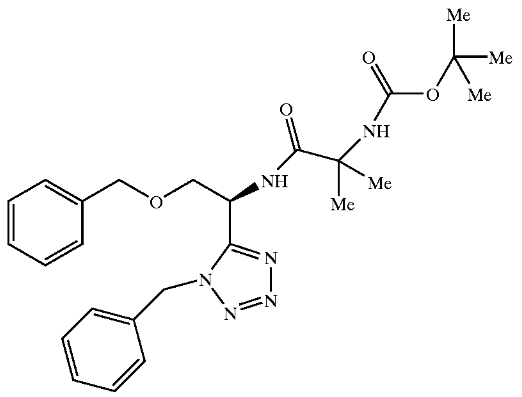

The isomeric mixture of Part B (122.2 mg, 0.30 mmol) was treated with 15% TFA (3.0 mL) for 2.0 h and evaporated. i-PrOH (2 mL) and brine (15.0 mL) were added to the residue and the pH of the aqueous solution was adjusted to 10 by addition of 1M $K_2CO_3$. The aqueous solution was extracted with $CH_2Cl_2$ (3x25 mL) and the combined organic layer was dried ($Na_2SO_4$) and evaporated to provide title amine (94 mg). This amine material was used in the next reaction without further purification. LC/MS (electrospray, +ions) m/z 310 (M+H).

N-Boc-methyl alanine (79 mg, 0.39 mmol), EDAC (75 mg, 0.39 mmol), HOAT (53 mg, 0.40 mmol), 1,2-DCE (0.7 mL) and DMF (60 μL) were mixed at 0° C. and stirred for 15 min. The resulting cloudy solution was transferred, via syringe, to a 0° C. solution of the crude amine (94 mg, 0.30 mmol) in 1,2-DCE (0.6 mL) and the mixture was stirred for 24 h at rt. The reaction mixture was diluted with EtOAc (30 mL) and washed with saturated $NaHCO_3$ (2x20 mL), water (20 mL) and brine (20 mL). The organic layer was dried ($Na_2SO_4$), evaporated and chromatographed ($SiO_2$ 230–400 mesh, 7/3 $CHCl_3$/ether) to provide the title compound (44.6 mg). LC/MS (electrospray, +ions) m/z 495 (M+H).

D.

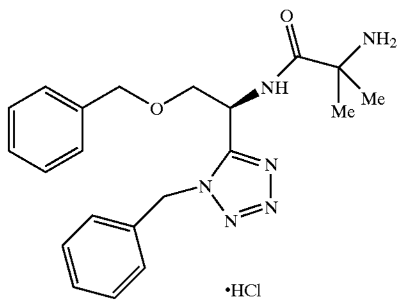

•HCl

Part C compound (44.6 mg, 0.09 mmol) was treated with ~2M $HCl/CH_2Cl_2$, MeOH, MeOAc (3.0 mL, prepared by addition of AcCl to 8/1 $CH_2Cl_2$/MeOH) for 2.3 h. and evaporated. The residue was further dried, under high vacuum, to afford the title compound as a colorless solid (41.1 mg): LC/MS (electrospray, +ions) m/z 395 (M+H).

EXAMPLE 4

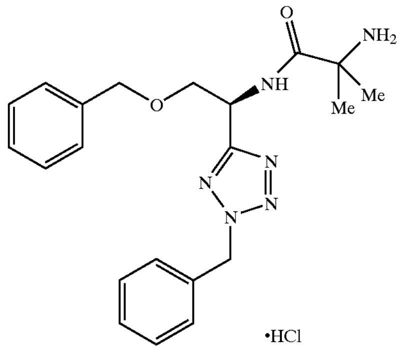

•HCl

A.

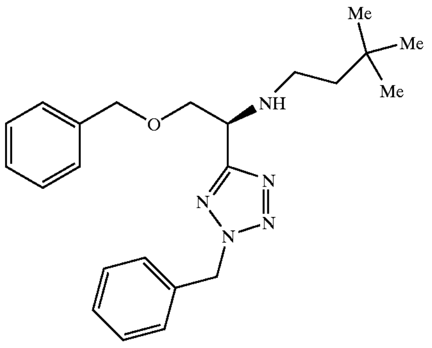

Benzyl bromide (54 μL, 0.45 mmol) was added to a stirred suspension of the Example 3 Part A compound,

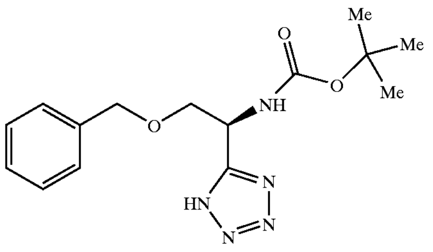

(115 mg, 0.36 mmol) and cesium carbonate (258 mg, 0.79 mmol) in $CH_3CN$ (1.0 mL), and the mixture was stirred for 18 h at rt. The reaction mixture was diluted with $CH_2Cl_2$ (20 mL) and washed with water (8 mL). The aqueous phase was back extracted with $CH_2Cl_2$ twice and the combined organic phase was dried ($Na_2SO_4$), evaporated and chromatographed ($SiO_2$ 230–400 mesh, 3/1 hexanes/EtOAc) to give the title compound as a mixture of N-1/N-2 tetrazole isomers (122 mg): LC/MS (electrospray, +ions) m/z 410 (M+H).

B.

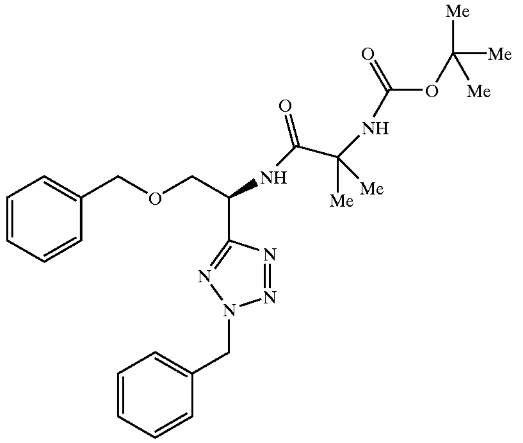

The isomeric mixture of Part A (122.2 mg, 0.30 mmol) was treated with 15% TFA (3.0 mL) for 2.0 h and evaporated. i-PrOH (2 mL) and brine (15.0 mL) were added to the residue and the pH of the aqueous solution was adjusted to 10 by addition of 1M $K_2CO_3$. The aqueous solution was extracted with $CH_2Cl_2$ (3×25 mL) and the combined organic layer was dried ($Na_2SO_4$) and evaporated to provide

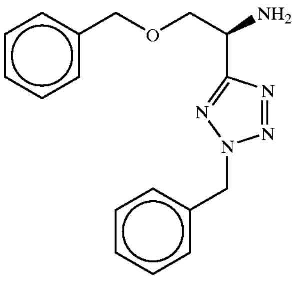

+

-continued

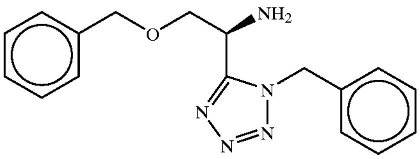

amine (94 mg). The material was used in the next reaction without further purification. LC/MS (electrospray, +ions) m/z 310 (M+H).

N-Boc-methyl alanine (79 mg, 0.39 mmol), EDAC (75 mg, 0.39 mmol), HOAT (53 mg, 0.40 mmol), 1,2-DCE (0.7 mL) and DMF (60 μL) were mixed at 0° C. and stirred for 15 min. The resulting cloudy solution was transferred, via syringe, to a 0° C. solution of the crude amine (94 mg, 0.30 mmol) in 1,2-DCE (0.6 mL) and the mixture was stirred for 24 h at rt. The reaction mixture was diluted with EtOAc (30 mL) and washed with saturated $NaHCO_3$ (2×20 mL), water (20 mL) and brine (20 mL). The organic layer was dried ($Na_2SO_4$), evaporated and chromatographed ($SiO_2$ 230–400 mesh, 7/3 $CHCl_3$/ether) to provide the title compound (81.0 mg) as a white solid. LC/MS (electrospray, +ions) m/z 495 (M+H).

C.

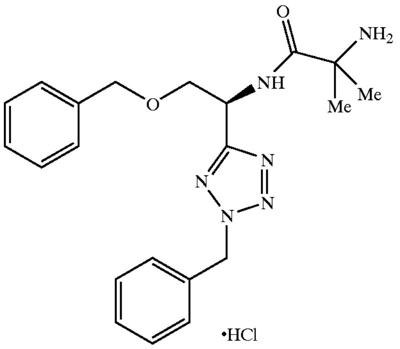

Part B compound (81.0 mg, 0.09 mmol) was treated with ~2M $HCl/CH_2Cl_2$, MeOH, MeOAc (3.0 mL, prepared by addition of AcCl to 8/1 $CH_2Cl_2$/MeOH) for 2.3 h. and evaporated. The residue was further dried, under high vacuum, to afford the title compound (72.4 mg) as a pale yellow solid: LC/MS (electrospray, +ions) m/z 395 (M+H).

EXAMPLE 5

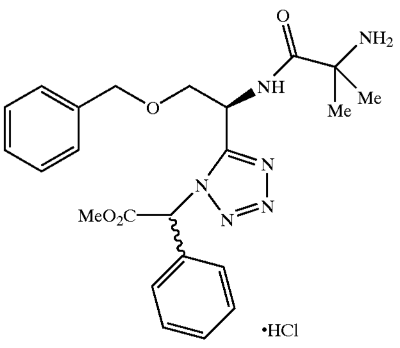

-continued

A.

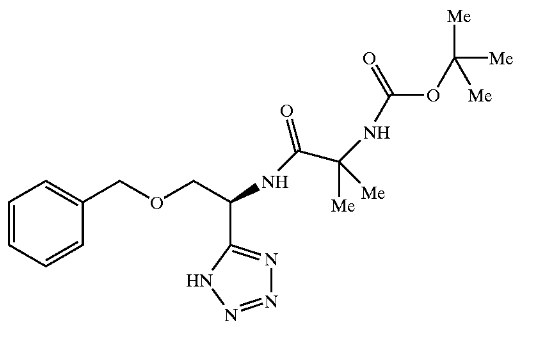

1M NaOH (0.67 mL) and i-PrOH (0.50 mL) were added to a solution of Example 2 Part D compound

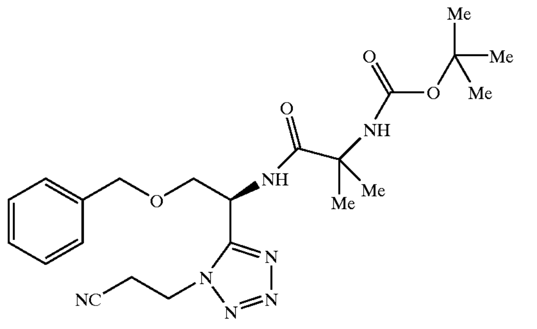

(308 mg, 0.67 mmol) in 6/1 THF/Dioxane (3.5 mL), and the mixture was stirred at rt. for 13 h. The reaction mixture was diluted with brine (30 mL) and the pH of the aqueous solution was adjusted to 3 by addition of 1M $H_3PO_4$. The aqueous solution was extracted with $CH_2Cl_2$ (3x50 mL) and the combined organic phase was dried ($Na_2SO_4$) and evaporated to yield the title compound (234 mg): LC/MS (electrospray, +ions) m/z 405 (M+H).

B.

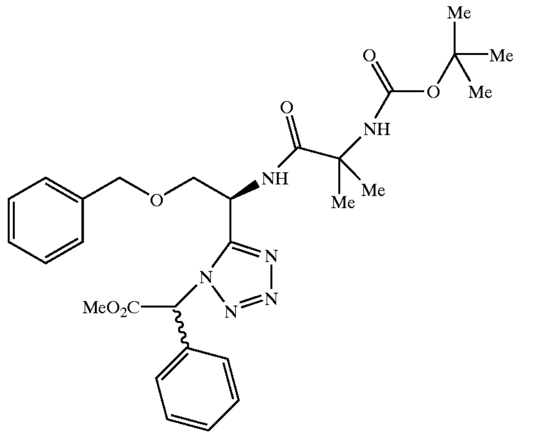

Diisopropylethyl amine (10 μL, 57 μmol) and diethylazodicarboxylate (53 μL, 0.34 mmol) were added to a solution of (+)-methyl-L-mandelate (56 mg, 0.34 mmol, Aldrich), Part A compound (118.5 mg, 0.29 mmol) and triphenylphosphine (87 mg, 0.33 mmol) in $CH_2Cl_2$ (0.9 mL), previously cooled at 0° C. After stirring the mixture at rt for 34 h, additional amounts of the reagents, triphenylphosphine (99 mg), of (+)-methyl-L-mandelate (56 mg) and diethylazodicarboxylate (53 μL), were added. The mixture was stirred at rt for an additional 24 h and concentrated in vacuo. The resulting residue was chromatographed ($SiO_2$ 230–400 mesh, 4/1 $CH_2Cl_2$/Ether) to afford a mixture containing the title compound (57.5 mg) contaminated with 1,2-dicarbethoxyhydrazide. The mixture was purified by chromatography ($SiO_2$ 230–400 mesh, 95/5 $CHCl_3$/MeOH) to provide the title compound (49.2 mg, 1/1 mixture of diastereomers) as a colorless oil: LC/MS (electrospray, +ions) m/z 553 (M+H).

C.

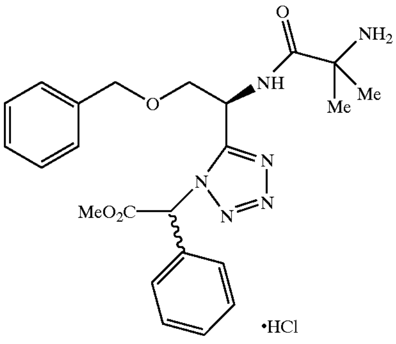

Part B compound (49.2 mg, 89 μmol) was treated with ~2M HCl/$CH_2Cl_2$, MeOH, MeOAc (3.0 mL, prepared by addition of AcCl to 8/1 $CH_2Cl_2$/MeOH) for 2.3 h and evaporated. The residue was further dried, under high vacuum, to afford the title compound (42.7 mg, 1/1 mixture of diastereomers) as a white solid: LC/MS (electrospray, +ions) m/z 453 (M+H).

EXAMPLE 6

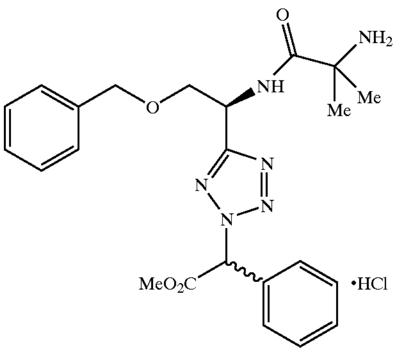

-continued

A.

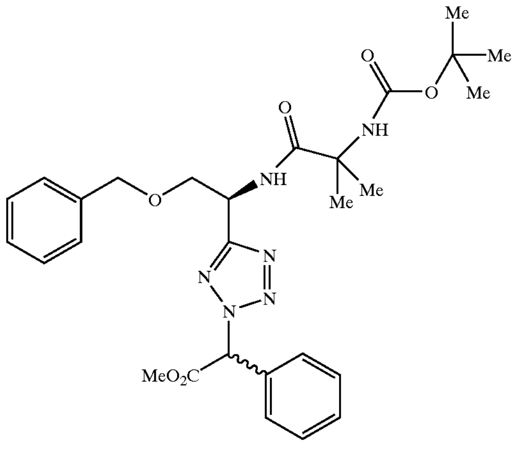

Diisopropylethyl amine (10 μL, 57 μmol) and diethylazodicarboxylate (53 μL, 0.34 mmol) were added to a solution of (+)-methyl-L-mandelate (56 mg, 0.34 mmol, Aldrich), compound Example 5 Part A

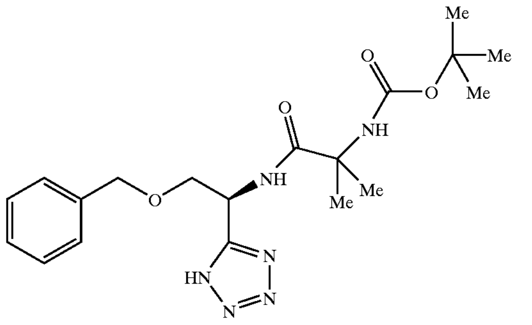

(118.5 mg, 0.29 mmol) and triphenylphosphine (87 mg, 0.33 mmol) in $CH_2Cl_2$ (0.9 mL), previously cooled at 0° C. After stirring the mixture at rt for 34 h, additional amounts of the reagents, triphenylphosphine (99 mg), of (+)-methyl-L-mandelate (56 mg) and diethylazodicarboxylate (53 μL), were added. The mixture was stirred at rt for an additional 24 h and concentrated in vacuo. The resulting residue was chromatographed ($SiO_2$ 230–400 mesh, 4/1 $CH_2Cl_2$/Eter) to afford the title compound (70.6 mg, 1/1 mixture of diastereomers) as a colorless oil: LC/MS (electrospray, +ions) m/z 553 (M+H).

B.

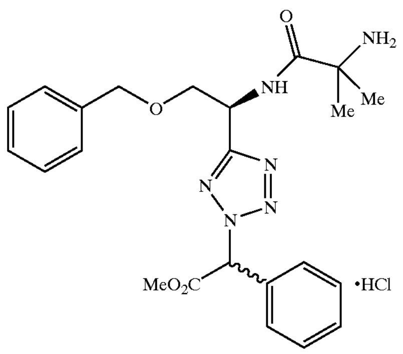

Part A compound (70.6 mg, 0.13 mmol) was treated with ~2M $HCl/CH_2Cl_2$, MeOH, MeOAc (3.0 mL, prepared by addition of AcCl to 8/1 $CH_2Cl_2$/MeOH) for 2.5 h and evaporated. The residue was further dried, under high vacuum, to afford the title compound (61.9 mg, 1/1 mixture of diastereomers) as a white solid: LC/MS (electrospray, +ions) m/z 453 (M+H).

EXAMPLE 7

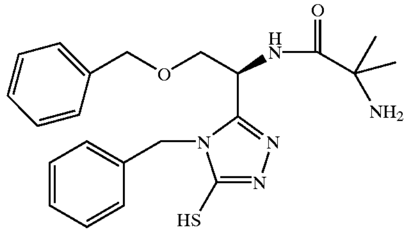

A.

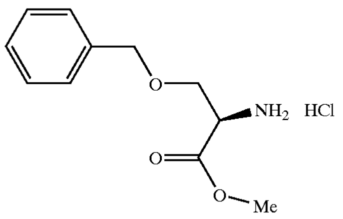

To a precooled 160 ml of methanol at 0° C. was added acetyl chloride (10 g, 128 mmol) slowly. After stirring at 0° C. for 15 min, O-benzyl-D-serine

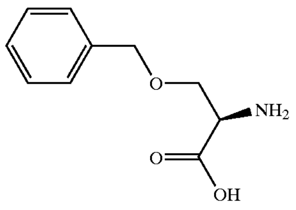

(5 g, 25.6 mmol) was added and the solution was heated to reflux for 2 days. The solvent was removed and the residue was dried under high vacuum to give title compound as a white solid (6.29 g, 100%). HPLCa rt=1.90 min.

B.

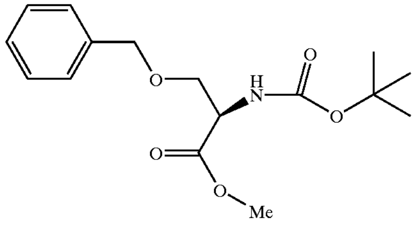

To a solution of Part A compound (3.65 g, 14.9 mmol) in 100 ml of dry methylene chloride was added di-t-butylcarboxymate (3.89 g, 17.8 mmol) followed by the addition of triethyl amine (2.25 g, 22.3 mmol). The reaction was stirred overnight and quenched with 50 ml of water and extracted with methylene chloride (3x100 ml). The combined organic layers were washed with brine, dried over Na2SO4, and concentrated to give crude title product as an oil (5.01 g). HPLCb rt=3.24 min.; LC/MS (electrospray, +ions) m/z 310 (M+H).

C.

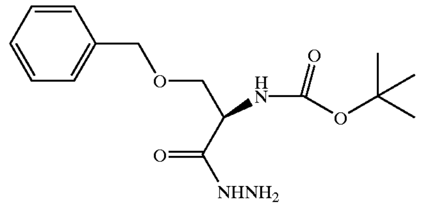

To a solution of crude Part B compound (0.98 g, 3.17 mol) in 10 ml of dry methyl alcohol was added hydrazine 0.447 g, 13.9 mmol). The reaction was stirred at rt for 3 h and heated to reflux for 5 h. The solvent was removed and the residue was dried under high vacuum to give title compound as an oil (0.96 g, 98%). HPLCb rt=3.21 min.; LC/MS (electrospray, +ions) m/z 310 (M+H).

D.

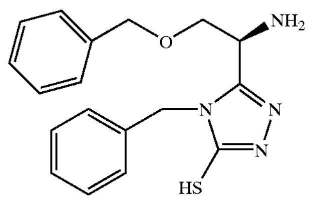

To a solution of crude Part C compound (0.53 g, 1.72 mmol) in 10 ml of dry ethyl alcohol was added benzyl isothiocyanate (307 mg, 2.06 mmol). The reaction was heated to reflux for 4 h. The reaction was allowed to cool to room temperature and the solvent was removed in vacuo. The residue was then treated with 1N NaOH and the resulting mixture was heated to 109° C. for 4 h. After cooling to rt, the resulting white precipitate was isolated by filtration. The solid was rinsed with water and dried under high vacuum to give title compound as a white solid (0.36 g, 62%). HPLCb rt=3.29 min.; LC/MS (electrospray, +ions) m/z 341 (M+H).

E.

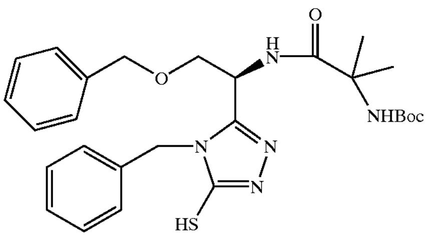

To a solution of Part D compound (153 mg, 0.45 mmol) in 4 ml of DMF was added Boc-methylalanine carboxylic acid (96 mg, 0.47 mmol, Sigma), HOAt (64 mg, 0.47 mmol), EDAC (91 mg, 0.47 mmol), and diisopropylethyl amine (61 mg, 0.47 mmol) at rt under nitrogen. The reaction mixture was stirred at rt for 20 h, and quenched with water (10 ml). The mixture was extracted with ethyl acetate (3x20 ml), the organic layer dried over sodium sulfate, and concentrated in vacuo to give a crude yellow oil. The crude residue was purified by flash chromatography, eluting with hexane/ethyl acetate (2:1) to give title compound as an oil (153 mg, 65%). HPLCb rt=4.13 min.; LC/MS (electrospray, +ions) m/z 526 (M+H).

F.

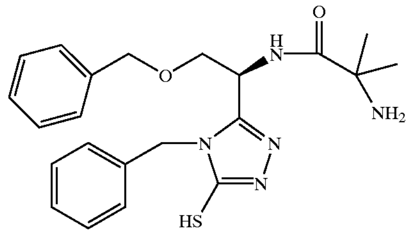

Part E compound (133 mg, 0.25 mmol) was treated with 2 ml of $TFA/CH_2Cl_2$ (1:3) at room temperature for 1 h, the solvent removed and the residue was purified by preparative HPLC (Shimadzu, 30–100% B, 30 min. gradient, 5 min. hold, 220 nM) to give the title compound (80 mg, 59%). HPLCb rt=3.25 min.; LC/MS (electrospray, +ions) m/z 425 (M+H).

EXAMPLE 8

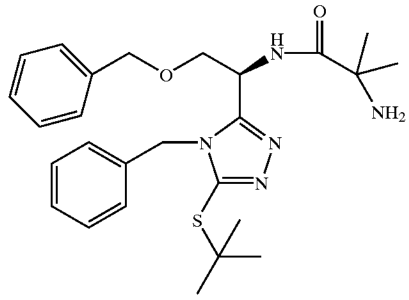

Example 7 Part E, compound (133 mg, 0.25 mmol) was treated with 2 ml of $TFA/CH_2Cl_2$ (1:3) at room temperature for 1 h, the solvent removed and the residue was purified by preparative HPLC (Shimadzu, 30–100% B, 30 min. gradient, 5 min. hold, 220 nM) to give the title compound (42 mg, 28%). HPLCb rt=3.80 min.; LC/MS (electrospray, +ions) m/z 481 (M+H).

EXAMPLE 9

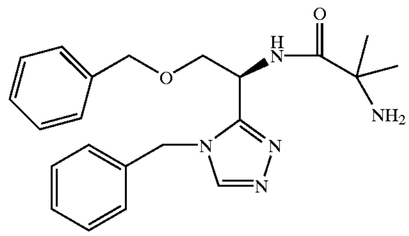

A solution of Example 7 Part E, compound (78 mg, 0.15 mmol) in 7.5 ml of THF was added to hydrogen peroxide (0.33 ml, 30% w/w). After stirring at rt for 2 days, the solvent was removed. The residue was then treated with 3 ml of TFA/CH2Cl2 (1:3) at room temperature for 1 h, the solvent removed, and the residue was purified by preparative HPLC (Shimadzu, 20–100% B, 30 min. gradient, 5 min. hold, 220 nM) to give the title compound (59 mg, 79%). HPLCb rt=2.99 min.; LC/MS (electrospray, +ions) m/z 394 (M+H).

EXAMPLE 10

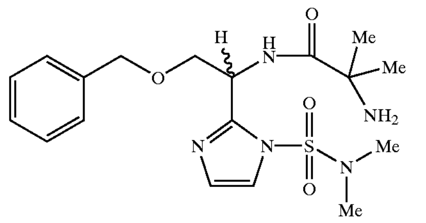

A.

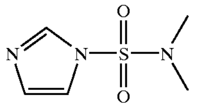

To a suspension of imidazole (19.08 g, 0.28 mol) in 300 ml of dry benzene was added dimethylchlorosulphonamide (26 ml, 0.24 mol) and triethylamine (36 ml, 0.26 mol). The reaction was stirred at rt under nitrogen for 24 h, the mixture filtered, and the filtrate was concentrated. The resulting crude product was distilled under reduced pressure (0.03 mmHg) to yield title compound (36.4 g, 86%). HPLCb rt=0.64 min.; LC/MS (electrospray, +ions) m/z 176 (M+H).

B.

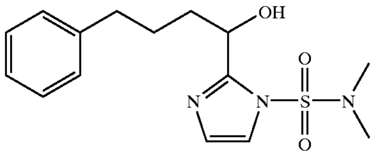

To a suspension of Part A compound (1.88 g, 10.75 mmol) in 100 ml of dry THF at −78° C. was added n-BuLi (4.60 ml, 2.5 M in hexane, 11.51 mmol) dropwise under nitrogen. The reaction was stirred at −78° C. for 1 h and 4-phenylbutyraldehyde

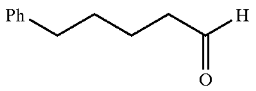

in 20 ml of dry ether was added in one portion. The mixture was stirred at −78° C. for 5 min. and then allowed to go to rt. After 3 hr at rt, the reaction was quenched with sat. NH4Cl solution. The mixture was extracted with ethyl acetate (3x20 ml), the organic layer dried over sodium sulfate, and concentrated in vacuo to give a crude yellow oil. The crude residue was purified by flash chromatography, eluting with hexane/ethyl acetate (1:3) to give title compound as an oil (3.24 g, 93%). HPLCb rt=3.44 min.; LC/MS (electrospray, +ions) m/z 324 (M+H).

C.

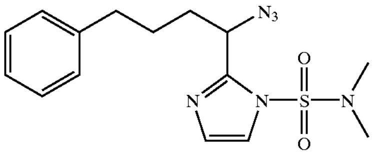

To a mixture of Part B compound (3.2 g, 9.91 mmol) and diphenyl phosphorazide (3.27 g, 11.89 mmol) in 17 ml of dry toluene at 0° C. under nitrogen was added 1,8-diazabicyclo[5.4.0]undec-7-ene (DBU) (1.81 g, 11.89 mmol). The reaction was stirred for 2 h at 0° C. and then 20 h at room temperature. The resulting two phase mixture was quenched with water and extracted with ethyl acetate (3x20 ml). The organic layer was washed with brine, dried over sodium sulfate, concentrated in vacuo and purified by flash chromatography using 3:1 hexane/ethyl acetate to afford title compound as an oil (1.64 g, 48%). HPLCb rt=4.15 min.; LC/MS (electrospray, +ions) m/z 349 (M+H).

D.

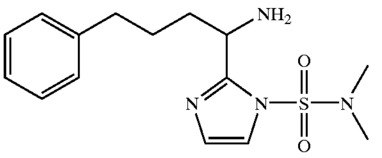

A mixture of Part C compound (232 mg, 0.67 mmol) and 5% Pd/C (50 mg) in 3 ml of EtOH was hydrogenated under 1 atmosphere of hydrogen. After 9 h, the solid was then filtered off and the filtrate was concentrated in vacuo to afford Part D compound as an oil (200 mg, 93%). HPLCb rt=3.10 min.: LC/MS (electrospray, +ions) m/z 323 (M+H).

E.

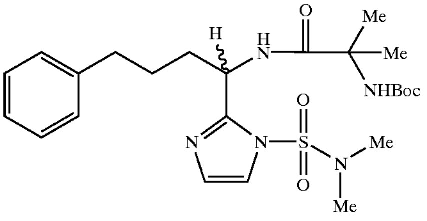

To a solution of Part D compound (172 mg, 0.53 mmol) and Boc-methylalanine carboxylic acid (114 mg, 0.56 mmol, Sigma) in 3 ml of acetonitrile was added benzotriazol-1-yloxy-bris(dimethylamine)phoshonium hexafluorophosphate (BOP) (248 mg, 0.56 mmol). After stirring for 20 min at rt, triethylamine (56.6 mg, 0.56 mmol) was added and the reaction was stirred for 5 h at room temperature. The solvent was removed via evaporation and the residue was purified by flash chromatography, eluting with hexane/ethyl acetate (1:1) to give Part E compound as an oil (238 mg, 88%). HPLCb rt=4.13 min.; LC/MS (electrospray, +ions) m/z 508 (M+H).

F.

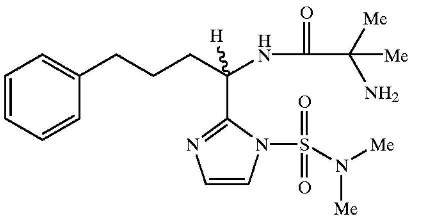

Part E compound (167 mg, 0.33 mmol) was treated with 2 ml of TFA/$CH_2Cl_2$ (1:3) at room temperature for 1 h, the solvent was removed and the residue was purified by preparative HPLC (Shimadzu, 30–100% B, 30 min. gradient, 5 min. hold, 220 nM) to give the title compound (137 mg). HPLCb rt=3.33 min.; LC/MS (electrospray, +ions) m/z 408 (M+H).

The following compounds were prepared employing the procedures described above and the working Examples.

EXAMPLES 11 TO 45

| Example No. | Structure | M + H positive ions |
|---|---|---|
| 11 | 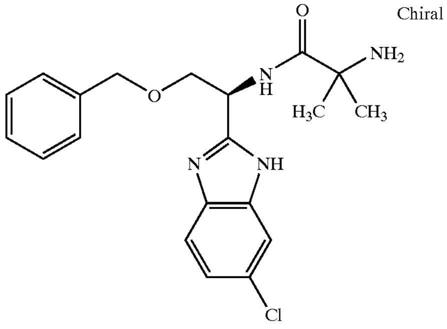 Chiral | 387 |
| 12 | 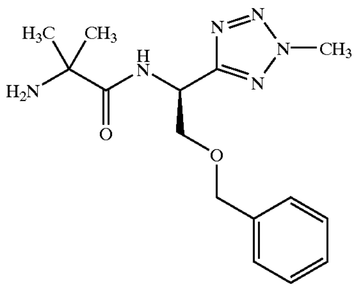 Chiral | 319 |
| 13 | 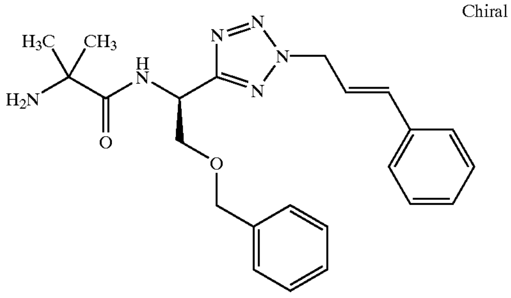 Chiral | 421 |

-continued
| Example No. | Structure | M + H positive ions |
|---|---|---|
| 14 | 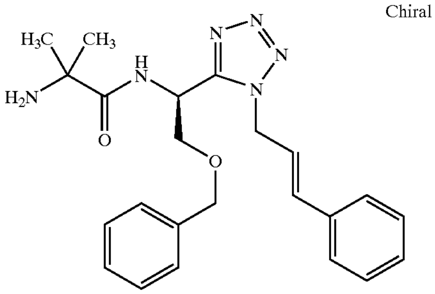 Chiral | 421 |
| 15 | 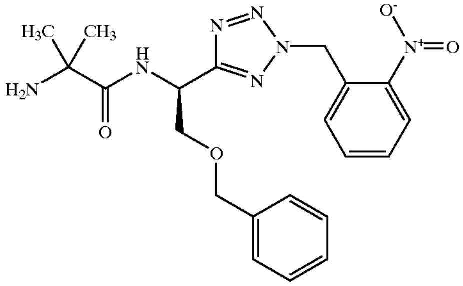 Chiral | 440 |
| 16 | 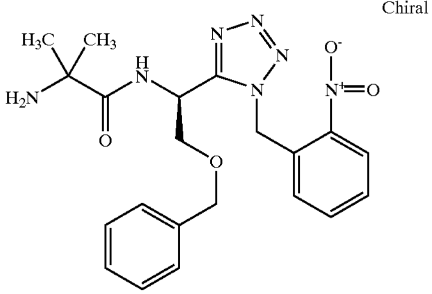 Chiral | 440 |
| 17 | 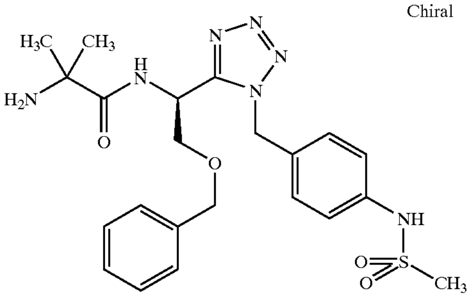 Chiral | 488 |
| 18 | 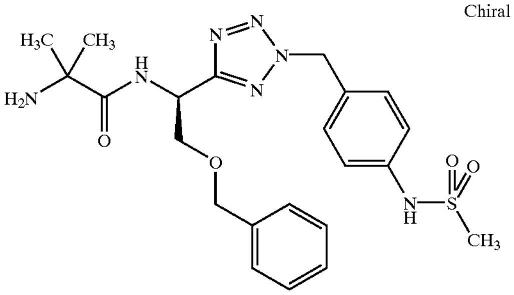 Chiral | 488 |

-continued
| Example No. | Structure | M + H positive ions |
|---|---|---|
| 19 | Chiral 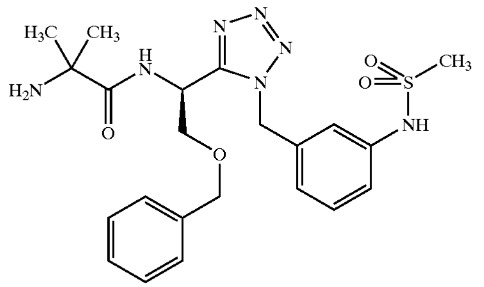 | 488 |
| 20 | Chiral 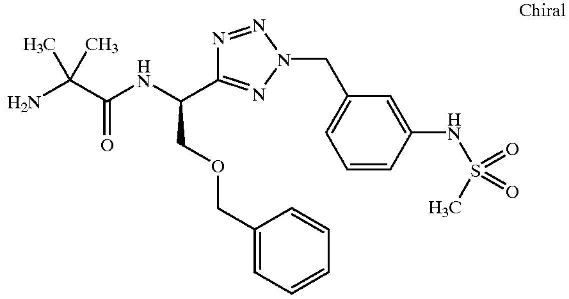 | 488 |
| 21 | Chiral 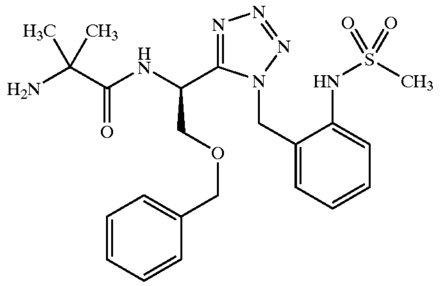 | 488 |
| 22 | Chiral 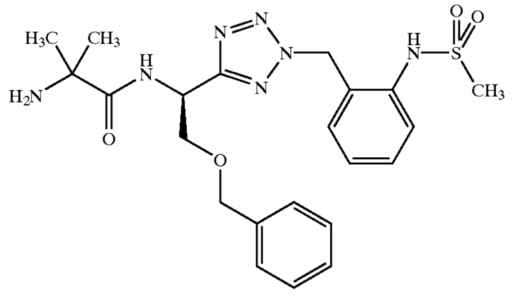 | 488 |

-continued
| Example No. | Structure | M + H positive ions |
|---|---|---|
| 23 | 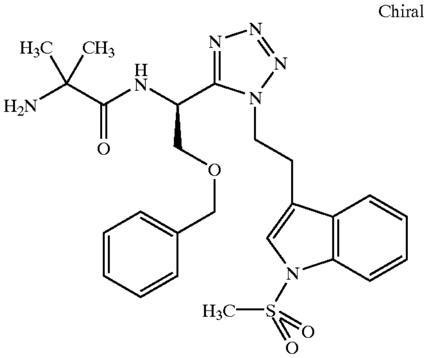 Chiral | 526 |
| 24 | 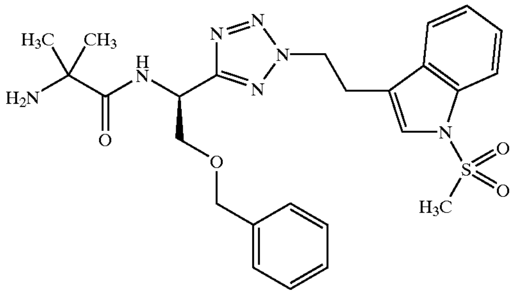 Chiral | 526 |
| 27 | 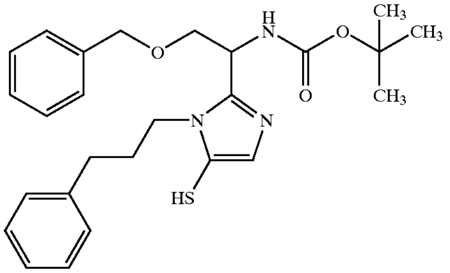 | 469 |
| 28 | 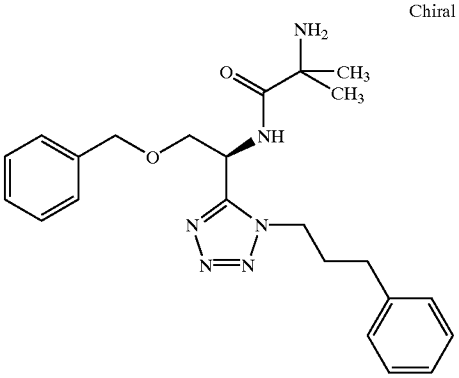 Chiral | 423 |

-continued
| Example No. | Structure | M + H positive ions |
|---|---|---|
| 29 | 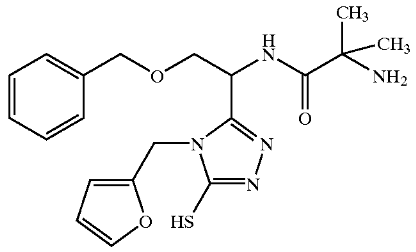 | 416 |
| 30 | 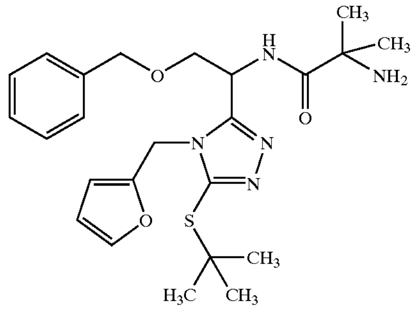 | 472 |
| 31 | 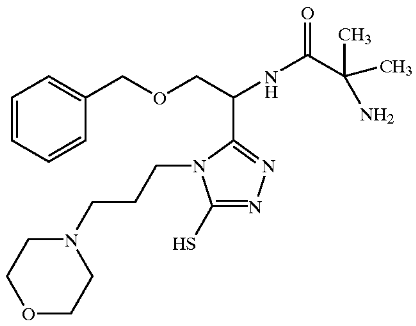 | 463 |
| 32 | 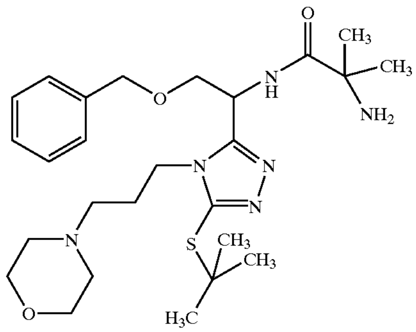 | 519 |

-continued
| Example No. | Structure | M + H positive ions |
|---|---|---|
| 33 | 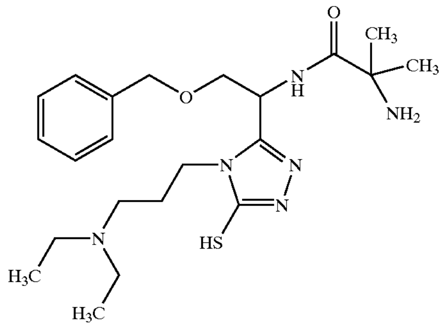 | 449 |
| 34 | 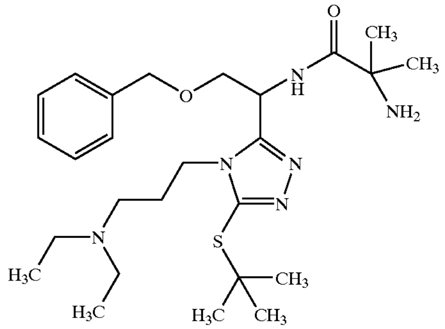 | 505 |
| 35 | 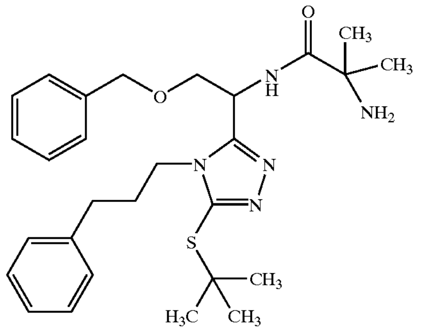 | 510 |
| 36 | Chiral 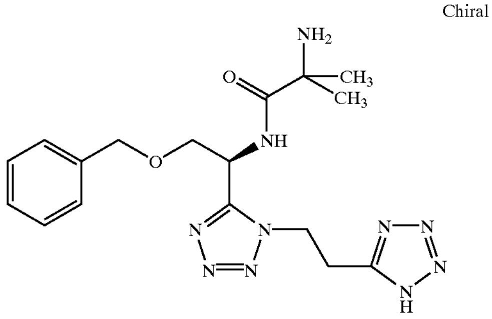 | 401 |

-continued
| Example No. | Structure | M + H positive ions |
|---|---|---|
| 37 | 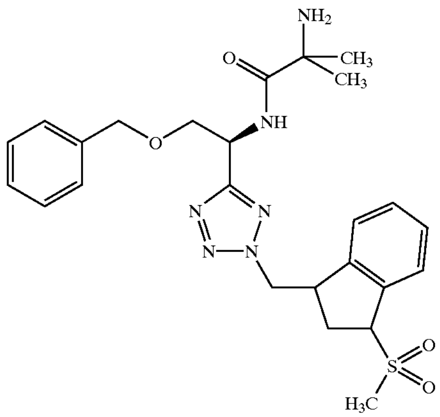 Chiral | 514 |
| 38 | 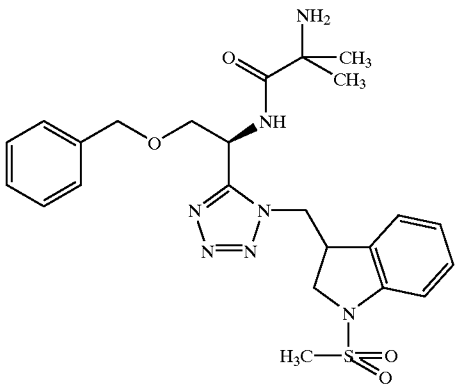 Chiral | 514 |
| 39 | 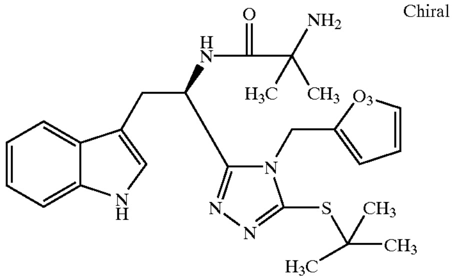 Chiral | 481 |
| 40 | 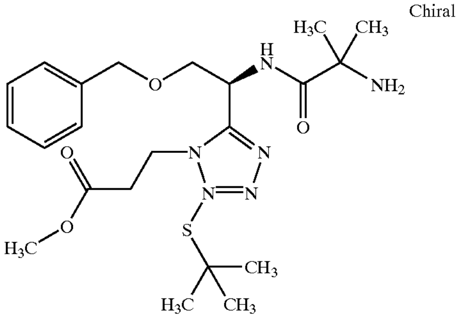 Chiral | 478 |

-continued
| Example No. | Structure | M + H positive ions |
|---|---|---|
| 41 | Chiral 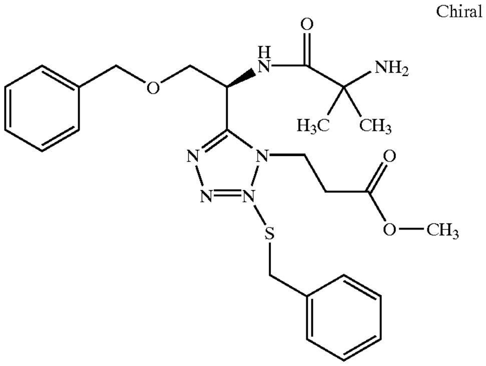 | 512 |
| 42 | Chiral 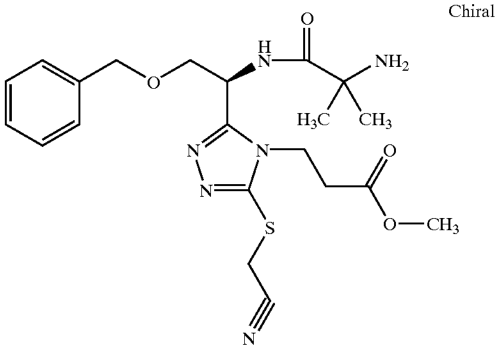 | 461 |
| 43 | Chiral 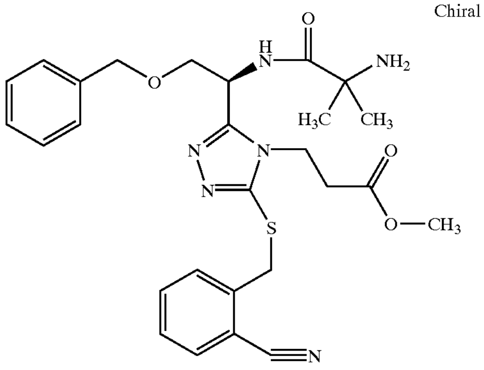 | 537 |
| 44 | Chiral 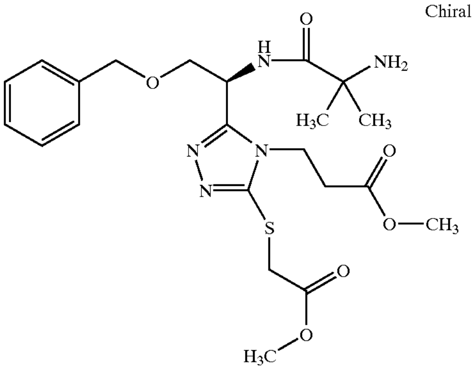 | 494 |

-continued

| Example No. | Structure | M + H positive ions |
|---|---|---|
| 45 | 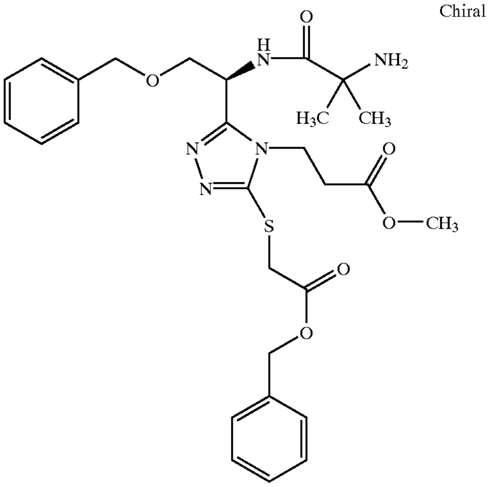 Chiral | 570 |

EXAMPLE 46

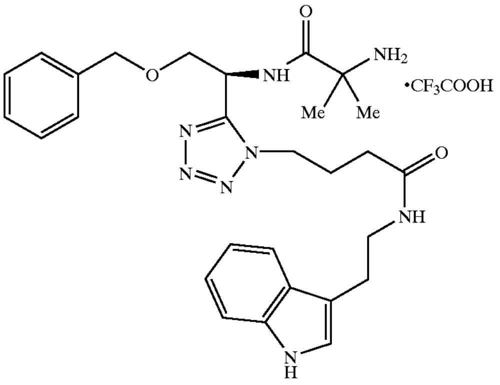

A.

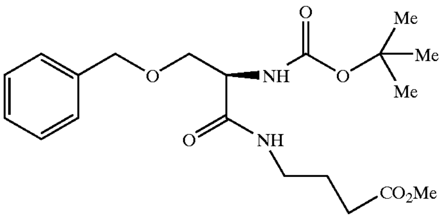

N-Methyl morpholine (2.5 mL) and isobutyl chloroformate (2.88 mL, 22.8 mmol) were added to a solution of N-Boc-O-benzyl-D-serine (6.73 g, 22.8 mmol, Sigma) in THF (35 mL), cooled at −18° C. After stirring the mixture for 0.5 h. at −18° C., a THF (15 mL) and DMF (25 mL) solution of methyl 4-aminobutyrate hydrochloride

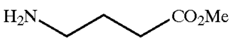

(3.53 g, 23 mmol) and N-methyl morpholine (5 mL) was added, keeping the reaction mixture below −10° C. The resulting mixture was stirred for 5 h. at between −10° to −15° C. The mixture was filtered, washing with ethyl acetate, and the solution was evaporated under reduced pressure. The residue was taken up in EtOAc (160 mL) and washed with 5% $NaHCO_3$ (2x40 mL), water (50 mL) and brine (50 mL). The organic solution was dried ($MgSO_4$), evaporated and chromatographed($SiO_2$ 230–400 mesh, 4% methanol/dichloromethane) to afford title compound (8.5 g) as a colorless syrup: LC/MS (electrospray, +ions) m/z 395 (M+H).

B.

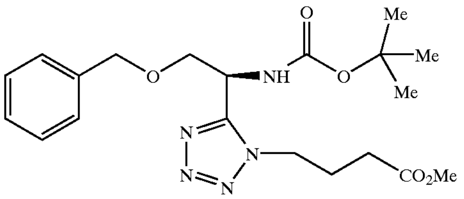

Diethylazodicarboxylate (13.4 mL, 21.6 mmol) and azidotrimethylsilane (2.87 mL, 21.6 mmol) were added to a 0° C. solution of Part A compound (8.5 g, 21.6 mmol), triphenylphosphine (5.7 g, 21.6 mmol) and diisopropylethyl amine (1 mL, 5.4 mmol) in THF (70 mL). The mixture was stirred at rt. for 24 h., and then cooled at 0° C. Another equivalent each of triphenylphosphine (5.7 g), diethylazodicarboxylate (13.4 mL) and azidotrimethylsilane (2.87 mL) was added and stirring was continued for an additional 48 h at rt. The reaction mixture was then concentrated in vacuo to one third the original volume, diluted with ethyl acetate (200 mL), then cooled to 0° C. An aqueous solution of ammonium cerium (IV) nitrate (65 g/250 mL) was added and the mixture stirred for 15 min. The organic layer was separated, the aqueous mixture was extracted with ethyl acetate (150 mL), and the combined organic phase was dried ($Na_2SO_4$). After concentration in vacuo, the residue was chromatographed ($SiO_2$ 230–400 mesh, 40% ethyl acetate/hexanes) to give solid title compound (5.5 g, contaminated with a less polar impurity) and recovered Part A compound (5.5 g, contaminated with triphenylphosphine oxide). The contaminated title compound could be used as is in the subsequent reaction. Alternatively, a portion of the impure title compound (4.2 g) was chromatographed ($SiO_2$ 230–400 mesh, 25% ethyl ether/dichloromethane) to give solid title compound (3.5 g) as a colorless solid: LC/MS (electrospray, +ions) m/z 420 (M+H).

C.

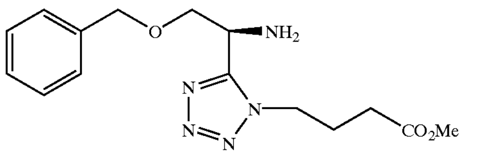

To a solution of Part B compound (3.5 g, 8.48 mmol) in dichloromethane (20 mL) was added a 4M HCl/dioxane solution (5 mL). After 3 h., more 4M HCl/dioxane solution (4 mL) was added and after a total of 5 h., the volatiles were removed in vacuo to give a syrup. The residue was dissolved in dichloromethane (200 mL), washed with 1N NaOH (75 mL), brine (2×80 mL), dried (sodium sulfate), and concentrated to give title compound (2.46 g) as a syrup. This material was used without further purification in the subsequent reaction: LC/MS (electrospray, +ions) m/z 320 (M+H).

D.

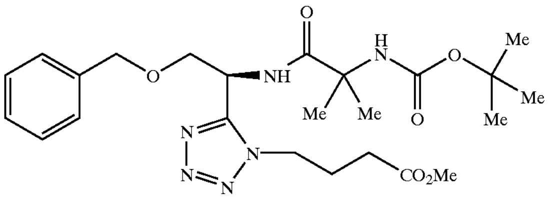

A DMF (30 mL) solution of N-Boc-methyl alanine

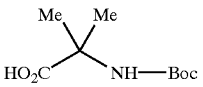

(1.88 g, 9.2 mmol, Sigma), Part C compound (2.46 g, 7.7 mmol), HOAT (1.17 g, 8.5 mmol), and EDAC (1.62 g, 8.5 mmol) was stirred at room temperature for 20 h. The reaction mixture was concentrated in vacuo and the residue dissolved in dichloromethane (200 mL). The organic layer was washed with water (3×100 mL), dried over magnesium sulfate, and concentrated in vacuo. The residue was chromatographed ($SiO_2$ 230–400 mesh) eluting with 40% ether/dichloromethane to give title compound (3.14 g) as a colorless oil: LC/MS (electrospray, +ions) m/z 505 (M+H).

E.

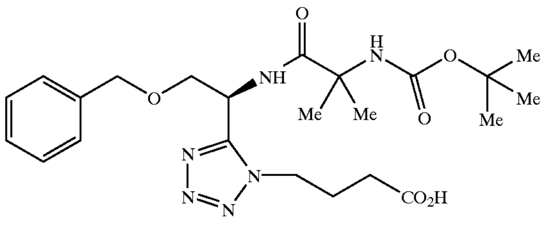

To a solution of Part D compound (1.4 g, 2.78 mmol) in THF (8 mL) was added an aqueous solution of lithium hydroxide (143 mg, 6 mmol, in 2 mL water) and the mixture was allowed to stir for 20 h. at room temperature. The reaction mixture was brought to pH 1–2 with 1N aq.HCl (5 mL) and the aqueous layer was extracted with ethyl acetate (200 mL). The organics were washed with water (60 mL), brine (100 mL), dried (magnesium sulfate), and concentrated in vacuo to give title compound (1.32 g) as a colorless solid. This material was used without further purification in the subsequent reaction: LC/MS (electrospray, +ions) m/z 491 (M+H).

F.

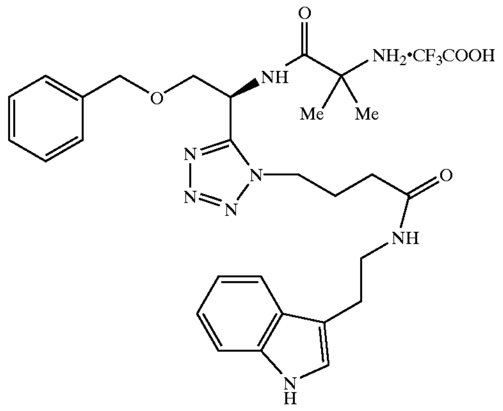

To tryptamine

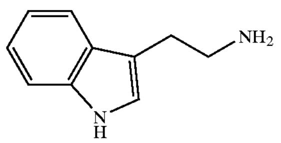

(24 mg, 0.15 mmol) was added a dichloromethane (1 mL) and DMF (0.5 mL) solution of Part E compound (50 mg, 0.1 mmol), EDAC (28.8 mg, 0.15 mmol), and dimethylamino pyridine (18.3 mg, 0.15 mmol, DMAP). The reaction mixture was shaken for 20 h., then diluted with methanol (5 mL).

The resulting solution was passed through a SCX resin column (1 g), eluting with methanol (15 mL), and the eluent was concentrated in vacuo to give the crude intermediate amide:

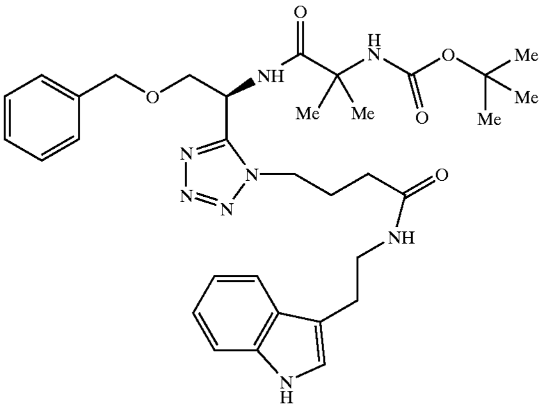

The resulting residue was dissolved in a dichloromethane/methanol HCl solution (1.5 mL, prepared from dissolving acetyl chloride (10.2 mL) in 3/2 dichloromethane/methanol (40 mL), 3.5 M) and stirred at rt. for 4 h. before removing the volatiles under reduced pressure. The resulting residue was purified by Prep HPLC to give the title compound as a dark colored foam (44 mg): LC/MS (electrospray, +ions) m/z 533 (M+H).

In a manner analogous to that of preparing the Example 46 compound, compounds of Examples 47 to 91 listed in the table below were prepared from Example 46 Part E compound (0.1 mmol) and the respective amine (0.15 to 0.2 mmol). Examples 47 to 50 were treated with trifluoroacetic acid (0.4 mL) and thioanisole (0.05 mL) in dichloromethane (1 mL) instead of HCl to form the final products. All but Example 70 were purified by preparative HPLC, eluting with a gradient system of methanol and water with 0.2% trifluoroacetic acid. All compounds were isolated as trifluoroacetic acid salts.

In the tables of compounds which follow, the $X_1$ designation refers to the point of attachment of the particular R moiety shown to the rest of the molecule.

EXAMPLES 47 TO 91

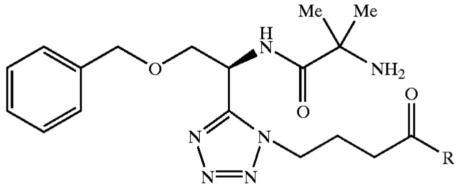

$= X_1—R$

| Example No. | $X_1$—R | M + H positive ions |
|---|---|---|
| 47 | 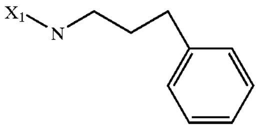 | 508 |
| 48 | 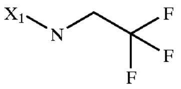 | 472 |
| 49 | 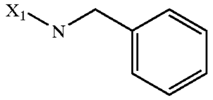 | 480 |
| 50 | 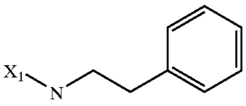 | 494 |
| 51 | 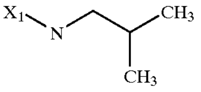 | 446 |
| 52 | 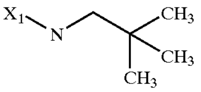 | 460 |
| 53 | 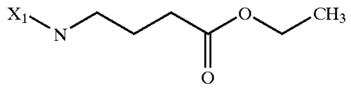 | 504 |

-continued

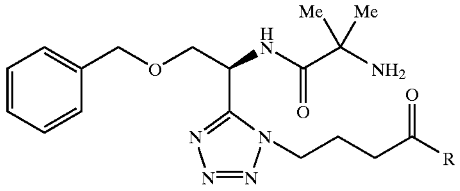

$= X_1—R$

| | | |
|---|---|---|
| 54 | 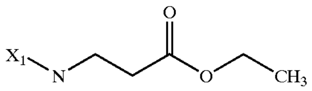 | 490 |
| 55 | 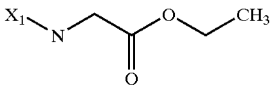 | 476 |
| 56 | 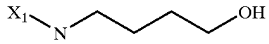 | 462 |
| 57 | 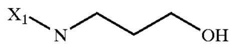 | 448 |
| 58 | 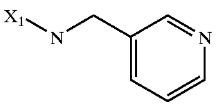 | 481 |
| 59 | 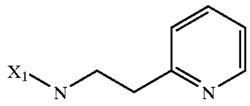 | 495 |
| 60 | 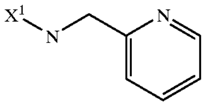 | 481 |
| 61 | 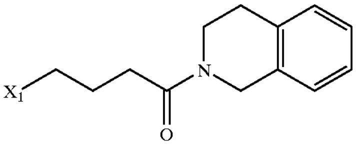 | 506 |
| 62 | 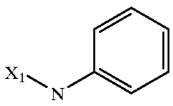 | 466 |
| 63 | 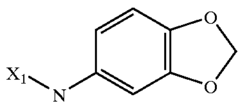 | 510 |
| 64 | 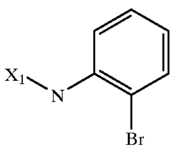 | 545 |

-continued
| | | |
|---|---|---|
| | 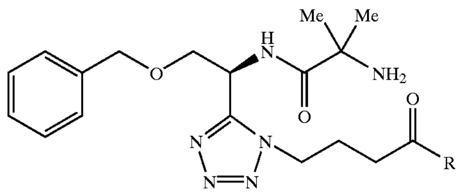 | = $X_1$—R |
| 65 | 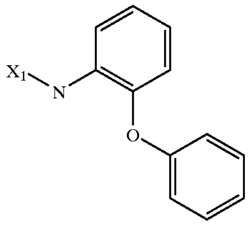 | 558 |
| 66 | 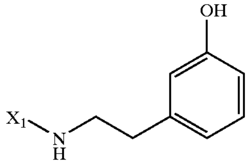 | 510 |
| 67 | 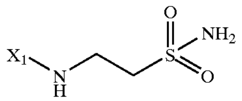 | 497 |
| 68 | 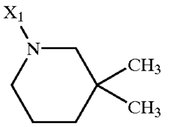 | 486 |
| 69 | 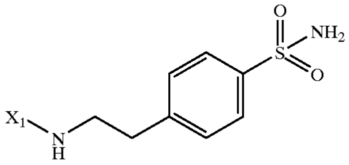 | 573 |
| 70 | 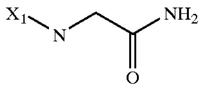 | 447 |
| 71 | 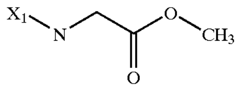 | 462 |
| 72 | 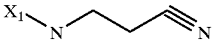 | 443 |
| 73 | 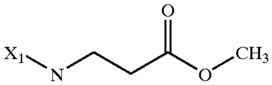 | 476 |
| 74 | 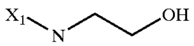 | 434 |
| 75 | 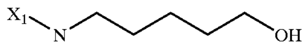 | 476 |
| 76 | 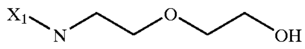 | 478 |
-continued
| | | |
|---|---|---|
| | 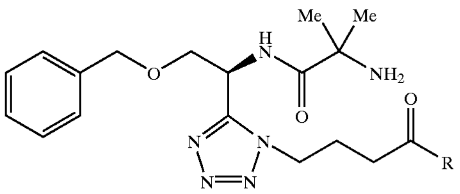 | = $X_1$—R |
| 77 | 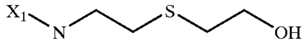 | 494 |
| 78 | 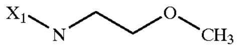 | 448 |
| 79 | 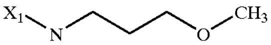 | 462 |
| 80 | 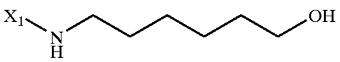 | 490 |
| 81 | 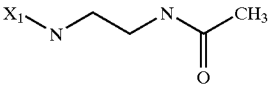 | 475 |
| 82 | 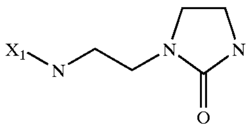 | 502 |
| 83 | 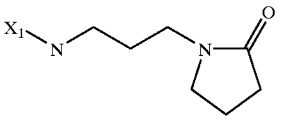 | 515 |
| 84 | 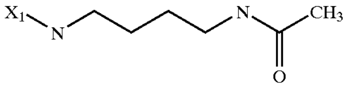 | 503 |
| 85 | 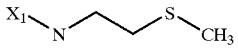 | 464 |
| 86 | 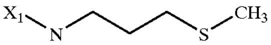 | 478 |
| 87 | 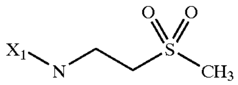 | 496 |
| 88 | 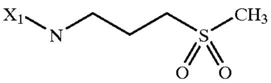 | 510 |
| 89 | 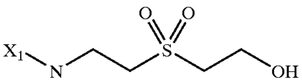 | 526 |
| 90 | 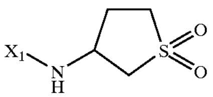 | 508 |
| 91 | 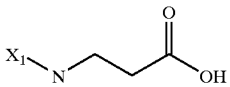 | 462 |

EXAMPLE 92

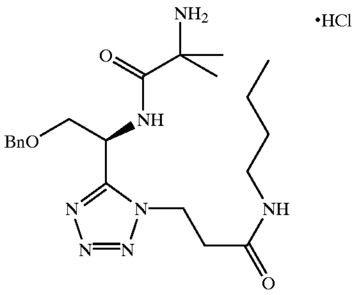

A.

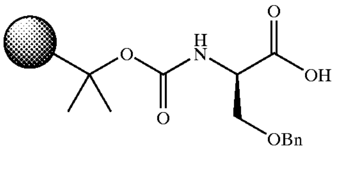

Methyl triflate (1.30 mL, 11.5 mmol) was added to a suspension of resin bound (tert-alkoxycarbonyl)imidazole (8.68 g, loading 0.72 mmol/g)

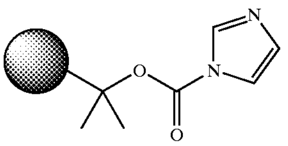

[Note: this procedure was adapted from Hernandez and Hodges. *J. Org. Chem.* 1997, 62, 3153] in dry 1,2-DCE (60.0 mL), cooled at 5° C. The mixture was stirred for 20 min at this temperature and for 15 min while being warmed to rt. After addition of DMAP (2.96 g, 24.2 mmol), stirring was continued for an additional 10 min.

N,O-Bis (trimethylsilyl)acetamide (4.48 mL, 18.1 mmol) was added to a suspension of O-benzyl-D-serine (3.54 g, 18.1 mmol) in DMF (21 mL) and the mixture was stirred for 30 min at rt. The resulting solution was transferred via syringe to the stirred resin suspension. The mixture was shaken for 8 h at rt and filtered. The resin bound O-benzyl-D-serine was washed with DMF (3 times), 5% AcOH/DMF, MeOH (3 times, 100 mL total), THF (3 times), and $CH_2Cl_2$ (3 times) and dried: 9.58 g; IR 1717 (broad) $cm^{-1}$; Anal. Found C, 80.78; H, 8.00; N, 0.91. Loading on N content: 0.65 mmol/g.

A portion of the resin (27 mg) was treated with 10% TFA/$CH_2Cl_2$ (1.0 mL) for 4.5 h and filtered. The resin was rinsed with $CH_2Cl_2$ (3 times) and MeOH (2 times) and the filtrates were evaporated and dried (vacuum, overnight) to give back O-benzyl-D-serine, as its TFA salt (4.4 mg): LC-MS 100% Area; LC/MS (electrospray, +ions) m/z 196 (M+H)E. Loading, on cleaved amount, of the resin bound O-benzyl-D-serine: 0.53 mmol/g.

B.

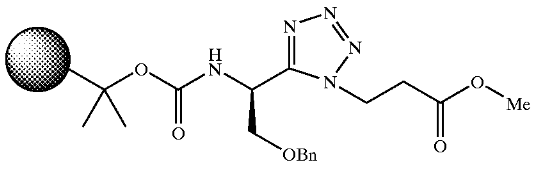

To the Part A resin bound O-benzyl-D-serine (1.75 g, 1.14 mmol) was added a solution of β-alanine methyl ester hydrochloride (315 mg, 2.27 mmol), diisopropylethylamine (0.39 mL, 2.24 mmol) and HOAT (308 mg, 2.26 mmol) in DMF (3.0 mL) and then, a solution of EDAC (433 mg, 2.26 mmol) in DMF (5.5 mL). The mixture was rocked for 24 h at rt and filtered. The polymer was washed 3 times each with DMF, THF and $CH_2Cl_2$ to give resin bound O-benzyl-D-serine-2-methoxy-carbonylethyl amide.

To the resin bound amide was added a solution of triphenylphosphine (955 mg, 3.64 mmol) in 1,2-DCE (3.0 mL) and a solution, previously cooled at 0° C., of trimethylslylazide (0.48 mL, 3.62 mmol) and diethyl azodicarboxylate (DEAD) (0.57 mL, 3.62 mmol) in 1,2- DCE (3.0 mL). The mixture was rocked for 24 h at rt and filtered. The resin was washed with DMF (3 times) and $CH_2Cl_2$ (6 times), and resubmitted to the above Mitsunobu reaction conditions twice. The polymer was finally washed with DMF (3 times), THF (3 times) and $CH_2Cl_2$ (3 times) to provide the resin bound 1-(2-methoxycarbonylethyl)-tetrazole.

C.

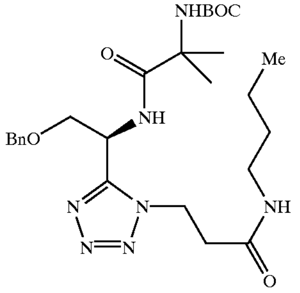

To the Part B resin bound methyl ester resin (307 mg, <0.20 mmol) in n-butyl amine (2.0 mL) was added a solution of tetra-n-butyl ammonium cyanide (40 mg, 0.15 mmol) in MeOH (0.3 mL) and the mixture was heated at 50° C. for 3.6 h. After filtratiion, the polymer was washed 3 times each with DMF, MeOH, THF and $CH_2Cl_2$ to give the resin bound amide.

The resin was treated with ~3M HCl/$CH_2Cl_2$, MeOH, methyl acetate (4.0 mL, prepared by addition of acetyl chloride (AcCl) to a 3/2 $CH_2Cl_2$/MeOH solution) for 4.5 h and filtered. The resin was rinsed with $CH_2Cl_2$ (3 times) and MeOH (twice), and the filtrates were evaporated to afford the amine HCl salt intermediate. This material was taken up in isopropanol (1.5 mL) and saturated NaCl (20 mL). The pH of the aqueous phase was adjusted to 10 by addition of 1M $K_2CO_3$ and the solution was extracted with $CH_2Cl_2$ (3x30 mL). The combined organic phase was dried ($Na_2SO_4$) and concentrated to give the free amine contaminated with triphenylphosphine oxide (30.7 mg).

N-Boc isobutyric acid (36 mg, 0.18 mmol), EDAC (34 mg, 0.18 mmol), HOAT (25 mg, 0.18 mmol), 1,2-DCE (0.3 mL) and DMF (30 uL) were mixed at 0° C. for 15 min. The resulting solution was added to a 0° C. solution of the crude amine (30.7 mg, <0.09 mmol) in 1,2-DCE (0.2 mL). The mixture was stirred for 22 h at rt and diluted with EtOAc (25 mL). The solution was washed with saturated $NaHCO_3$ (2x20 mL), water (20 mL) and saturated NaCl (20 mL), dried and evaporated to give crude Part C compound (44.4 mg). Preparative HPLC (solvent B: start 30%, final 90%; gradient time: 15 min; flow rate 20 mL/min; wavelenght 220 nm; column YMC S5 ODS 20x100 mm) gave the Part C compound (19.0 mg): LC/MS (electrospray, +ions) m/z 532 (M+H).

D.

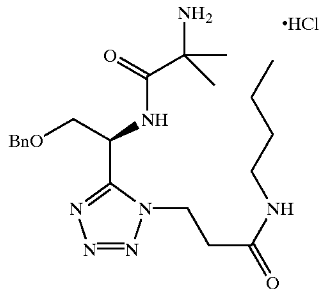

The Part C compound (19.0 mg, 0.036 mmol) was treated with ~3M HCl in $CH_2Cl_2$, MeOH, MeOAc (2.0 mL, prepared by addition of AcCl to a 3/2 $CH_2Cl_2$/MeOH solution) for 2.2 h and concentrated. The residue was further dried (vacuum, 2 h) to afford the title compound (16.6 mg) as a colorless solid: LC-MS 96% Area; LC/MS (electrospray, +ions) m/z 432 (M+H).

EXAMPLE 93

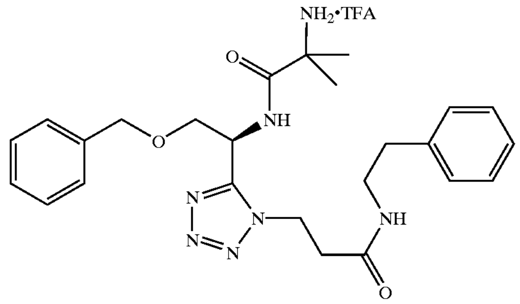

A.

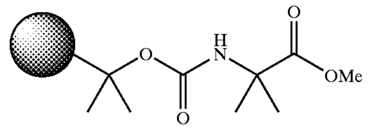

Methyl triflate (0.80 mL, 7.11 mmol) was added to a suspension of resin bound (tert-alkoxycarbonyl)imidazole (5.06 g, Loading 0.70 mmol/g)

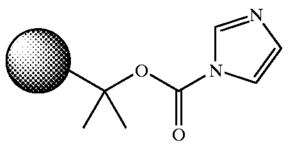

in dry 1,2-DCE (30 mL), cooled at 10° C. The mixture was stirred for 15 min at this temperature and for 10 min while being warmed to rt. After addition of $Et_3N$ (2.40 mL, 17.2 mmol), stirring was continued for an additional 10 min. A suspension of methyl 2-aminoisobutyrate (1.14 g, 7.42 mmol) and $Et_3N$ (0.98 mL, 7.04 mmol) in DMF (13 mL) was filtered and transferred via syringe to the stirred resin suspension. The mixture was shaken for 5.5 h at rt and filtered. The resin bound Part A compound was washed with THF (3 times), 1/1 THF/MeOH, THF (3 times), and $CH_2Cl_2$ (3 times) and dried: IR 1728 $cm^{-1}$; Anal. Found C, 82.02; H, 7.96; N, 0.89. Loading on N content: 0.64 mmol/g.

B.

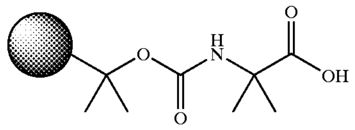

A 3/2 dioxane/0.25 M KOH solution (40 mL) was added to the Part A compound (2.63 g, Loading 0.64 mmol/g) and the suspension was heated at 75° C. for 4.5 h. After filtration, the polymer was washed with DMF (3 times), 5% AcOH/DMF (3 times, 50 mL total), MeOH (3 times), THF (3 times) and $CH_2Cl_2$ (3 times) and dried to provide the Part B compound (2.50 g).

A portion of the resin (53 mg) was treated with 10% TFA/$CH_2Cl_2$ (1.5 mL) for 5 h and filtered. The resin was rinsed with $CH_2Cl_2$ (3 times) and MeOH (2 times) and the filtrates were evaporated and dried (vacuum, overnight) to give pure 2-aminoisobutyric acid, as its TFA salt (6.3 mg): $^1$H NMR 5 ($CD_3OD$, ppm) 1.55 (s, 6H).

Loading, on cleaved amount, of the resin bound 2-aminoisobutyric acid Part B compound: 0.53 mmol/g.

C.

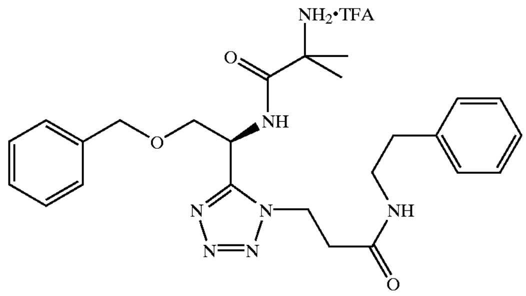

To a suspension of Example 92, Part B compound in phenethylamine (1.4.0 mL) was added a solution of tetra-n-butyl ammonium cyanide (22 mg, 0.08 mmol) in MeOH (0.3 mL) and the mixture was heated at 60–65° C. for 3 h. After filtration, the polymer was washed 3 times each with DMF, 1/1 THF/MeOH, THF and $CH_2Cl_2$to give the resin bound amide.

The resin was treated with ~3M HCl in $CH_2CH_2$, MeOH, MeOAc (3.0 mL, prepared by addition of AcCl to a 3/2 $CH_2Cl_2$/MeOH solution) for 5 h and filtered. The resin was rinsed with $CH_2Cl_2$ (3 times) and MeOH (twice), and the filtrates were evaporated to afford the intermediate

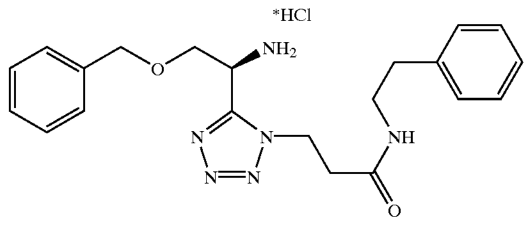

(69.3 mg).

The above intermediate (69.3 mg, 0.18 mmol), Part A compound(400 mg, loading 0.53 mmol/g) and a solution of EDAC(115 mg, 0.60 mmol), HOAT (82 mg, 0.60 mmol) and diisopropylethylamine (0.10 mL, 0.60 mmol) in DMF (3.0 mL) were mixed and the resulting suspension was rocked at rt for 24 h. After filtration, the resin was washed with DMF (3 times) and dioxane (3 times). The resin was swollen with 3/2 dioxane/$H_2O$, rocked overnight, filtered and washed with THF (3 times) and $CH_2Cl_2$ (3 times).

The resin was treated with ~3M HCl in $CH_2Cl_2$, MeOH, MeOAc (4.0 mL, prepared by addition of AcCl to a 3/2 $CH_2Cl_2$/MeOH solution) for 6 h and filtered. The resin was rinsed with $CH_2Cl_2$ (2 times) and MeOH and the filtrates were evaporated to give the crude title compound. This crude mixture was dissolved in acetonitrile/MeOH and passed through an anion exchange cartridge (3.0 g, CHQAX) by eluting wit h acetonitrile (18 mL) to provide the amine (22.2 mg). Further elution with 1/1 acetonitrile/MeOH (20 mL) gave an additional amount of amine (29.8 mg). The combined amine was further purified by preparative HPLC (solvent B: start 30%, final 80%; gradient time: 20 min; flow rate 20 mL/min; wavelenght 220 nm; column YMC S5 ODS 20×100 mm) to afford the tittle compound (20.7 mg): HPLC 100% Area; LC/MS (electrospray, +ions) m/z 480 (M+H).

EXAMPLES 94 AND 95

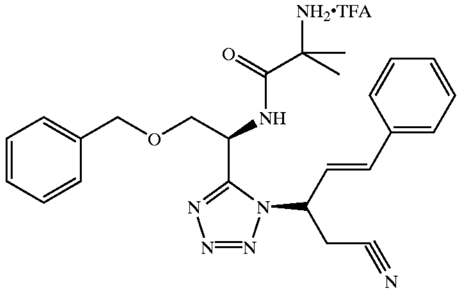

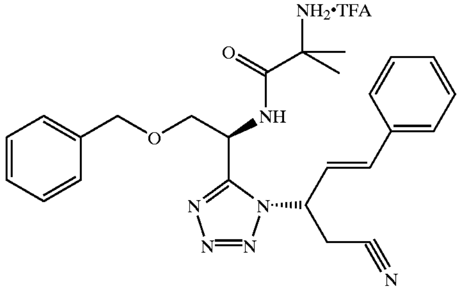

A.

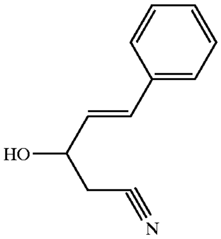

Sodium borohydride (110 mg, 2.92 mmol) was added to a solution of cinnamoyl acetonitrile (1.0 g, 5.84 mmol, Maybridge) in 4/1 MeOH/$H_2O$ (30 mL), cooled at 0° C., and the mixture was stirred for 1.5 h. After warming to rt, small portions of sodium borohydride were added at 45 min intervals until reaction completion (additional 90 min). After evaporating in vacuo most of the MeOH, potassium phosphate buffer (pH 3, 45 mL) was added and the mixture was stirred for 15 min. 5% $NaHCO_3$ (45 mL) was added and the aqueous mixture was extracted with $CH_2Cl_2$. The organic phases were combined, dried ($Na_2SO_4$) and concentrated. The residue was chromatographed ($SiO_2$ 230–400 mesh, 1/1

Hex/EtOAC) to give the Part A compound (842.5 mg) as a yellow liquid: LC/MS 98% Area; LC/MS (electrospray, +ions) m/z 156 (M—OH).

B.

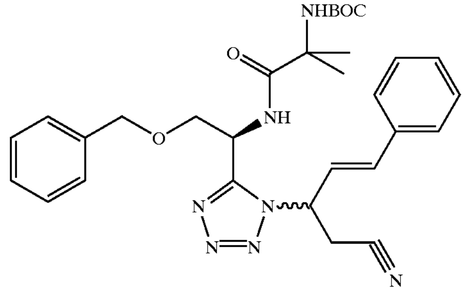

Diisopropylethylamine (31 μL, 0.18 mol) and diethylazodicarboxylate (0.18 mL, 1.14 mmol) were added to a solution of the Part A alcohol (198 mg, 1.14 mmol), Example 5 Part A compound

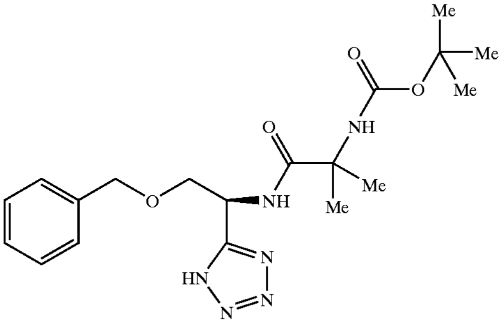

(360 mg, 0.89 mmol) and $Ph_3P$ (303 mg, 1.15 mmol) in $CH_2Cl_2$ (2.6 mL), previously cooled at 0° C. The mixture was stirred at rt for 24 h and evaporated. The residue was chromatographed ($SiO_2$ 230–400 mesh, 1/1 Hex/EtOAC) to afford the Part B N-1 substituted tetrazoles (98.3 mg, 20% yield, 2 diastereomers): HPLC 98% diastereomer combined Area; LC/MS (electrospray, +ions) m/z 560 (M+H).

C.

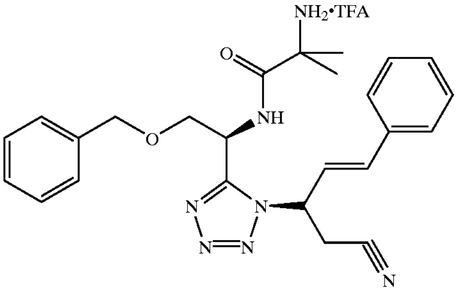

and

D.

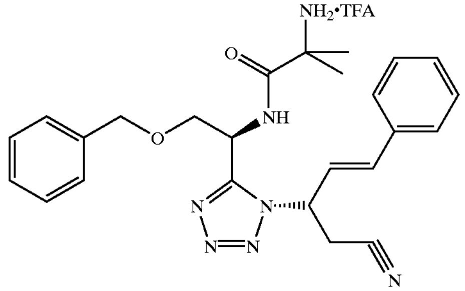

A solution of the Part B compound (72 mg, 0.13 mmol, 2 diastereomers) and thioanisole (45 μL, 0.38 mmol) in $CH_2Cl_2$ (1.5 mL) was treated with 4M HCl/dioxane solution (1.5 mL) for 1.2 h and concentrated. Preparative HPLC (solvent B: start 40%, final 90%; gradient time: 30 min; flow rate 20 mL/min; wavelength 220 nm; column YMC S5 ODS 20×100 mm) afforded Example 94 title compound (23.8 mg, 32% yield, single diastereomer) as a colorless solid: LC/MS 100% Area; LC/MS (electrospray, +ions) m/z 460 (M+H), and Example 95 title compound (26.7 mg, 36% yield, the other diastereomer) as a colorless solid: LC/MS 100% Area; LC/MS (electrospray, +ions) m/z 460 (M+H).

The following compounds were prepared employing procedures as described in Examples 96 to 101.

| Example No. | Structure | | M + H positive ions |
|---|---|---|---|
| 96 | 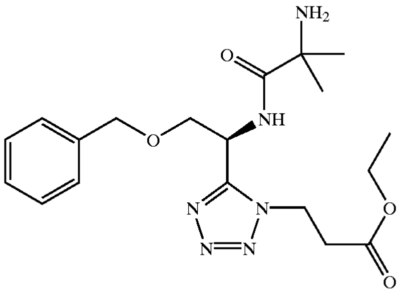 | Chiral | 405 |
| 97 | 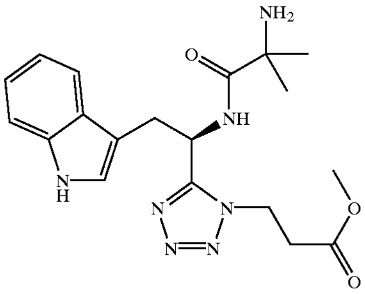 | Chiral | 400 |
| 98 | 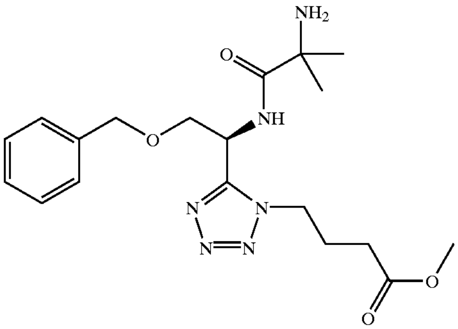 | Chiral | 405 |
| 99 | 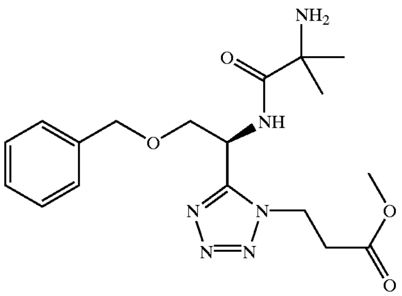 | Chiral | 391 |

-continued
| Example No. | Structure | | M + H positive ions |
|---|---|---|---|
| 100 | 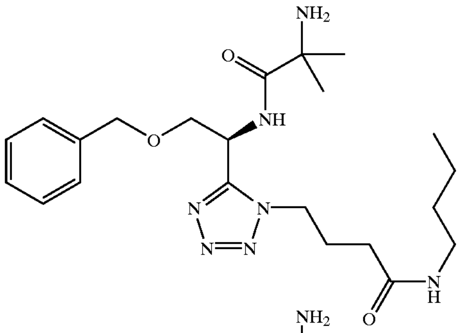 | Chiral | 446 |
| 101 | 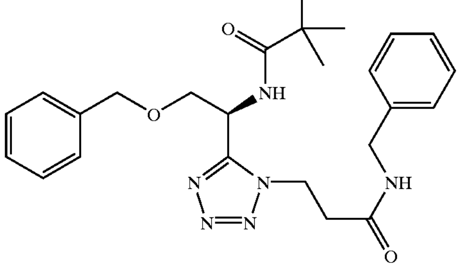 | Chiral | 466 |
The following compounds were prepared employing the procedures described in Examples 102 to 117 and general procedures detailed in the working examples.
| Example No. | Structure | | M + H positive ions |
|---|---|---|---|
| 102 | 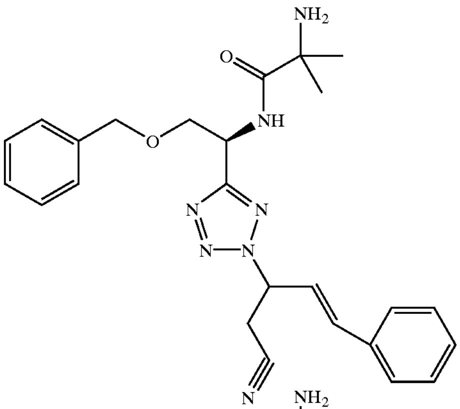 | Chiral | 460 |
| 103 | 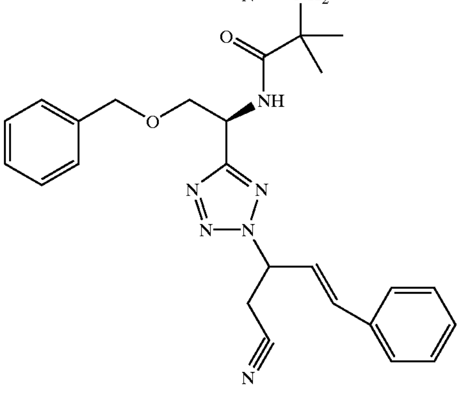 | Chiral | 460 |

-continued
| Example No. | Structure | | M + H positive ions |
|---|---|---|---|
| 104 | 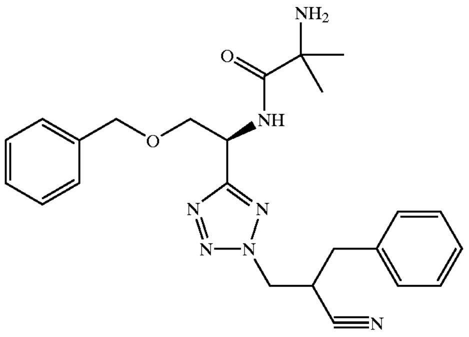 | Chiral | 448 |
| 105 | 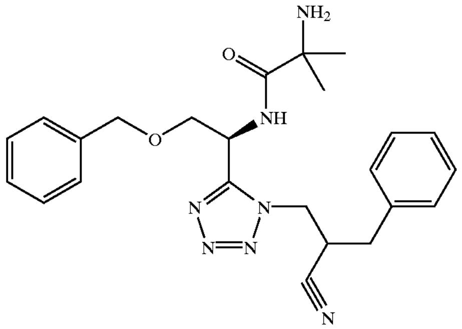 | Chiral | 448 |
| 106 | 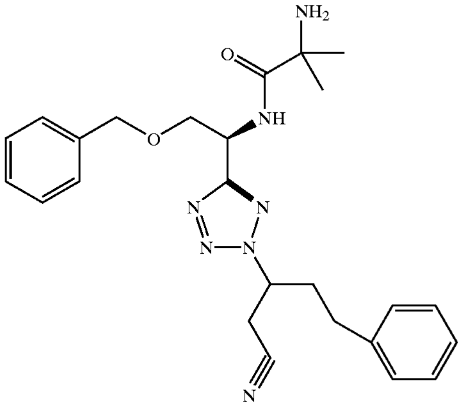 | Chiral | 462 |
| 107 | 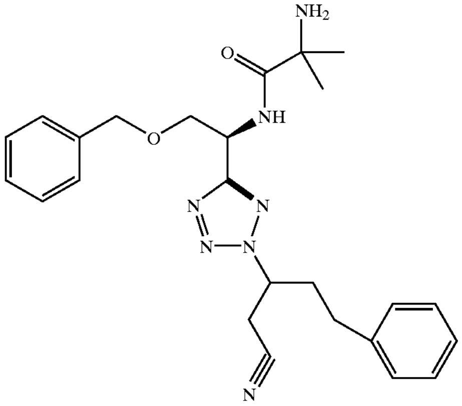 | Chiral | 462 |

-continued
| Example No. | Structure | | M + H positive ions |
|---|---|---|---|
| 108 | 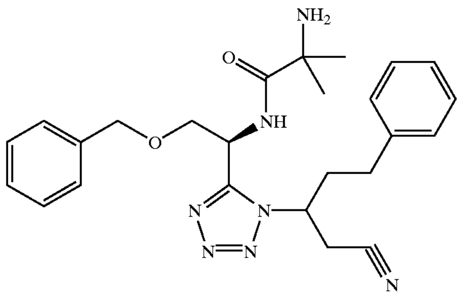 | Chiral | 462 |
| 109 | 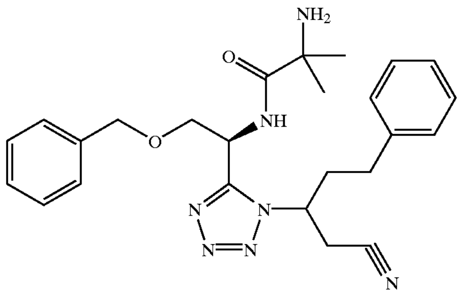 | Chiral | 462 |
| 110 | 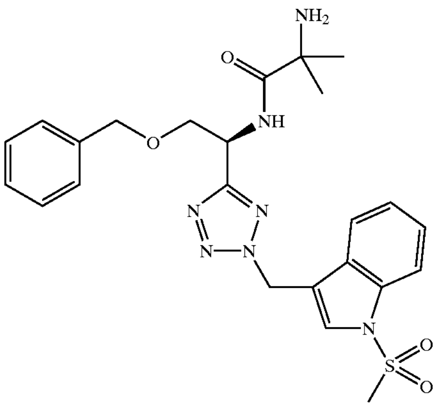 | Chiral | 512 |
| 111 | 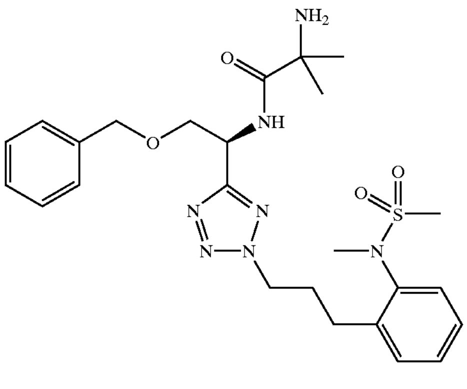 | Chiral | 530 |

-continued
| Example No. | Structure | | M + H positive ions |
|---|---|---|---|
| 112 | 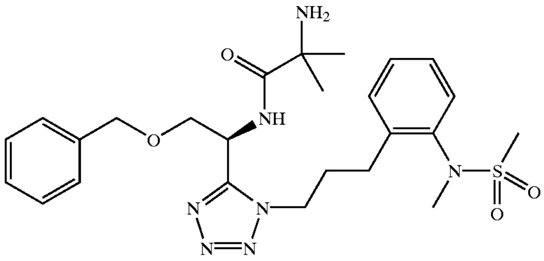 | Chiral | 530 |
| 113 | 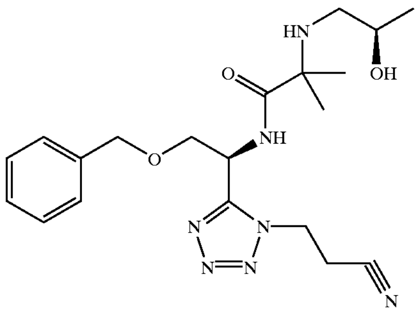 | Chiral | 416 |
| 114 | 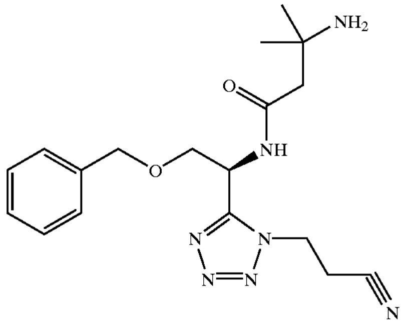 | Chiral | 372 |
| 115 | 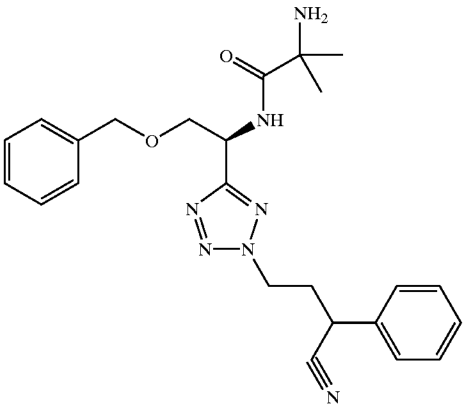 | Chiral | 448 |

-continued

| Example No. | Structure | | M + H positive ions |
|---|---|---|---|
| 116 | 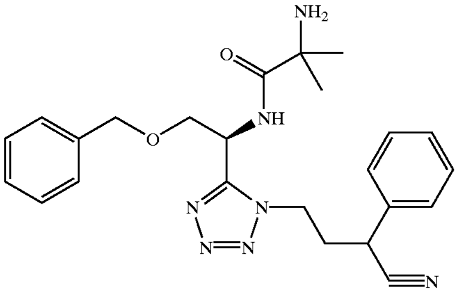 | Chiral | 448 |
| 117 | 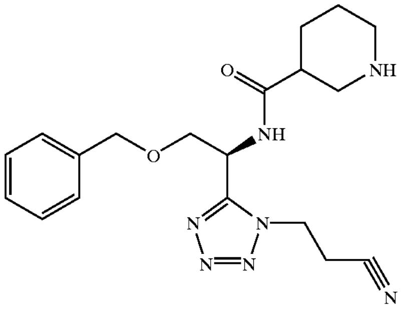 | Chiral | 384 |

EXAMPLE 118

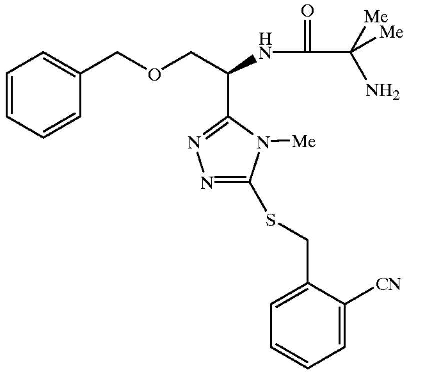

A.

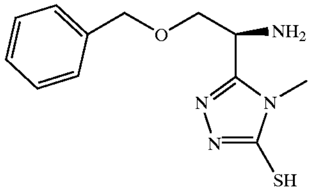

To a solution of crude

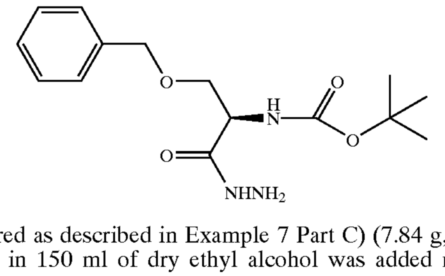

(prepared as described in Example 7 Part C) (7.84 g, 25.37 mmol) in 150 ml of dry ethyl alcohol was added methyl isothiocyanate (2.04 g, 27.91 mmol). The reaction was heated to reflux for 6 h. The reaction was allowed to cool to room temperature and the solvent was removed via the evaporator. The residue was then treated with 1N NaOH (70 ml), the resulting mixture was heated to reflux (113° C. oil bath) for 12 h. The reaction was cooled to room temperature and the solvent was removed via vacuum. The residue was treated with 300 ml of methyl chloride/methanol (100:7.5). The mixture was stirred at room temperature for 1 h and filtered. The filtrate was concentrated and co-evaporated with toluene to give crude title compound (7.54 g). HPLCb retention time (rt)=2.37 min. LC/MS (electrospray, +ions) m/z 265 (M+H).

B.

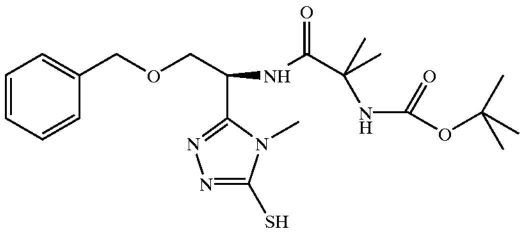

To a solution of Part A compound (7.54 g, 28.6 mmol) and Boc-methylalanine carboxylic acid (6.96 g, 34.3 mmol, Sigma) in 100 ml of DMF was added HOAt (5.05 g, 37.1 mmol) nitrogen and the reaction mixture was stirred at rt. overnight. The solvent was removed via vacuum and the residue was diluted with water (100 ml). The mixture was extracted with 1/1 ethyl acetate/ether (3×200 ml), the organic layer was dried over magnesium sulfate, and filtered. The filtrate was stored at 0° C. and the resulting solid recovered by filtration to give Part B compound (1.45 g). The resulting filtrate was then concentrated and the residue was purified by flash chromatography, eluting with hexanes/ethyl acetate (2:1) to give further Part B compound as a white solid (6.92 g). HPLCb retention time (rt)=3.19 min. LC/MS (electrospray, +ions) m/z 450 (M+H).

C.

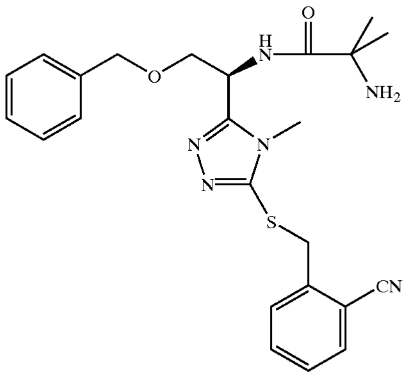

To a solution of Part B compound (67.4 mg, 0.15 mol) in 1 ml of dry dioxane was added triethyl amine 30.3 mg, 0.3 mmol) and 2-cyanobenzyl bromide (58.8 mg, 0.3 mmol) at rt. The reaction was shaken overnight and the solvent was removed via vacuum to give the intermediate:

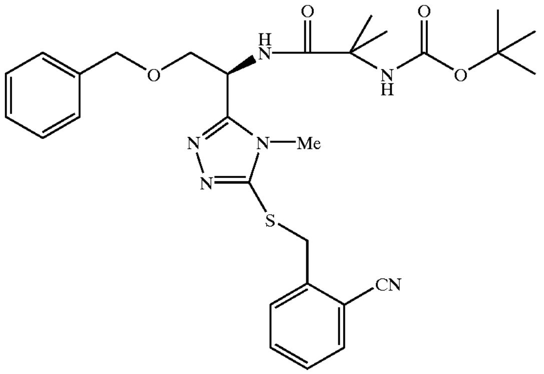

The residue was then treated with TFA/dichloro-methane (1 ml, 1:3) at rt for 2 h. The solvent was evaporated and the reaction mixture was purified by a SCX column (2 g) as follows: The column was conditioned by rinsing with methanol (10 mL). The reaction mixture in 1 mL of methanol was loaded onto the column followed by methanol (30 mL). The product was then eluted with 2 N ammonia in methanol (7 mL). The solvent was removed from the sample by the use of a speed vacuum to give the title compound (53 mg, 76%) as an oil: HPLCb rt=3.15 min, LC/MS (electrospray, +ions) m/z 465 (M+H).

EXAMPLE 119

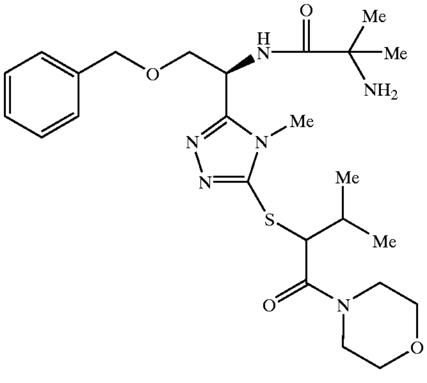

To a solution of Example 118 Part B compound (67.4 mg, 0.15 mmol) in 1 mL of dry dioxane was added triethyl amine (30.3 mg, 0.3 mmol) and 4-(2-bromoisovaleryl)-morpholine (75 mg, 0.3 mmol) at rt. The reaction was shaken overnight, then potassium carbonate (103 mg, 0.75 mmol) was added and the reaction was continually shaken for another 24 h. The solid was filtered off, the filtrate was collected, and the solvent was removed via vacuum. The residue was then treated with TFA/methylene chloride (1 ml, 1:3) at rt for 2 h. The solvent was evaporated and the reaction mixture was purified by a SCX column (2 g) as follows: The column was conditioned by rinsing with methanol (10 mL). The reaction mixture in 1 ml of methanol was loaded onto the column followed by methanol (30 mL). The product was then eluted with 2 N ammonia in methanol (7 mL). The solvent was removed from the sample by the use of a speed vacuum to give the title compound (41 mg, 53%) as an oil: HPLCb rt=3.06 min, LC/MS (electrospray, +ions) m/z 519 (M+H).

EXAMPLE 120

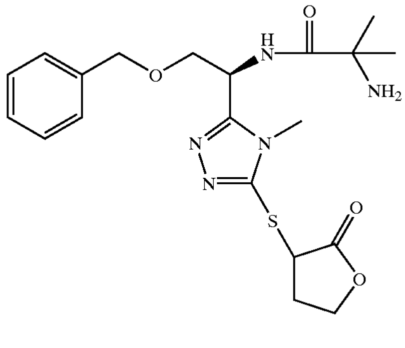

To a solution of Example 118 Part B compound (67.4 mg, 0.15 mmol) in 1 ml of dry dioxane was added triethyl amine (30.3 mg, 0.3 mmol) and 2-bromobutyrolactone (49.5 mg, 0.3 mmol) at rt. The reaction was shaken overnight, then potassium carbonate (103 mg, 0.75 mmol) was added and the reaction was continually shaken for another 24 h. The solid was filtered off, the filtrate was collected, and the solvent was removed via vacuum. The reaction mixture was purified by a short silica gel cartridge column (2 g) as follows: The column was conditioned by rinsing with ethyl acetate (10 ml). The reaction mixture in 1 ml of ethyl acetate was loaded onto the column followed by ethyl acetate (7 ml). The solution was collected and the solvent was removed from the sample by the use of a speed vacuum. The residue was then treated with TFA/methyl chloride (1 ml, 1:3) at rt for 2 h. The solvent was removed via vacuum to give the title compound as TFA salt (47.1 mg, 57%): HPLC rt=2.56 min, LC/MS (electrospray, +ions) m/z 434(M+H).

In a manner analogous to that of compounds of Example 118 to 120, compounds of Examples 121 to 172 listed in the table below were prepared from Example 118 Part B compound (0.15 mmol) and the respective bromide (0.3 mmol). Examples 159–172 required further elaboration before deprotection with TFA. A few examples were purified by preparative HPLC, eluting with a gradient system of methanol and water with 0.2% trifluoroacetic acid. Examples 121 to 172 were isolated as trifluoroacetic acid salts or as a free base.

EXAMPLES 121 TO 172

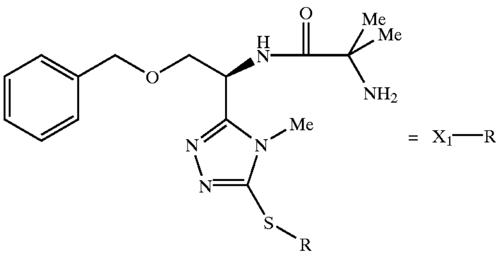

| Example No. | $X_1$—R | M + H positive ions |
| --- | --- | --- |
| 121 | 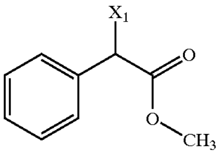 | 498 |
| 122 | 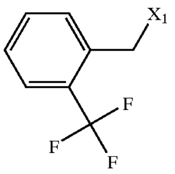 | 508 |
| 123 | 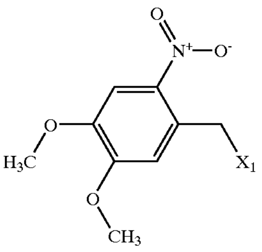 | 545 |
| 124 | 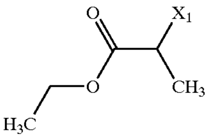 | 450 |
| 125 | 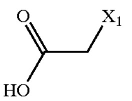 | 408 |

-continued
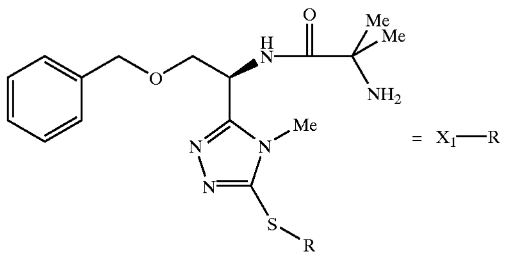
| Example No. | $X_1$—R | M + H positive ions |
|---|---|---|
| 126 | 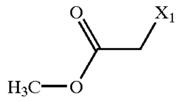 | 422 |
| 127 | 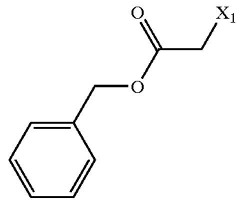 | 498 |
| 128 | 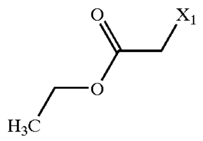 | 436 |
| 129 | 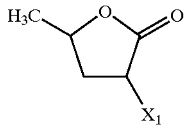 | 448 |
| 130 | 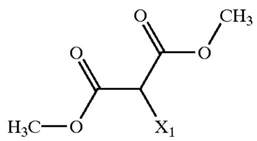 | 480 |
| 131 | 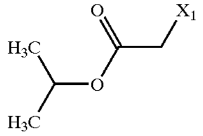 | 450 |
| 132 | 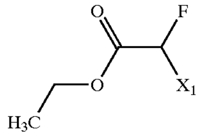 | 454 |

-continued
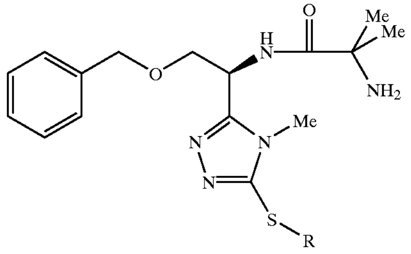
= $X_1$—R
| Example No. | $X_1$—R | M + H positive ions |
|---|---|---|
| 133 | 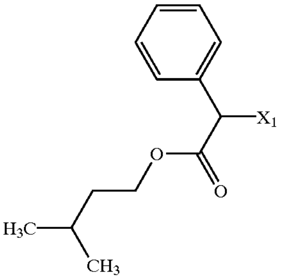 | 554 |
| 134 | 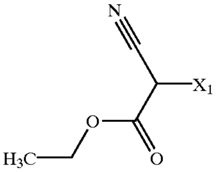 | 461 |
| 135 | 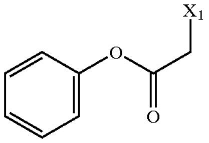 | 484 |
| 136 | 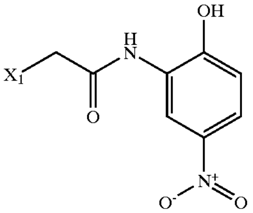 | 544 |
| 137 | 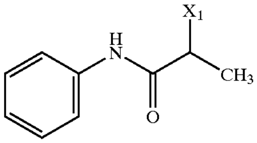 | 497 |
| 138 | 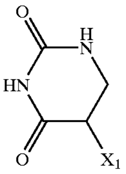 | 462 |

-continued
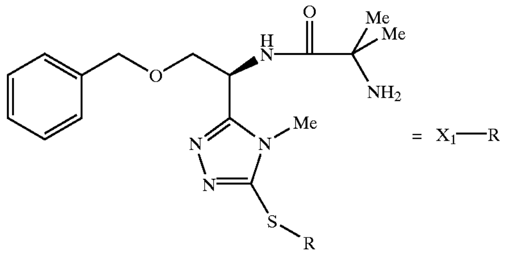
| Example No. | $X_1$—R | M + H positive ions |
|---|---|---|
| 139 | 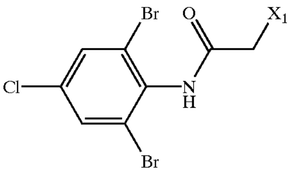 | 675 |
| 140 | 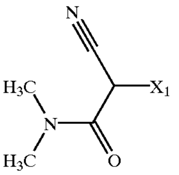 | 460 |
| 141 | 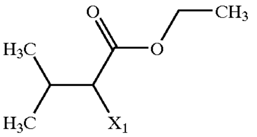 | 478 |
| 142 | 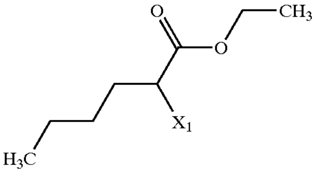 | 492 |
| 143 | 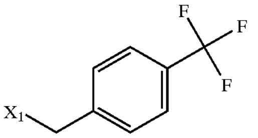 | 508 |
| 144 | 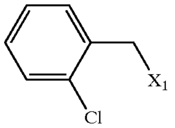 | 475 |
| 145 | 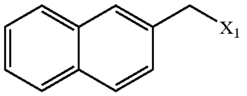 | 490 |
| 146 | 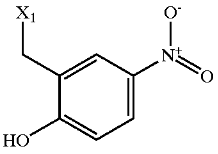 | 501 |

-continued
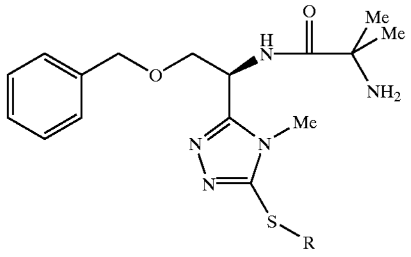
= $X_1$—R
| Example No. | $X_1$—R | M + H positive ions |
|---|---|---|
| 147 | 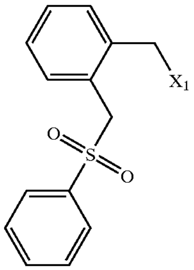 | 594 |
| 148 | 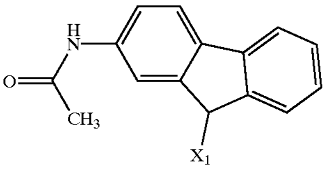 | 571 |
| 149 | 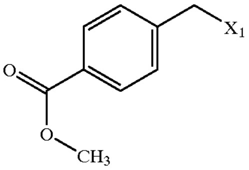 | 498 |
| 150 | 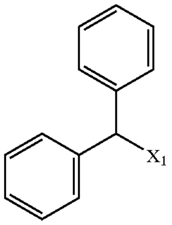 | 516 |
| 151 | 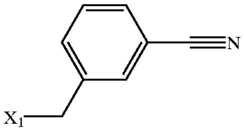 | 465 |
| 152 | 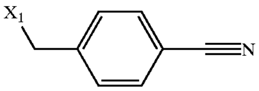 | 465 |

-continued
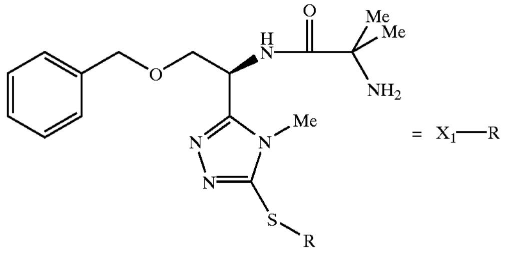
| Example No. | $X_1$—R | M + H positive ions |
|---|---|---|
| 153 | 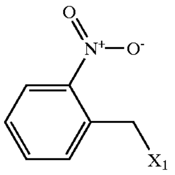 | 485 |
| 154 | 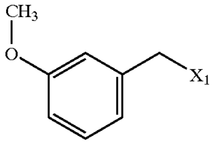 | 470 |
| 155 | 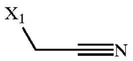 | 389 |
| 156 | 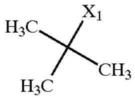 | 406 |
| 157 | 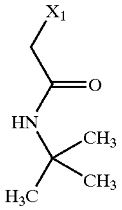 | 463 |
| 158 | 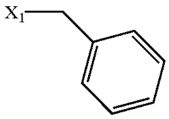 | 440 |
| 159 | 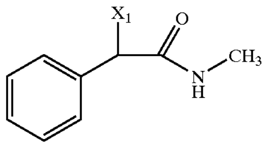 | 497 |
| 160 | 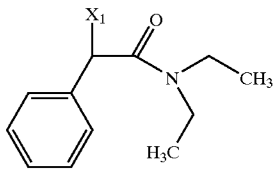 | 539 |

-continued
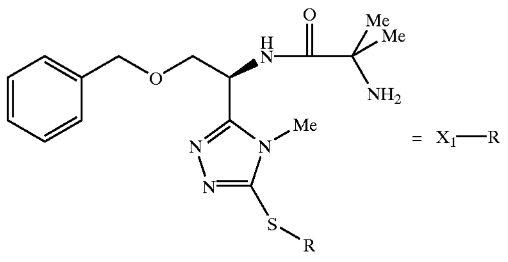
| Example No. | $X_1$—R | M + H positive ions |
|---|---|---|
| 161 | 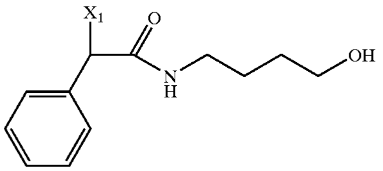 | 555 |
| 162 | 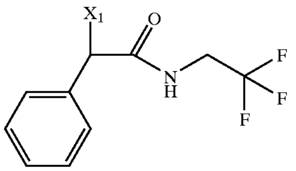 | 565 |
| 163 | 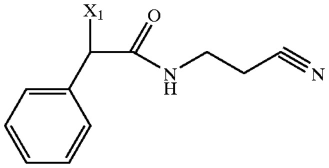 | 536 |
| 164 | 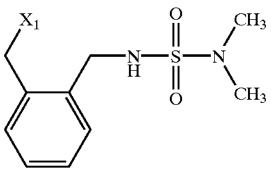 | 576 |
| 165 | 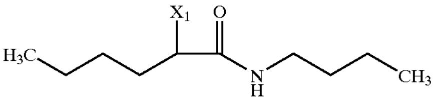 | 519 |
| 166 | 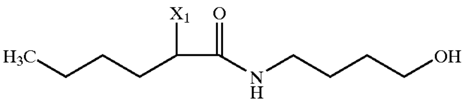 | 535 |

-continued
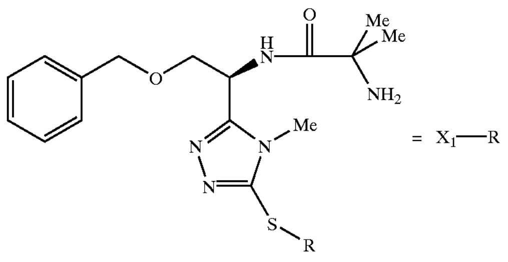
| Example No. | $X_1$—R | M + H positive ions |
|---|---|---|
| 167 | 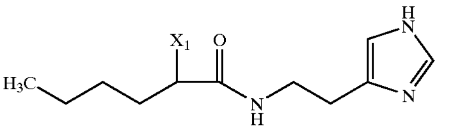 | 557 |
| 168 | 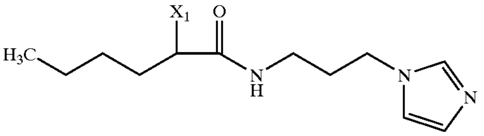 | 571 |
| 169 | 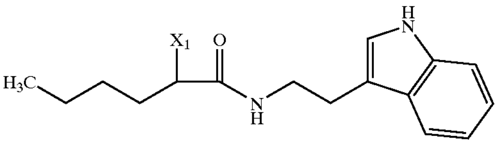 | 606 |
| 170 | 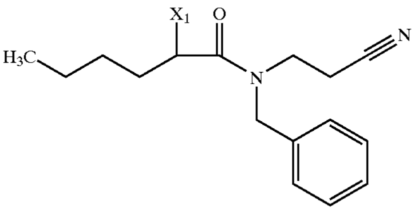 | 606 |
| 171 | 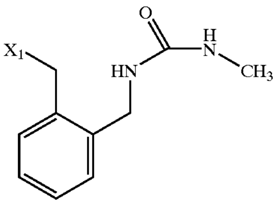 | 526 |
| 172 | 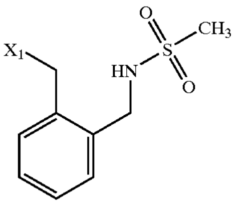 | 547 |

Compounds of Examples 173 to 216 listed in the table below were prepared in a manner analogous to that of compounds of Example 118 to 172.
EXAMPLES 173 TO 216
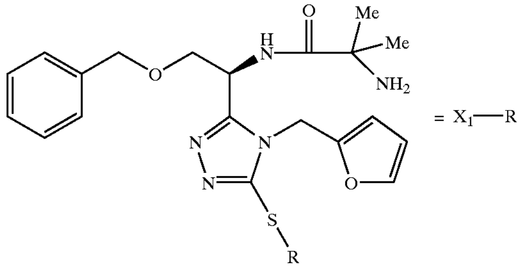
| Example No. | $X_1$-R | M + H positive ions |
|---|---|---|
| 173 | 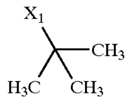 | 472 |
| 174 | 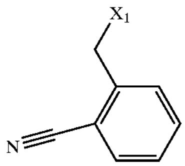 | 531 |
| 175 | 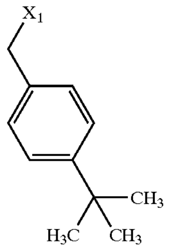 | 562 |
| 176 | 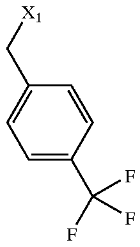 | 574 |
| 177 | 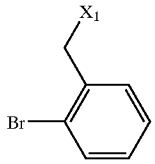 | 585 |
-continued
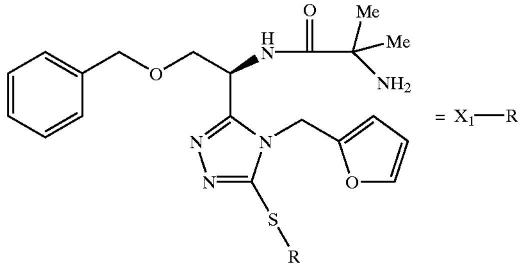
| Example No. | $X_1$-R | M + H positive ions |
|---|---|---|
| 178 | 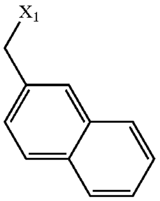 | 556 |
| 179 | 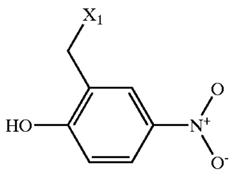 | 567 |
| 180 | 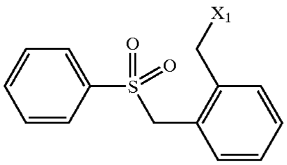 | 660 |
| 181 | 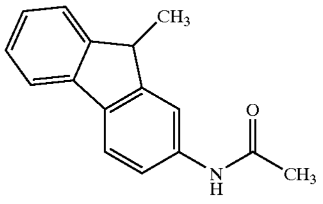 | 651 |
| 182 | 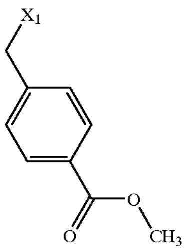 | 564 |

-continued
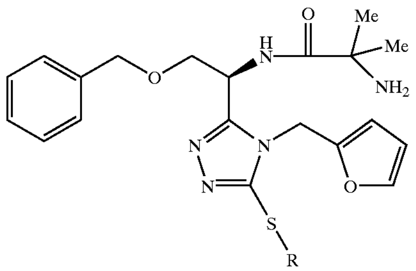
= $X_1$—R
| Example No. | $X_1$-R | M + H positive ions |
|---|---|---|
| 183 | 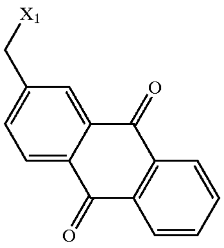 | 636 |
| 184 | 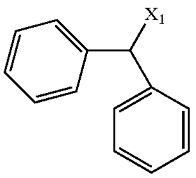 | 582 |
| 185 | 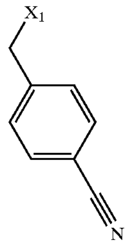 | 531 |
| 186 | 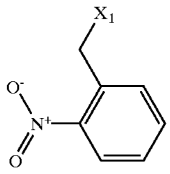 | 551 |
| 187 | 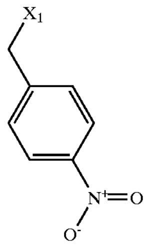 | 551 |
-continued
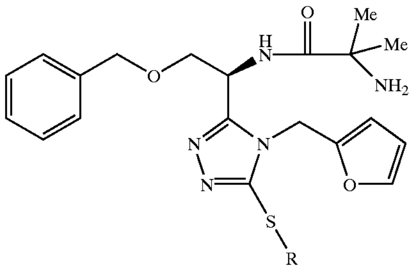
= $X_1$—R
| Example No. | $X_1$-R | M + H positive ions |
|---|---|---|
| 188 | 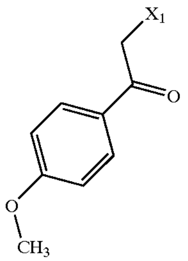 | 564 |
| 189 | 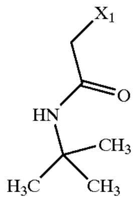 | 529 |
| 190 | 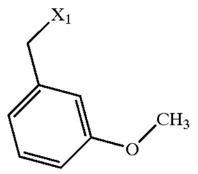 | 536 |
| 191 | 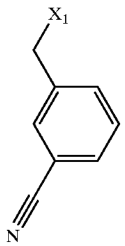 | 531 |
| 192 | 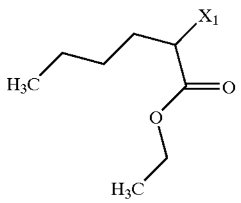 | 558 |
| 193 | 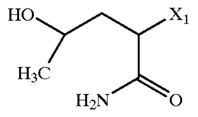 | 531 |

-continued
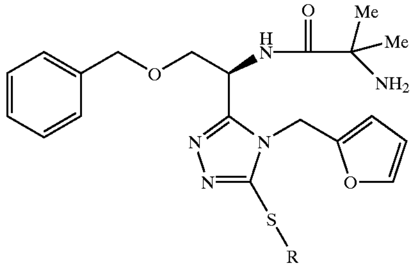
= $X_1$—R
| Example No. | $X_1$-R | M + H positive ions |
|---|---|---|
| 194 | 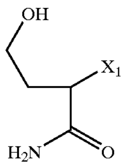 | 517 |
| 195 | 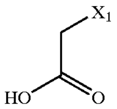 | 474 |
| 196 | 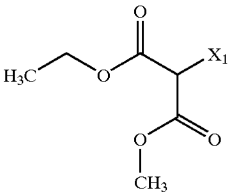 | 560 |
| 197 | 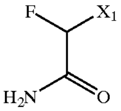 | 491 |
| 198 | 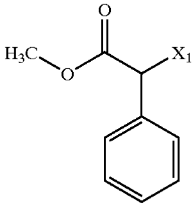 | 564 |
| 199 | 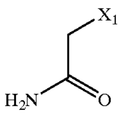 | 473 |
| 200 | 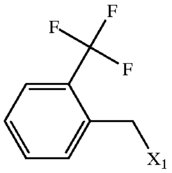 | 574 |
-continued
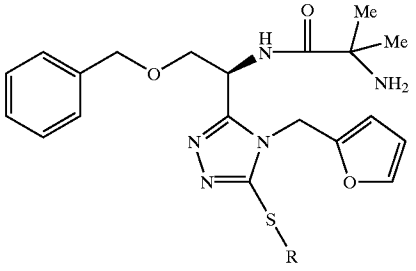
= $X_1$—R
| Example No. | $X_1$-R | M + H positive ions |
|---|---|---|
| 201 | 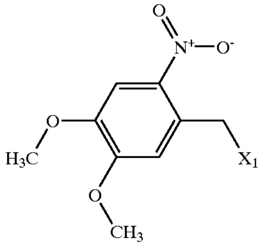 | 611 |
| 202 | 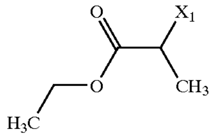 | 516 |
| 203 | 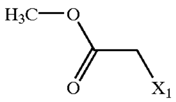 | 488 |
| 204 | 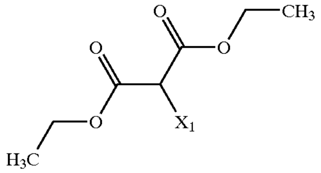 | 574 |
| 205 | 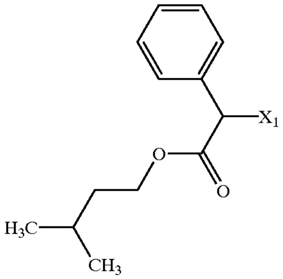 | 620 |
| 206 | 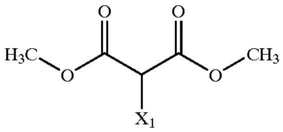 | 546 |

-continued
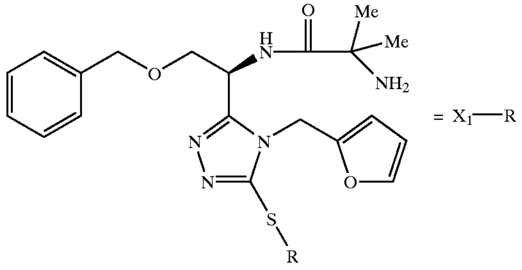
| Example No. | $X_1$-R | M + H positive ions |
|---|---|---|
| 207 | 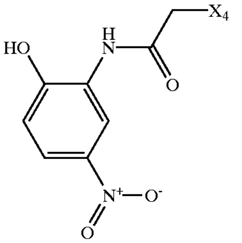 | 610 |
| 208 | 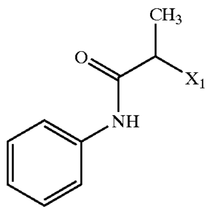 | 563 |
| 209 | 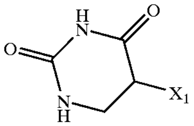 | 528 |
| 210 | 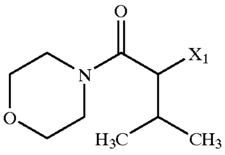 | 585 |
| 211 | 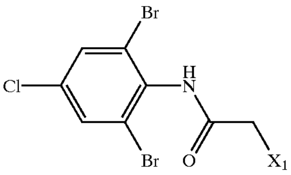 | 741 |
| 212 | 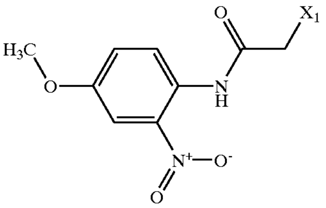 | 624 |
-continued
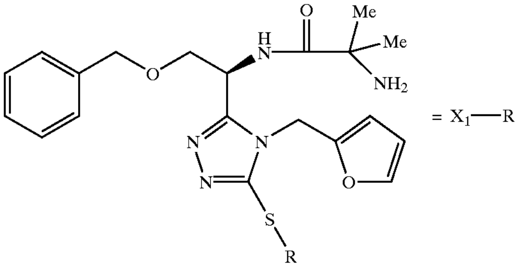
| Example No. | $X_1$-R | M + H positive ions |
|---|---|---|
| 213 | 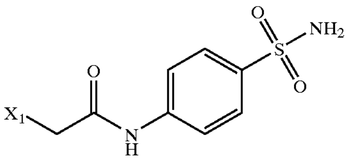 | 628 |
| 214 | 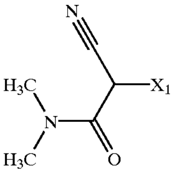 | 526 |
| 215 | 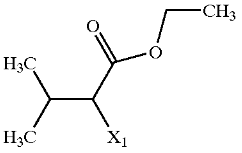 | 544 |
| 216 | 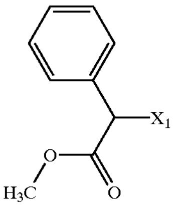 | 564 |
EXAMPLE 217
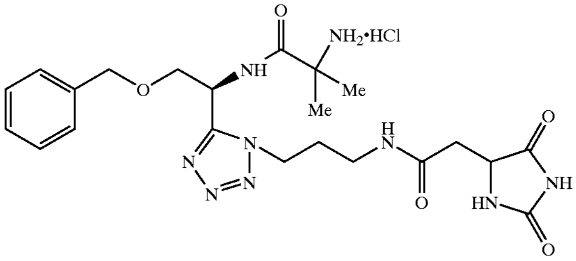

-continued

A.

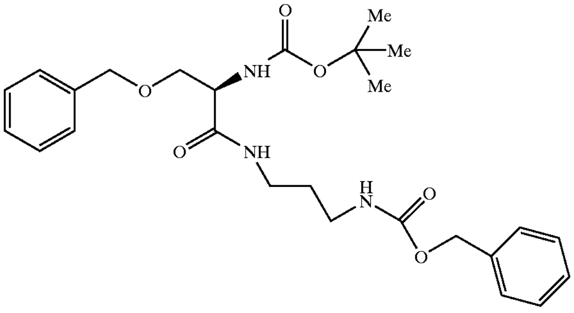

N-Methyl morpholine (1.86 mL, 16.9 mmol) and isobutyl chloroformate (2.19 mL, 16.9 mmol) were added to a solution of N-Boc-O-benzyl-D-serine (5 g, 16.9 mmol, ChemImpex) in THF (35 mL), cooled at −18° C. under nitrogen. After stirring the mixture for 0.5 h. at −18° C., a solution of N-Cbz-1-3-diaminobutane hydrochloride

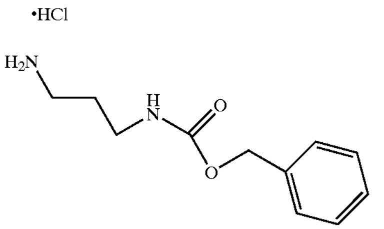

(4.14 g, 16.9 mmol) and N-methyl morpholine (1.86 mL, 16.9 mmol) in DMF (10 mL) was added and the resulting mixture was allowed to warm up to −5° C. over a period of 4 h. The mixture was filtered and the solution was evaporated near to dryness. The residue was taken up in EtOAc and washed with 5% $NaHCO_3$ (3×50 mL), water and brine. The organic solution was dried ($Na_2SO_4$), and evaporated to afford Part A compound (7.84 g, 97% yield): LC/MS (electrospray, +ions) m/z 486 (M+H).

B.

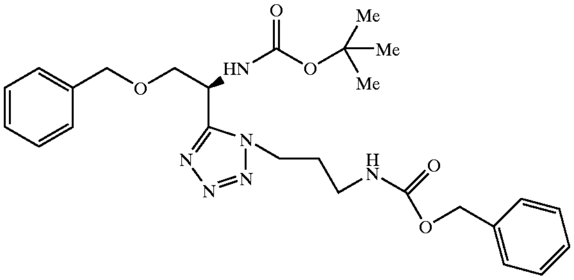

Diethylazodicarboxylate (2.57 mL, 16.3 mmol) and azidotrimethylsilane (2.16 mL, 16.3 mmol) were added to a solution of Part A compound (7.92 g, 16.3 mmol) and triphenylphosphine (4.28 g, 16.3 mmol) in THF (60 mL), previously cooled at 0° C. under nitrogen. The mixture was stirred at rt overnight and then cooled at 0° C. Another equivalent each of triphenylphosphine (4.28 g), diethylazodicarboxylate (2.57 mL) and azidotrimethylsilane (2.16 mL) was added and stirring was continued for an additional 24 h at rt. The reaction mixture was cooled at 0° C. and an aqueous solution (75 ml) of ammonium cerium (IV) nitrate (2.63 g/100 mL) was added and stirred for 1 h. The aqueous mixture was extracted with $CH_2Cl_2$ and the organic phase was dried ($Na_2SO_4$), evaporated and chromatographed ($SiO_2$ 230–400 mesh, 1/1 hexanes/EtOAc) to give the impure Part B compound. The contaminated tetrazole was dissolved in $CHCl_3$ and ether was added to precipitate Part B compound (2.6 g) as a colorless solid: MS (electrospray, +ions) m/z 511 (M+H).

C.

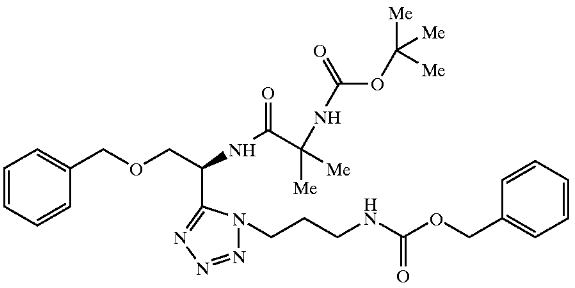

To a solution of Part B compound (2.5 g, 4.80 mmol) in $CH_2Cl_2$ was added a 4M HCl/dioxane solution (14.7 mL) and stirred for 3 h. The solvents were removed at reduce pressure, the residue concentrated from $CH_2Cl_2$ and the residue was taken up in minimal i-PrOH. Brine (150 mL) was added and the pH of the aqueous solution was adjusted to 10 by addition of 1M $K_2CO_3$. The aqueous solution was extracted with $CH_2Cl_2$, dried ($Na_2SO_4$), and evaporated to provide the amine intermediate,

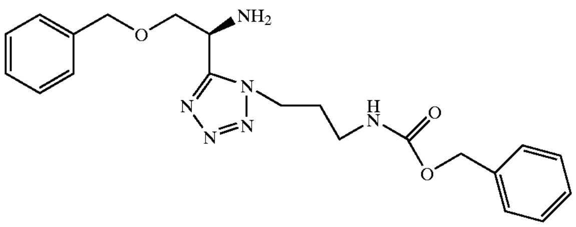

used without further purification in the subsequent reaction.

N-Boc-methyl alanine (1.49 g, 7.35 mmol, Sigma), EDAC (1.14 g, 7.35 mmol), HOAt (1 g, 7.35 mmol), 1,2-DCE and DMF (1.29 mL) were mixed at 0° C. and stirred for 15 min. The resulting solution was transferred to a 0° C. solution of the crude amine intermediate (prepared above) in 1,2-DCE and the mixture was stirred overnight at rt. The reaction mixture was diluted with EtOAc and washed with saturated $NaHCO_3$, water and brine. The organic layer was dried ($Na_2SO_4$), evaporated and chromatographed ($SiO_2$230–400 mesh, 1/1 hexanes/EtOAc) to provide Part C compound (1.58 g) as a colorless oil: MS (electrospray, +ions) m/z 596 (M+H).

D.

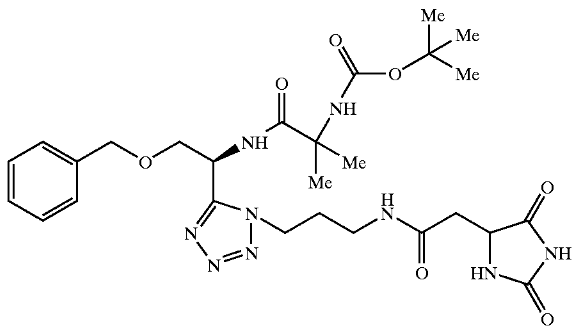

A methanol (3 mL) solution of Part C compound (100 mg, 0.17 mmol) and 5% palladium on carbon (50 mg) was hydrogenated for 1 h at 45 psi hydrogen. The reaction mixture was filtered through Celite and concentrated affording intermediate compound

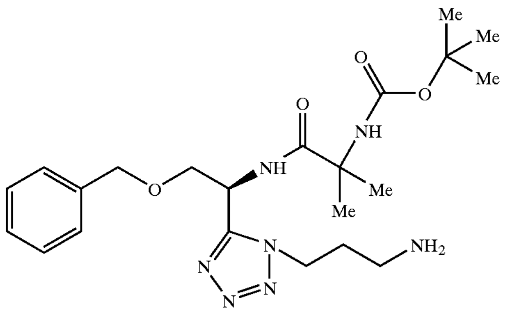

(68.1 mg). The resulting residue could be purifired by auto Prep HPLC to give pure intermediate compound (47.6 mg): MS (electrospray, +ions) m/z 462 (M+H).

A $CH_2Cl_2$ (1 mL) and DMF (0.5 mL) solution of hydantoin

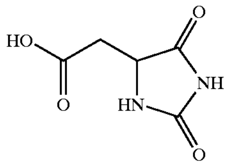

(25.3 mg, 0.16 mmol), EDAC (31.3 mg, 0.16 mmol), and dimethylamino pyridine (DMAP) (20.4 mg, 0.16 mmol) was added to a $CH_2Cl_2$ (1 mL) solution of the intermediate compound (75 mg, 0.16 mmol) at rt under nitrogen. The reaction mixture was allowed to stir at rt overnight and the volatiles were removed under vacuum. The resulting residue was dissolved in methanol and passed through a SCX resin column to give Part D compound (72 mg): MS (electrospray, +ions) m/z 602 (M+H).

E.

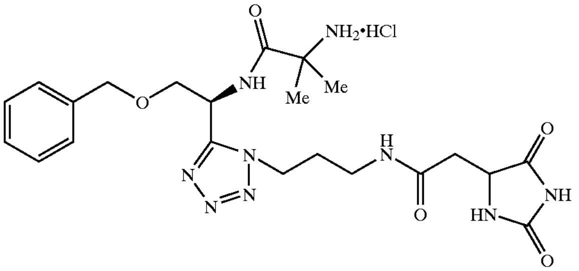

A $CH_2Cl_2$ solution of Part D compound (64.3 mg, 0.107 mmol) was treated with an HCl solution (3.0 mL; 10.2 ml of AcCl in 40 ml of 3/2 $CH_2Cl_2$/MeOH) for 3 h and evaporated in vacuo. The residue was coevaporated four times with $CH_2Cl_2$ to give the title compound (51.4 mg) as a white solid: LC/MS (electrospray, +ions) m/z 502 (M+H).

EXAMPLE 218

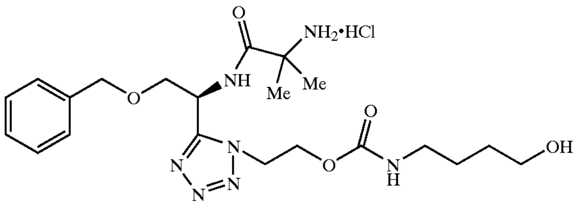

A.

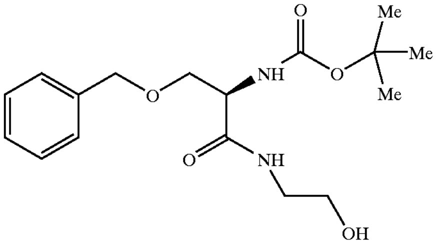

N-Methyl morpholine (2.23 mL, 20.3 mmol) and isobutyl chloroformate (2.64 mL, 20.3 mmol) were added to a solution of N-Boc-O-benzyl-D-serine (6 g, 20.3 mmol, ChemImpex) in THF (30 mL), cooled at −20° C. under nitrogen. After stirring the mixture for 45 min. at −20° C., a solution of ethanolamine (1.3 g, 21.4 mmol) in THF (20 mL) was added and the resulting mixture was allowed to warm up to rt over a period of 4 h. After stirring overnight, the mixture was filtered and the solution was evaporated near to dryness. The residue was purified by flash column chromatography (silica gel), eluting with hexanes:ethyl acetate (1:4) to afford the Part A compound (7.3 g): LC/MS (electrospray, +ions) m/z 339 (M+H).

B.

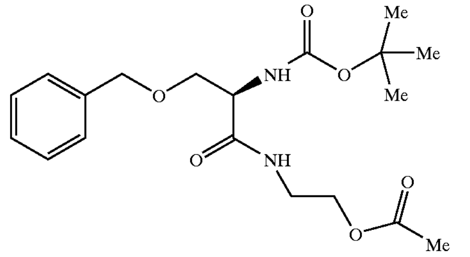

To a CH2$Cl_2$ (20 mL) solution of Part A compound (3.60 g, 10.7 mmol) at rt under nitrogen was added pyridine (3.44 mL, 42.6 mmol) and acetic anhydride (1.1 mL, 11.7 mmol). After 14 h, the volatiles were removed under vacuum. The resulting residue was purified by flash column chromatography (silica gel), eluting with hexanes:ethyl acetate (2:1) to afford the Part B compound (3.85 g): LC/MS (electrospray, +ions) m/z 381 (M+H).

C.

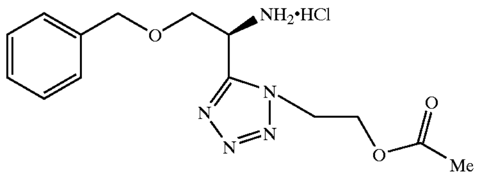

To a THF (30 mL) solution of Part B compound (3.83 g, 10.1 mmol) was added triphenylphosphine (2.64 g, 10.1 mmol), diethylazodicarboxylate (1.24 mL, 10.1 mmol) and azidotrimethylsilane (1.34 mL, 10.1 mmol). The mixture was stirred at room temperature (rt) for 24 h and then another equivalent each of triphenylphosphine (2.64 g), diethylazodicarboxylate (1.24 mL) and azidotrimethylsilane (1.34 mL) was added and stirring was continued for an additional 24 h at rt. The volatiles were removed under vacuum and the residue was purified by flash chromatography ($SiO_2$ 230–400 mesh, 8/1 hexanes/EtOAc) to give somewhat impure intermediate compound

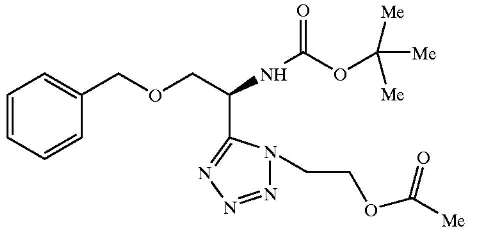

(2.71 g). The contaminated tetrazole was sufficiently pure for the subsequent reaction.

A 4M HCl/dioxane solution (10 mL) was added to the above intermediate compound (2.71 g, ≦6.69 mmol) and stirred for 1.5 h. The solvents were removed at reduce pressure and the residue co-evaporated twice with a mixture of toluene and methanol to provide Part C compound (2.28 g) as a colorless solid: LC/MS (electrospray, +ions) m/z 381 (M+H).

D.

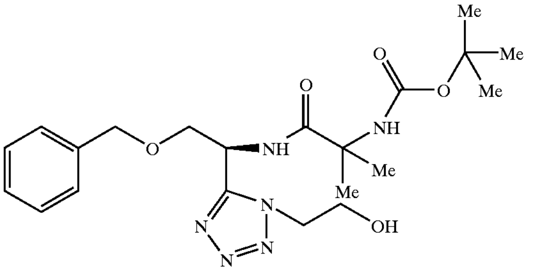

To a $CH_2Cl_2$ (25 mL) solution of Part C compound (2.28 g, 6.7 mmol) was added diisopropylethylamine (2.33 mL, 13.4 mmol), N-Boc-methyl alanine (2.04 g, 10 mmol, ChemImpex), HOAt (1.36 g, 10 mmol), and EDAC (1.92 g, 10 mmol) and the mixture was stirred overnight at rt. The reaction mixture was quenched with saturated ammonium chloride, and the aqueous layer was washed three times with $CH_2Cl_2$. The combined organic layers were washed with brine, dried ($Na_2SO_4$), and evaporated to provide intermediate compound

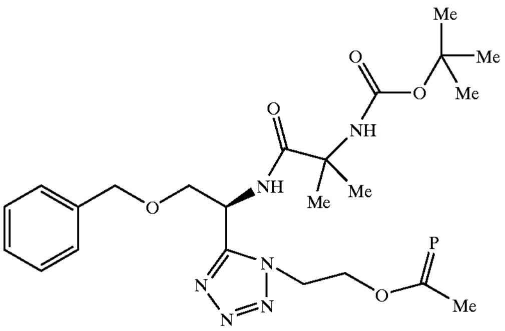

sufficiently pure for the subsequent reaction.

The above intermediate compound in a solution of THF/MeOH (20 mL, 20/1) was treated with 2N lithium hydroxide (10 mL) for 1 h. After cooling to 0° C., the reaction mixture was neutralized to pH 7 and the aqueous layer extracted with $CH_2Cl_2$ (3 times 100 mL). The combined organics were dried ($MgSO_4$), filtered, and concentrated under vacuum. The residue was purified by flash chromatography ($SiO_2$ 230–400 mesh, 1/1 hexanes/EtOAc) to give Part D compound (1.69 g): MS (electrospray, +ions) m/z 449 (M+H).

E.

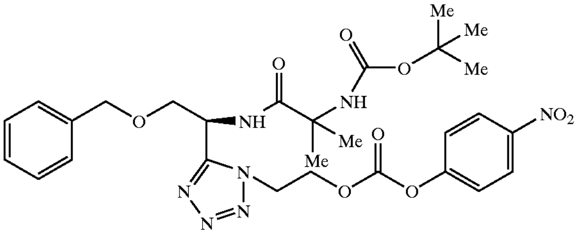

To a THF (20 mL) solution at 0° C. of Part D compound (1.34 g, 3.0 mmol) was added pyridine (0.53 mL, 6.6 mmol). After 3 min, a THF (10 mL) solution of para-nitrochloroformate (1.33 g, 6.6 mmol) was added and the mixture was stirred at 0° C. for 1 h and 2 h at rt. The reaction mixture was then filtered and the filtrate concentrated under vacuum. The resulting residue was purified by flash chromatography ($SiO_2$, 230–400 mesh) eluting with 1/1 hexanes/EtOAc to give Part E compound (1.52 g): LC/MS (electrospray, +ions) m/z 614 (M+H).

F.

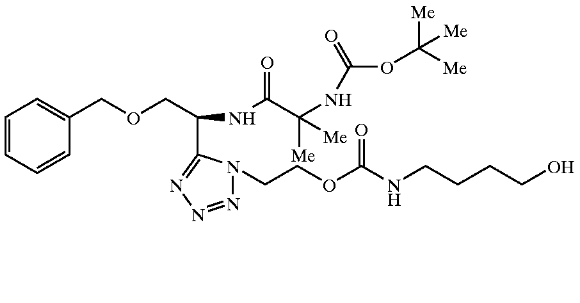

To a THF (20 mL) solution of Part E compound (3.4 g, 5.55 mmol) was added

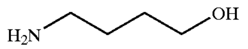

(0.74 g, 8.32 mmol) and after 3 h at RT, the volatiles were removed under vacuum. The resulting residue was purified by flash chromatography ($SiO_2$ 230–400 mesh) eluting with 1/2 hexanes/EtOAc (4/1 to 1/1) to give pure Part F compound (2.325 g), as well as some less pure material (1.03 g): LC/MS (electrospray, +ions) m/z 564 (M+H).

G.

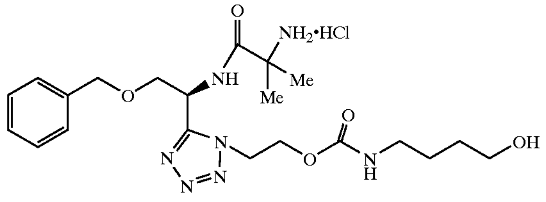

Part F compound (1.59 g, 2.82 mmol) was treated with a 4N HCl/dioxane solution (15 mL) for 1.5 h. The volatiles were evaporated in vacuo to give the title compound (1.44 g) as a colorless solid: LC/MS (electrospray, +ions) m/z 464 (M+H).

The above intermediate was treated with a 4N HCl/dioxane solution for 3 h and evaporated in vacuo. The residue was purified by preparative HPLC to give the title compound (85 mg) as a white solid: MS (electrospray, +ions) m/z 566 (M+H).

The intermediate Example 218, Part F can be prepared with the modified conditions as described in Example 219.

EXAMPLE 219

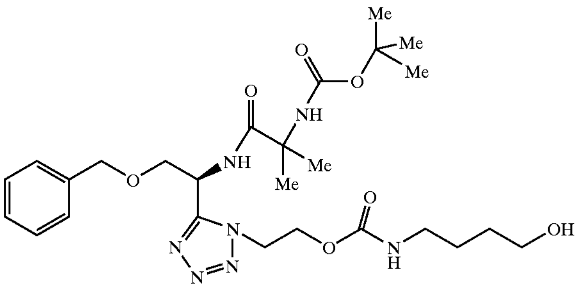

A.

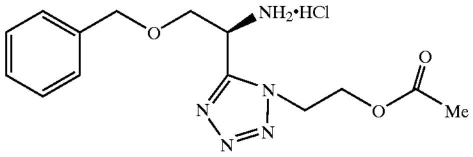

To a THF (250 mL) solution of Example 218 Part B compound (47.0 g, 120 mmol) cooled to 1° C. was added triphenylphosphine (32.6 g, 123 mmol) and diisopropylethylamine (5.4 mL, 32 mmol). Diethylazodicarboxylate (19.6 mL, 123 mmol, DEAD) was added dropwise over 15 minutes keeping temperature under 5° C. followed by the addition azidotrimethylsilane (16.5 mL, 123 mmol). The mixture was stirred at room temperature (rt) for 24 h and then another equivalent each of triphenylphosphine (32.6 g), DEAD(19.6 mL) and azidotrimethylsilane (16.5 mL) was added as before and stirring was continued for an additional 24 h at rt. Another equivalent each of triphenylphosphine (32.6 g), DEAD (19.6 mL) and azidotrimethylsilane (16.5 mL) was added as before and stirring was continued for an additional 24 h at rt. The reaction was cooled to 1° C. and quenched with a solution of ammonium cerium(IV) nitrate (136 g) in water (500 ml) over 45 minutes. The resulting mixture was filtered through celite and concentrated in vacuo and extracted twice with ethyl acetate (250 mL). The combined organic extracts were washed with brine, dried over magnesium sulfate and concentrated in vacuo to give an orange oil (236 g). This oil was dissolved in methyl t-butyl ether (1 L, MTBE), washed twice with 1N NaOH (500 mL), once with water (500 mL) and once with brine (500 mL), dried over magnesium sulfate and concentrated in vacuo to give a yellow solid (166 g). This solid was purified through a silica gel pad (500 g, 230–400 mesh) eluting with 15–40% ethyl acetate in hexanes to give the acetate intermediate as a yellow oil (20.6 g, 41% yield).

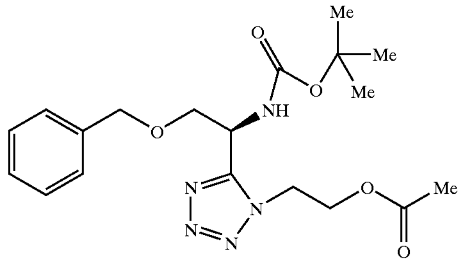

A 4M HCl/dioxane solution (325 mL) was added to a solution of the above intermediate compound (106.6 g, 263 mmol, combined from numerous reactions) in $CH_2Cl_2$ (600 mL) and stirred overnight. The solvents were removed in vacuo and the residue co-evaporated twice with a mixture of toluene and methanol to provide desired compound (89.3 g, 100% yield)) as a brown foam: LC/MS (electrospray, +ions) m/z 381 (M+H).

B.

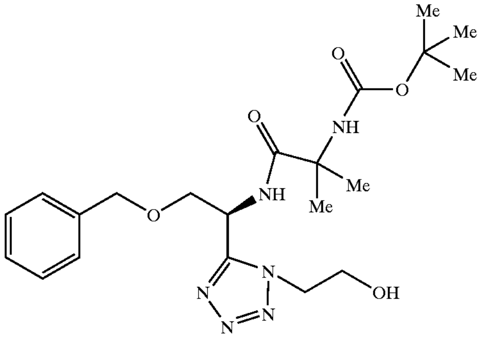

To a $CH_2Cl_2$ (1 L) solution of Part A compound (80.0 g, 262 mmol) was added diisopropylethylamine (120 mL, 262 mmol), N-Boc-methyl alanine (80.0 g, 393 mmol), HOAt (53.5 g, 393 mmol), and EDAC (75.3 g, 393 mmol) and the mixture was stirred 1 hour at rt. The reaction mixture was washed with water (500 mL), 0.5 M HCl (500 mL) and saturated $NaHCO_3$ (500 mL), dried ($MgSO_4$), and evaporated to provide intermediate compound as a yellow foam (146.8 g)

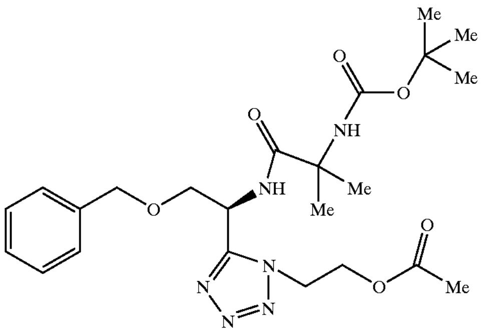

sufficiently pure for the subsequent reaction.

The above intermediate compound in a solution of THF/MeOH (1.25 L, 4/1) was placed in a water bath and 2N lithium hydroxide (65 mL) was added over 15 minutes maintaining the internal temperature below 25° C. The reaction stirred at room temperature for lh. The reaction mixture was concentrated in vacuo to an oil/solid mixture which was dissolved in water (500 mL) and the pH was adjusted to 5.5 with 1N HCl (40 mL). Dichloromethane was added (500 mL)and the mixture stirred for 30 minutes. The organic layer was separated and the aqueous layer extracted with $CH_2Cl_2$ (250 mL). The combined organics were washed with water (400 mL) and brine (400 mL), dried ($MgSO_4$), filtered, and concentrated under vacuum to give Part D compound (123.2 g) as a light yellow foam: MS (electrospray, +ions) m/z 449 (M+H).

C.

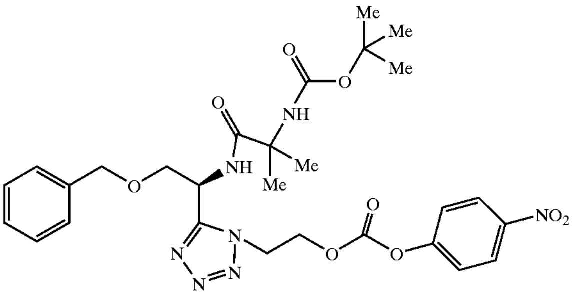

To a $CH_2Cl_2$ (350 mL) solution at 0° C. of Part B compound (123 g, 260 mmol) was added pyridine (32.0 mL, 391 mmol). After 10 min, a $CH_2Cl_2$ (150 mL) solution of para-nitrochloroformate (63.0 g, 313 mmol) was added over 1 hour, and the mixture was stirred at room temperature for 1 hour. The reaction mixture was washed with water (300 mL), 1N HCl (300 mL), and brine (300 mL), dried ($MgSO_4$), and concentrated in vacuo to a brown oil (187.3 g). This crude material was purified through a silica gel pad (500 g, 230–400 mesh) eluted with 30–50% ethyl acetate in hexanes to give Part E compound as an off-white foam (130.98 g, 81.9% yield): LC/MS (electrospray, +ions) m/z 614 (M+H).

D.

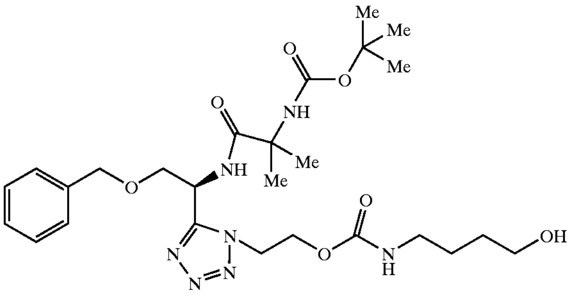

To a THF (600 mL) solution of Part C compound (117.5 g, 190 mmol) in a water bath was added aminobutanol

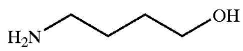

(19.4 mL, 210 mmol) dropwise over 30 minutes and after 1 h at RT, an additional aliquot of 4-amino-1-butanol (1.7 mL, 18 mmol) was added. After stirring an additional 30 minutes at rt, the volatiles were removed under vacuum. The resulting residue was dissolved in EtOAc (600 mL) and washed with 1N HCl (200 mL), saturated $NaHCO_3$ (1×400 mL and 2×200 mL, emulsion), and brine (3×200 mL, slow separation), dried ($MgSO_4$), and concentrated in vacuo to give an oil. This oil was dissolved in MTBE (600 mL) and washed with saturated $NaHCO_3$ (1×300 mL), and brine (2×500 mL), dried ($Na_2SO_4$), and concentrated in vacuo to give a yellow oil (156.52 g). This oil was dissolved in MTBE (1 L) and washed with 1N NaOH (500 mL) and water. The organic layer was washed again with 1N NaOH (500 mL) and the combined NaOH washes were extracted with MTBE (400 mL). The combined MTBE layers were washed with water (500 mL) and brine (500 mL), dried ($MgSO_4$), and concentrated in vacuo to give pure title Part D compound as a light yellow oil (103.08 g, 95.5% yield): LC/MS (electrospray, +ions) m/z 564 (M+H).

Examples 220–352 were prepared in a manner analogous to that of compounds described previously in the invention and by methods known in the art.
EXAMPLES 220 TO 352
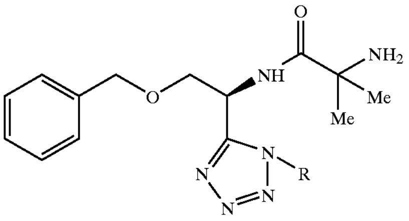 = $X_1$—R
| Example No. | $X_1$—R | M + H positive ions |
|---|---|---|
| 220 | 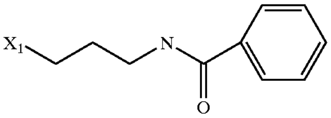 | 466 |
| 221 | 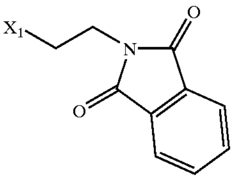 | 478 |
| 222 | 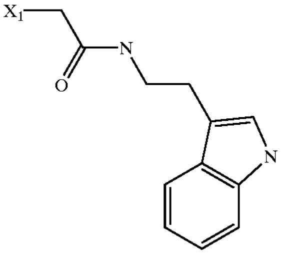 | 505 |
| 223 | 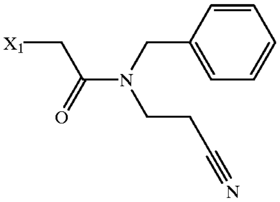 | 505 |
| 224 | 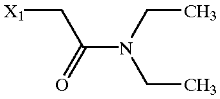 | 418 |
| 225 | 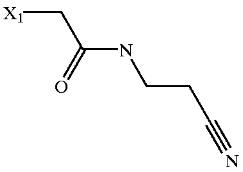 | 415 |

-continued
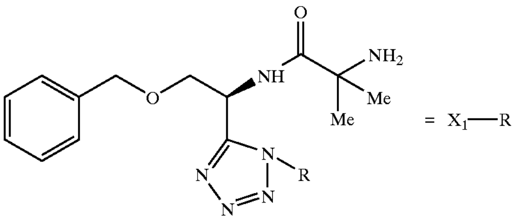
| Example No. | $X_1$—R | M + H positive ions |
|---|---|---|
| 226 | 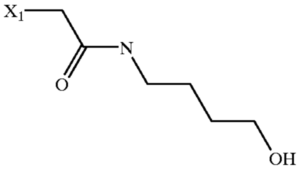 | 434 |
| 227 | 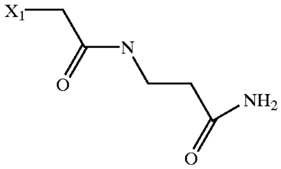 | 433 |
| 228 | 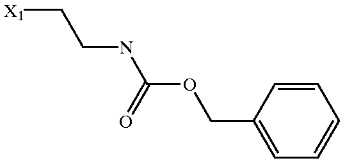 | 482 |
| 229 | 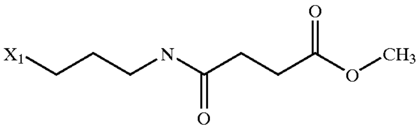 | 476 |
| 230 | 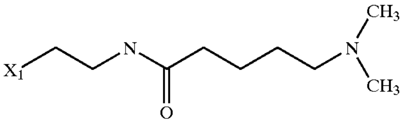 | 475 |
| 231 | 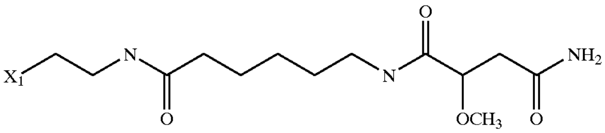 | 590 |
| 232 | 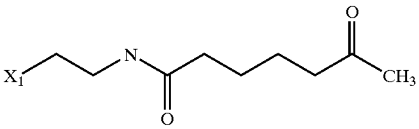 | 474 |
| 233 | 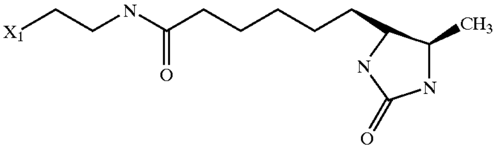 | 544 |

-continued
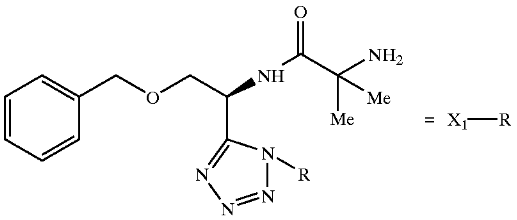
| Example No. | $X_1$—R | M + H positive ions |
|---|---|---|
| 234 | 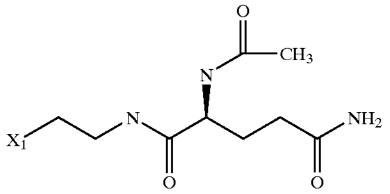 | 518 |
| 235 | 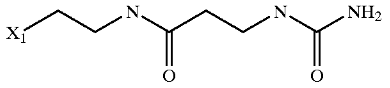 | 462 |
| 236 | 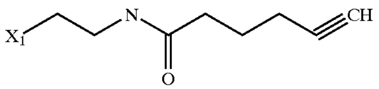 | 442 |
| 237 | 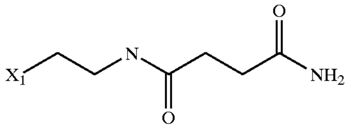 | 447 |
| 238 | 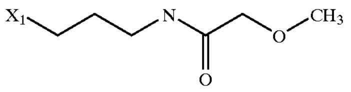 | 434 |
| 239 | 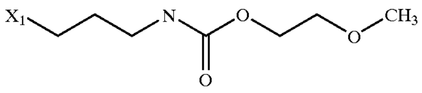 | 464 |
| 240 | 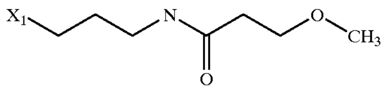 | 448 |
| 241 | 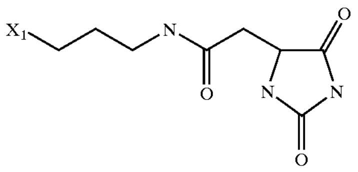 | 502 |
| 242 | 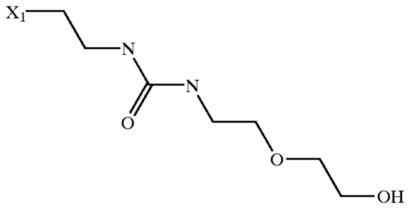 | 479 |

-continued
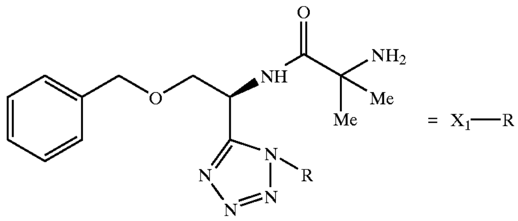
| Example No. | $X_1$—R | M + H positive ions |
|---|---|---|
| 243 | 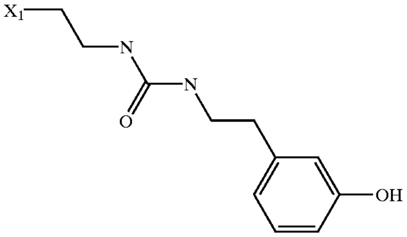 | 511 |
| 244 | 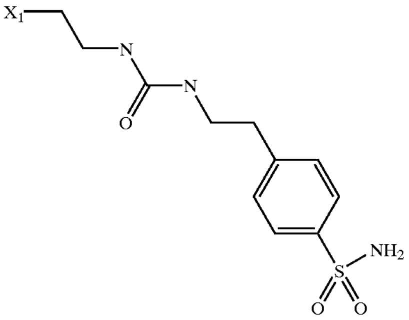 | 574 |
| 245 | 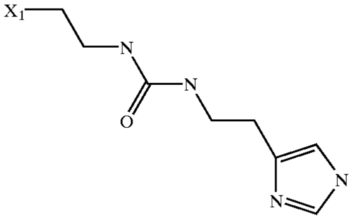 | 485 |
| 246 | 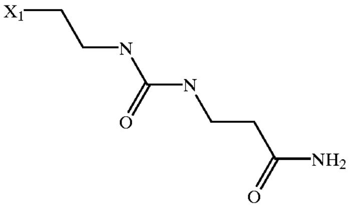 | 462 |
| 247 | 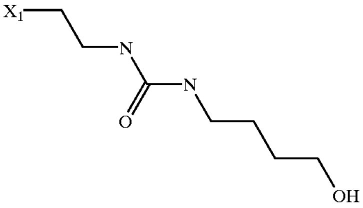 | 463 |
| 248 | 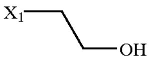 | 349 |

-continued
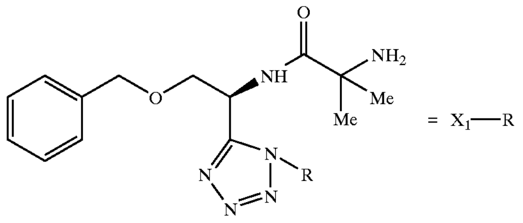
| Example No. | $X_1$—R | M + H positive ions |
|---|---|---|
| 249 | 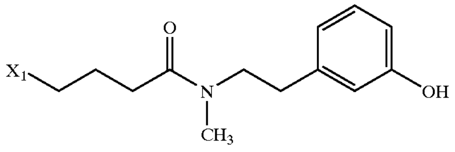 | 524 |
| 250 | 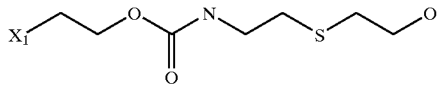 | 496 |
| 251 | 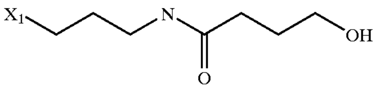 | 448 |
| 252 | 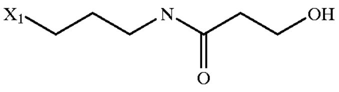 | 434 |
| 253 | 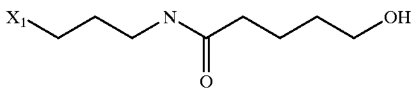 | 462 |
| 254 | 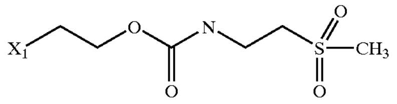 | 498 |
| 255 | 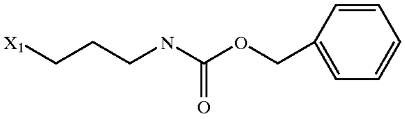 | 496 |
| 256 | 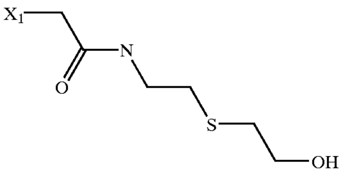 | 466 |
| 257 | 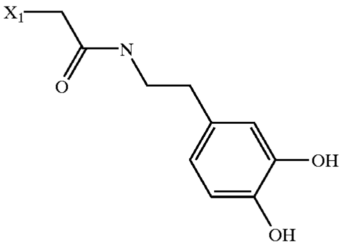 | 498 |

-continued
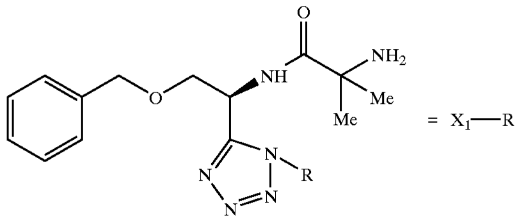
| Example No. | $X_1$—R | M + H positive ions |
|---|---|---|
| 258 | 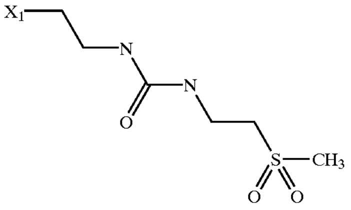 | 497 |
| 259 | 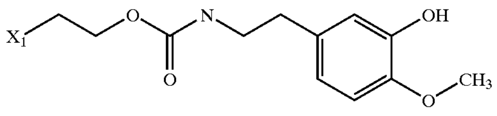 | 542 |
| 260 | 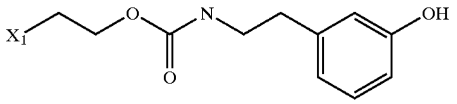 | 512 |
| 261 | 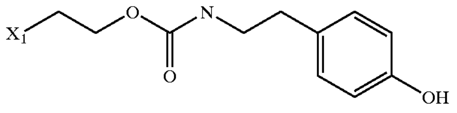 | 512 |
| 262 | 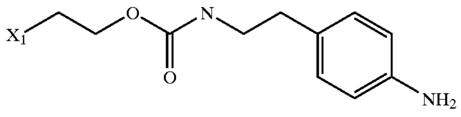 | 511 |
| 263 | 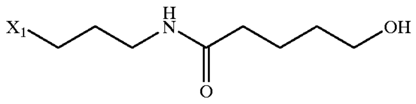 | 462 |
| 264 | 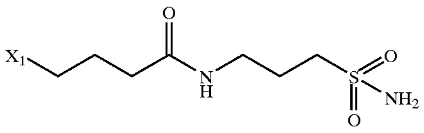 | 511 |
| 265 | 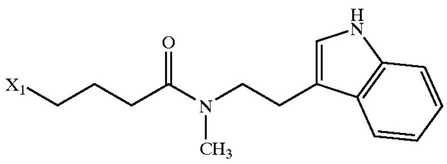 | 547 |
| 266 | 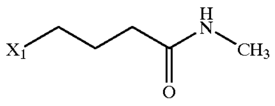 | 404 |

-continued
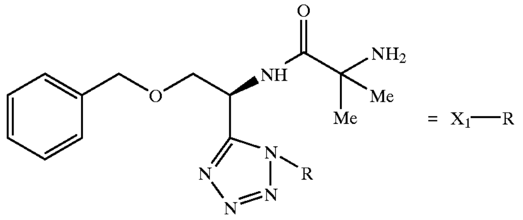
| Example No. | $X_1$—R | M + H positive ions |
|---|---|---|
| 267 | 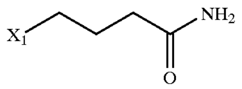 | 390 |
| 268 | 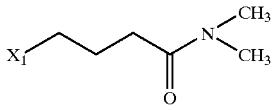 | 418 |
| 269 | 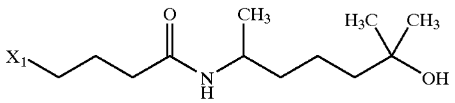 | 518 |
| 270 | 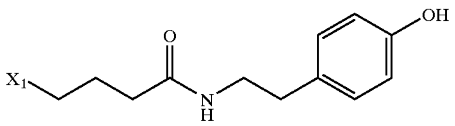 | 510 |
| 271 | 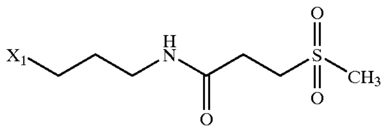 | 496 |
| 272 | 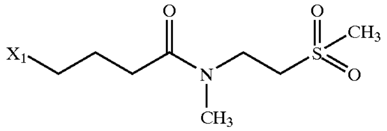 | 510 |
| 273 | 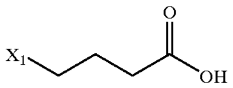 | 391 |
| 274 | 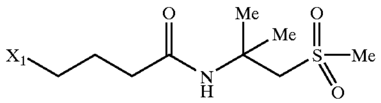 | 524 |
| 275 | 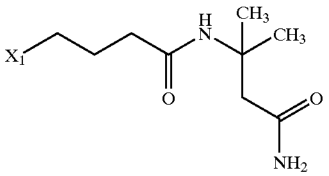 | 489 |

-continued
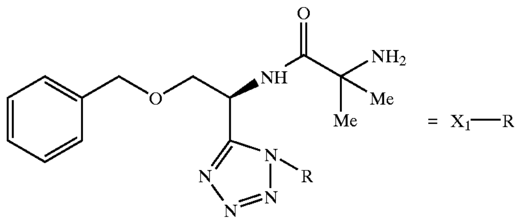
| Example No. | $X_1$—R | M + H positive ions |
|---|---|---|
| 276 | 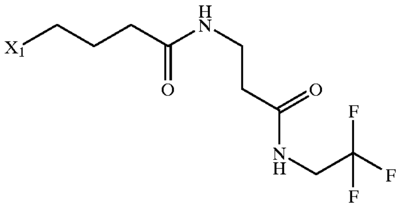 | 543 |
| 277 | 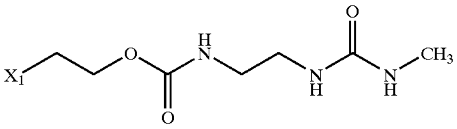 | 492 |
| 278 | 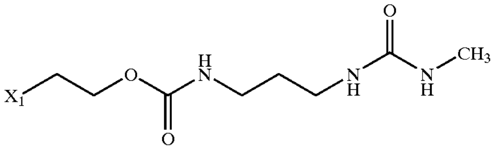 | 506 |
| 279 | 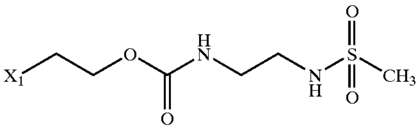 | 513 |
| 280 | 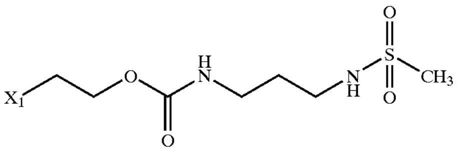 | 527 |
| 281 | 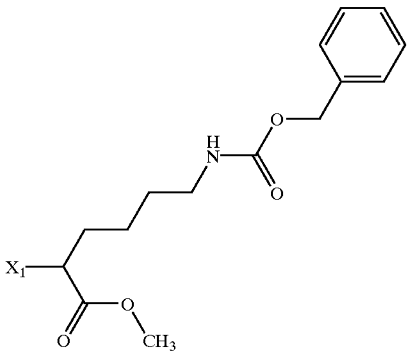 | 582 |

-continued
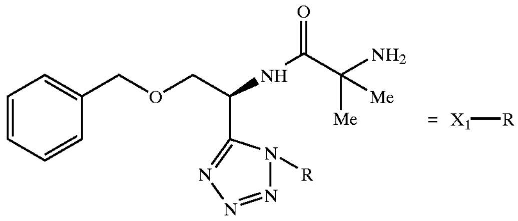
| Example No. | $X_1$—R | M + H positive ions |
|---|---|---|
| 282 | 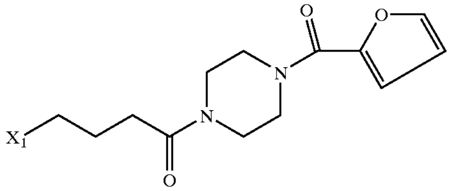 | 553 |
| 283 | 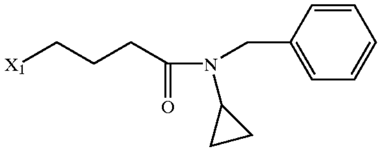 | 520 |
| 284 | 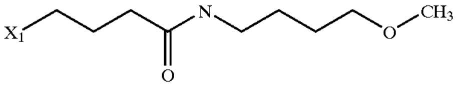 | 476 |
| 285 | 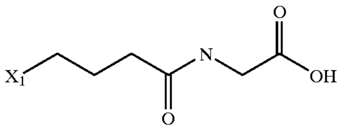 | 448 |
| 286 | 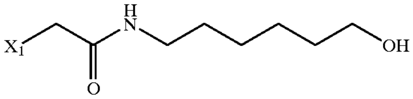 | 462 |
| 287 | 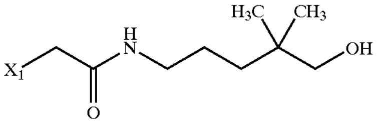 | 476 |
| 288 | 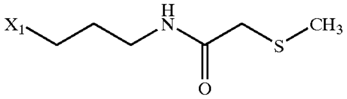 | 450 |
| 289 | 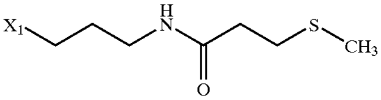 | 464 |
| 290 | 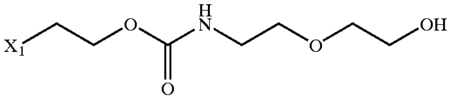 | 480 |
| 291 | 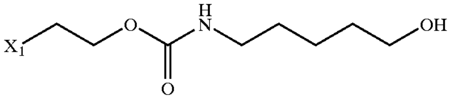 | 478 |

-continued
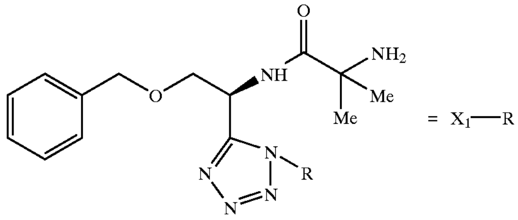
| Example No. | $X_1$—R | M + H positive ions |
|---|---|---|
| 292 | 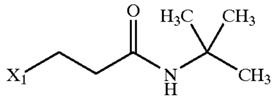 | 432 |
| 293 | 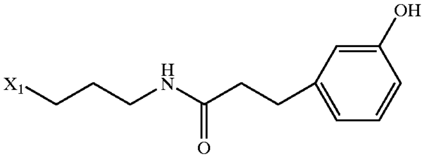 | 510 |
| 294 | 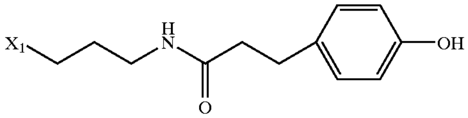 | 510 |
| 295 | 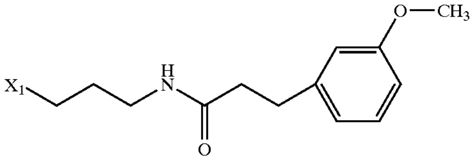 | 524 |
| 296 | 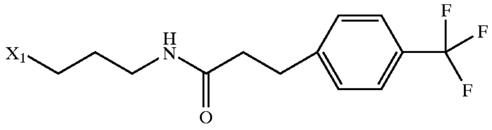 | 562 |
| 297 | 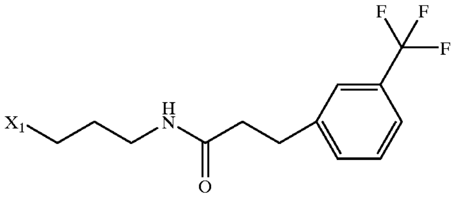 | 562 |
| 298 | 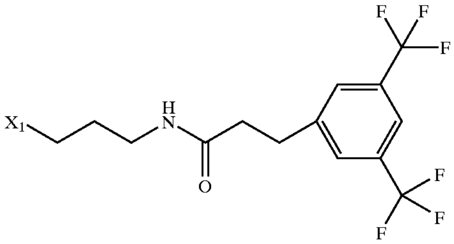 | 630 |

-continued
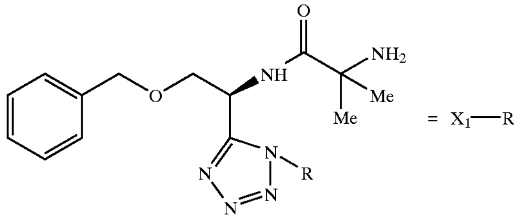
| Example No. | $X_1$—R | M + H positive ions |
|---|---|---|
| 299 | 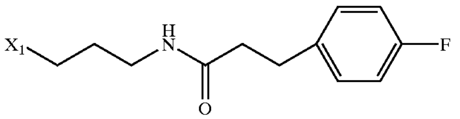 | 512 |
| 300 | 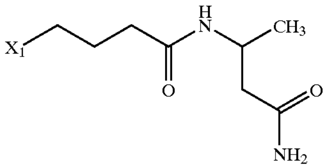 | 475 |
| 301 | 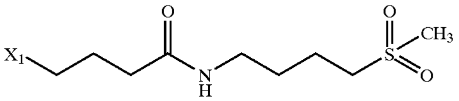 | 524 |
| 302 | 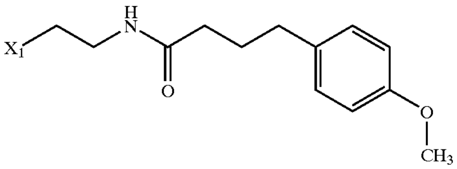 | 524 |
| 303 | 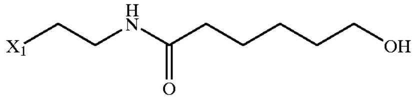 | 462 |
| 304 | 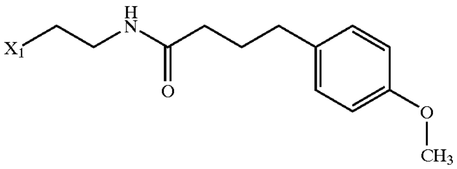 | 524 |
| 305 | 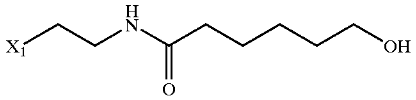 | 462 |
| 306 | 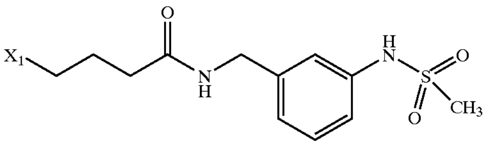 | 573 |

-continued
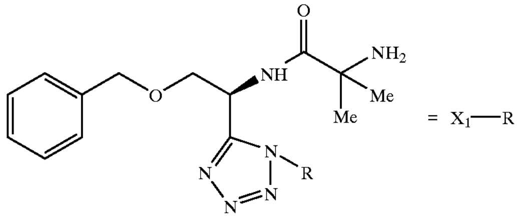
| Example No. | $X_1$—R | M + H positive ions |
|---|---|---|
| 307 | 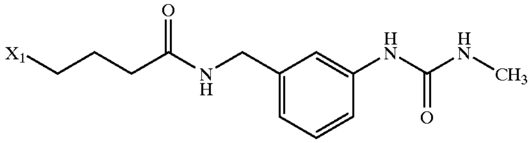 | 552 |
| 308 | 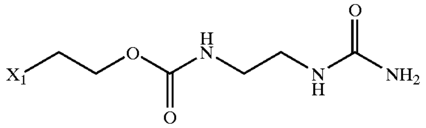 | 478 |
| 309 | 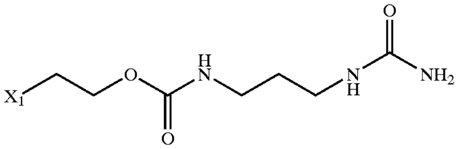 | 492 |
| 310 | 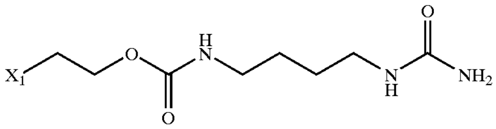 | 506 |
| 311 | 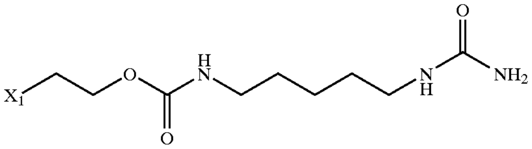 | 520 |
| 312 | 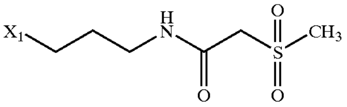 | 482 |
| 313 | 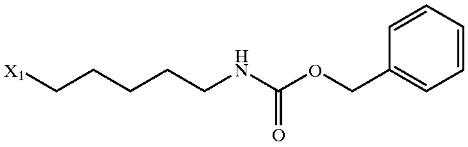 | 524 |
| 314 | 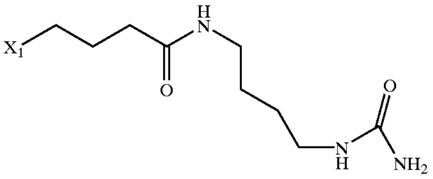 | 504 |

-continued
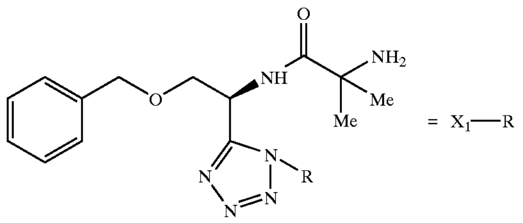
| Example No. | $X_1$—R | M + H positive ions |
|---|---|---|
| 315 | 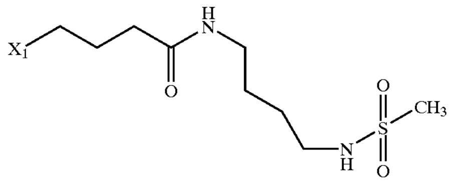 | 539 |
| 316 | 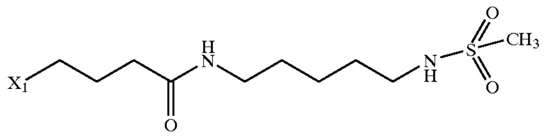 | 553 |
| 317 | 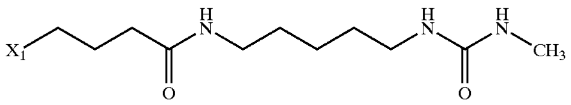 | 532 |
| 318 | 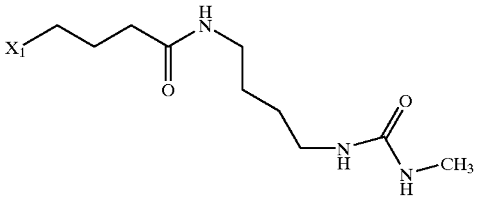 | 518 |
| 319 | 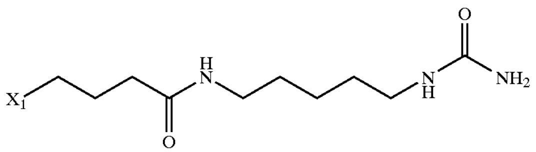 | 518 |
| 320 | 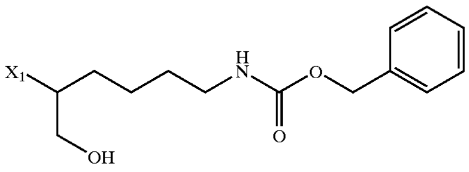 | 554 |
| 321 | 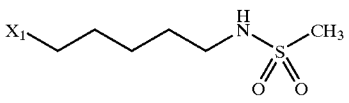 | 468 |

-continued
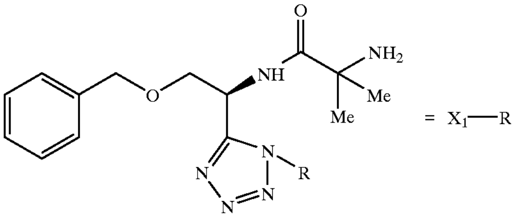
| Example No. | $X_1$—R | M + H positive ions |
|---|---|---|
| 322 | 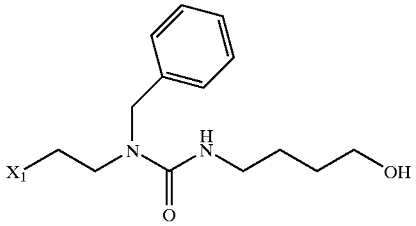 | 553 |
| 323 | 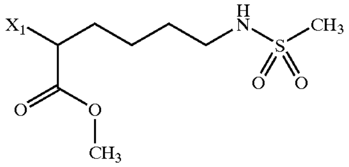 | 526 |
| 324 | 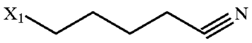 | 386 |
| 325 | 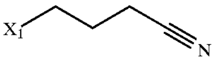 | 372 |
| 326 | 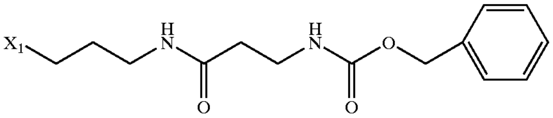 | 567 |
| 327 | 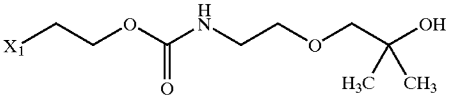 | 508 |
| 328 | 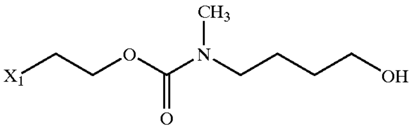 | 478 |
| 329 | 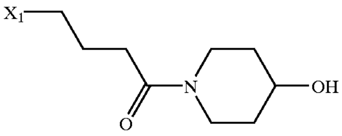 | 474 |
| 330 | 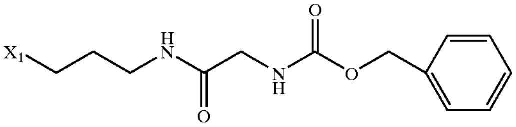 | 553 |

-continued
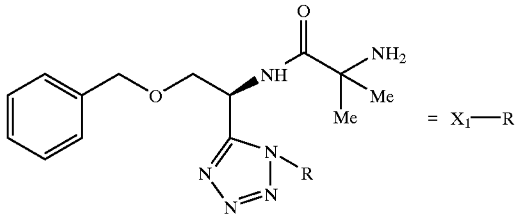
| Example No. | $X_1$—R | M + H positive ions |
|---|---|---|
| 331 | 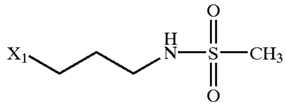 | 440 |
| 332 | 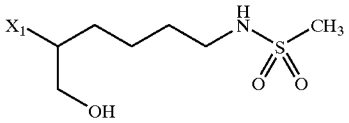 | 498 |
| 333 | 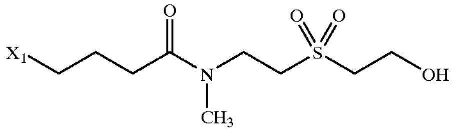 | 540 |
| 334 | 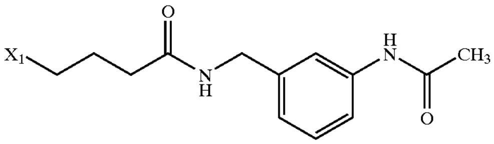 | 537 |
| 335 | 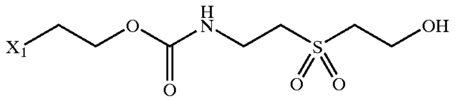 | 528 |
| 336 | 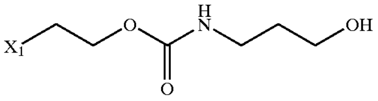 | 450 |
| 337 | 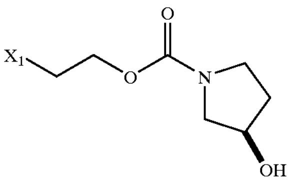 | 462 |
| 338 | 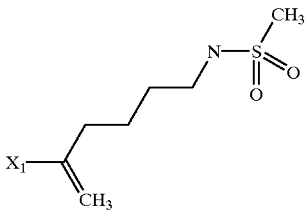 | 480 |

-continued
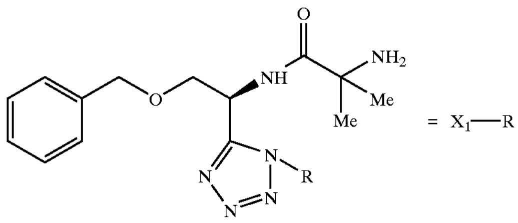
| Example No. | $X_1$—R | M + H positive ions |
|---|---|---|
| 339 | 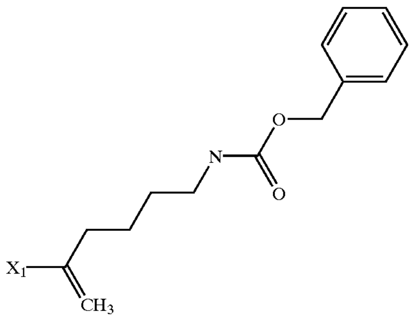 | 536 |
| 340 | 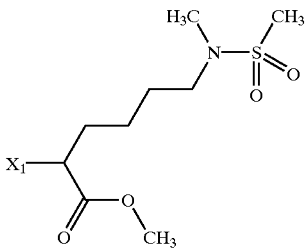 | 540 |
| 341 | 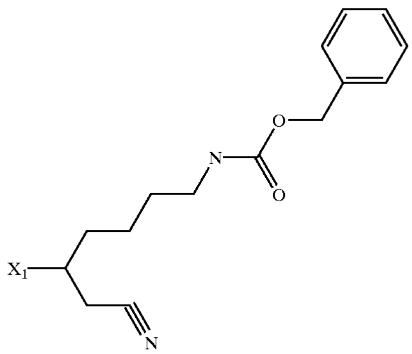 | 563 |
| 342 | 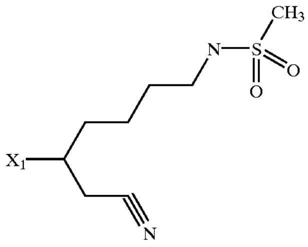 | 507 |

-continued
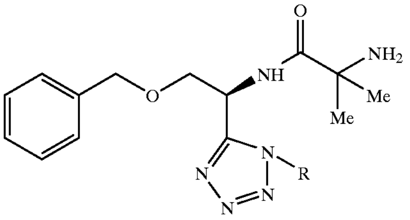 = $X_1$—R
| Example No. | $X_1$—R | M + H positive ions |
|---|---|---|
| 343 | 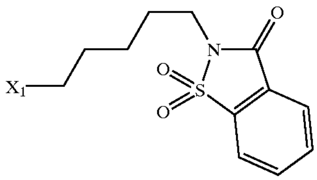 | 556 |
| 344 | 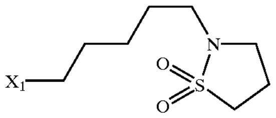 | 494 |
| 345 | 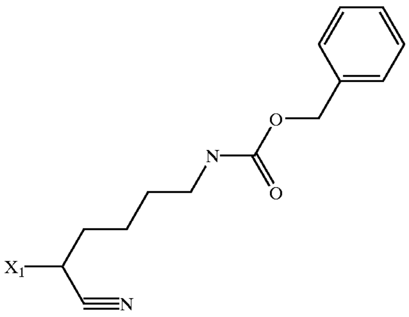 | 549 |
| 346 | 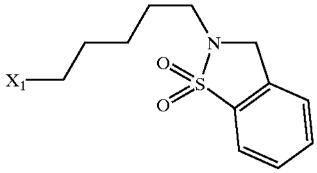 | 542 |
| 347 | 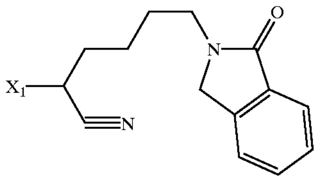 | 531 |

-continued
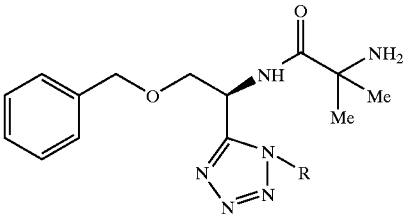 = $X_1$—R
| Example No. | $X_1$—R | M + H positive ions |
|---|---|---|
| 348 | 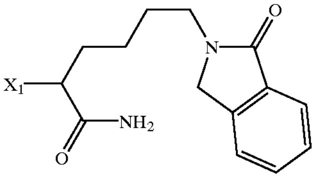 | 549 |
| 349 | 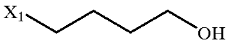 | 377 |
| 350 | 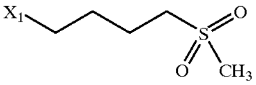 | 439 |
| Example No. | Structure | M + H positive ions |
|---|---|---|
| 351 | 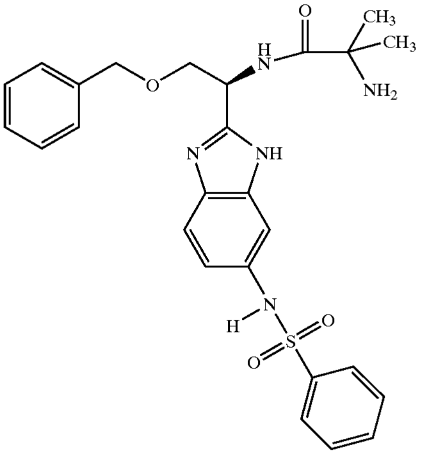 Chiral | 508 |
| 352 | 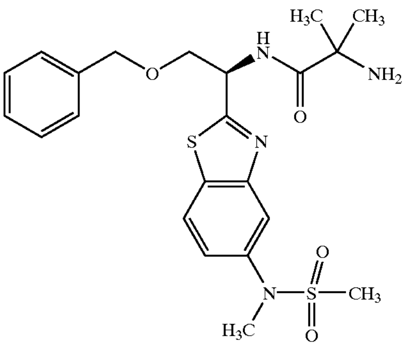 Chiral | 477 |

EXAMPLE 353

A.

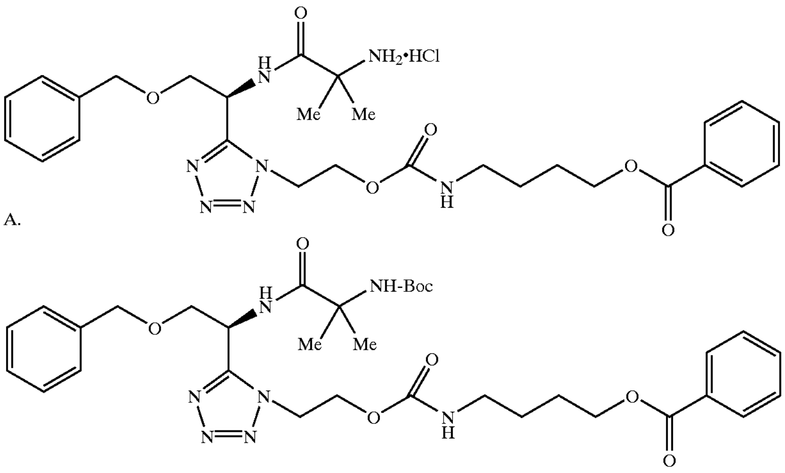

To a solution of Compound 218 Part F (929 mg, 1.65 mmol) in anhydrous $CH_2Cl_2$ (8 mL) was added pyridine (400 μl, 4.95 mmol) and DMAP (40 mg, 0.33 mmol) followed by the addition of benzoyl chloride (2871 μl, 2.48 mmol). After stirring for 5 h at room temperature, the solvent was removed in vacuo, and the residue was purified by flash column chromatography ($SiO_2$, 20%–50% EtOAc in hexanes) to give the desired product (1.09 g, 99% yield).

B.

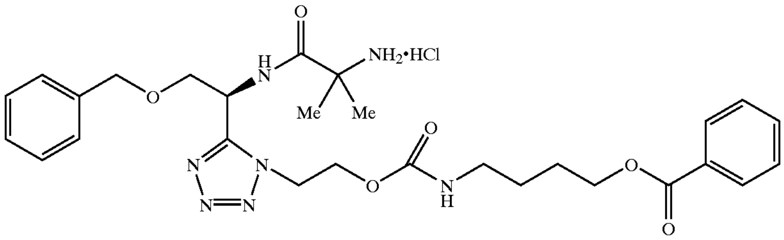

To a solution of Part A compound (580 mg) in $CH_2Cl_2$ (3 ml) was added 4N HCl in dioxane (3 ml). The reaction mixture stirred at room temperature for 1.5 h. The solvent was removed in vacuo to give the desired product. (469 mg, 89% yield). LC/MS (electrospray, +ions) m/z 567 (M+H).

EXAMPLE 353

Alternate Preparation

A.

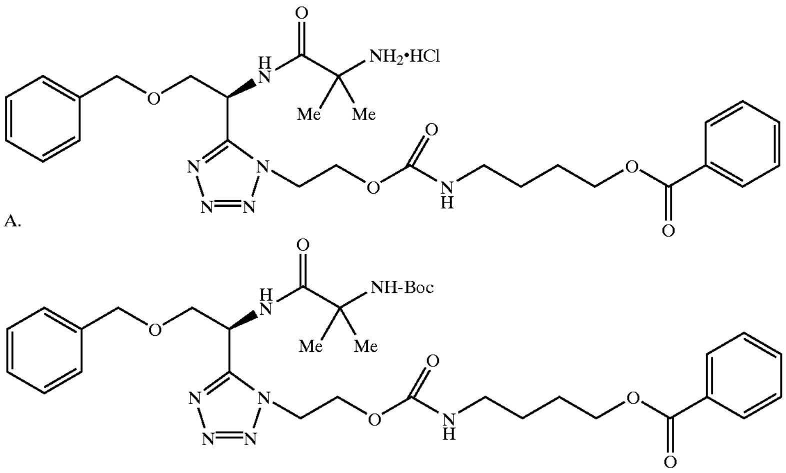

To a solution of Example 219 compound (102.66 g, 182 mmol) in anhydrous $CH_2Cl_2$ (650 mL) was added pyridine (37.0 mL, 455 mmol) and DMAP (2.23 g, 18.2 mmol). The flask was immersed in a water bath and benzoyl chloride (25 mL, 219 mmol) was added dropwise over 20 minutes. After stirring for 2 h at room temperature, additional benzoyl chloride (6.0 mL, 54 mmol) was added dropwise and the reaction continued to stir at room temperature overnight. The reaction mixture was washed with 1N HCl (300 mL), saturated $NaHCO_3$ (300 mL), and brine (300 mL), dried ($MgSO_4$), and concentrated in vacuo, and the residue was purified by silica gel pad filtration (SiO2, 650 g, 10%–85% EtOAc in hexanes) to give the desired product (116.34 g, 97% yield) as a colorless foam.

B.

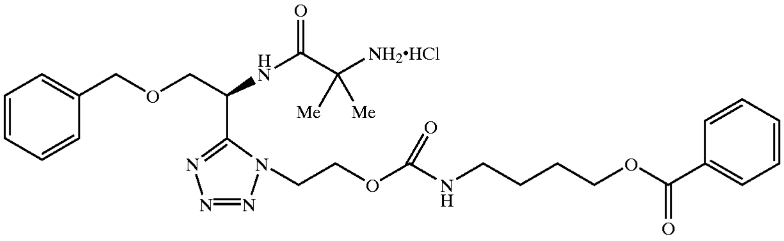

To a solution of Part A compound (116.0 g, 174 mmol) in $CH_2Cl_2$ (700 ml) was added 4N HCl in dioxane (218 ml, 870 mmol) dropwise over 30 minutes. The reaction mixture stirred at room temperature for 4 h. The solvent was removed in vacuo. The residue was dissolved in water (500 mL) and washed with MTBE (250 mL). The aqueous layer was mixed with $CH_2Cl_2$ (300 mL) and the pH adjusted to 11 with 1N NaOH (190 mL). The $CH_2Cl_2$ layer was separated and the aqueous layer was extracted with $CH_2Cl_2$ (300 mL). The combined $CH_2Cl_2$ layers were washed with brine (2×300 mL), dried ($MgSO_4$) and concentrated in vacuo to give the desired product (92.8 g, 94% yield) as a yellow oil. LC/MS (electrospray, +ions) m/z 567 (M+H).

EXAMPLE 354

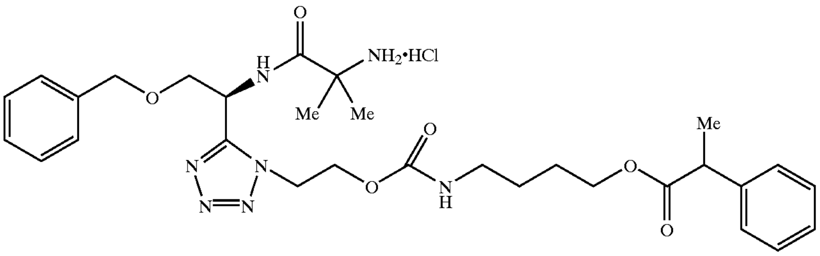

A.

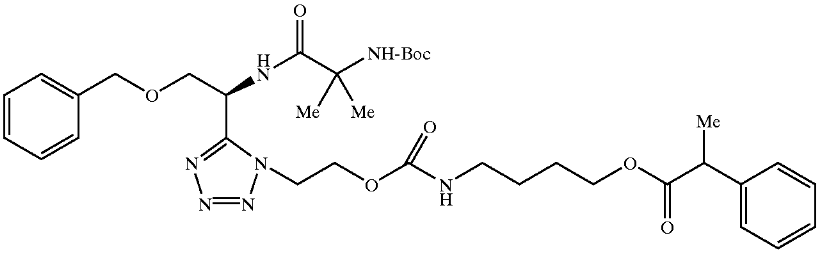

To a solution of Compound 219 (100 mg, 0.18 mmol) in 1,2-dichloroethane (250 μl) at 0° C. is added a solution of 2-phenylpropionic acid (50 μl, 0.37 mmol), EDAC (69 mg, 0.36 mmol), and DMAP (44 mg, 0.36 mmol) in 1,2-dichloroethane (250 μl). The reaction mixture stirred for 36 hours at room temperature. The reaction was diluted with EtOAc (50 ml) and washed with saturated $NaHCO_3$ (2×25 ml), water (25 ml) and brine (25 ml), dried ($Na_2SO_4$) and evaporated to give the crude product (128 mg). This material was purified by flash column chromatography eluted with 1:1 hexanes:EtOAc to give the product (122.4 mg, 99% yield).

B.

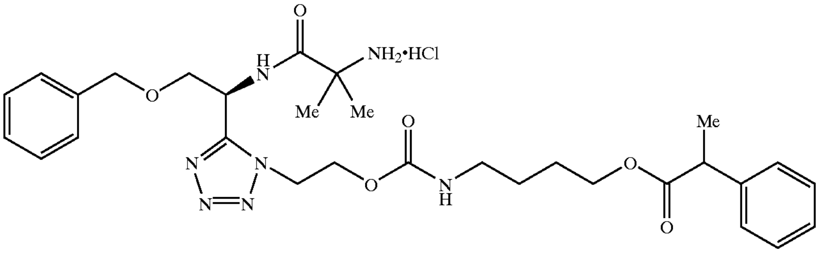

Part A compound (122 mg, 0.18 mmol) was stirred in a 10%TFA in $CH_2Cl_2$ solution (4.0 ml) for 2.5 h. The solvent was removed in vacuo. The residual TFA was removed by coevapoation with $CH_2Cl_2$ (4×3 ml) and MeOH (2×3 ml). The residue was dissolved in MeOH and heated at 60° C. for 8 h. The solvent was removed in vacuo, and the residue was purified by prepartive HPLC (20%–100% B, 12 min. gradient, 20 ml/min, YMCS5 ODS 20×100 mm) to give the desired product (115.4 mg, 93% yield). LC/MS (electrospray, +ions) m/z 596 (M+H).

In a manner analogous to that of compounds of Example 353 and 354, compounds of Examples 355 to 392 listed in the table below were prepared from Example 218 Part F compound and the respective acid or acid chloride.

EXAMPLES 355 TO 392

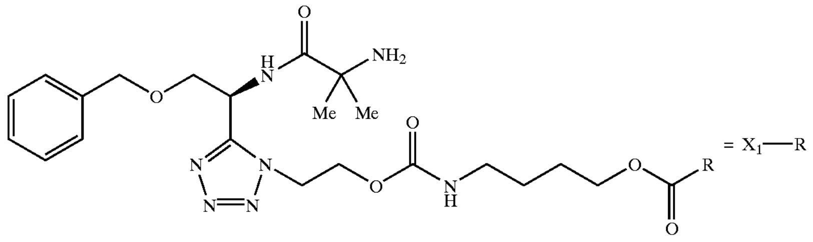

| Example No. | $X_1$— R | M + H positive ions |
|---|---|---|
| 355 | 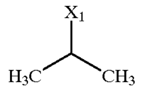 | 534 |
| 356 | 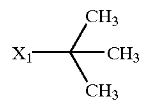 | 548 |
| 357 | 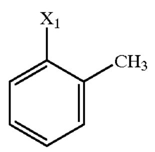 | 582 |

-continued
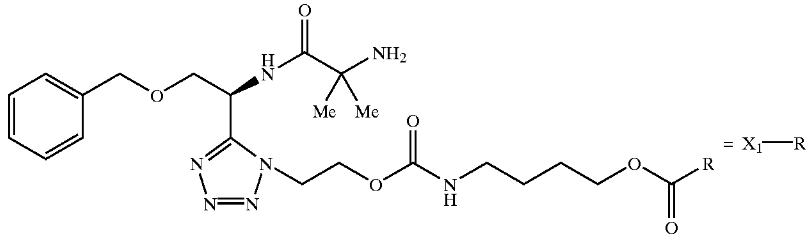
| Example No. | $X_1$— R | M + H positive ions |
|---|---|---|
| 358 | 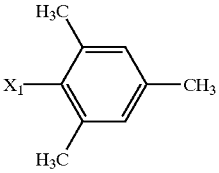 | 610 |
| 359 | $X_1$—$CH_3$ | 506 |
| 360 | 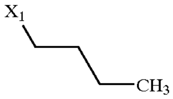 | 548 |
| 361 | 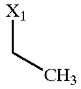 | 520 |
| 362 | 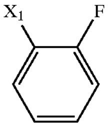 | 586 |
| 363 | 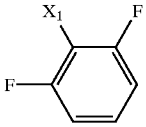 | 604 |
| 364 | 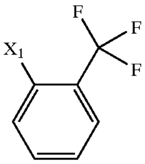 | 636 |
| 365 | 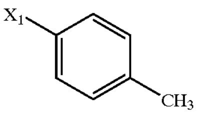 | 582 |
| 366 | 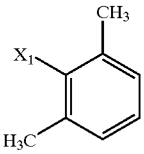 | 596 |

-continued
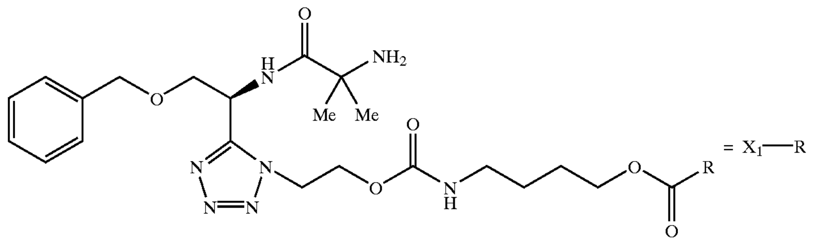
| Example No. | $X_1$— R | M + H positive ions |
|---|---|---|
| 367 | 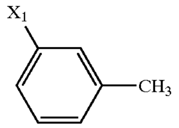 | 582 |
| 368 | 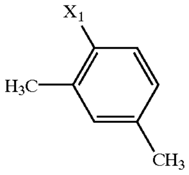 | 596 |
| 369 | 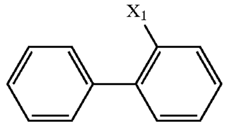 | 644 |
| 370 | 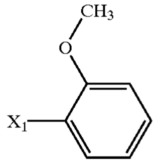 | 598 |
| 371 | 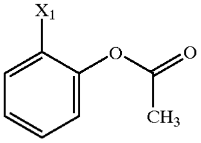 | 626 |
| 372 | 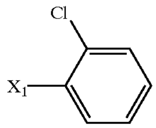 | 603 |
| 373 | 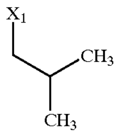 | 548 |
| 374 | 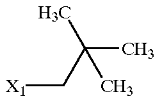 | 562 |

-continued
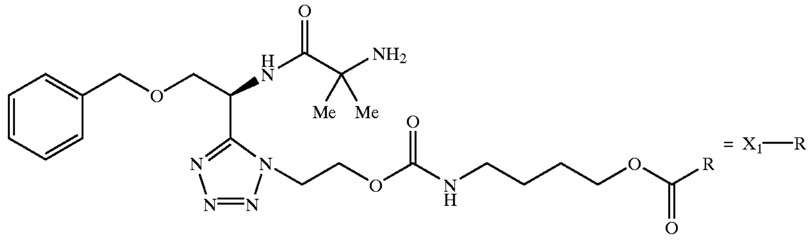
| Example No. | $X_1$— R | M + H positive ions |
|---|---|---|
| 375 | 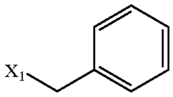 | 582 |
| 376 | 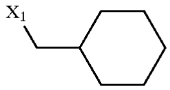 | 588 |
| 377 | 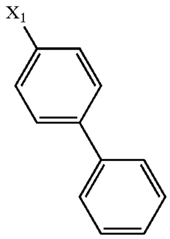 | 644 |
| 378 | 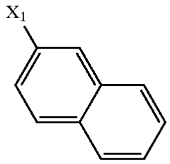 | 618 |
| 379 | 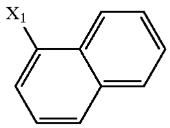 | 618 |
| 380 | 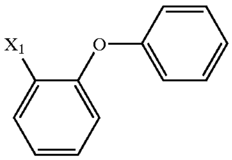 | 660 |
| 381 | 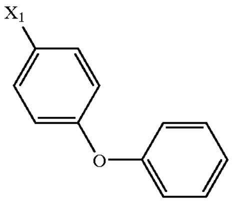 | 660 |
| 382 | 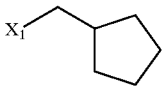 | 574 |

-continued
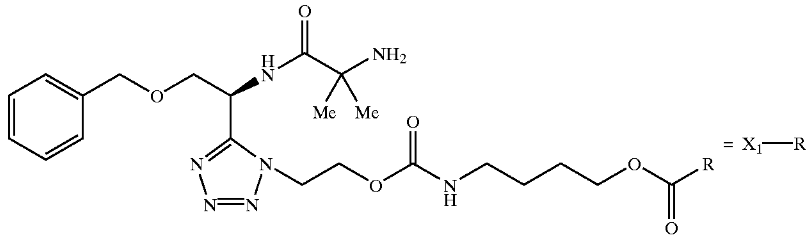
| Example No. | $X_1$— R | M + H positive ions |
|---|---|---|
| 383 | 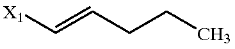 | 560 |
| 384 | 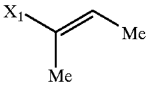 | 546 |
| 385 | 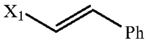 | 594 |
| 386 | 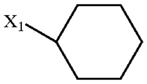 | 574 |
| 387 | 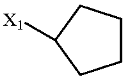 | 560 |
| 388 | 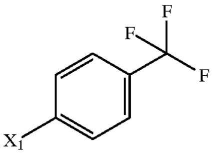 | 636 |
| 389 | 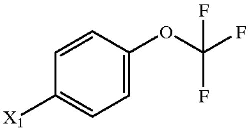 | 652 |
| 390 | 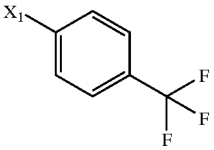 | 650 |
| 391 | 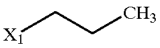 | 534 |
| 392 | 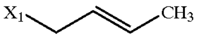 | 546 |

Compounds of Examples 393 to 424 listed in the tables below were prepared in a manner analogous to that of compounds of Example 353 and 354.
EXAMPLES 393 TO 424
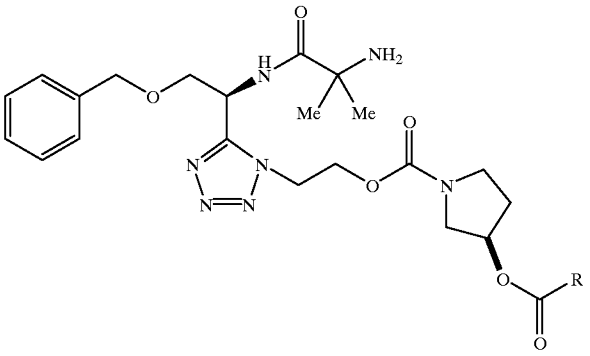
= $X_1$-R
| Example No. | $X_1$-R | M + H positive ions |
|---|---|---|
| 393 | 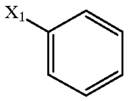 | 566 |
| 394 | 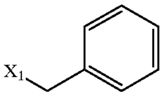 | 580 |
| 395 | 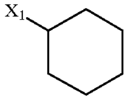 | 572 |
| 396 | 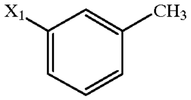 | 580 |
| 397 | 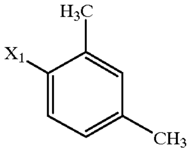 | 594 |
| 398 | 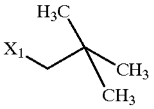 | 560 |
| 399 | 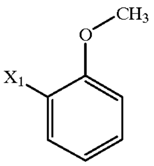 | 596 |

-continued
| Example No. | $X_1$-R | M + H positive ions |
|---|---|---|
| 400 | 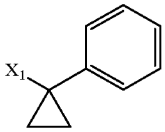 | 606 |
| 401 | 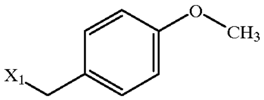 | 610 |
| 402 | 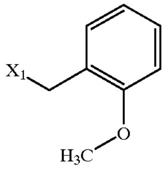 | 610 |
| 403 | 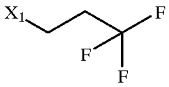 | 586 |
| 404 | 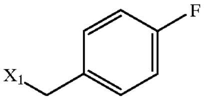 | 598 |
| 405 | 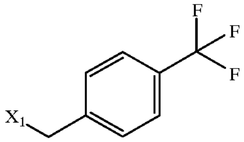 | 648 |
| 406 | 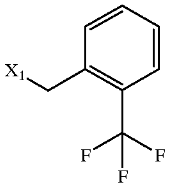 | 648 |
| 407 | 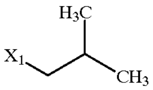 | 546 |
| 408 | 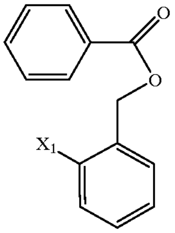 | 700 |
| 409 | 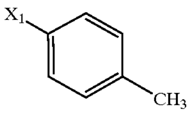 | 580 |

-continued
| Example No. | $X_1$-R | M + H positive ions |
| --- | --- | --- |
| 410 | 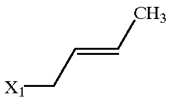 | 544 |
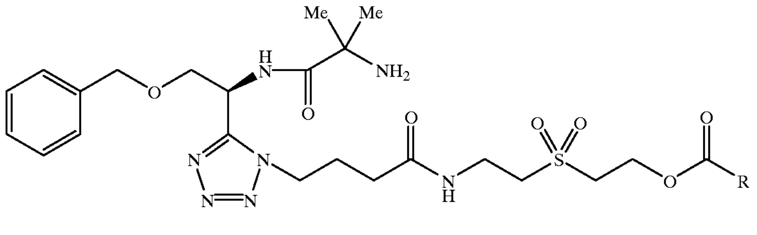 $= X_1$-R
| | | |
| --- | --- | --- |
| 411 | 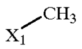 | 568 |
| 412 | 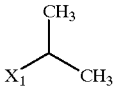 | 596 |
| 413 | 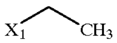 | 582 |
| 414 | 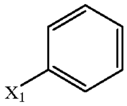 | 630 |
| 415 | 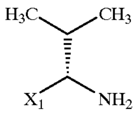 | 625 |
| 416 | 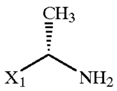 | 597 |
| 417 | 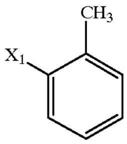 | 644 |
| 418 | 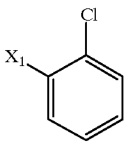 | 665 |
| 419 | 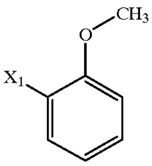 | 660 |

-continued

| Example No. | $X_1$-R | M + H positive ions |
|---|---|---|
| 420 | 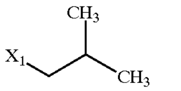 | 610 |
| 421 | 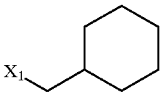 | 650 |
| 422 | 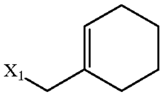 | 648 |
| 423 | 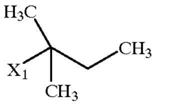 | 624 |
| 424 | 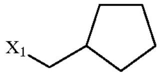 | 636 |

EXAMPLE 425

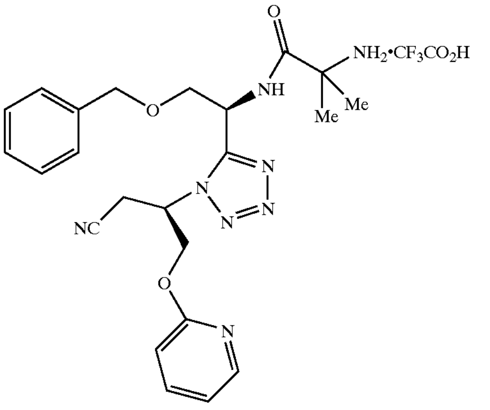

A.

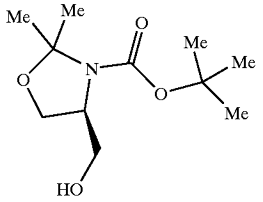

To a solution of methyl R-(+)-3-BOC-2,2-dimethyl-4-oxazolidine carboxylate

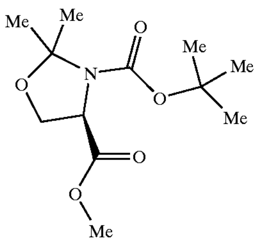

(2.05 g, 7.75 mmol, Aldrich, 98%) in THF (24.0 mL) was added a light suspension of calcium chloride (437 mg, 3.94 mmol) in EtOH (16.5 mL) and the resulting solution was cooled to 0° C. Sodium borohydride was added and the mixture was stirred at 0° C. for 2 h. and for 4 h at rt. The final mixture was cooled to 0° C. and potassium phosphate buffer (pH 3, 40 mL) was added. The aqueous mixture was stirred for 30 min at rt. and then extracted with $CH_2Cl_2$ (3×70 mL). The combined organic phase was dried ($Na_2SO_4$) and evaporated to a crude which was chromatographed ($SiO_2$ 230–400 mesh, 3/2 to 1/1 hexanes/EtOAc) to give the starting ester (409 mg, 20% recovery) and the desired alcohol (1.46 g, 80% yield): $^1H$ NMR a ($CDCl_3$,ppm, rotamers) 4.18–3.56 (4m, 6H), 1.55 and 1.50 (2s, 15 H).

B.

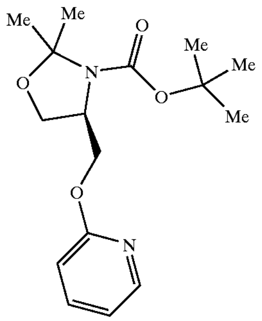

To a solution of Part A compound(2.90 g, 12.5 mmol), 2-hydroxypyridine (1.54 g, 15.7 mmol)and triphenylphosphine (4.11 g, 15.7 mmol) in THF (27 mL) was added diethylazo-dicarboxylate (2.47 mL, 15.7 mmol) dropwise. The solution was stirred at rt. for 13.5 h. and then partially evaporated. The remaining solution was passed through a $SiO_2$ (230–400 mesh) column, eluting with 7/3 hexanes/EtOAc, to provide the desired compound (1.88 g, 49% yield) as a solid: $^1H$ NMR δ ($CDCl_3$,ppm, rotamers) 8.15 (m, 1H), 7.57 (m,1H), 6.88 (m, 1H), 6.74 (d, J=8.2 Hz, 1H), 4.50 (m, 1H), 4.25–3.95 (several m, 4H), 1.61–1.45 (several s, 15H).

C.

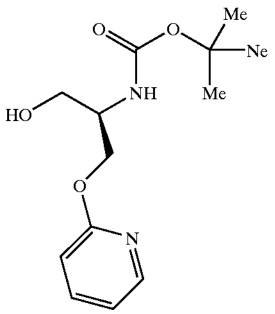

A solution of Part B compound(434 mg, 1.41 mmol) and p-toluenesulfonic acid monohydrate (295 mg, 1.55 mmol) in dry MeOH (14.1 mL) was heated at 35° C. for 7 h and then stirred at rt. for 3.8 h. After cooling to 0° C., a 1M $K_2CO_3$ solution (0.8 mL) was added and the mixture volume was reduced in vacuo to 4 mL. Brine (50 mL) was added and the pH of the aqueous solution was adjusted to 10 by addition of 1M $K_2CO_3$. Extraction with $CH_2Cl_2$ (4×50 mL), drying ($Na_2SO_4$), evaporation and chromatography ($SiO_2$ 230–400 mesh, 1/1 hexanes/EtOAc) of the crude gave starting Part B compound (93 mg, 21% recovery) and the desired alcohol (249 mg, 66% yield) as a white solid: LC-MS 99% Area; LC/MS (electrospray, +ions) m/z 269 (M+H).

D.

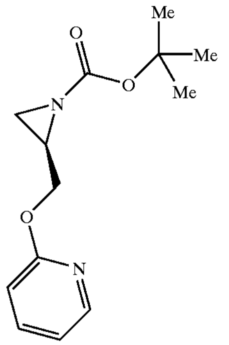

To a solution of Part C compound (1.34 g, 5.00 mmol) and triphenylphosphine (1.58 g, 6.02 mmol) in $CH_2Cl_2$ (34.0 mL), cooled at 0° C., was added diethylazodicarboxylate (0.95 mL, 6.03) dropwise and the mixture was stirred at rt. for 3.75 h. The mixture volume was reduced to 8 mL in vacuo and the remaining solution was passed through a $SiO_2$ (230–400 mesh) column, eluting with 7/3 hexanes/EtOAc to obtain the desired compound (862 mg, 70% yield) as a yellow oil: $^1$H NMR δ ($CDCl_3$,ppm) 8.13 (m, 1H), 7.57 (m, 1H), 6.88 (m, 1H), 6.78 (d, J=8.2 Hz, 1H), 4.45 (dd, J=11.6, 4.4 Hz,1H), 4.36 (dd, J=11.6, 5.5 Hz,1H), 2.88 (m, 1H), 2.35 (d, J=6.0 Hz,1H), 2.22 (d, J=3.9 Hz,1H), 1.43 (s, 9H).

E.

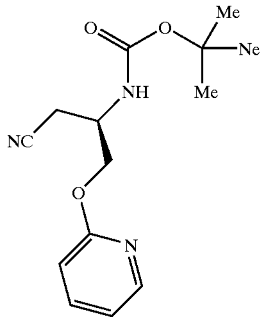

To a suspension of Part D compound (97 mg, 0.39 mmol) and potassium cyanide (51 mg, 0.78 mmol) in DMSO (2.6 mL) was added water (7 μL) and the mixture was heated at 30–40° C. for 11 h. Stirring was continued for an additional 9 h. at rt. and the mixture was diluted with 1/9 hexanes/EtOAc (60 mL). The solution was washed with water (2×30 mL) and brine (30 mL), dried ($Na_2SO_4$) and evaporated to give 92 mg crude. Chromatography ($SiO_2$ 230–400 mesh, 7/3 hexanes/EtOAc) provided starting aziridine (8.0 mg, 8% recovery) and the desired compound (75.6 mg, 72% yield) as a colorless solid: LC-MS 100% Area; LC/MS (electrospray, +ions) m/z 278 (M+H).

F.

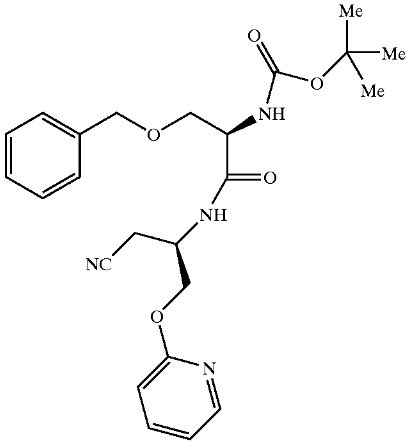

15% TFA/$CH_2Cl_2$ solution (6.0 mL) was added to a flask containing Part E compound(199 mg, 0.72 mmol) and thioanisole (0.254 mL, 2.16 mmol), and the resulting solution was allowed to stand at rt. for 4 h. The solution was evaporated and the residual TFA was removed by co-evaporation with $CH_2Cl_2$ (2×5 mL) and MeOH (3×5 mL), and dryinaunder high vacuum for 1 h. The crude amine salt material,

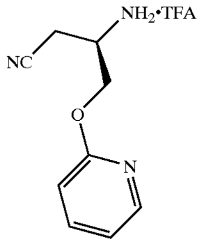

was used without further purification in the subsequent reaction.

N-Boc-O-benzyl-D-serine (298 mg, 1.00 mmol), EDAC (194 mg, 1.01 mmol), HOAT (137 mg, 1.01 mmol), 1,2-DCE (0.47 mL), and DMF (0.94 mL) were mixed at 0° C. and stirred for 15 min. The resulting cloudy solution was transferred, via syringe, to a 0° C. solution of the crude amine (from above) in 1,2-DCE (0.4 mL) and DMF (0.47 mL), and the mixture was stirred for 10 min. at 0° C. Diisopropylethylamine (0.32 mL, 1.84 mmol) was added and stirring was continued at rt. for 36 h. The reaction mixture was diluted with EtOAc (80 mL) and washed with saturated $NaHCO_3$ (2x40 mL), water (40 mL) and brine (40 mL). The organic layer was dried ($Na_2SO_4$), evaporated and chromatographed ($SiO_2$ 230–400 mesh, 1/1 hexanes/EtOAc) to provide the desired compound (311 mg, 95% yield) as a colorless oil: $^1$H NMR δ ($CDCl_3$,ppm) 8.17 (s, 1H), 7.84 (s, 1H), 7.61 (m, 1H), 7.30 (m, 5H), 6.94 (m, 1H), 6.76 (d, J=7.9 Hz, 1H), 5.37 (s, 1H), 4.52 (m, 5H), 4.31 (broad s, 1H), 3.88 (m, 1H), 3.58 (m, 1H), 2.80 (m, 2H), 1.43 (s, 9H).

G.

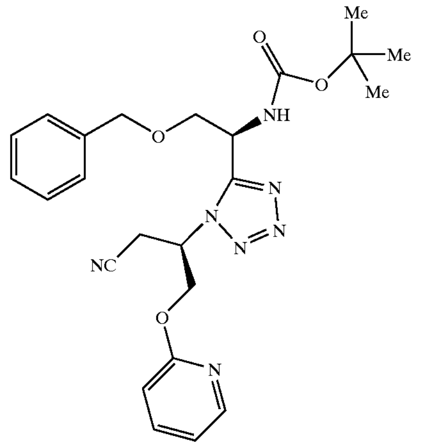

Diethylazodicarboxylate (131 pL, 0.83 mmol, DEAD) and azidotrimethylsilane (110 μL, 0.83 mmol) were added to a solution of Part F compound(311 mg, 0.69 mmol) and triphenylphosphine (217 mg, 0.83 mmol) in $CH_2Cl_2$ (1.4 mL). The mixture was stirred at rt. for 22 h. and additional amounts of triphenylphosphine (217 mg), DEAD (131 μL) and azidotrimethylsilane (110 μL) were added. Stirring was continued for an additional 24 h at rt. and the final mixture was passed through a $SiO_2$ (230–400 mesh) column, eluting with 3/2 to 1/1 hexanes/EtOAc, to give the desired compound (248 mg, 76%) as a thick colorless oil: $^1$H NMR δ($CDCl_3$,ppm) 8.11 (m, 1H), 7.55 (m, 1H), 7.33 (m, 3H), 7.20 (m, 2H), 6.92 (t, J=7.9 Hz, 1H), 6.76 (d, J=8.3 Hz, 1H), 5.45 (d, J=8.3 Hz, 1H), 5.44 (m, 2H), 4.73 (dd, J=11.6, 4.9 Hz, 1H), 4.63 (dd, J=11.6, 8.3 Hz, 1H), 4.50 (d, J=11.0 Hz, 1H), 4.44 (d, J=11.0 Hz, 1H), 4.00 (dd, J=8.3, 5.5 Hz, 1H), 3.58 (t, J=8.8 Hz, 1H), 3.04 (dd, J=17.0, 7.1 Hz, 1H), 2.86 (dd, J=17.0, 7.1 Hz, 1H), 1.43 (s, 9H).

H.

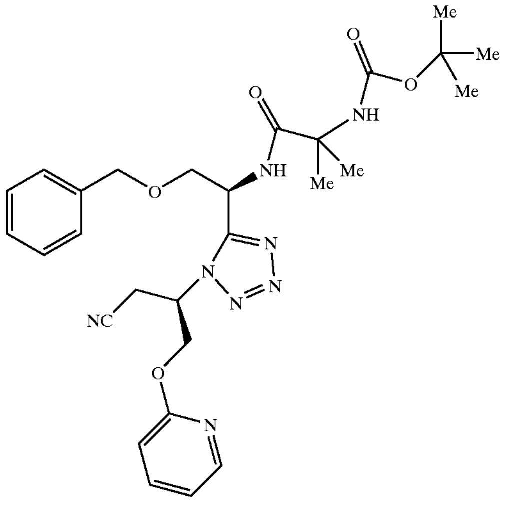

15% TFA/$CH_2Cl_2$ solution (6.2 mL) was added to a flask containing the Part G compound (227 mg, 0.47 mmol) and thioanisole (0.17 mL, 1.41 mmol), and the resulting solution was allowed to stand at rt. for 4 h. The solution was evaporated and the residual TFA was removed by co-evaporation with $CH_2Cl_2$ (2x8 mL) and MeOH (3x8 mL), and drying under high vacuum for 1 h The residue was heated at 60° C. in MeOH (25 mL) for 11.5 and the solution concentrated. The crude amine material,

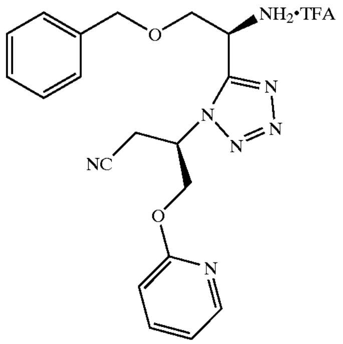

was used without further purification in the subsequent reaction.

N-Boc-methyl alanine

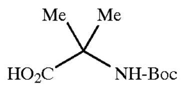

($_{125}$ mg, 0.62 mmol), EDAC (117 mg, 0.61 mmol), HOAT (84 mg, 0.62 mmol), 1,2-DCE (350 μL) and DMF (700 μL) were mixed at 0° C. and stirred for 15 min. The resulting solution was transferred, via syringe, to a 0° C. solution of the crude amine (from above) in 1,2-DCE (300 μL) and DMF (400 μL), and the mixture was stirred at 0° C. for 15 min. Diisopropylethylamine (205 μL, 1.18 mmol) was added and stirring was continued for 25 h at rt. The final mixture was diluted with EtOAc (75 mL) and washed with saturated $NaHCO_3$ (2x30 mL), water (30 mL) and brine (30 mL). The organic layer was dried ($Na_2SO_4$), evaporated and chromatographed ($SiO_2$ 230–400 mesh, 3/2 to 2/3 hexanes/EtOAc) to provide desired compound (175.4 mg, 66% yield) as a colorless foam: $^1$H NMR δ ($CDCl_3$,ppm) 8.13 (m, 1H), 7.57 (m, 1H), 7.42 (d, J=8.8 H, 1H), 7.31 (m, 3H), 7.19 (m, 2H), 6.93 (m, 1H), 6.77 (d, J=8.2 Hz, 1H), 5.75 (m, 1H), 5.49 (m, 1H), 4.97 (s, 1H), 4.73 (dd, J=11.6, 5.5 Hz, 1H), 4.66 (dd, J=11.6, 7.7 Hz, 1H), 4.50 (d, J=11.6 Hz, 1H), 4.43 (d, J=11.5 Hz, 1H), 4.04 (m, 1H), 3.52 (t, J=8.8 Hz, 1H), 3.02 (dd, J=17.1, 6.6 Hz, 1H), 2.85 (dd, J=17.0, 7.7 Hz, 1H), 1.50 (s, 3H), 1.44 (s, 3H), 1.36 (s, 9H).

I.

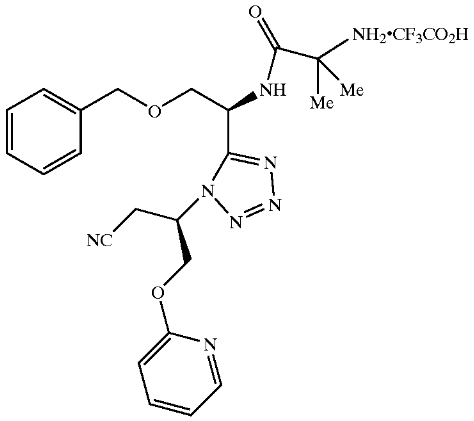

Part H compound (492 mg, 0.87 mmol) was treated with 15% TFA/$CH_2Cl_2$ (14.0 mL) for 2.5 h and the solution concentrated in vacuo. The residual TFA was co-evaporated with $CH_2Cl_2$ (3×10 mL) and MeOH (2×10 mL), and drying under high vacuum for 1 h The residue was heated at 60° C. in MeOH (40 mL) for 10 h. and the solution concentrated to give the crude desired compound. Successive precipitation from MeOH/ether provided the pure desired compound (418 mg). The mother liquor was evaporated and the residue was purified by preparative HPLC (Shimadzu, 10–100% B [90%MeOH:10%H2O:0.1% TFA], 30 min. gradient, 20 mL/min. flow rate, 220 nm, YMC S5 ODS 20×100 mm) to give an additional amount of the title compound (67.6 mg) as a white solid: Combined yield, 96%; LC-MS 99% Area; LC/MS (electrospray, +ions) m/z 465 (M+H).

The following compounds were prepared employing the procedures described above and the working Examples.

EXAMPLES 426 TO 477

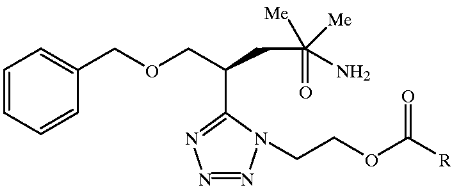 = $X_1$-R

| Example No. | $X_1$-R | M + H positive ions |
|---|---|---|
| 426 | 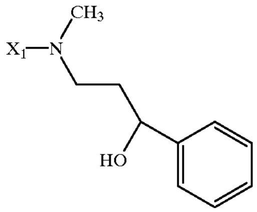 | 540 |
| 427 | 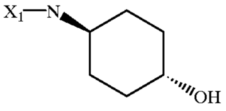 | 490 |
| 428 | 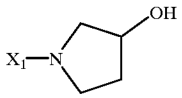 | 462 |
| 429 | 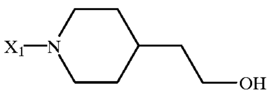 | 504 |

-continued
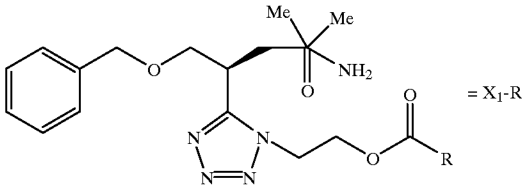
| Example No. | $X_1$-R | M + H positive ions |
|---|---|---|
| 430 | 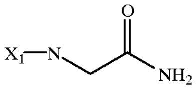 | 449 |
| 431 | 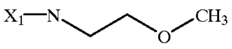 | 450 |
| 432 | 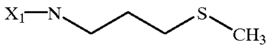 | 480 |
| 433 | 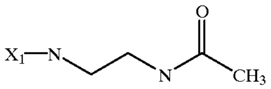 | 477 |
| 434 | 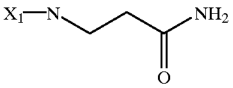 | 463 |
| 435 | 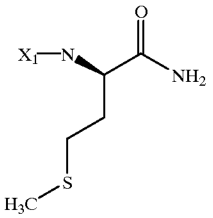 | 523 |
| 436 | 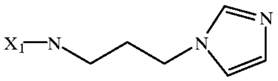 | 500 |
| 437 | 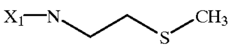 | 466 |
| 438 | 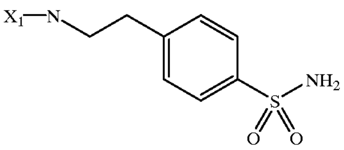 | 575 |
| 439 | 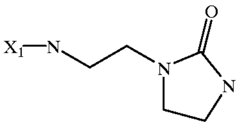 | 504 |
| 440 | 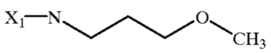 | 464 |

-continued
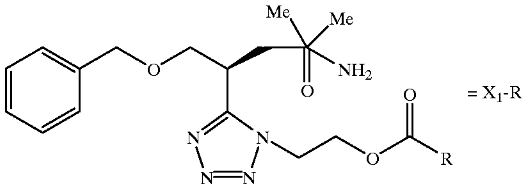
| Example No. | $X_1$-R | M + H positive ions |
|---|---|---|
| 441 | 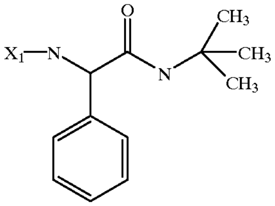 | 581 |
| 442 | 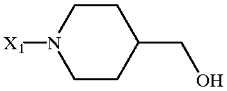 | 490 |
| 443 | 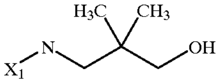 | 478 |
| 444 | 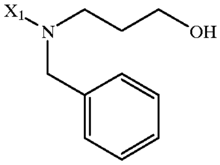 | 540 |
| 445 | 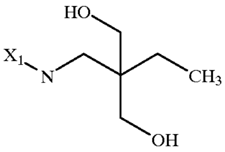 | 508 |
| 446 | 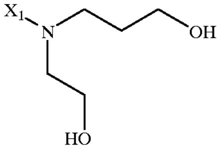 | 494 |
| 447 | 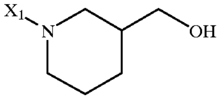 | 490 |
| 448 | 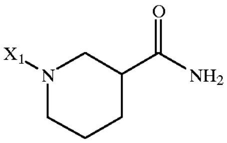 | 503 |

-continued
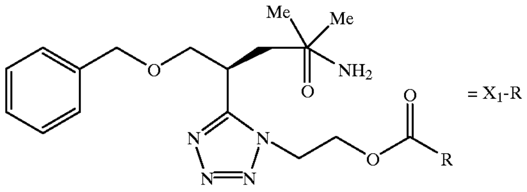
| Example No. | $X_1$-R | M + H positive ions |
|---|---|---|
| 449 | 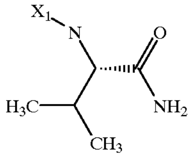 | 491 |
| 450 | 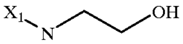 | 436 |
| 451 | 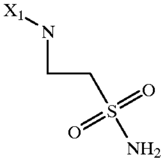 | 499 |
| 452 | 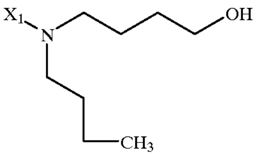 | 520 |
| 453 | 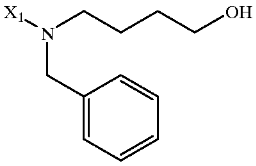 | 554 |
| 454 | 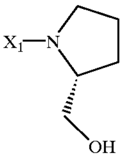 | 476 |
| 455 | 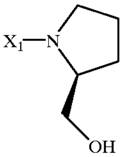 | 476 |
| 456 | 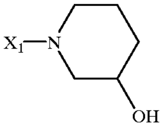 | 476 |

-continued
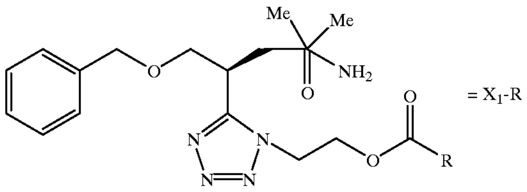
| Example No. | $X_1$-R | M + H positive ions |
|---|---|---|
| 457 | 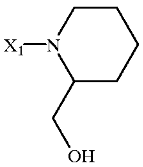 | 490 |
| 458 | 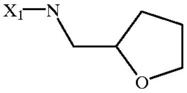 | 476 |
| 459 | 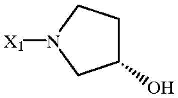 | 462 |
| 460 | 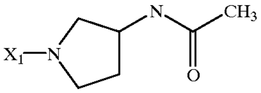 | 503 |
| 461 | 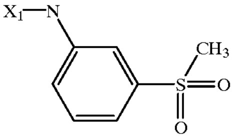 | 546 |
| 462 | 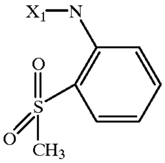 | 546 |
| 463 | 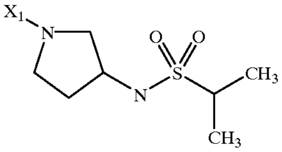 | 567 |
| 464 | 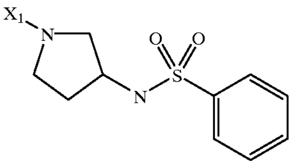 | 601 |
| 465 | 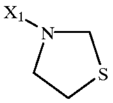 | 464 |

-continued
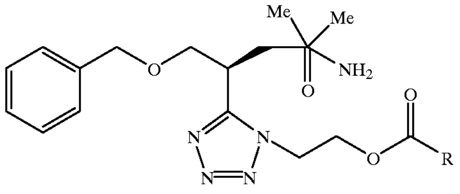
$= X_1\text{-}R$
| Example No. | $X_1$-R | M + H positive ions |
|---|---|---|
| 466 | 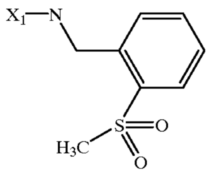 | 560 |
| 467 | 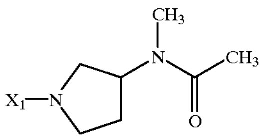 | 517 |
| 468 | 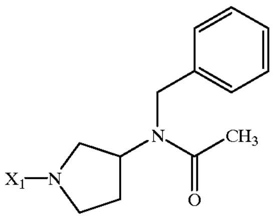 | 593 |
| 469 | 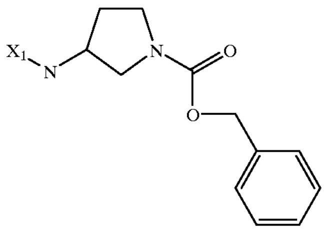 | 595 |
| 470 | 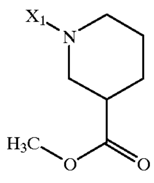 | 518 |
| 471 | 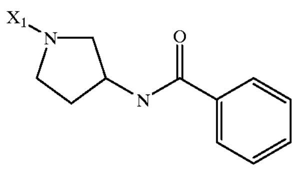 | 565 |
| 472 | 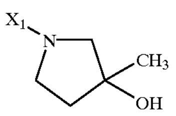 | 476 |

-continued
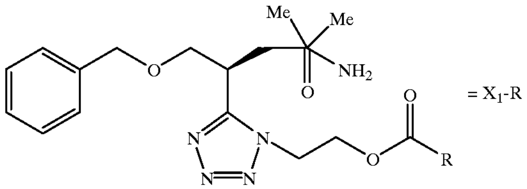
| Example No. | $X_1$-R | M + H positive ions |
|---|---|---|
| 473 | 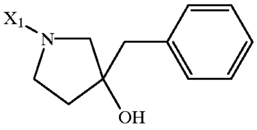 | 552 |
| 474 | 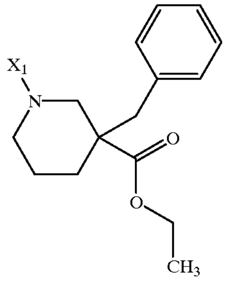 | 622 |
| 475 | 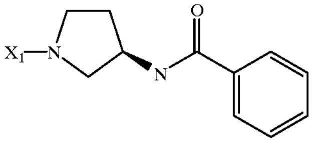 | 565 |
| 476 | 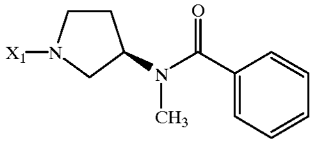 | 579 |
| 477 | 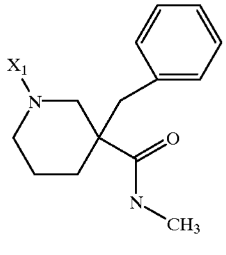 | 607 |

EXAMPLES 478 TO 498
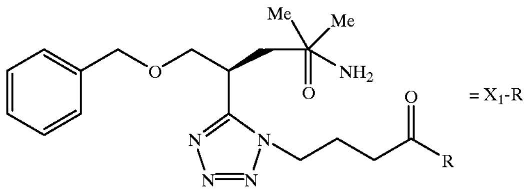
= $X_1$-R
| Example No. | $X_1$-R | M + H positive ions |
|---|---|---|
| 478 | 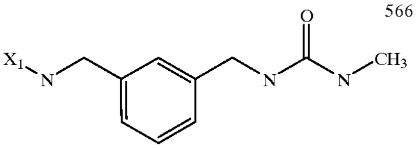 | 566 |
| 479 | 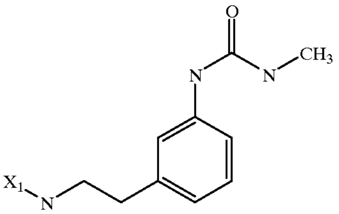 | 566 |
| 480 | 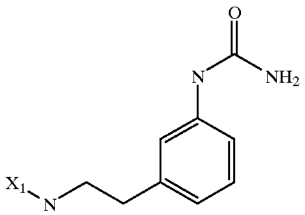 | 552 |
| 481 | 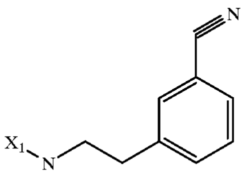 | 519 |
| 482 | 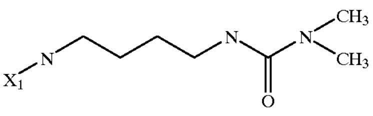 | 532 |
| 483 | 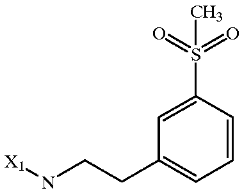 | 572 |
| 484 | 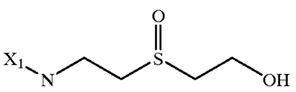 | 510 |
-continued
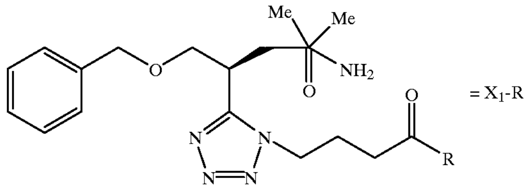
= $X_1$-R
| Example No. | $X_1$-R | M + H positive ions |
|---|---|---|
| 485 | 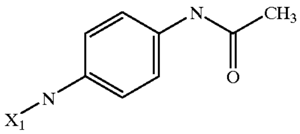 | 523 |
| 486 | 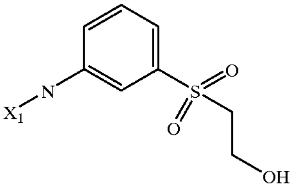 | 574 |
| 487 | 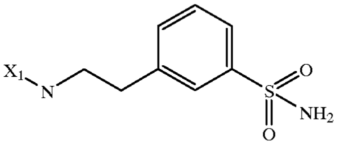 | 573 |
| 488 | 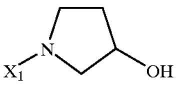 | 460 |
| 489 | 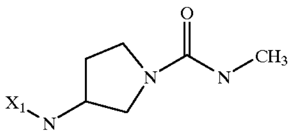 | 516 |
| 490 | 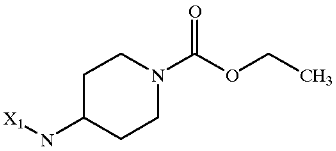 | 545 |
| 491 | 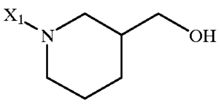 | 488 |
| 492 | 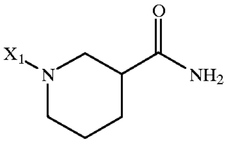 | 501 |

-continued
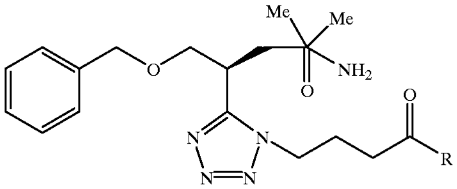
= $X_1$-R
| Example No. | $X_1$-R | M + H positive ions |
|---|---|---|
| 493 | 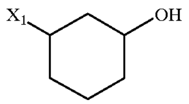 | 474 |
| 494 | 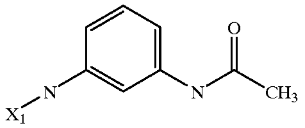 | 523 |
| 495 | 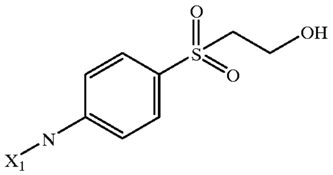 | 574 |
| 496 | 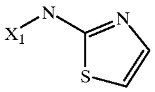 | 473 |
| 497 | 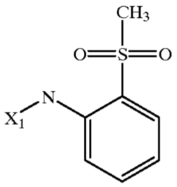 | 544 |
| 498 | 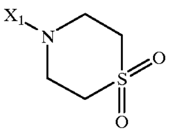 | 508 |
EXAMPLES 499 TO 530
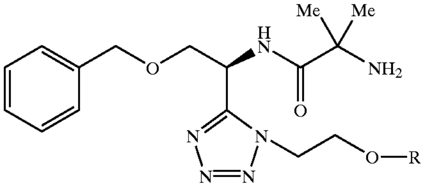
= $X_2$—R
| Example No. | $X_1$—R | M + H positive ions |
|---|---|---|
| 499 | 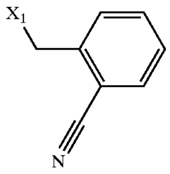 | 464 |
| 500 | 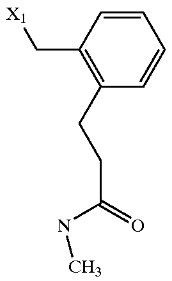 | 525 |
| 501 | 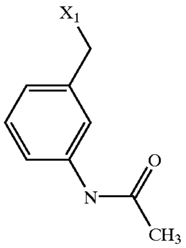 | 496 |
| 502 | 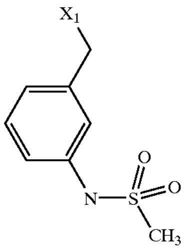 | 532 |
| 503 | 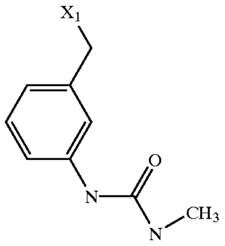 | 511 |

-continued
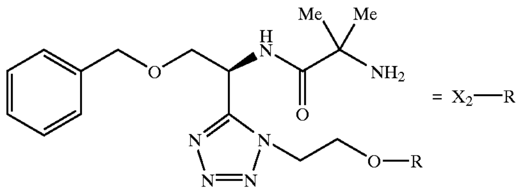
| Example No. | X1—R | M + H positive ions |
|---|---|---|
| 504 | 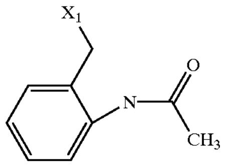 | 496 |
| 505 | 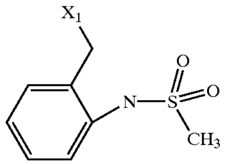 | 532 |
| 506 | 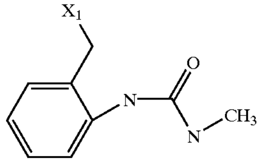 | 511 |
| 507 | 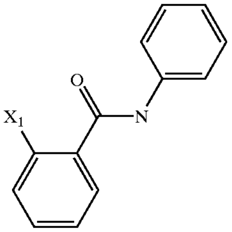 | 544 |
| 508 | 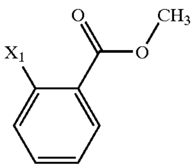 | 483 |
| 509 | 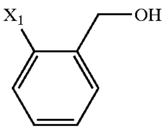 | 455 |
| 510 | 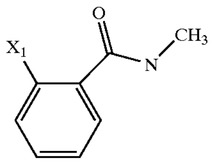 | 482 |
-continued
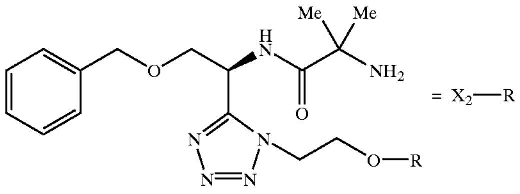
| Example No. | X1—R | M + H positive ions |
|---|---|---|
| 511 | 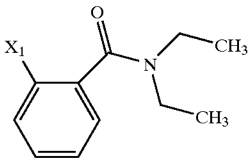 | 524 |
| 512 | 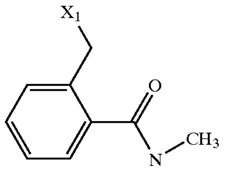 | 496 |
| 513 | 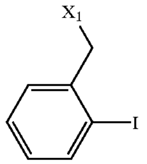 | 565 |
| 514 | 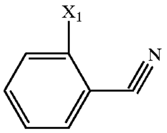 | 450 |
| 515 | 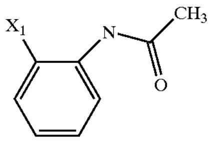 | 482 |
| 516 | 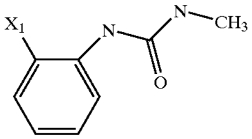 | 497 |
| 517 | 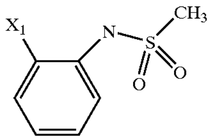 | 518 |
| 518 | 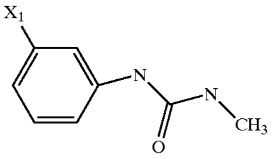 | 497 |

-continued
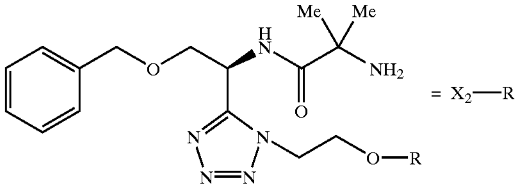
| Example No. | $X_1$—R | M + H positive ions |
|---|---|---|
| 519 | 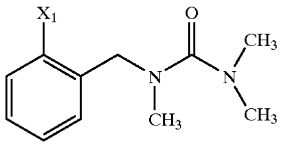 | 539 |
| 520 | 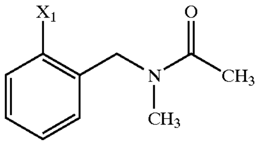 | 510 |
| 521 | 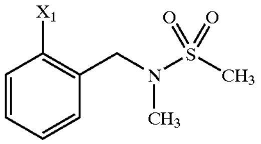 | 546 |
| 522 | 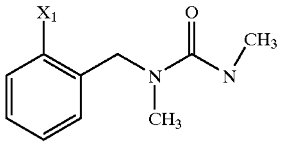 | 525 |
| 523 | 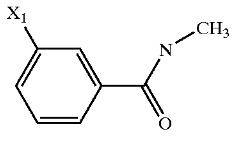 | 482 |
| 524 | 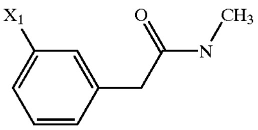 | 496 |
-continued
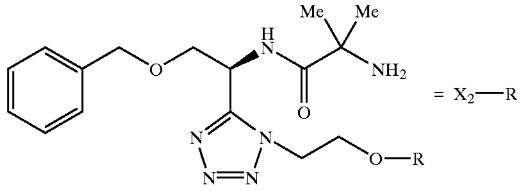
| Example No. | $X_1$—R | M + H positive ions |
|---|---|---|
| 525 | 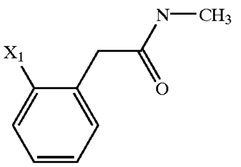 | 496 |
| 526 | 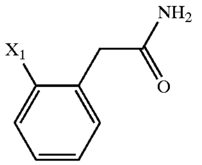 | 482 |
| 527 | 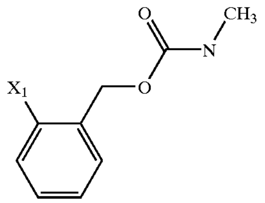 | 512 |
| 528 | 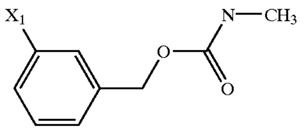 | 512 |
| 529 | 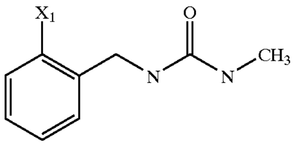 | 511 |
| 530 | 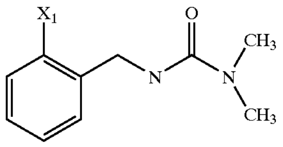 | 525 |

EXAMPLES 531 TO 554
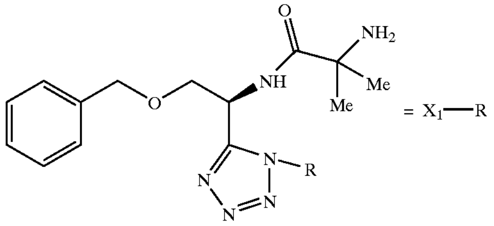
| Example No. | $X_1$—R | M + H positive ions |
|---|---|---|
| 531 | 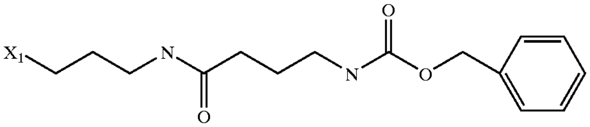 | 581 |
| 532 | 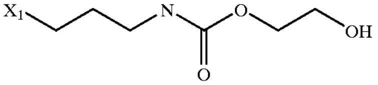 | 450 |
| 533 | 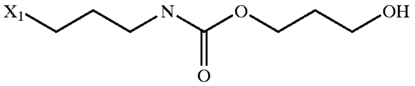 | 464 |
| 534 | 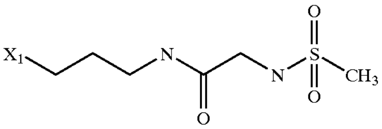 | 497 |
| 535 | 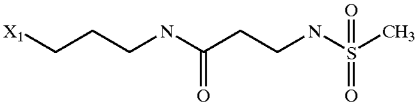 | 511 |
| 536 | 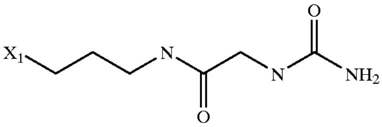 | 462 |
| 537 | 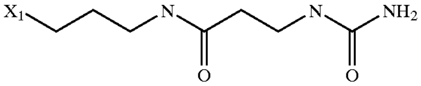 | 476 |
| 538 | 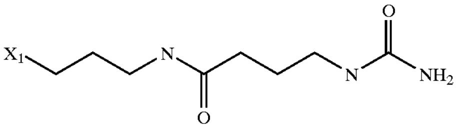 | 490 |
| 539 | 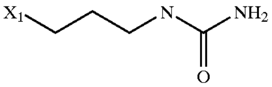 | 405 |
| 540 | 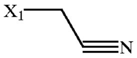 | 344 |
| 541 | 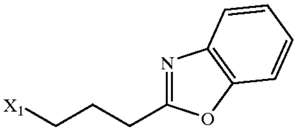 | 464 |

-continued
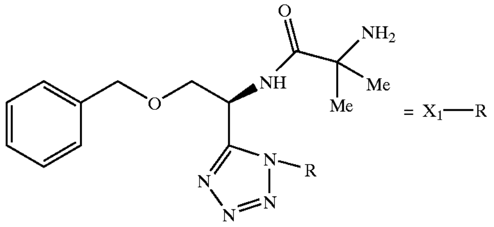
| Example No. | $X_1$—R | M + H positive ions |
|---|---|---|
| 542 | 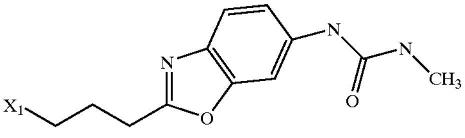 | 536 |
| 543 | 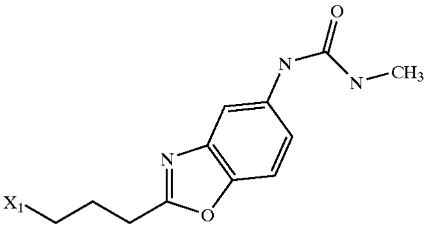 | 536 |
| 544 | 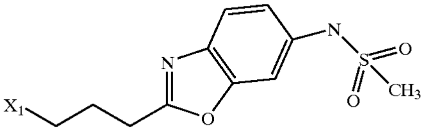 | 557 |
| 545 | 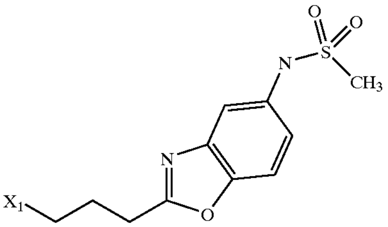 | 557 |
| 546 | 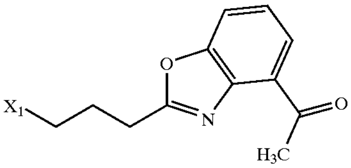 | 506 |
| 547 | 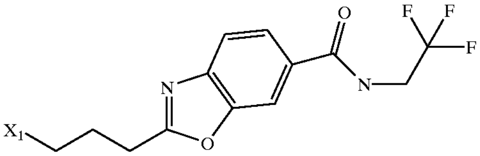 | 589 |
| 548 | 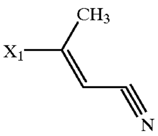 | 370 |

-continued
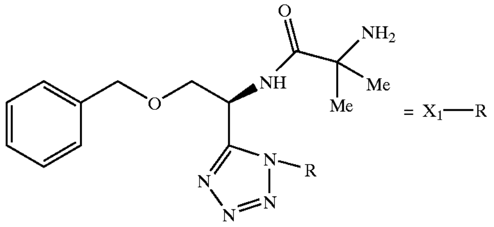
| Example No. | $X_1$—R | M + H positive ions |
|---|---|---|
| 549 | 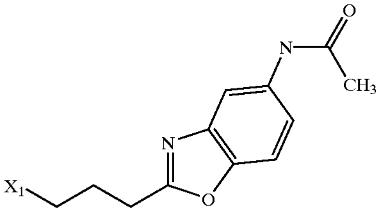 | 521 |
| 550 | 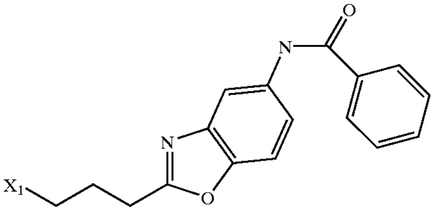 | 583 |
| 551 | 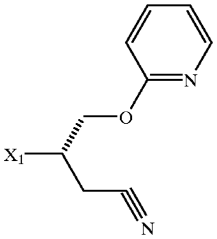 | 465 |
| 552 | 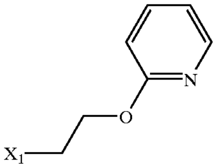 | 426 |
| 553 | 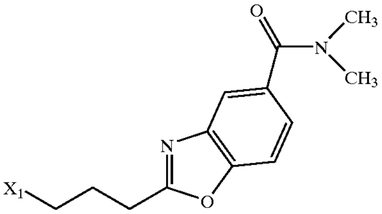 | 535 |
| 554 | 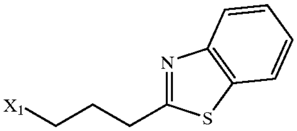 | 480 |

EXAMPLES 555 TO 583
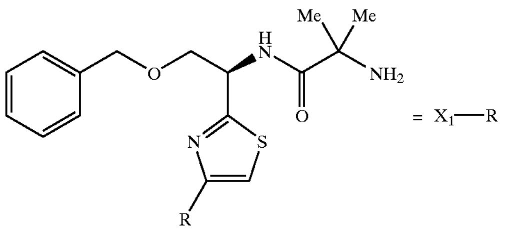
| Example No. | $X_1$—R | M + H positive ions |
|---|---|---|
| 555 | 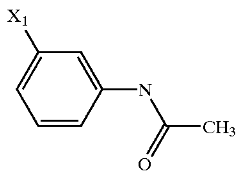 | 453 |
| 556 | 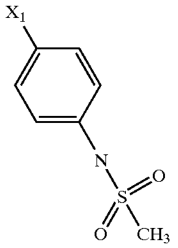 | 489 |
| 557 | 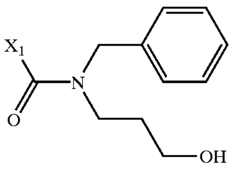 | 511 |
| 558 | 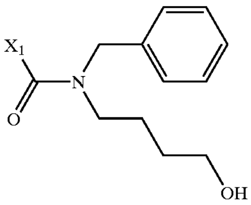 | 525 |
| 559 | 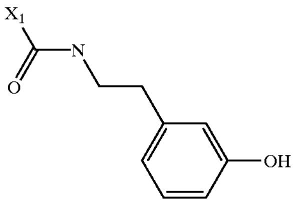 | 483 |
| 560 | 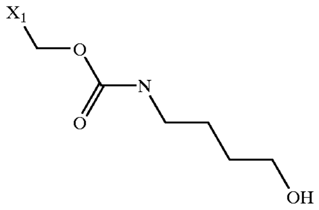 | 465 |

-continued
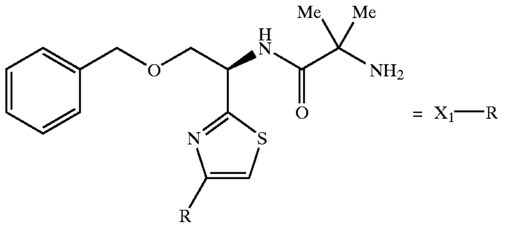
| Example No. | $X_1$—R | M + H positive ions |
|---|---|---|
| 561 | 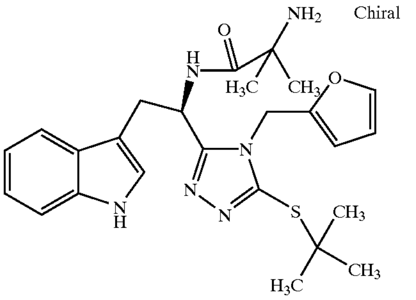 | 481 |
| 562 | 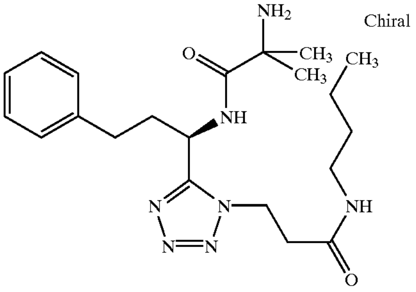 | 416 |
| 563 | 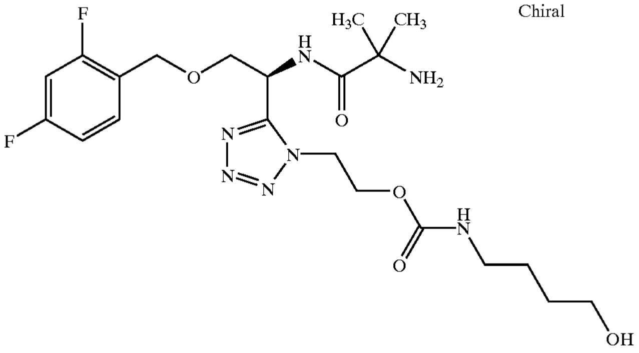 | 500 |
| 564 | 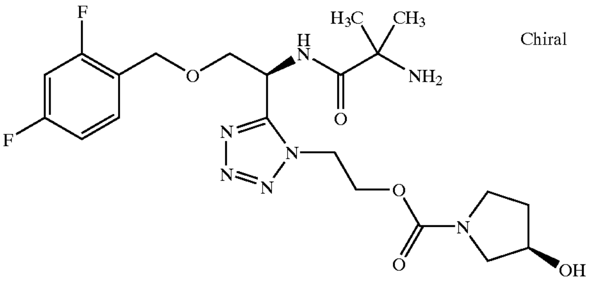 | 498 |

-continued
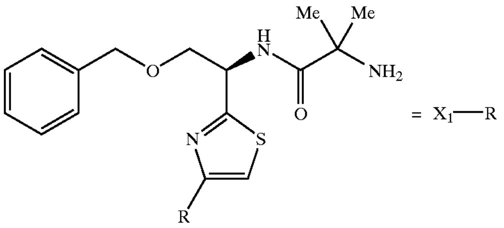
| Example No. | $X_1$—R | | M + H positive ions |
|---|---|---|---|
| 565 | 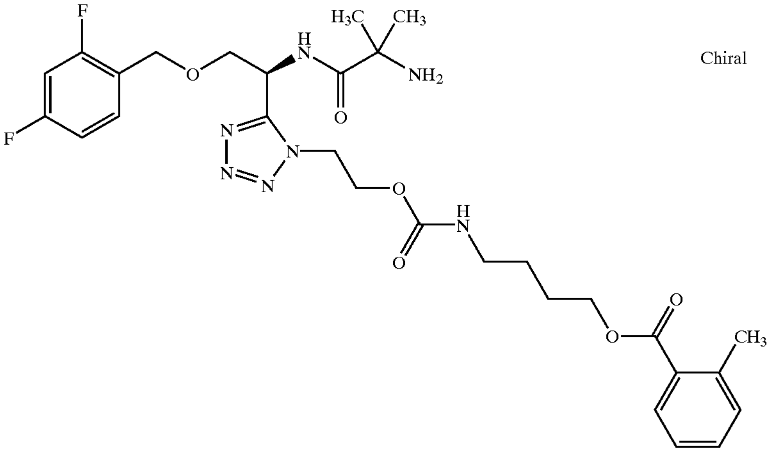 | Chiral | 618 |
| 566 | 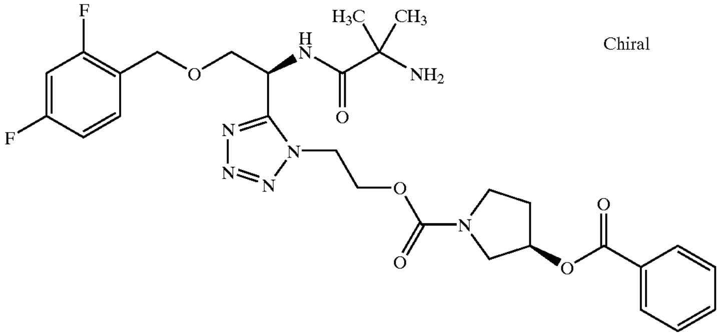 | Chiral | 602 |
| 567 | 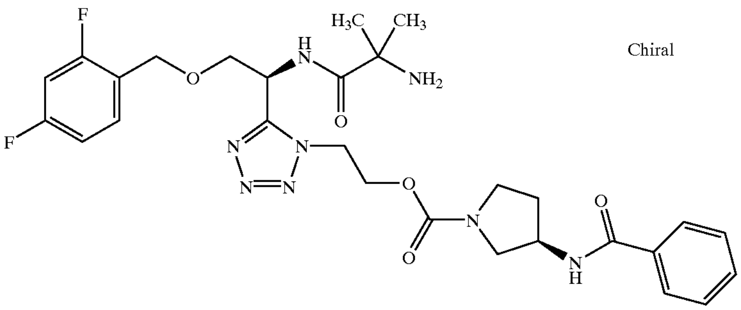 | Chiral | 601 |

-continued
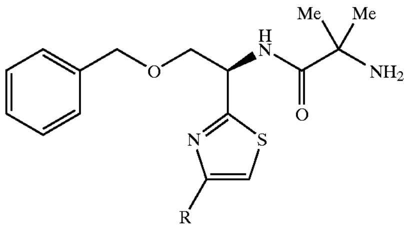 = $X_1$—R
| Example No. | $X_1$—R | M + H positive ions |
| --- | --- | --- |
| 568 | 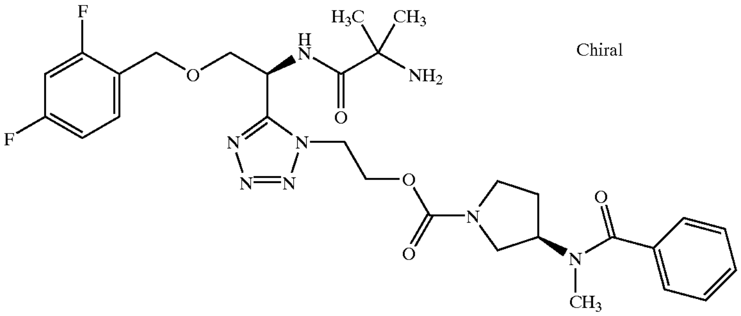 Chiral | 615 |
| 569 | 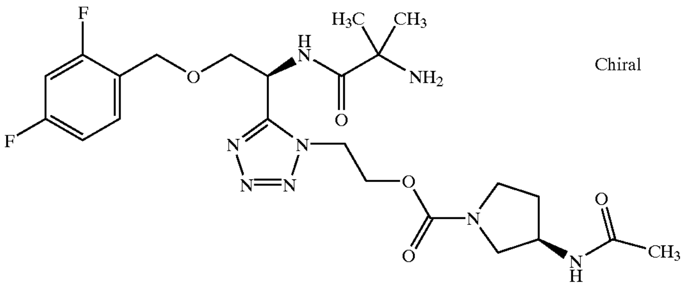 Chiral | 539 |
| 570 | 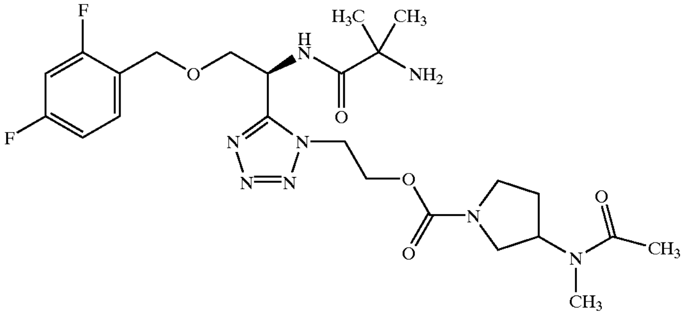 | 553 |
| 571 | 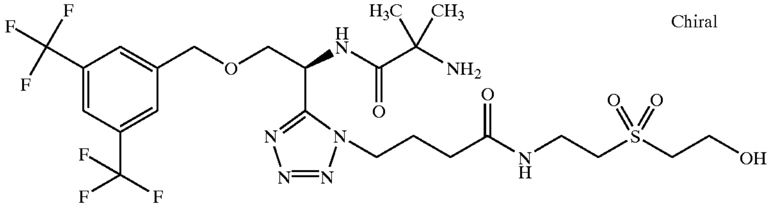 Chiral | 662 |

-continued
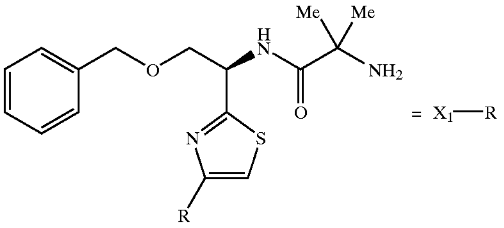
| Example No. | $X_1$—R | M + H positive ions |
|---|---|---|
| 572 | 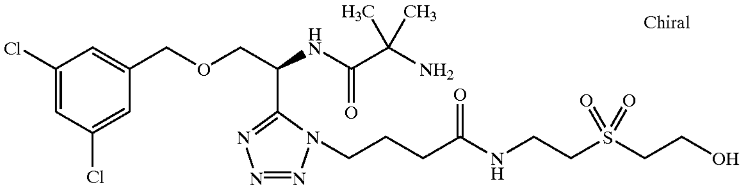 Chiral | 595 |
| 573 | 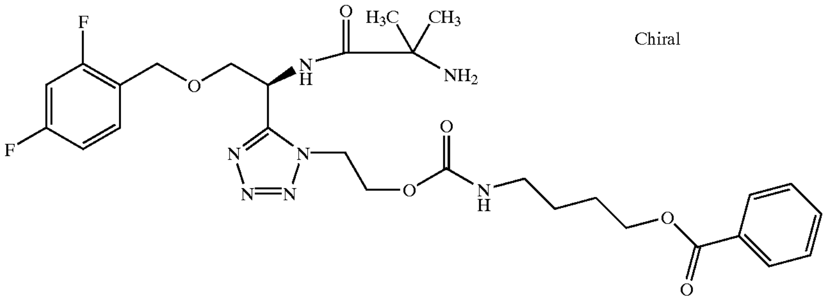 Chiral | 604 |
| 574 | 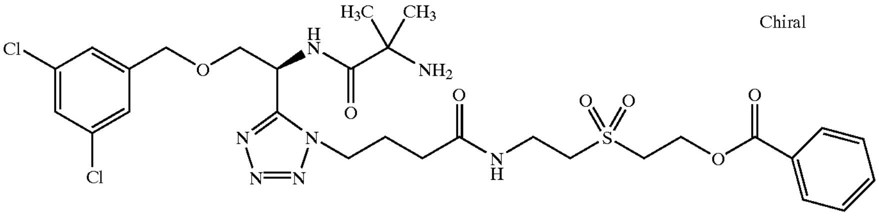 Chiral | 699 |
| 575 | 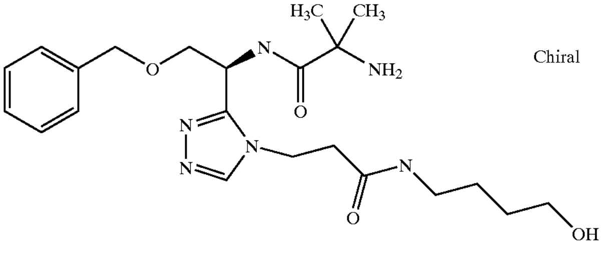 Chiral | 447 |

-continued
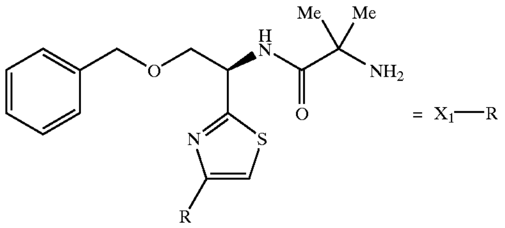
| Example No. | $X_1$—R | | M + H positive ions |
|---|---|---|---|
| 576 | 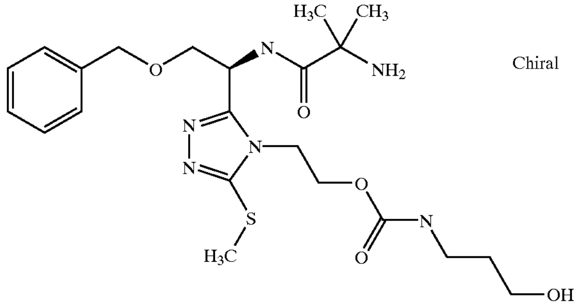 | Chiral | 495 |
| 577 | 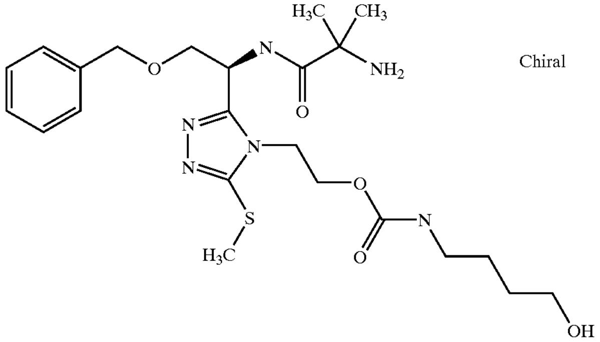 | Chiral | 509 |
| 578 | 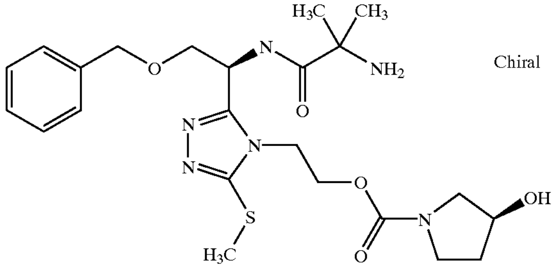 | Chiral | 507 |
| 579 | 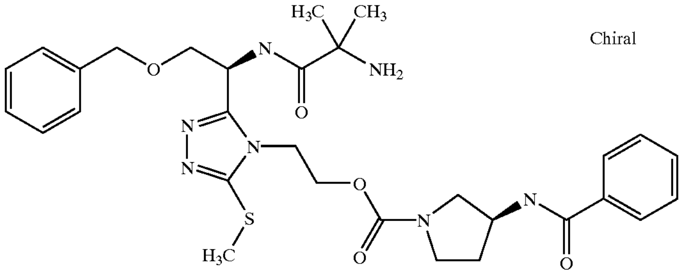 | Chiral | 610 |

-continued
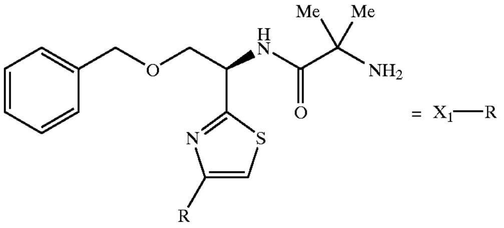
| Example No. | $X_1$—R | M + H positive ions |
|---|---|---|
| 580 | 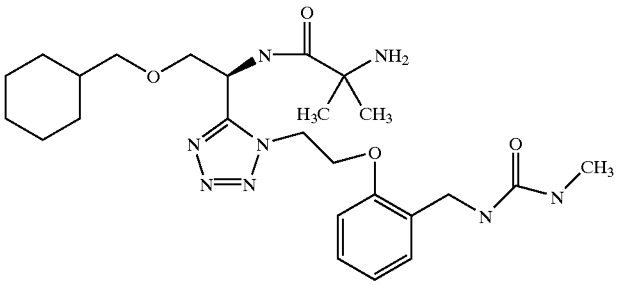 | 517 |
| 581 | 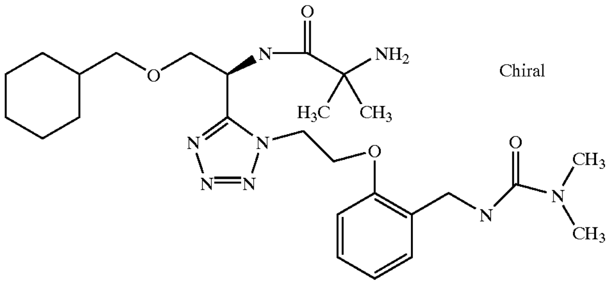 Chiral | 531 |
| 582 | 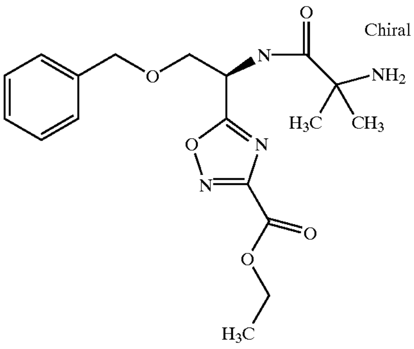 Chiral | 377 |
| 583 | 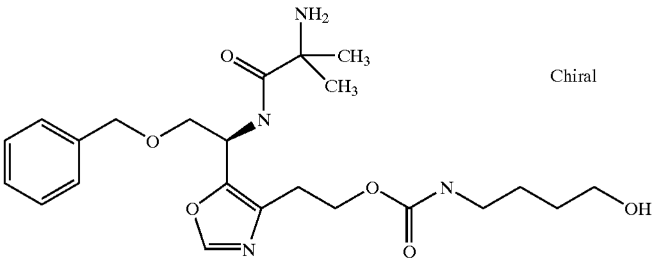 Chiral | 463 |

EXAMPLE 584

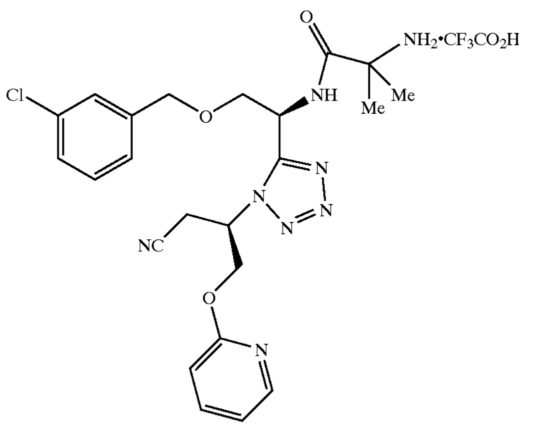

A.

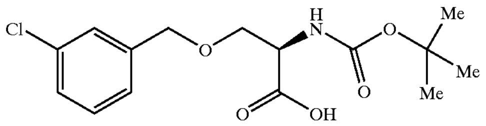

To a 0° C. solution of Boc-D-serine

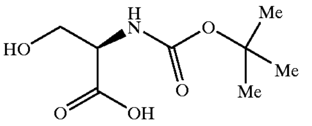

(2 g, 9.76 mmol, Aldrich) in DMF (40 mL) was added sodium hydride (0.78 g, 19.52 mmol, 60% oil dispersion) slowly over 30 min. The reaction mixture was kept at 0° C. for 1 h, room temperature for 30 ma then re-cooled to 0° C. and meta-chlorobenzyl bromide

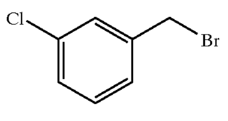

(2 g, 9.76 mmol) was added. The final mixture was allowed to warm to room temperature overnight. The reaction was then brought to ~pH 3 with iN HCl, the aqueous layer extracted with ethyl acetate (3×150 mL), and the combined organics dried over magnesium sulfate. The volatiles were removed in vacuo to give crude title compound. The crude compound was purified by preparative HPLC to give pure desired product (1.1 g, 34% yield); LC/MS (electrospray, +ions) m/z 330(M+H).

B.

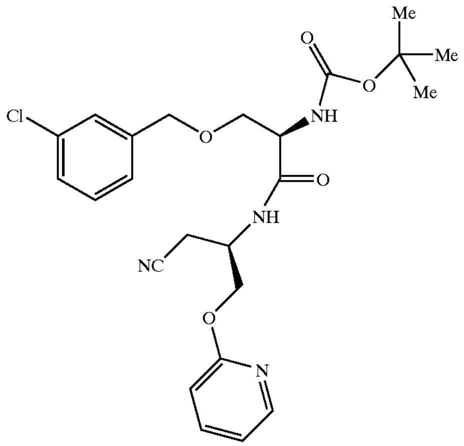

15% TFA/$CH_2Cl_2$ solution (6.0 mL) was added to a flask containing Example 425,Part E compound(570 mg, 2.05 mmol) and thioanisole (0.72 mL, 6.15 mmol), and the resulting solution was allowed to stand at rt. for 4 h. The solution was evaporated and the residual TFA was removed by co-evaporation with $CH_2Cl_2$ (2×5 mL) and MeOH (3×5 mL), and drying under high vacuum for 1 h The crude amine salt material,

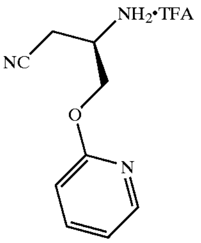

was used without further purification in the subsequent reaction.

Part A compound (1.05 g, 3.19 mmol), EDAC (607 mg, 3.19 mmol), HOAT (432 mg, 3.19 mmol), 1,2-DCE (0.47 mL), and DMF (0.94 mL) were mixed at 0° C. and stirred for 15 min. The resulting cloudy solution was transferred, via syringe, to a 0° C. solution of the crude amine (from above) in 1,2-DCE (0.4 mL) and DMF (0.47 mL), and the mixture was stirred for 10 min. at 0° C. Diisopropylethylamine (1.09 mL, 6.38 mmol) was added and stirring was continued at rt. for 36 h. The reaction mixture was diluted with EtOAc (80 mL) and washed with saturated $NaHCO_3$ (2×40 mL), water (40 mL) and brine (40 mL). The organic layer was dried ($Na_2SO_4$), evaporated and chromatographed ($SiO_2$ 230–400 mesh, 1/1 hexanes/EtOAc) to provide the desired compound (850 mg, 84% yield) as a colorless oil; LC/MS (electrospray, +ions) m/z 489 (M+H).

C.

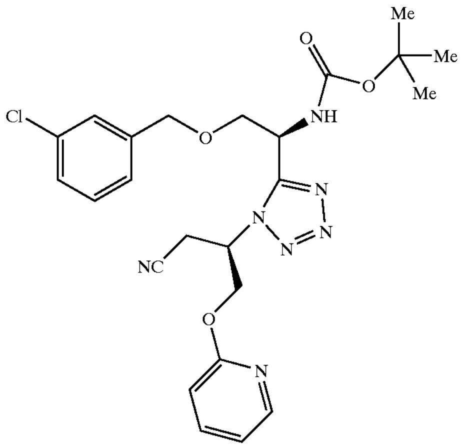

Diethylazodicarboxylate (0.34 mL, 2.09 mmol, DEAD) and azidotrimethylsilane (0.31 mL, 2.09 mmol) were added to a solution of Part B compound(850 mg, 1.74 mmol) and triphenylphosphine (547 mg, 2.09 mmol) in $CH_2Cl_2$ (1.4 mL) The mixture was stirred at rt. for 22 h. and additional amounts of triphenylphosphine (547 mg), DEAD (0.34 mL) and azidotrimethylsilane (0.31 mL) were added. Stirring was continued for an additional 24 h at rt. and the final mixture was passed through a $SiO_2$ (230–400 mesh) column, eluting with 3/2 to 1/1 hexanes/EtOAc, to give the desired compound (580 mg, 65%) as a thick colorless oil; LC/MS (electrospray, +ions) m/z 514 (M+H).

D.

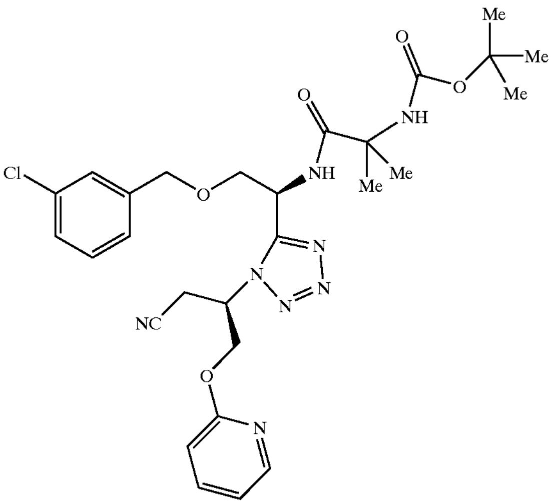

15TFA/$CH_2Cl_2$ solution (6.2 mL) was added to a flask containing the Part C compound (580 mg, 1.13 mmol) and thioanisole (0.4 mL, 3.39 mmol), and the resulting solution was allowed to stand at rt. for 4 h. The solution was evaporated and the residual TFA was removed by co-evaporation with $CH_2Cl_2$ (2x8 mL) and MeOH (3x8 mL), and drying under high vacuum for 1 h The residue was heated at 60° C. in MeOH (25 mL) for 11 h. and the solution concentrated. The crude amine material,

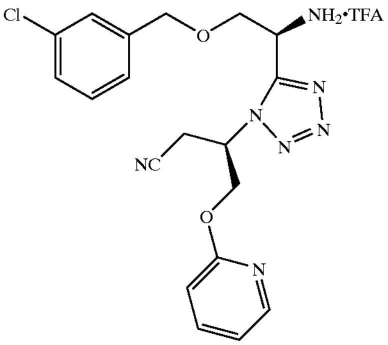

was used without further purification in the subsequent reaction.

N-Boc-methyl alanine

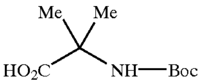

(300 mg, 1.46 mmol), EDAC (280 mg, 1.46 mmol), HOAT (200 mg, 1.46 mmol), 1,2-DCE (350 μL) and DMF (700 μL) were mixed at 0° C. and stirred for 15 min. The resulting solution was transferred, via syringe, to a 0° C. solution of the crude amine (from above) in 1,2-DCE (300 μL) and DMF (400 μL), and the mixture was stirred at 0° C. for 15 min. Diisopropylethylamine (507 μL, 2.92 mmol) was added and stirring was continued for 25 h at rt. The final mixture was diluted with EtOAc (75 mL) and washed with saturated $NaHCO_3$ (2x30 mL), water (30 mL) and brine (30 mL). The organic layer was dried ($Na_2SO_4$), evaporated and chromatographed ($SiO_2$ 230–400 mesh, 3/2 to 2/3 hexanes/EtOAc) to provide desired compound (419 mg, 62% yield) as a colorless foam; LC/MS (electrospray, +ions) m/z 599 (M+H).

E.

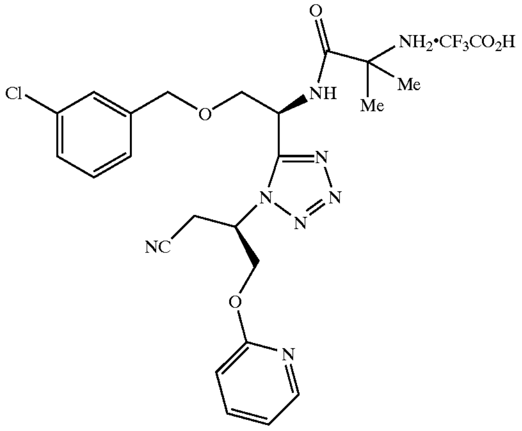

Part D compound (418 mg, 0.7 mmol) was treated with 10% TFA/$CH_2Cl_2$ (14.0 mL) for 2.5 h and the solution concentrated in vacuo. The residual TFA was co-evaporated with $CH_2Cl_2$ (3x10 mL) and MeOH (2x10 mL), and drying under high vacuum for 1 h The residue was heated at 60° C. in MeOH (40 mL) for 10 h. and the solution concentrated to give the crude desired compound. The crude material was purified by preparative HPLC to give the title compound (385 mg, 90% yield) as a colorless oil: MS (electrospray, +ions) m/z 499 (M+H).

EXAMPLE 585

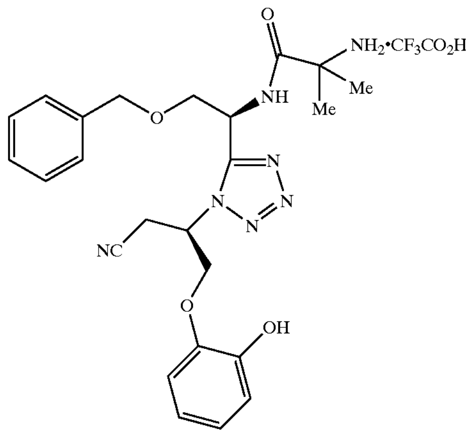

A.

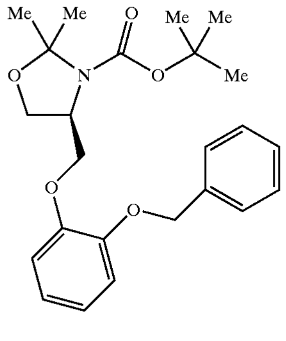

To a solution of Example 425 Part A compound(1.00 g, 4.33 mmol), 2-(benzyloxy)phenol (0.97 mL, 5.32 mmol, Aldrich, 96%) and triphenylphosphine (1.38 g, 5.26 mmol) in $CH_2Cl_2$ (9.5 mL), cooled at 0° C., was added diethylazodicarboxylate (0.83 mL, 5.27 mmol) dropwise. The solution was stirred at rt. for 4.5 h. and then diisopropylethylamine (0.79 mL, 4.54 mmol)was added. After stirring for an additional 14.5 h., the solution was partially evaporated. The remaining solution was passed through a $SiO_2$ (230–400 mesh) column, eluting with 9/1 hexanes/EtOAc, to provide a mixture of 2-(benzyloxy)phenol and the desired compound.

Chromatography (230–400 mesh, 4/1 hexanes/Ether) of the above mixture afforded the desired compound (1.17 g, 65% yield) as an oil: $^1$H NMR δ ($CDCl_3$,ppm, rotamers) 7.43–7.30 (m,5H), 7.07, 7.01 and 6.91 (3m, 4H) 5.10 and 5.11 (2s, 2H), 4.31, 4.19 and 3.92 (3m, 5H), 1.61, 1.55, 1.52, 1.50, 1.49 and 1.46 (6s, 15H).

B.

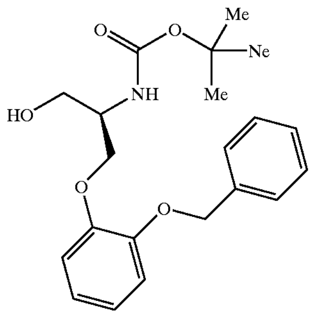

A solution of Part A compound(1.17 g, 4.33 mmol) and p-toluenesulfonic acid monohydrate (81.0 mg, 0.43 mmol) in dry MeOH (28.4 mL) was stirred at rt. for 10.5 h. 1M $K_2CO_3$ solution (0.22 mL) was added and the mixture volume was reduced, in vacuo, to almost dryness. The residue was taken up in EtOAc (120 mL) and washed with saturated $NaHCO_3$ (2×40 mL) and brine (40 mL). Drying ($Na_2SO_4$), evaporation and chromatography ($SiO_2$ 230–400 mesh, 3/2 hexanes/EtOAc) of the crude gave the desired alcohol (792 mg, 75% yield) as a colorless oil:. $^1$H NMR δ($CDCl_3$,ppm) 7.38 (m,5H), 6.92 (m, 4H) 5.50 (d, J=7.2 Hz, 2H), 5.10 (s, 2H), 4.21 and 4.13 (2m, 2H) 3.93 (m, 2H), 3.74 (m, 1H), 3.03 (s, 1H), 1.44 (s, 9H).

C.

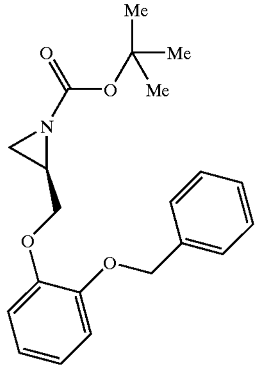

To a solution of Part B compound (792 mg, 2.12 mmol) and triphenylphosphine (612 mg, 2.33 mmol, $Ph_3P$) in $CH_2Cl_2$ (14.0 mL), cooled at 0° C., was added diethylazodicarboxylate (370 μL, 2.35 mmol, DEAD) dropwise. After stirring at rt for 2.2 h, additional amounts of $Ph_3P$ (306 mg, 1.17 mmol) and DEAD (185 μL, 1.18 mmol) were added and stirring was continued for an additional 1.3 h. The mixture volume was reduced to 4 mL in vacuo and the remaining solution was passed through a $SiO_2$ (230–400 mesh, deactivated with 80/20/1 hexanes/EtOAc/$Et_3N$) column, eluting with 7/3 hexanes/EtOAc to obtain the desired compound (595 mg, 79% yield) as a colorless oil: $^1$H NMR δ ($CDCl_3$,ppm) 7.44 (d, J=7.7 Hz, 2H), 7.36 (t, J=7.4 Hz, 2H), 7.29 (t, J=7.4 Hz,1H), 6.91 (m, 4H), 5.11 (s, 2H), 4.2 (dd, J=11.0, 5.0 Hz, 1H) and 4.01 (dd, J=11.0, 5.5 Hz, 1H) 2.85 (m, 1H), 2.35 (d, J=6.1 Hz, 1H), 2.22 (d, J=3.9 Hz, 1H), 1.42 (s, 9H).

D.

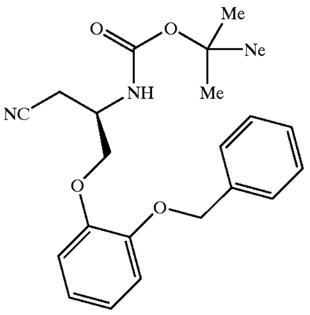

Potassium cyanide (140 mg, 2.15 mmol) was dissolved in water (258 μL, 14.3 mmol) and heated to 65° C. DMSO (8.0 mL) was added and the light suspension was stirred at 65° C. for 15 min. Then, a solution of Part C. compound 5 (595 mg, 1.68 mmol) in DMSO (1 mL+2×0.4 mL rinses)was added dropwise and stirring was continued at 65° C. for 6 h. and at rt for 4 h. After cooling to rt, the reaction mixture was diluted with 1/9 hexanes/EtOAc (125 mL) and washed with water (2×50 mL) and brine (30 mL). Drying ($Na_2SO_4$), evaporation and chromatography ($SiO_2$ 230–400 mesh, 7/3 hexanes/EtOAc) of the crude yielded the desired compound (444 mg, 69%) as a colorless oil: 1H NMR δ($CDCl_3$,ppm) 7.40 (m,5H), 6.97 (m, 4H) 5.32 (s, 1H), 5.12 (s, 2H), 4.22 (m, 2H), 4.06 (m, 1H) 2.79 (d, J=6.1 Hz, 2H), 1.43 (s, 9H).

E.

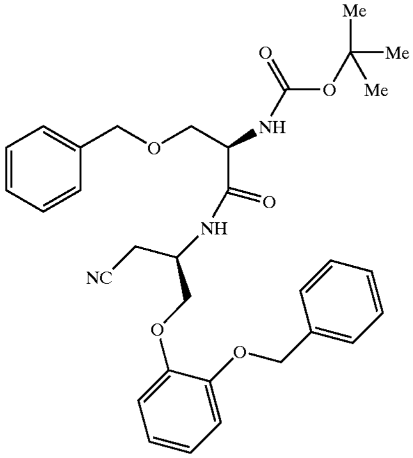

15% TFA/$CH_2Cl_2$ solution (9.5 mL) was added to a flask containing Part D compound (444 mg, 1.16 mmol) and thioanisole (0.41 mL, 3.49 mmol), and the resulting solution was allowed to stand at rt. for 3.5 h. The solution was evaporated and the residual TFA was removed by co-evaporation with $CH_2Cl_2$ (5×6 mL) and drying under high vacuum for 1.2 h. The crude amine salt material,

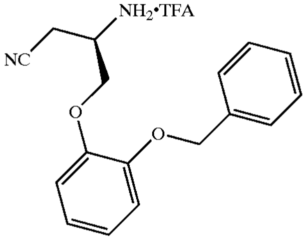

was used without further purification in the subsequent reaction.

N-Boc-O-benzyl-D-serine (445 mg, 1.51 mmol), EDAC (290 mg, 1.51 mmol), HOAT (205 mg, 1.51 mmol), 1,2-DCE (0.76 mL), and DMF (1.50 mL) were mixed at 0° C. and stirred for 15 min. The resulting cloudy solution was transferred, via syringe, to a 0° C. solution of the crude amine (from above) in 1,2-DCE (0.64 mL) and DMF (0.76 mL), and the mixture was stirred for 10 min. at 0° C. Diisopropylethylamine (0.61 mL, 3.50 mmol) was added and stirring was continued at rt. for 36 h. The reaction mixture was diluted with EtOAc (125 mL) and washed with saturated $NaHCO_3$ (2×40 mL), water (40 mL) and brine (40 mL). The organic layer was dried ($Na_2SO_4$), evaporated and chromatographed ($SiO_2$ 230–400 mesh, 3/2 hexanes/EtOAc) to provide the desired compound (394 mg, 61% yield) as a thick colorless oil: $^1$H NMR δ ($CDCl_3$,ppm) 7.38 (m,5H), 7.24 (m, 5H), 7.12 (d, J=8.3 Hz, 1H), 6.95 (m, 4H), 5.30 (s, 1H), 5.07 (s, 2H), 4.47 (m, 3H), 4.21 (m, 2H), 4.02 (dd, J=9.4, 4.6 Hz, 1H), 3.81 (m, 1H), 3.51 (dd, J=9.4, 6.0 Hz, 1H), 2.75 (m, 2H), 1.40 (s, 9H).

F.

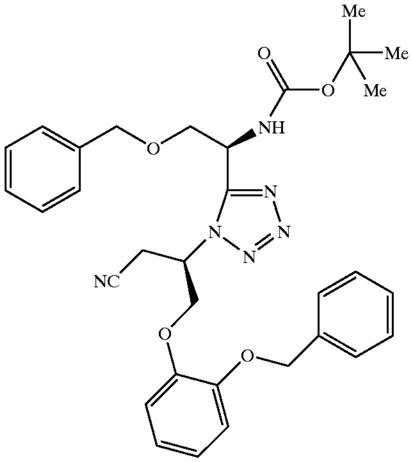

Diethylazodicarboxylate (155 μL, 0.98 mmol, DEAD) was added, dropwise, to a solution of Part E compound(457 mg, 0.82 mmol), triphenylphosphine (258 mg, 0.98 mmol) and azidotrimethylsilane (144 μL, 0.99 mmol, Sigma, 91%) in $CH_2Cl_2$ (1.8 mL). The mixture was stirred at rt. for 20 h. and additional amounts of $CH_2Cl_2$ (0.57 mL), triphenylphosphine (258 mg), azidotrimethylsilane (144 uL) and DEAD (155 μL) were added. Stirring was continued for an additional 21.2 h at rt. and the final mixture was passed through a $SiO_2$ (230–400 mesh) column, eluting with 7/3 hexanes/EtOAc, to give the desired compound (336 mg, 70% yield) as a thick colorless oil: $^1$H NMR δ ($CDCl_3$,ppm)

7.43–7.21 (m, 10H), 6.91 (m, 4H) 5.44 (d, J=7.4 Hz, 1H), 5.35 (m, 1H), 5.26 (m, 1H), 5.03 (s, 2H), 4.48 (m, 3H), 4.35 (m, 1H), 3.94 (dd, J 8.8, 6.2 Hz, 1H) 3.67 (t, J=8.7 Hz, 1H), 3.12 (dd, J=17.1, 6.4 Hz, 1H), 2.88 (dd, J=17.1, 7.9 Hz, 1H), 1.34 (s, 9H).

G.

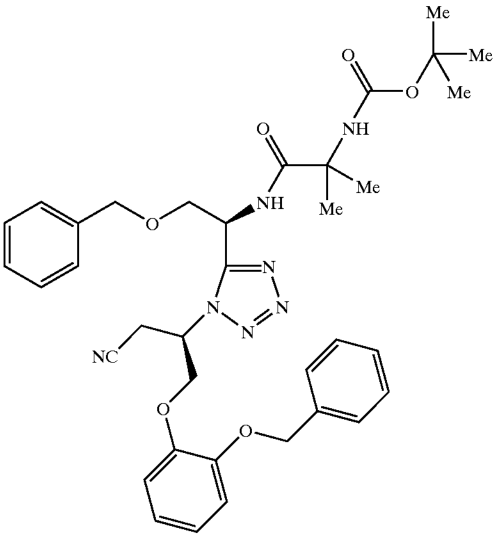

15% TFA/$CH_2Cl_2$ solution (7.6 mL) was added to a flask containing the Part F compound (336 mg, 0.58 mmol) and thioanisole (203 μL, 1.73 mmol), and the resulting solution was allowed to stand at rt. for 3.5 h. The solution was evaporated and the residual TFA was removed by co-evaporation with $CH_2Cl_2$ (2×6 mL) and MeOH (2×6 mL), and drying under high vacuum for 1.5 h. The residue was heated at 65° C. in MeOH (25 mL) for 9 h. and the solution concentrated. The crude amine material,

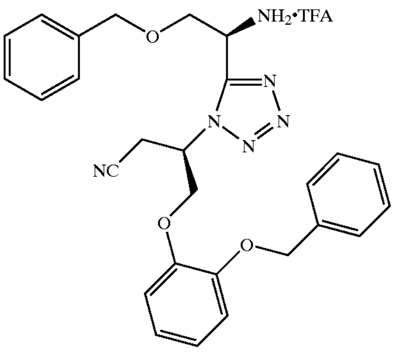

was used without further purification in the subsequent reaction.

N-Boc-methyl alanine

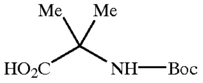

(153 mg, 0.75 mmol), EDAC (145 mg, 0.76 mmol), HOAT (103 mg, 0.76 mmol), 1,2-DCE (0.58 mL) and DMF (1.10 mL) were mixed at 0° C. and stirred for 15 min. The resulting solution was transferred, via syringe, to a 0° C. solution of the crude amine (from above) in 1,2-DCE (0.40 mL) and DMF (0.58 mL), and the mixture was stirred at 0° C. for 10 min. Diisopropylethylamine (0.28 mL, 1.61 mmol) was added and stirring was continued for 48.5 h at rt. The final mixture was diluted with EtOAc (100 mL) and washed with saturated $NaHCO_3$ (2×30 mL), water (30 mL) and brine (30 mL). The organic layer was dried ($Na_2SO_4$), evaporated and chromatographed ($SiO_2$ 230–400 mesh, 3/2 hexanes/EtOAc) to provide desired compound (293 mg, 76% yield) as a white foam: $^1H$ NMR δ ($CDCl_3$,ppm) 7.40–7.22 (m, 11H), 6.97–6.84 (m, 4H) 5.56 (m, 1H), 5.39 (m, 1H), 5.07 (s, 2H), 4.79 (s, 1H), 4.46 (m, 4H), 4.03 (dd, J=8.8, 6.0 Hz, 1H) 3.67 (t, J=8.6 Hz, 1H), 3.11 (dd, J=17.1, 6.0 Hz, 1H), 2.88 (dd, J=17.1, 7.7 Hz, 1H), 1.42, 1.35 and 1.32 (3s, 15H).

H.

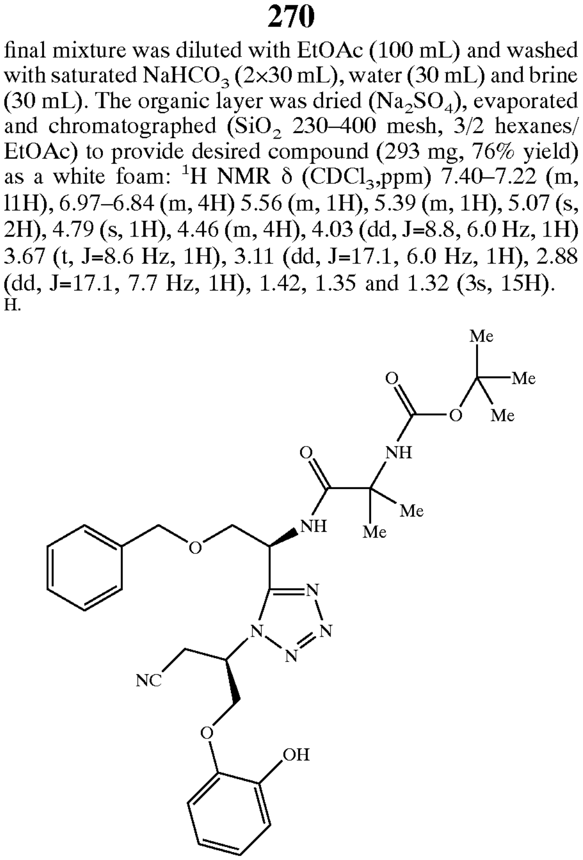

A solution of Part G compound (293 mg, 0.44 mmol) in THF (4.0 mL) and MeOH (4.0 mL) was degassed by purging with vacuum followed by $N_2$ addition three times. 5% Pd-C (Degussa type, 50% water content) was added and the resulting suspension was purged with vacuum followed by $H_2$ addition three times. The mixture was hydrogenated (1 atm., balloon) for 13.5 h. and filtered through celite. The filter cake was rinsed with MeOH (30 mL) and EtOAc (20 mL) and the combined filtrate was evaporated. The residue was chromatographed ($SiO_2$ 230–400 mesh, 1/1 hexanes/EtOAc)to obtain the desired compound (212 mg, 85% yield) as a colorless thick oil: $^1H$ NMR δ ($CDCl_3$,ppm) 7.66 (s, 1H), 7.34–7.19 (m, 6H), 6.85–6.73 (m, 4H) 5.48 (m, 2H), 4.99 (s, 1H), 4.64 (s, 1H), 4.43 (m, 3H), 4.04 (m, 1H), 3.80 (t, J=8.3 Hz, 1H), 2.96 (m, 1H), 2.77 (m, 1H), 1.47, 1.39 and 1.32 (3s, 15H).

I.

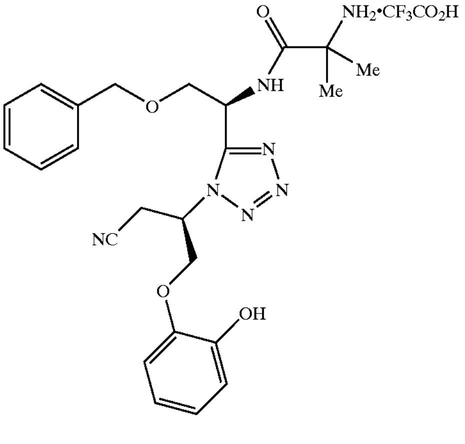

Part H compound (212 mg, 0.37 mmol) was treated with 10% TFA/$CH_2Cl_2$ (6.5 mL) for 2 h. and the solution concentrated in vacuo. The residual TFA was co-evaporated with $CH_2Cl_2$ (2×8 mL) and MeOH (2×8 mL), and drying under high vacuum for 1.2 h. The residue was heated at 65° C. in MeOH (40 mL) for 8 h. and the solution concentrated to give the crude desired compound. Purification by preparative HPLC (Shimadzu, 10–100% B [90%MeOH:10%H2O:0.2% TFA], 25 min. gradient, 20 mL/min. flow rate, 220 nm, Shimadzu VP ODS 20×100 mm) afforded the title compound (191 mg, 88% yield) as a slightly yellow solid: LC-MS 100% Area; LC/MS (electrospray, +ions) m/z 480 (M+H).

EXAMPLE 586

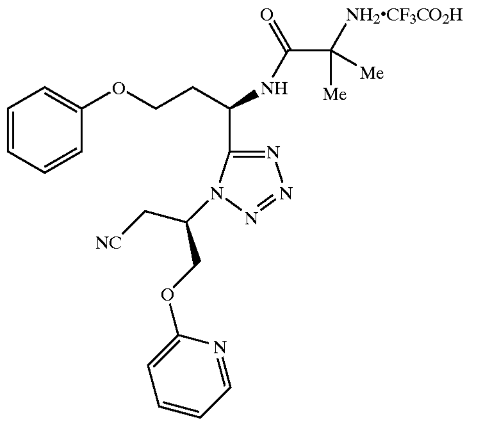

A.

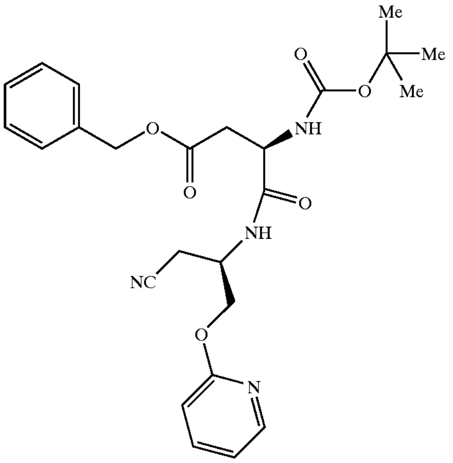

15% TFA/$CH_2Cl_2$ solution (11.6 mL) was added to a flask containing Example 425 Part E compound(1.1 g, 3.97 mmol) and thioanisole (1.48 mL, 11.9 mmol), and the resulting solution was allowed to stand at rt. for 4 h. The solution was evaporated and the residual TFA was removed by co-evaporation with $CH_2Cl_2$ (3×15 mL) and MeOH (3×15 mL), and dryinunder high vacuum for 1 h The crude amine salt material,

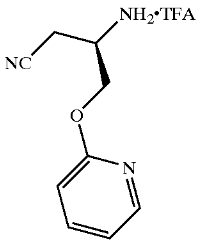

was used without further purification in the subsequent reaction.

N-BOC-D-aspartic acid 0-benzyl ester (1.80 g, 5.55 mmol), EDAC (1.07 g, 5.59 mmol), HOAT (0.76 g, 5.59 mmol), 1,2-DCE (1.0 mL), and DMF (2.0 mL) were mixed at 0° C. and stirred for 20 min. The resulting cloudy solution was transferred, via syringe, to a 0° C. solution of the crude amine (from above) in 1,2-DCE (1.0 mL) and DMF (2.0 mL), and the mixture was stirred for 10 min. at 0° C. Diisopropylethylamine (1.73 ml, 9.92 mmol) was added and stirring was continued at rt. for 18 h. The solution was concentrated in vacuo and the residue was chromatographed ($SiO_2$ 230–400 mesh, 1/1 hexanes/EtOAc) to provide the desired compound (1.72 g, 90% yield) as a white solid: LC-MS 81% Area; LC-MS (electrospray, +ions) m/z 483 (M+H).

B.

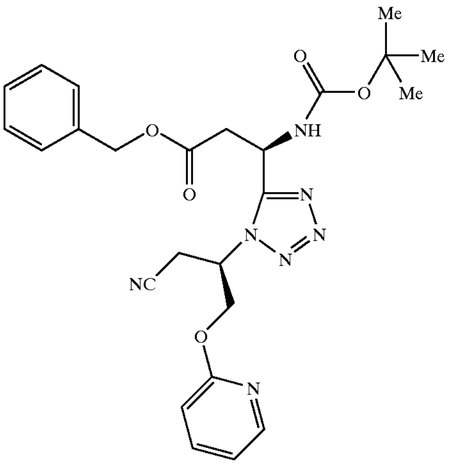

Diethylazodicarboxylate (0.61 mL, 3.78 mmol, DEAD) and azidotrimethylsilane (0.60 mL, 4.13 mmol) were added to a solution, cooled at 0° C., of Part A compound (1.66 g, 3.44 mmol) and triphenylphosphine (1.08 g, 4.13 mmol) in $CH_2Cl_2$ (10 mL). After stirring at rt. for 24 h., additional amounts of triphenylphosphine (1.08 g), DEAD (0.61 mL) and azidotrimethylsilane (0.60 mL) were added and stirring was continued for an additional 24 h. The final solution was partially evaporated in vacuo and passed through a $SiO_2$ (230–400 mesh) column, eluting with 1/1 hexanes/EtOAc, to give the desired compound (552 mg, 32% yield) as a white solid: LC-MS 73% Area; LC-MS (electrospray, +ions) m/z 508 (M+H).

C.

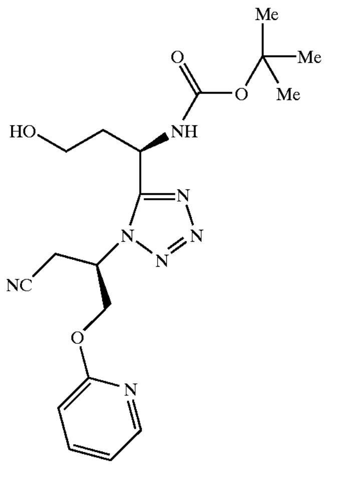

Sodium borohydride (30.4 mg, 0.81 mmol, $NaBH_4$) was added to a suspension, cooled at 0° C., of calcium chloride (44.7 mg, 0.40 mmol, $CaCl_2$) in EtOH(1.5 mL) and the mixture was stirred for 30 min at 0° C. A solution of the Part B compound (204 mg, 0.40 mmol) in THF (2.0 ml) was added and stirring was continued at 0° C. for 4 h. and at rt. for 2 h. After cooling back to 0° C., additional calcium borohydride solution (prepared, as above, from $CaCl_2$ 22.4 mg, EtOH 0.75 mL, and $NaBH_4$ 15.2 mg) was added and stirring was continued for 2 h. at 0° C. and for 2 h. at rt. The final mixture was cooled to 0° C. and quenched with potassium phosphate buffer (pH 3). The mixture was concentrated in vacuo, diluted with brine(25 mL) and extracted with EtOAc(3x 25mL). The combined EtOAc layer was dried ($Na_2SO_4$), concentrated, and chromatographed ($SiO_2$ 230–400 mesh, 1/1 hexanes/EtOAc to EtOAc) to afford the desired compound (92.8 mg, 57% yield) as a white solid: LC-MS 100% Area; LC-MS (electrospray, +ions) m/z 404 (M+H).

D.

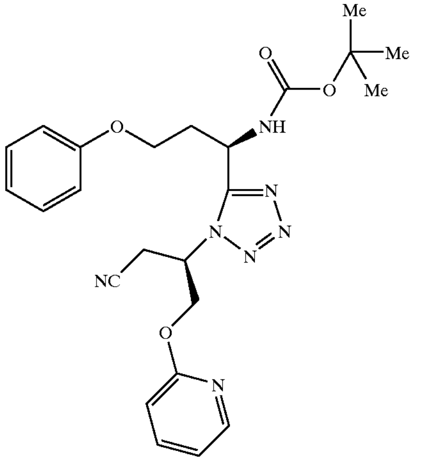

Diethylazodicarboxylate (48.3 μL, 0.30 mmol) was added to a solution, cooled at 0° C., of Part C compound (100 mg, 0.25 mmol), phenol (25.7 mg, 0.27 mmol), and triphenylphosphine (78.4 mg, 0.30 mmol) in $CH_2Cl_2$ (2.0 ml). After stirring at rt for 48 h., the solution was partially evaporated in vacuo and passed through a SiO2 (230–400 mesh) column eluting with 1/1 hexanes/EtOAc to provide the desired compound (52 mg, 43% yield) as a white solid: LC-MS 95% Area; LC-MS (electrospray, +ions) m/z 480 (M+H).

E.

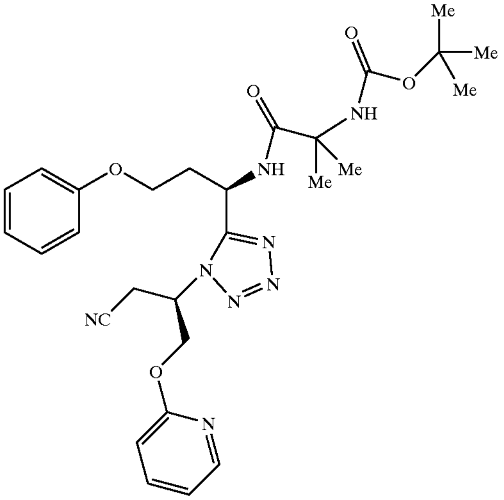

15% TFA/$CH_2Cl_2$ solution (5.0 mL) was added to a flask containing Part D compound (49.8 mg, 0.10 mmol) and thioanisole (36.6 μL, 0.31 mmol), and the resulting solution was allowed to stand at rt. for 4 h. The solution was evaporated and the residual TFA was removed by co-evaporation with $CH_2Cl_2$ (4×5 mL) and MeOH (2×5 mL), and drying under high vacuum for 1 h. The residue was heated at 60° C. in MeOH (5 mL) for 18 h. and the solution concentrated. The crude amine material,

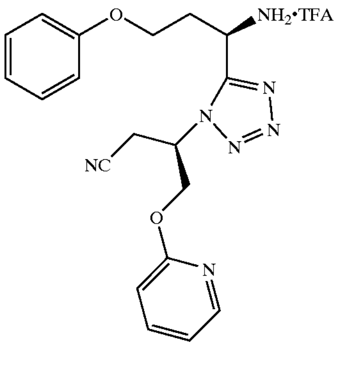

was used without further purification in the subsequent reaction.

N-Boc-methyl alanine

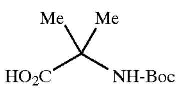

(29.5 mg, 0.15 mmol), EDAG (27.9 mg, 0.15 mmol), HOAT (19.8 mg, 0.15 mmol), 1,2-DCE (1.0 mL) and DMF (0.5 mL) were mixed at 0° C. and stirred for 30 min. The resulting solution was transferred, via syringe, to a 0° C. solution of the crude amine (from above) in 1,2-DCE (1.0 mL) and DMF (0.5 mL), and the mixture was stirred at 0° C. for 15 min. Diisopropylethylamine (54.2 μL, 0.31 mmol) was added and stirring was continued for 24 h at rt. The final mixture was diluted with EtOAc (15 mL) and washed with saturated $NaHCO_3$ (2×20 mL), water (20 mL), and brine (20 mL). The organic layer was dried ($Na_2SO_4$), concentrated and purified by two consecutive chromatographies (both on $SiO_2$ 230–400 mesh; 1st with 1/1 hexanes/EtOAc, $_2$nd with 9/1 $CH_2Cl_2$/EtOAc) to afford the desired compound (35.8 mg, 61% yield) as a white solid: LC-MS 100% Area; LC-MS (electrospray, +ions) m/z 565 (M+H).

F.

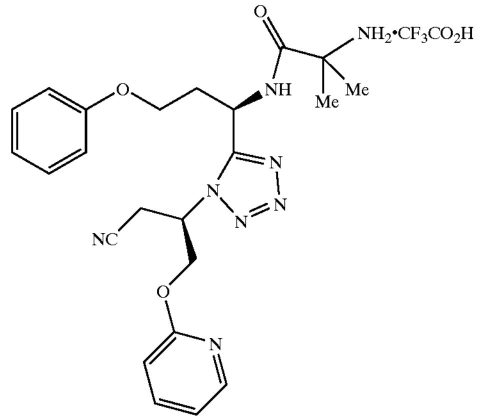

10% TFA/$CH_2Cl_2$ Solution (1.0 mL) was added to a flask containing the Part E compound (32.2 mg, 0.06 mmol) and the resulting solution was allowed to stand at rt. for 4 h. The solution was evaporated and the residual TFA was removed by co-evaporation with $CH_2Cl_2$ (3×1 mL) and MeOH (3×1 mL), and drying under high vacuum for 1 h. The residue was heated at 60° C. in MeOH (10 mL) for 18 h. and the solution concentrated. The crude was taken up in a minimal amount of $CH_2Cl_2$ and precipitation, by addition of hexanes, provided the title compound (31.3 mg, 94%) as a white solid: LC-MS 93% Area; LC-MS(electrospray, +ions) m/z 465 (M+H).

EXAMPLE 587

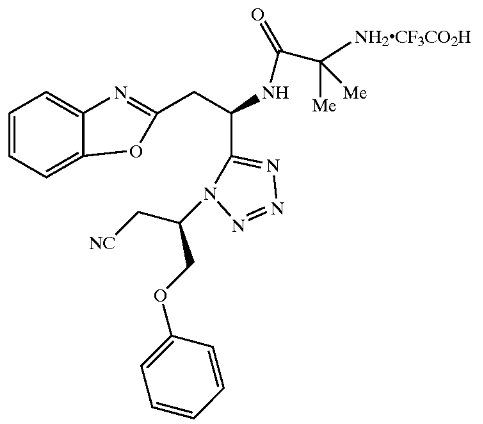

-continued

A.

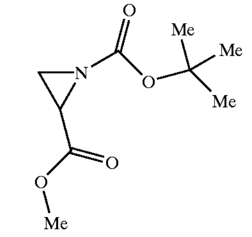

To a solution of aziridine-2-carboxylic acid methyl ester

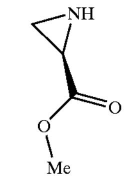

(4.40 g, 43.5 mmol, TCI America) and $Et_3N$ (10.0 mL, 71.7 mmol) in $CH_2Cl_2$ (60.0 mL) was added di-t-butyl dicarbonate (10.9 g, 50.0 mmol) and the resulting solution was stirred at rt for 29 h. The mixture was diluted with EtOAc (200 mL) and washed with saturated $NaHCO_3$ (2×60 mL) and brine (60 mL). The organic layer was dried ($Na_2SO_4$), evaporated and chromatographed ($SiO_2$ 230–400 mesh, 4/1 hexanes/EtOAc) to provide desired compound (8.81 g, 100% yield) as a colorless liquid: $^1$H NMR δ ($CDCl_3$,ppm) 3.78 (s, 3H), 3.04 (dd, J=5.5, 3.3 Hz, 1H), 2.53 (dd, J=3.3, 1.1 Hz, 1H) 2.42 (dd, J=5.5, 1.1 Hz, 1H), 1.46 (s, 9H).

B.

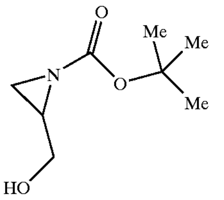

To a solution of Part A compound (2.33 g, 11.6 mmol) in THF (35.0 mL) was added a light suspension of calcium chloride (901 mg, 8.12 mmol) in EtOH (23.0 mL) and the resulting solution was cooled to 0° C. Sodium borohydride (615 mg, 16.3 mmol) was added and the mixture was stirred at 0° C. for 1.75 h. and at rt for 1.25 h. After cooling to 0° C., EtOAc (5 mL) was added and stirring was continued for 1 h at rt. Additional EtOAc (125 mL) was added and the mixture was filtered. The filtrate was evaporated and the residue chromatographed ($SiO_2$ 230–400 mesh; deactivated with 50/50/1 hexanes/EtOAc/$Et_3N$; eluting with 1/1 to 2/3 hexanes/EtOAc) to afford the desired alcohol (1.57 g, 78% yield): $^1$H NMR δ.3.97 (m, 1H), 3.50 (m, 1H), 2.68 (m, 1H), 2.30 (d, J=5.5 Hz, 1H) 2.15 (d, J=3.8 Hz, 1H), 2.13 (t, J 6.1 Hz, 1H overlapped) 1.47 (s, 9H).

C.

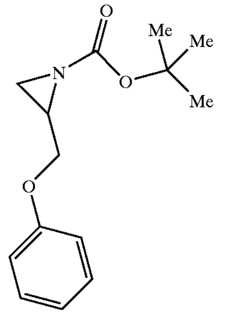

To a solution of Part B compound (1.57 g, 9.08 mmol), phenol (1.01 g, 10.7 mmol) and triphenylphosphine (2. 82 g, 10. 8 mmol, $Ph_3P$) in $CH_2Cl_2$ (19. 5 mL), cooled at 0° C., was added duisopropyletylamine (1.63 mL, 9.36 mmol) and diethylazodicarboxylate (1.70 mL, 10.8 mmol, DEAD). After stirring at rt. for 15 h., additional amounts of phenol (1.01 g), $Ph_3P$ (2.82 g) and DEAD (1.7 mL) were added. Stirring was continued for 2.5 h. and the mixture volume was reduced to 8 mL in vacuo. The remaining solution was passed through a SiO2 (230–400 mesh; deactivated with 85/15/1 hexanes/EtOAc/$Et_3N$) column, eluting with 85/15 hexanes/ EtOAc, to give the desired compound (1.87 g) contaminated with phenol as an oil: LC-MS (neutral buffer) 72% Area; LC/MS (electrospray, +ions) m/z 250 (M+H).

D.

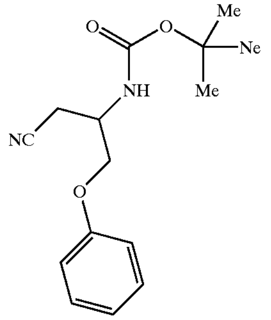

Potassium cyanide (500 mg, 7.68 mmol) was dissolved in water (0.86 mL, 47.8 mmol) and heated to 65° C. DMSO (24.0 mL) was added and the mixture was stirred at 65° C. for 20 min. to obtain a light suspension. Then, a solution of Part C compound (1.87 g, <7.51 mmol) in DMSO (4 mL +2x1 mL rinses)was added, dropwise, and stirring was continued at 65° C. for 4.7 h. After cooling to rt, the reaction mixture was diluted with EtOAc (200 mL) and washed with water (2x80 mL) and brine (80 mL). Drying ($Na_2SO_4$), evaporation and chromatography (SiO2 230–400 mesh, 7/3 hexanes/EtOAc) of the crude provided the desired compound (996 mg, 40% yield from Part B alcohol) as a white solid: LC-MS 100% Area; LC/MS (electrospray, +ions) m/z 299 (M+Na).

E.

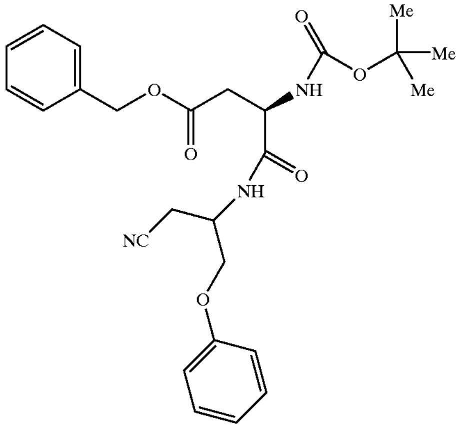

15% TFA/$CH_2Cl_2$ solution (15.0 mL) was added to a flask containing Part D compound (596 mg, 2.16 mmol) and thioanisole (0.76 mL, 6.47 mmol), and the resulting solution was allowed to stand at rt. for 3.5 h. The solution was evaporated and the residual TFA was removed by co-evaporation with $CH_2Cl_2$ (2x10 mL) and MeOH (2x10 mL), and drying under high vacuum for 3 h. The crude amine salt material,

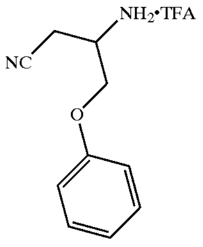

was used without further purification in the subsequent reaction.

N-Boc-D-aspartic acid P-benzyl ester (908 mg, 2.81 mmol), EDAC (538 mg, 2.81 mmol), HOAT (383 mg, 2.81 mmol), 1,2-DCE (1.30 mL), and DMF (2.70 mL) were mixed at 0° C. and stirred for 15 min. The resulting cloudy solution was transferred, via syringe, to a 0° C. solution of the crude amine (from above) in 1,2-DCE (1.00 mL) and DMF (1.30 mL), and the mixture was stirred for 10 min. at 0° C. Diisopropylethylamine (1.00 mL, 5.74 mmol) was added and stirring was continued at rt. for 44 h. The reaction mixture was diluted with EtOAc (125 mL) and washed with saturated $NaHCO_3$ (2x50 mL), water (50 mL) and brine (50 mL). The organic layer was dried ($Na_2SO_4$), evaporated and chromatographed ($SiO_2$ 230–400 mesh, 7/3 to 1/1 hexanes/EtOAc) to provide the desired compound (795 mg, 77% yield, 1/1 diasteromeric mixture) as a white solid: LC-MS 100% Area; LC/MS (electrospray, +ions) m/z 504 (M+Na).

F.

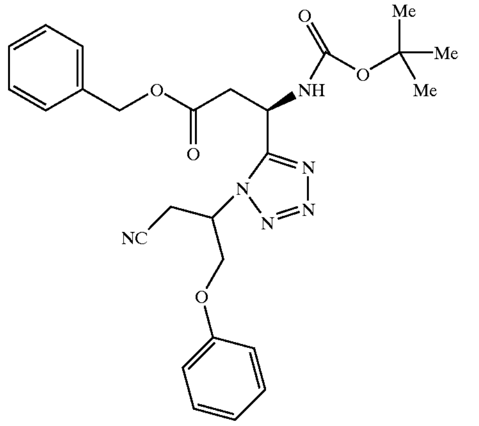

Diethylazodicarboxylate (310 $\mu$L, 1.97 mmol, DEAD) was added, dropwise, to a solution of Part E compound (795 mg, 1.65 mmol), triphenylphosphine (519 mg, 1.98 mmol) and azidotrimethylsilane (290 uL, 1.99 mmol, Sigma, 91%) in $CH_2Cl_2$ (3.5 mL). After stirring at rt. for 20.5 h., additional amounts of $CH_2Cl_2$ (1.20 mL), triphenylphosphine (519 mg), azidotrimethylsilane (290 $\mu$L) and DEAD (310 $\mu$L) were added and stirring was continued for an additional 41.5 h at rt. The final mixture was passed through a SiO2 (230–400 mesh) column, eluting with 3/2 hexanes/EtOAc, to afford the desired compound (204 mg, 25% yield, 1/1 diastereomeric mixture) as a thick oil: $^1$H NMR $\delta$ ($CDCl_3$,ppm, diastereomers) 7.32 (m, 7H), 7.00 (t, J=7.5 Hz, 1H), 6.85 (2d, J=8.8 Hz, 2H), 5.62 (m, 3H), 5.10 (m, 2H), 4.43 (m, 2H), 3.46 (m, 4H), 1.42 and 1.37 (2s, 9H).

G.

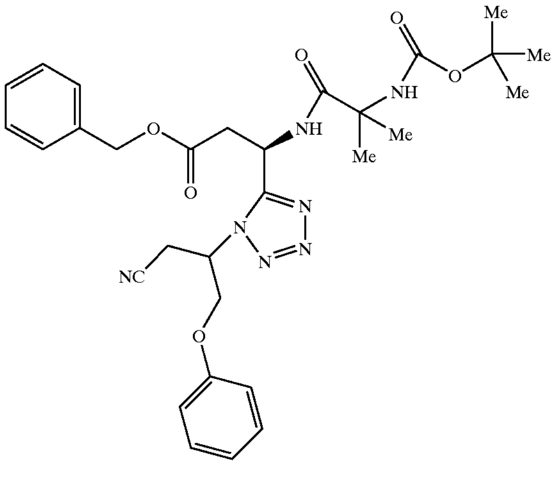

15% TFA/$CH_2Cl_2$ solution (5.3 mL) was added to a flask containing the Part F compound (204 mg, 0.40 mmol) and thioanisole (141 $\mu$L, 1.20 mmol), and the resulting solution was allowed to stand at rt. for 3.5 h. The solution was evaporated and the residual TFA was removed by co-evaporation with $CH_2Cl_2$ (2x8 mL) and MeOH (2x8 mL), and drying under high vacuum for 2 h. The residue was heated at 65° C. in MeOH (25 mL) for 12 h. and the solution concentrated. The crude amine material,

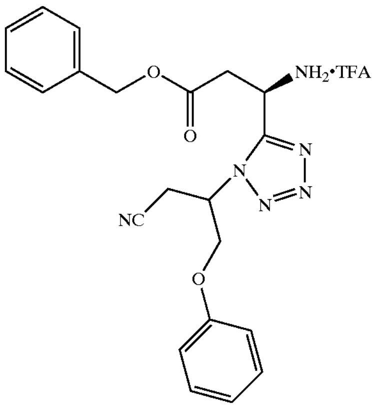

was used without further purification in the subsequent reaction.

N-Boc-methyl alanine

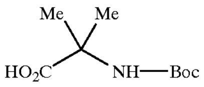

(123 mg, 0.61 mmol), EDAC (115 mg, 0.60 mmol), HOAT (82 mg, 0.60 mmol), 1,2-DCE (0.40 mL) and DMF (0.74 mL) were mixed at 0° C. and stirred for 15 min. The resulting solution was transferred, via syringe, to a 0° C. solution of the crude amine (from above) in 1,2-DCE (0.35 mL) and DMF (0.45 mL), and the mixture was stirred at 0° C. for 10 min. Diisopropylethylamine (0.17 mL, 0.98 mmol) was added and stirring was continued for 46 h at rt. The final mixture was diluted with EtOAc (75 mL) and washed with saturated $NaHCO_3$ (2x30 mL), water (30 mL) and brine (30 mL). The organic layer was dried ($Na_2SO_4$), evaporated and chromatographed ($SiO_2$ 230–400 mesh, 85/15 $CH_2Cl_2$/Ether) to provide desired compound (160 mg, 67% yield, 1/1 diastereomeric mixture) as a thick oil: $^1$H NMR $\delta$ ($CDCl_3$, ppm) 7.57 (s, 1H), 7.32 (m, 7H), 6.98 (m, 1H), 6.91 and 6.83 (2d, J=7.7 Hz, 2H), 5.84, 5.75 and 5.64 (3m, 2H), 5.11 (m, 2H), 4.88 (m, 1H),4.49 and 4.36 (2m, 2H) 3.44–3.14 (m, 4H), 1.40, 1.31, 1.30 and 1.28 (4s, 15H).

H.

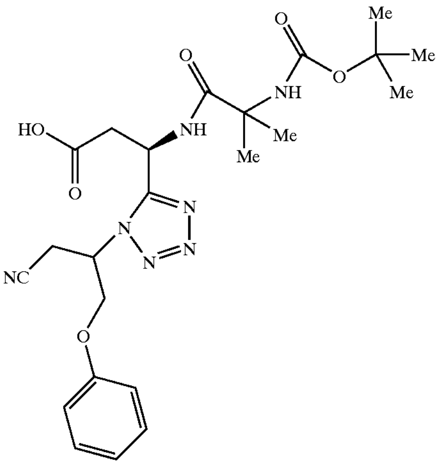

A solution of Part G compound (160 mg, 0.27 mmol) in THF (2.4 mL) and MeOH (2.4 mL) was degassed by purging with vacuum followed by $N_2$ addition three times. 5Pd-C (Degussa type, 500 water content) was added and the resulting suspension was purged with vacuum followed by $H_2$ addition three times. The mixture was hydrogenated (1 atm., balloon) for 3 h. and filtered through celite. The filter cake was rinsed with MeOH (15 mL) and EtOAc (10 mL) and the combined filtrate was evaporated to give the desired acid (147 mg, 100% yield) as a colorless thick oil: $^1H$ NMR δ ($CDCl_3$, ppm) 7.73 and 7.63 (2s, 1H), 7.26 (m, 2H), 6.98 (t, J=7.2 Hz, 1H), 6.91 and 6.83 (2d, J=7.7 Hz, 2H), 5.88, 5.74 and 5.68 (3m, 2H), 5.13 and 5.01 (2s, 1H), 4.50 and 4.39 (2m, 2H) 3.55–3.10 (m, 4H), 1.44 1.43 1.41, 1.39, 1,30 and 1,27 (6s, 15H).

I.

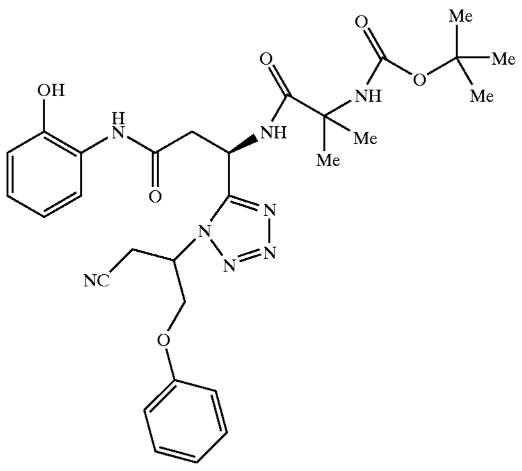

Diisopropylethylamine (0.17 mL, 0.98 mmol) was added to a mixture, cooled at 0° C., of Part H compound (147 mg, 0.27 mmol), 2-aminophenol (36 mg, 0.33 mmol), benzotriazole-lyl-oxy-tris-pyrrolidino-phosphonium hexafluorophospate (155 mg, 0.30 mmol) and DMF (50 μL) in 1,2-DCE (1.0 mL). After stirring at 0° C. for 2 min. and at rt. for 22 h. the mixture was diluted with EtOAc (80 mL) and washed with 0.38 M citric acid (5.0 mL, emulsion), water (20 mL) and brine (20 mL). The organic layer was dried ($Na_2SO_4$), evaporated and chromatographed ($SiO_2$ 230–400 mesh, 3/7 hexanes/EtOAc) to provide desired compound (151 mg, 87% yield, diastereomeric mixture) as a thick oil: $^1H$ NMR δ ($CDCl_3$,ppm) 8.79–8.17 (5s, 3H), 7.24 (m, 3H), 7.10–6.72 (3m, 6H), 5.82 (m, 2H), 5.04 and 4.99 (2s, 1H), 4.51 and 4.40 (2m, 2H) 3.50–3.20 (m, 4H), 1.44, 1.43, 1.42–1.23 (several broad s, 15H).

J.

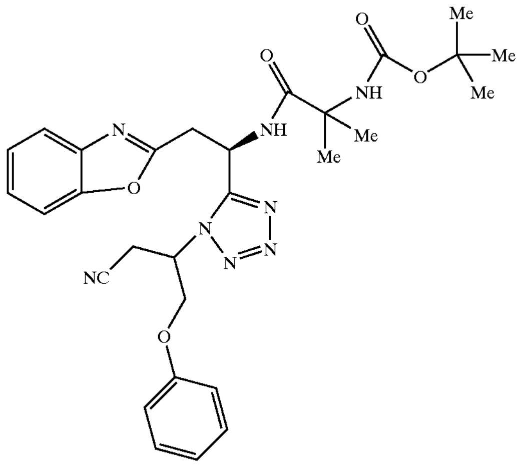

Diethylazodicarboxylate (37 μL, 0.23 mmol, DEAD) was added dropwise to a solution, cooled at 0° C., of Part I compound (108 mg, 0.18 mmol), and triphenylphosphine (62 mg, 0.24 mmol) in $CH_2Cl_2$ (0.9 mL). After stirring at rt. for 12.8 h., diisopropylethylamine (20 μL, 0.11 mmol) and additional amounts of $CH_2Cl_2$ (0.2 mL), triphenylphosphine (62 mg) and DEAD (37 μL) were added. Stirring was continued for an additional 6.7 h at rt. and the solution was evaporated. Chromatography ($SiO_2$ 230–400 mesh, 1/1 to 2/3 hexanes/EtOAc) afforded the desired compound (22.7 mg, 22% yield, 3/4 diastereomeric mixture) as an oil: $^1H$ NMR δ($CDCl_3$,ppm, diastereomers) 7.87 (s, 1H), 7.64, 7.50 and 7.30 (3m, 6H), 7.00 (m, 1H), 6.94 and 6.87 (2d, J=8.2 Hz, 2H), 4.83. (broad s, 1H), 4.58 and 4.47 (2m, 2H), 3.83 (m, 2H), 3.42 (m, 2H), 1.39, 1.33, 1.31, 1.25 and 1.23 (5s, 15H).

K.

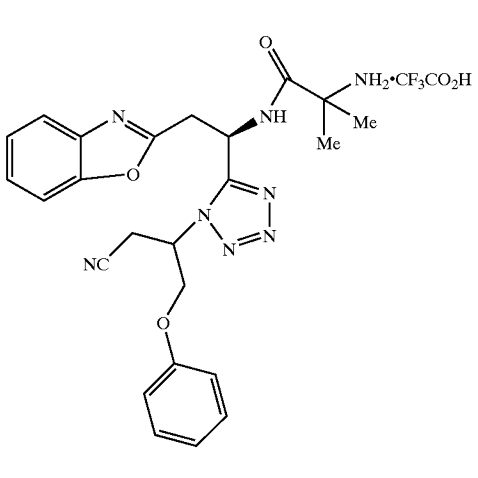

Part J compound (24.1 mg, 0.093 mmol) was treated with 10% TFA/$CH_2Cl_2$ (2.0 mL) for 2 h. and the solution concentrated in vacuo. The residual TFA was co-evaporated with $CH_2Cl_2$ (2x3 mL) and MeOH (2x3 mL), and drying under high vacuum for 2 h. The residue was heated at 65° C. in MeOH (15 mL) for 12 h. and the solution concentrated to give a mixture of the desired compound and its diastereomer. Separation by preparative HPLC (Shimadzu, 10–100% B [90%MeOH:10%H2O:0.2% TFA], 25 min. gradient, 20 mL/min. flow rate, 220nm, Shimadzu VP ODS 20x100 mm) afforded the title compound (10.3 mg, 42% yield, RR configuration) as a slightly reddish oil: LC-MS 93% Area; LC/MS (electrospray, +ions) m/z 475 (M+H). Analytical HPLC (0–100% B [90%MeOH:10%H2O:0.2% TFA], 8 min. gradient, 2.5 mL/min. flow rate, 220nm, Zorbax SBC.18, 4.6x75 mm) 4.48 min. retention time.

EXAMPLES 588–628

The following compounds were prepared employing the procedures described above and the working Examples.

The identified diasteriomers were separated by HPLC. HPLC retention times were measured on a Shimadzu HPLC using a Zorbax SB C18 column (4.6x75 mm) with an eight minute gradient (10% MeOH:90% $H_2O$ to 90%MeOH:10% $H_2O$, with 0.2% phosphoric acid). The following retention times characterize ther diastereomers:

| Example | $R_t$ (min) |
|---|---|
| 588 | 5.08 |
| 589 | 5.59 |
| 591 | 6.31 |
| 592 | 5.82 |
| 594 | 5.03 |
| 595 | 5.31 |
| 603 | 5.26 |
| 604 | 5.68 |
| 606 | 5.89 |
| 607 | 6.38 |
| 612 | 5.78 |
| 613 | 6.30 |
| 619 | 6.95 |
| 620 | 7.24 |

| Example No. | Structure | M + H positive ions |
|---|---|---|
| 588 | 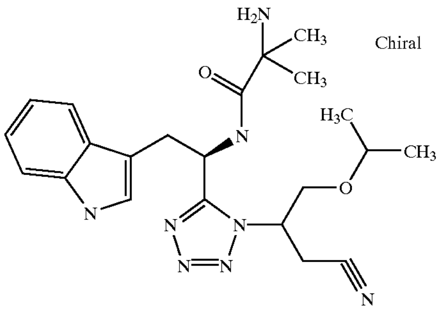 Diastereomer A | 439 |
| 589 | 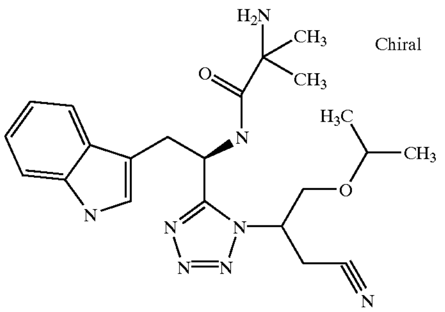 Diastereomer B | 439 |

-continued
| Example No. | Structure | M + H positive ions |
| --- | --- | --- |
| 590 | 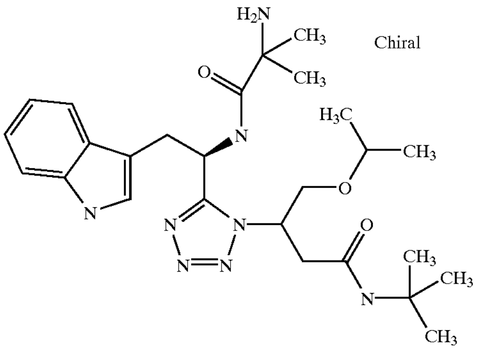 | 513 |
| 591 | 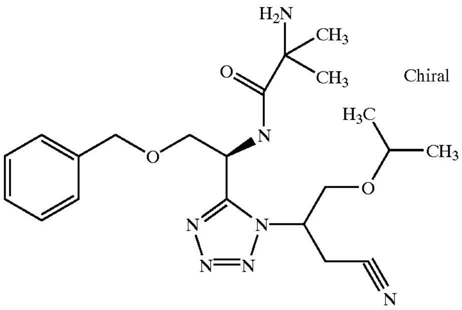 Diastereomer A | 430 |
| 592 | 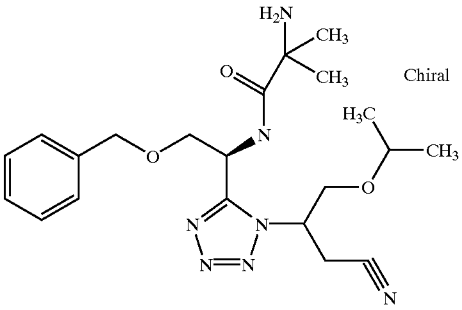 Diastereomer B | 430 |
| 593 | 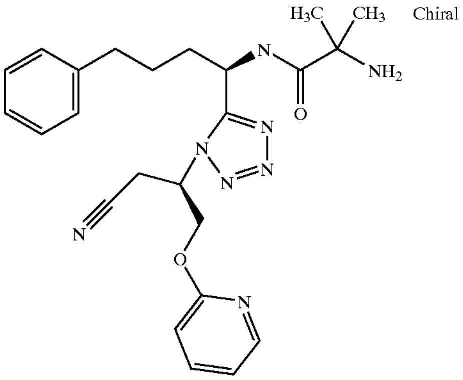 | 463 |

-continued
| Example No. | Structure | M + H positive ions |
|---|---|---|
| 594 | 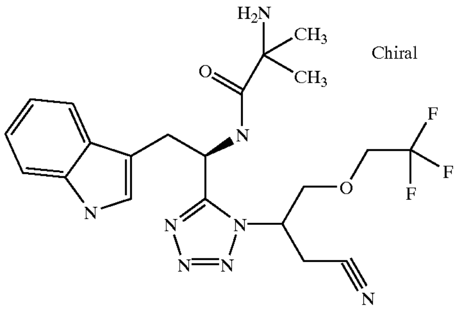 Chiral<br>Diastereomer A | 479 |
| 595 | 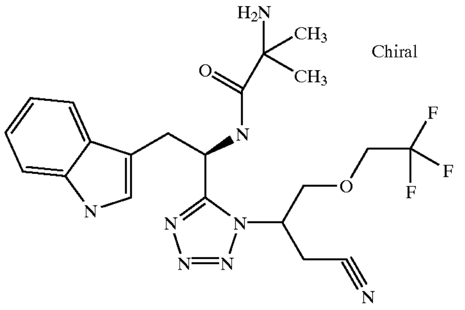 Chiral<br>Diastereomer B | 479 |
| 596 | Chiral 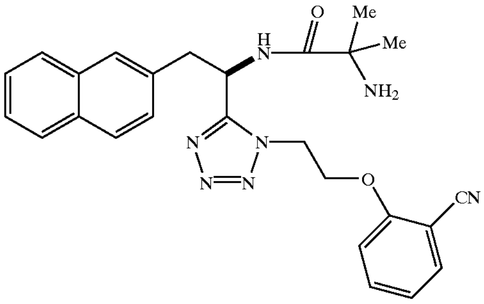 | 470 |
| 597 | 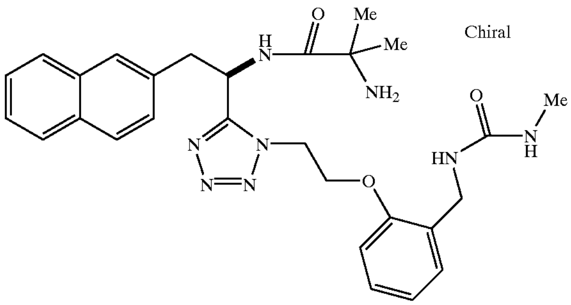 Chiral | 531 |

-continued
| Example No. | Structure | M + H positive ions |
| --- | --- | --- |
| 598 | 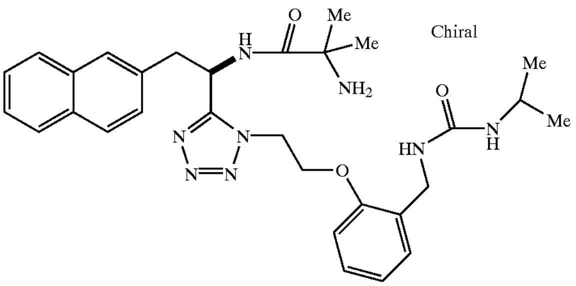 | 559 |
| 599 | 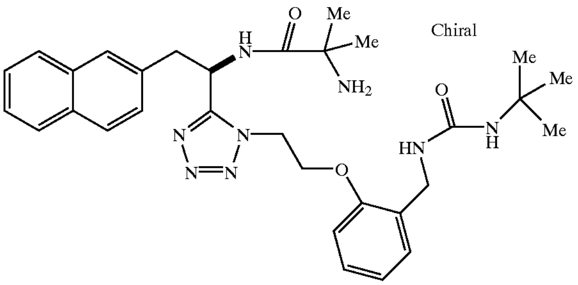 | 573 |
| 600 | 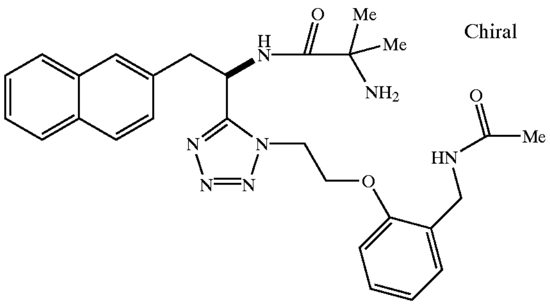 | 516 |
| 601 | 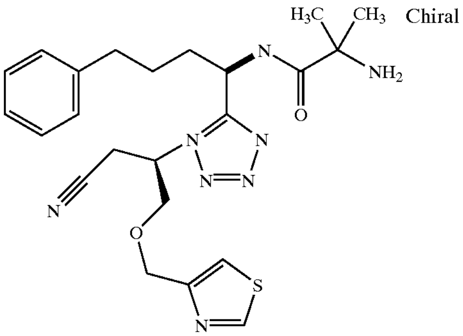 | 483 |
| 602 | 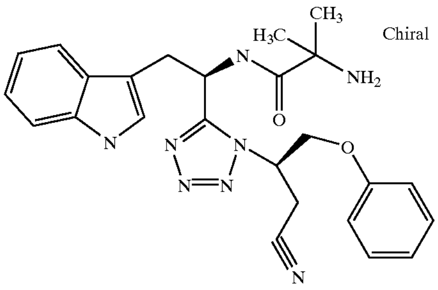 | 473 |

-continued
| Example No. | Structure | M + H positive ions |
|---|---|---|
| 603 | 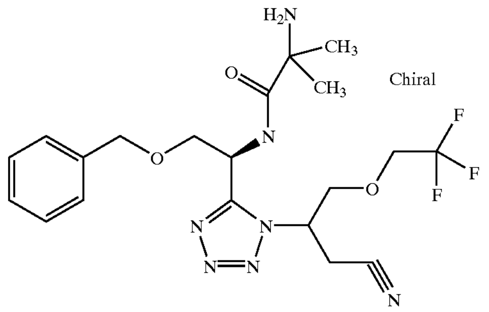 Diastereomer A | 470 |
| 604 | 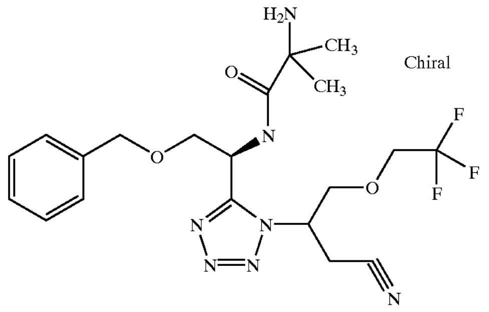 Diastereomer B | 470 |
| 605 | 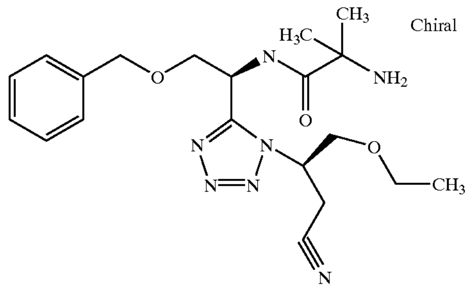 | 416 |
| 606 | 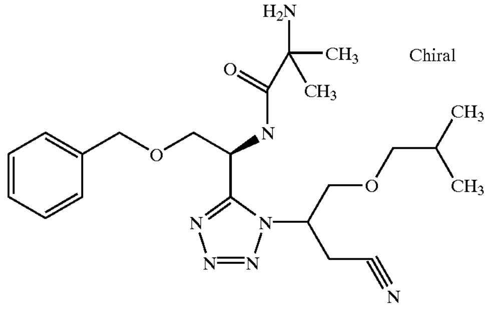 Diastereomer A | 444 |

-continued
| Example No. | Structure | M + H positive ions |
|---|---|---|
| 607 | 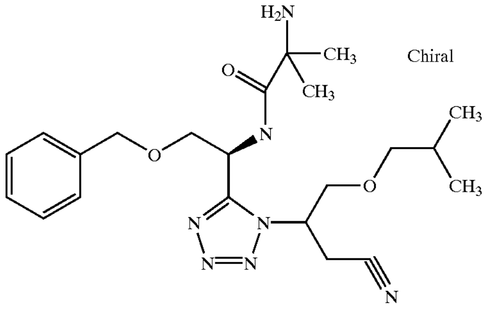 Chiral Diastereomer B | 444 |
| 608 | 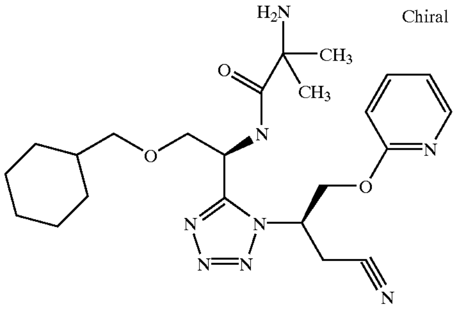 Chiral | 471 |
| 609 | 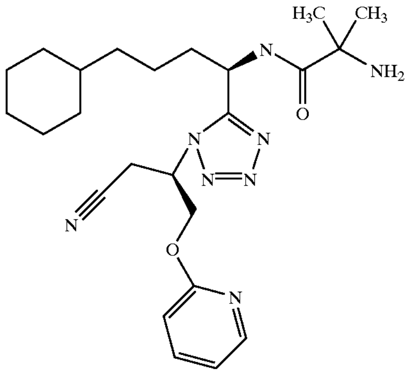 Chiral | 469 |
| 610 | 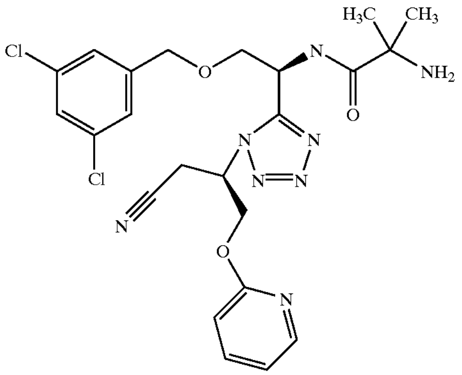 Chiral | 534 |

-continued
| Example No. | Structure | M + H positive ions |
|---|---|---|
| 611 | 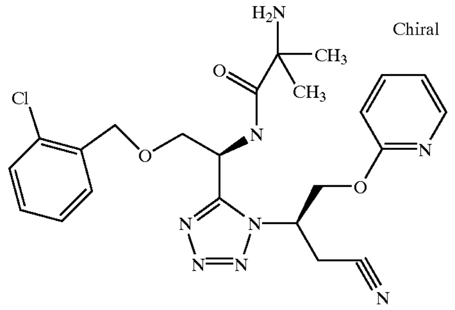 Chiral | 499 |
| 612 | 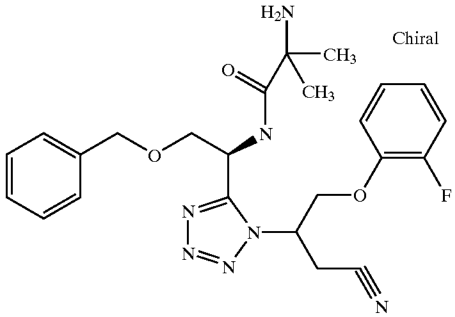 Chiral<br>Diastereomer A | 482 |
| 613 | 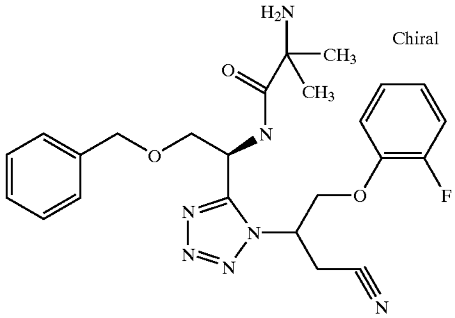 Chiral<br>Diastereomer B | 482 |
| 614 | 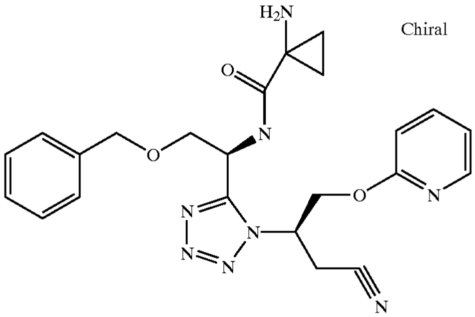 Chiral | 463 |

-continued
| Example No. | Structure | M + H positive ions |
|---|---|---|
| 615 | 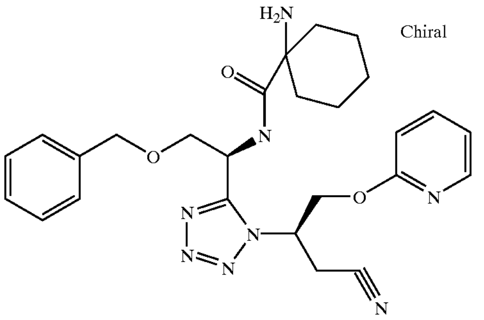 | 505 |
| 616 | 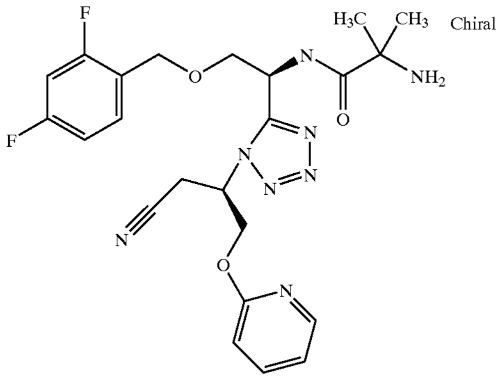 | 501 |
| 617 | 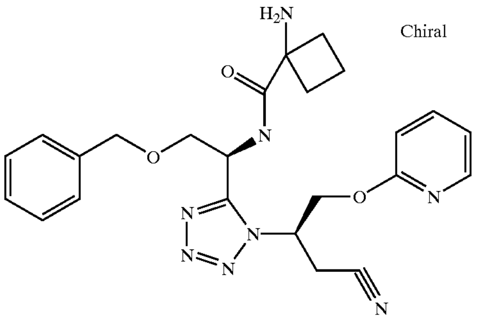 | 477 |
| 618 | 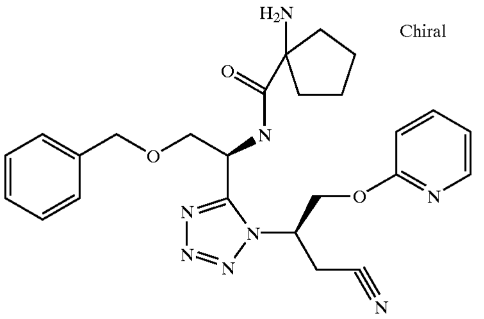 | 491 |

-continued
| Example No. | Structure | M + H positive ions |
|---|---|---|
| 619 | 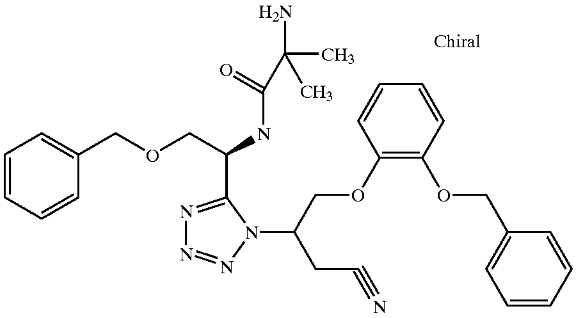 Diastereomer A | 570 |
| 620 | 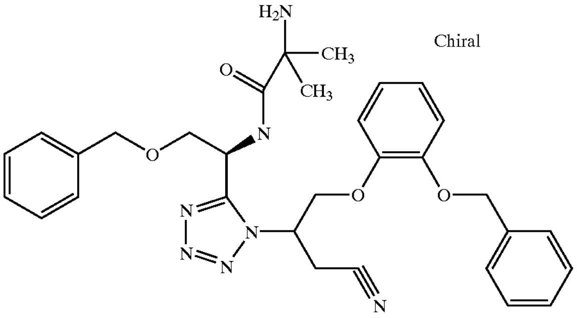 Diastereomer B | 570 |
| 621 | 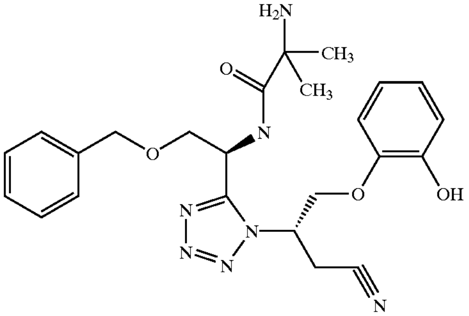 | 480 |
| 622 | 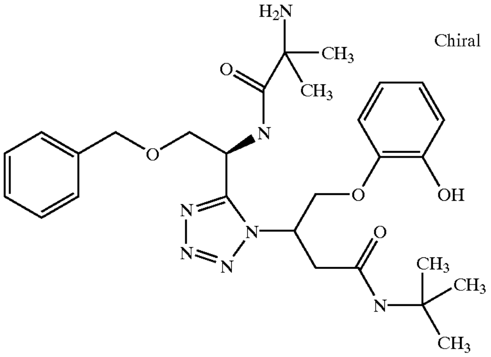 | 554 |

-continued
| Example No. | Structure | M + H positive ions |
|---|---|---|
| 623 | 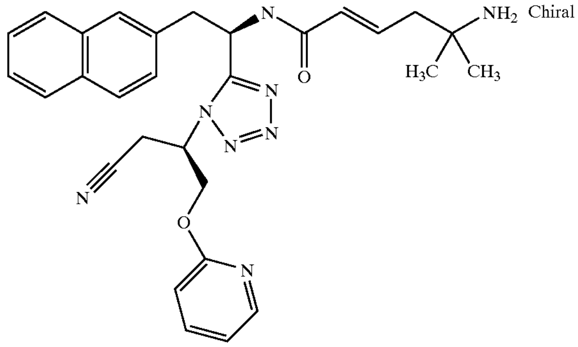 Chiral | 525 |
| 624 | 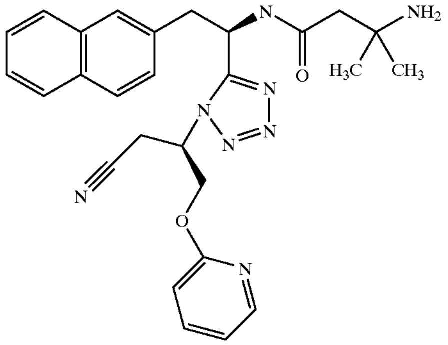 Chiral | 499 |
| 625 | 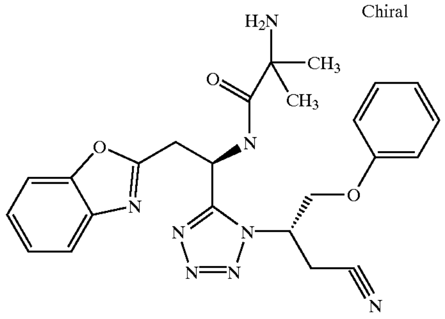 Chiral | 475 |
| 626 | 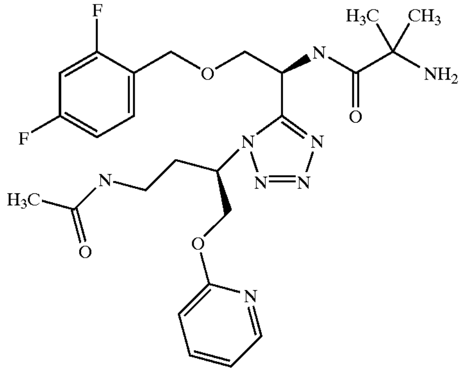 Chiral | 547 |

-continued
| Example No. | Structure | | M + H positive ions |
|---|---|---|---|
| 627 | 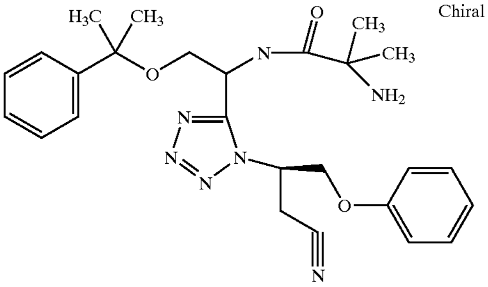 | Chiral | 493 |
| 628 | 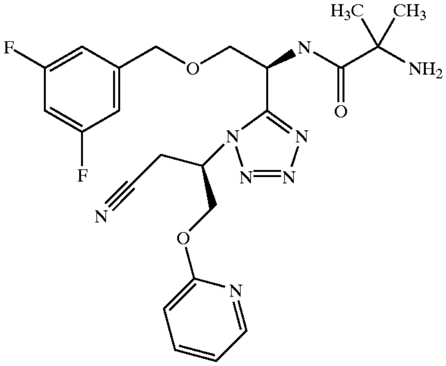 | Chiral | 501 |
EXAMPLES 629–641
The following compounds are prepared employing the procedures described above and the working Examples.
629
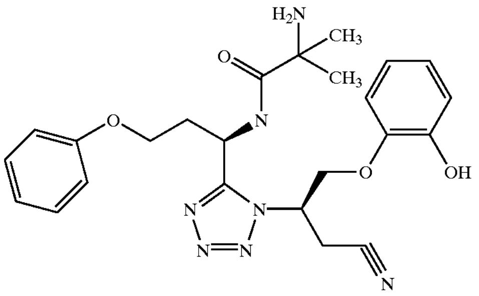
630
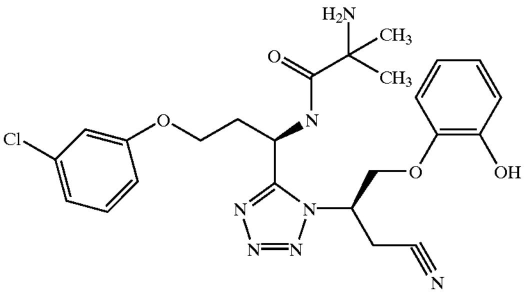
-continued
631
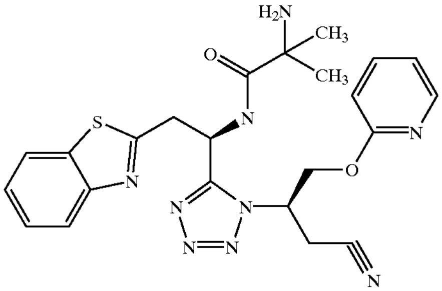
631
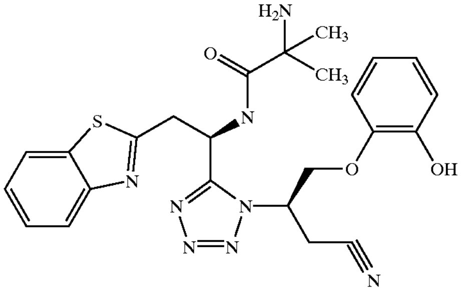

-continued
633
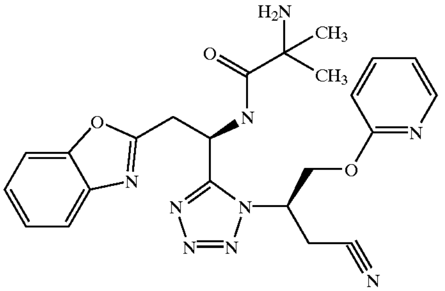
634
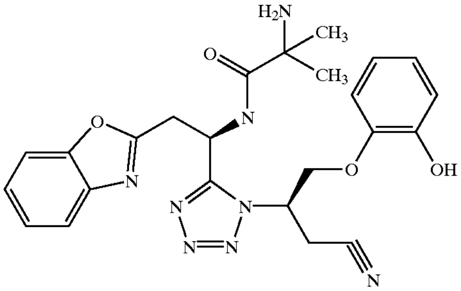
635
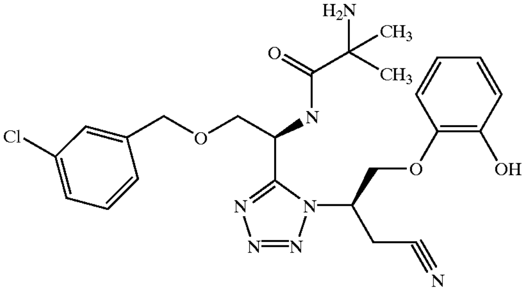
636
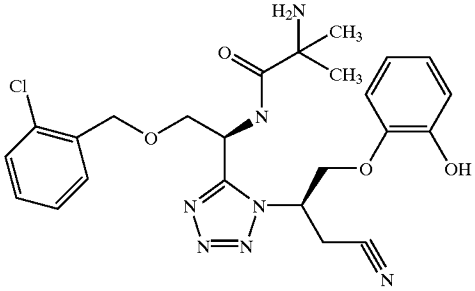
637
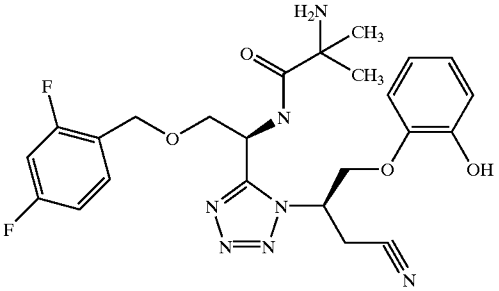
-continued
638
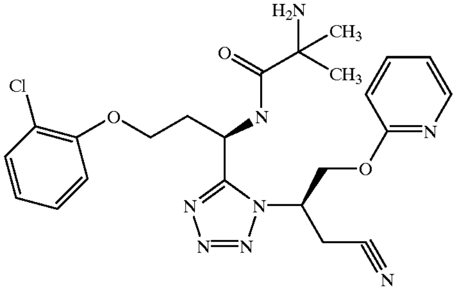
639
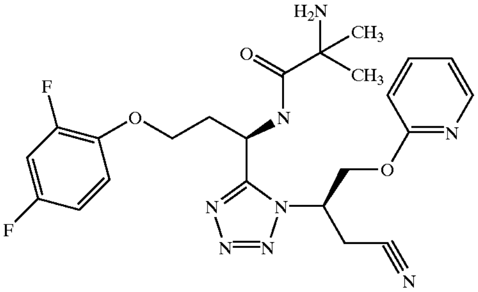
640
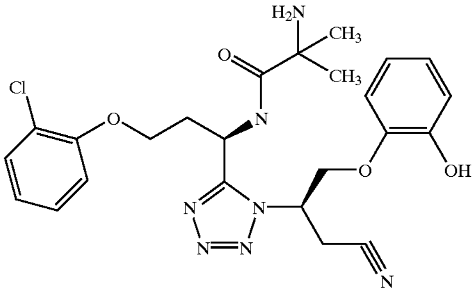
641
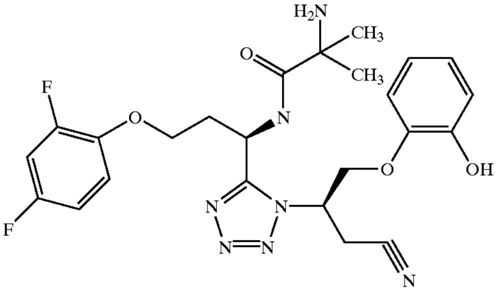
What is claimed is:
1. A compound of the structure
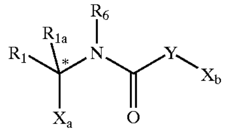
including pharmaceutically acceptable salts thereof, prodrug esters thereof, and all stereoisomers thereof,
wherein $R_1$ is alkyl, aryl, alkenyl, alkynyl, arylalkyl, cycloalkyl, cycloalkylalkyl, alkoxyalkyl, arylalkyloxyalkyl, aryloxyalkyl, heteroaryl, cycloalkylalkoxyalkyl, heteroarylalkyl, cycloheteroalkyl or cycloheteroalkylalkyl, and these groups may be optionally substituted by 1,2 or 3-substituents selected from halogen, —$OR_8$, —$OC(O)R_8$, alkyl, phenyl, phenoxy, halophenyl, —$CF_3$, —$OCF_3$, —$N(R_{8a})C(O)(R_8)$, or —$N(R_8)(R_{8a})$;

$R_{1a}$ is H, alkyl, or cycloalkyl;

$X_a$ is

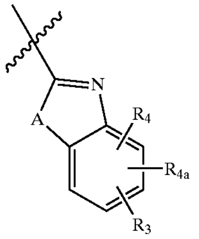

A is oxygen, sulfur, —NH—, —N—$R_5$, or —NC(O)—$R_2$;

$R_2$ is alkyl, aryl, alkenyl, alkynyl, arylalkyl, cycloalkyl, cycloalkylalkyl, alkoxyalkyl, aryloxyalkyl, heteroaryl, or heteroarylalkyl, and these groups may optionally be substituted by 1,2 or 3-substituents selected from halogen, —$OR_{8b}$, —$OC(O)R_{8b}$, alkyl, phenyl, phenoxy, halophenyl, —$CF_3$, —$OCF_3$, —$N(R_{8c})C(O)(R_{8b})$, or —$N(R_{8c})(R_{8b})$;

$R_3$ is halogen, alkyl, aryl, alkenyl, alkynyl, alkaryl, alkoxy, aryloxy or J1, and where alkyl, aryl, alkenyl, alkynyl, arylalkyl, alkoxy, or aryloxy may be optionally substituted with 1 to 3 J1;

$R_4$ and $R_{4a}$ are the same or different and are independently selected from H, halogen, —$CF_3$, alkyl, or aryl;

Y is

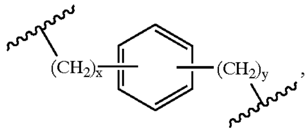
,

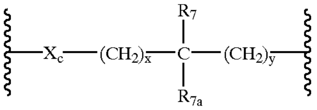
or

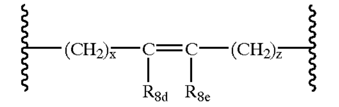

where x and y are independently 0 to 3 and z is 1 to 3;

$X_c$ is a bond, —N—$R_{6a}$ or —O—;

$R_7$ and $R_{7a}$ are the same or different and are independently selected from H, alkyl, —$CF_3$, phenyl, aryl, arylalkyl, and cycloalkyl; or one or both of $R_7$ and $R_{7a}$ can be independently joined to one or both of $R_9$ and $R_{10}$ groups (of $X_b$) to form an alkylene bridge of 1 to 5 carbon atoms; or $R_7$ and $R_{7a}$ are joined together to form a ring of from 3–7 carbon atoms;

$R_6$, $R_{6a}$, $R_{6b}$, $R_{6c}$, $R_8$, $R_{8a}$, $R_{8b}$, $R_{8c}$, $R_{8d}$, $R_{8e}$, $R_{8f}$, $R_{8g}$, $R_{8h}$, $R_{8i}$, $R_{8k}$, $R_{8l}$, and $R_{8m}$ are the same or different and are independently H, alkyl, cycloalkyl, alkenyl or aryl;

$R_{8j}$ is H, alkyl, aryl, hydroxy or —$OC(O)R_{8k}$;

$X_b$ is

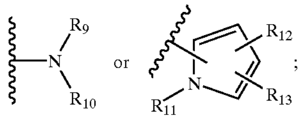

$R_9$ and $R_{10}$ are the same or different and are independently selected from H, alkyl, and substituted alkyl where the substituents may be 1 to 3 hydroxy, 1 to 3 $C_1$–$C_{10}$-alkanoyloxy, 1 to 3 $C_{1-6}$ alkoxy, phenyl, phenoxy, $C_1$–$C_6$-alkoxycarbonyl; or $R_9$ and $R_{10}$ can together form —$(CH_2)_tX_d(CH_2)_u$— where $X_d$ is $C(R_{8h})(R_{8j})$, —O— or —$N(R_{6b})$, t and u are independently 1–3;

$R_{11}$ is H, $C_1$–$C_6$alkyl, —$CF_3$, arylalkyl, or aryl, and with the alkyl and aryl groups being optionally substituted with 1 to 3 hydroxy, 1 to 3 $C_{1-10}$alkanoyloxy, 1 to 3 $C_{1-6}$ alkoxy, phenyl, phenoxy or $C_1$–$C_6$ alkoxycarbonyl;

$R_{12}$ and $R_{13}$ are independently H, $C_1$–$C_6$alkyl, —$CF_3$, aryl, or halogen, and with the alkyl and aryl groups being optionally substituted with 1 to 3 hydroxy, 1 to 3 $C_1$–$C_{10}$-alkanoyloxy, 1 to 3 $C_{1-6}$ alkoxy, or $C_1$–$C_6$ alkoxycarbonyl;

J1 is nitro, —$(CH_2)vN(T_{1a})C(O)T_1$, —$(CH_2)_vCN$, —$(CH_2)_vN(T_{1a})C(O)OT_1$, —$(CH_2)_vN(T_{1a})C(O)N(T_{1b})T_1$, —$(CH_2)_vN(T_{1a})SO_2T_1$, —$(CH_2)_vC(O)N(T_{1a})T_1$, —$(CH_2)_vC(O)OT_1$, —$(CH_2)_vOC(O)OT_1$, —$(CH_2)_vOC(O)T_1$, —$(CH_2)_vOC(O)N(T_{1a})T_1$, —$(CH_2)_vN(T_{1a})SO_2N(T_{1b})T_1$, —$(CH_2)_vOT_1$, —$(CH_2)_vSO_2T_1$, —$(CH_2)vSO_2N(T_{1a})T_1$, —$(CH_2)vC(O)T_1$, —$(CH_2)vCH(OH)T_1$, cycloheteroalkyl or heteroaryl, with v being 0–5;

$T_1$, $T_{1a}$ and $T_{1b}$ are the same or different and are independently H, alkyl, alkenyl, alkynyl, lower alkythioalkyl, alkoxyalkyl, aryl, arylalkyl, heteroaryl, heteroarylalkyl, cycloheteroalkyl, or cycloalkyl, each of which may be optionally substituted with 1, 2 or 3 substituents selected from halogen, hydroxyl, —$NR_{8f}C(O)NR_{8g}R_{8i}$, —$C(O)NR_{8f}R_{8g}$, —$NR_{8f}C(O)R_{8g}$, —CN, —$N(R_{8f})SO_2R_{14}$, —$OC(O)R_{8f}$, —$SO_2NR_{8f}R_{8g}$, —$SOR_{14}$, —$SO_2R_{14}$, alkoxy, —COOH, cycloheteroalkyl, or —$C(O)OR_{14}$; or $T_1$ and $T_{1a}$ or $T_1$ and $T_{1b}$ can together form —$(CH_2)wXe(CH_2)_z$— where $X_e$ is —$C(R_{8m})(R_{8l})$, —O—, —S—, —SO—, —$SO_2$—, —$NC(O)OR_{14a}$, —$NC(O)NR_{14a}R_{14b}$, —$NC(O)R_{14a}$ or —$N(R_{6c})$ where w and z are each independently 1–3; with the proviso that $T_1$ can not be hydrogen when it is connected to carbonyl or sulfur, as in —$C(O)T_1$ or —$SO_2T_1$;

$R_{14}$, $R_{14a}$, and $R_{14b}$ are independently $C_1$–$C_6$alkyl, heteroaryl, or aryl, each optionally substituted with —$(CH_2)_sOH$, with s being 0–5.

2. The compound as defined in claim 1 wherein $R_1$ is aralkyl, arylalkyloxyalkyl, cycloheteroalkylalkyl, aryloxyalkyl or heteroarylalkyl.

3. The compound as defined in claim 1 wherein $R_{1a}$ is H or alkyl.

4. The compound as defined in claim 1 wherein $R_1$ is arylalkyloxyalkyl and $R_{1a}$ is H.

5. The compound as defined in claim 1 wherein $R_6$ is H.

6. The compound as defined in claim 4 wherein A is NH, $R_4$ and $R_{4a}$ are H and $R_3$ is J1.

7. The compound as defined in claim 1 wherein Y is

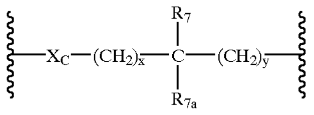

where x and y are 0, $X_c$ is a bond, and $R_7$ and $R_{7a}$ are independently alkyl.

8. The compound as defined in claim 1 wherein $X_b$ is

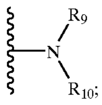

$R_9$ and $R_{10}$ are the same or different and are independently selected from H and substituted alkyl where the substituents may be 1 to 2 hydroxyls.

9. The compound as defined in claim 1 wherein J1 is $-(CH_2)_vCN$, $-(CH_2)_vC(O)N(T_{1a})T_1$, $-(CH_2)_vN(T_{1a})C(O)T_1$, $-(CH_2)_vOC(O)N(T_{1a})T_1$, $-(CH_2)_vN(T_{1a})C(O)N(T_{1b})T_1$, or heteroaryl, with v being 0–4;

$T_1$, $T_{1a}$ and $T_{1b}$ are the same or different and are independently selected from alkyl, lower alkythioalkyl, alkoxyalkyl, aryl, arylalkyl, heteroarylalkyl, or cycloheteroalkyl, each of which may be optionally substituted with $-OC(O)R_{8f}$, $-C(O)NR_{8f}R_{8g}$, $-(CH_2)_sOH$, with s being 0–2, $-SO_2NR_{8f}R_{8g}$, or $-SO_2R_{14}$; or $T_1$ and $T_{1a}$ or $T_1$ and $T_{1b}$ can together form $-(CH_2)_wX_e(CH_2)_z-$ where $X_e$ is $C(R_{8m})(R_{8l})$;

$R_{8f}$ is alkyl or aryl.

10. The compound as defined in claim 1 having the structure

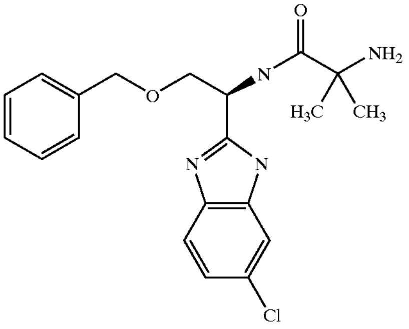

Chiral,

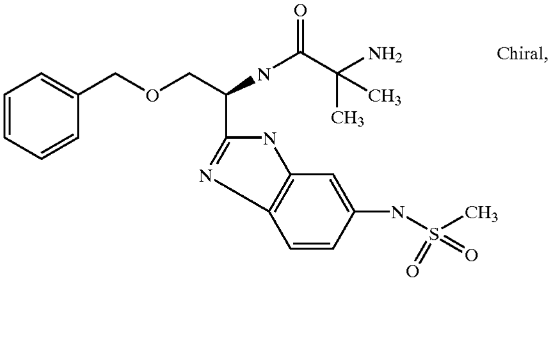

Chiral,

-continued

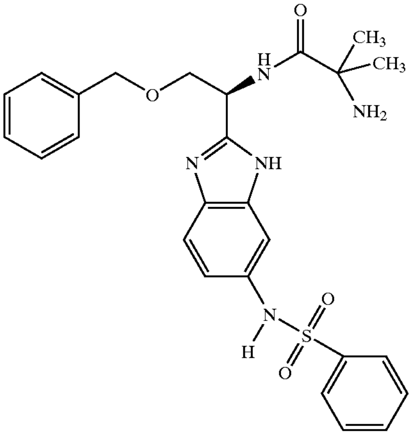

Chiral,

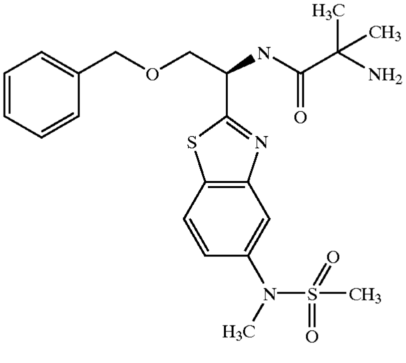

Chiral, or a pharmaceutically acceptable salt thereof.

11. The compound as defined in claim 1 having the structure

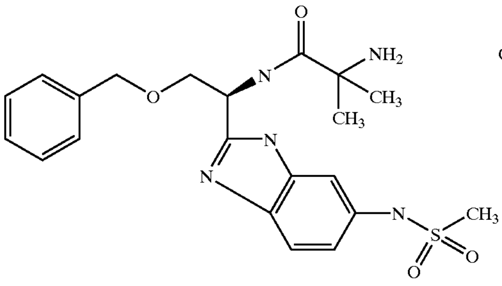

Chiral or a pharmaceutically acceptable salt thereof.

12. A pharmaceutical composition comprising a compound as defined in claim 1 and a pharmaceutically acceptable carrier therefor.

13. A method for increasing levels of endogenous growth hormone, which comprises administering to a patient in need of treatment a therapeutically effective amount of a compound as defined in claim 1.

14. A method for treating obesity, osteoporosis, renal disease, cardiac myopathy, cachexia, HIV wasting syndrome, long term critical illness, sarcopenia, and/or stimulating wound healing and/or the immune system, or increasing muscle mass and/or muscle strength, or maintenance of muscle strength and function in the elderly, or reversal or prevention of frailty in the elderly, which comprises administering to a patient in need of treatment a therapeutically effective amount of a compound as defined in claim 1.

15. A method for treating Syndrome X, which comprises administering to a patient in need of treatment a therapeutically effective amount of a compound as defined in claim 1.

16. A method for prophylaxis and/or treatment of diabetes and/or increasing lean body mass, which comprises administering to a patient in need of treatment a therapeutically effective amount of a compound as defined in claim 1.

17. A method for preventing or treating osteoporosis, which comprises administering to a patient in need of treatment a therapeutically effective amount of a compound as defined in claim 1.

18. A method for treating osteoporosis, which comprises administering to a patient in need of treatment a therapeutically effective amount of a compound as defined in claim 1 in combination with parathyroid hormone or a bisphosphonate.

19. A method for treating Syndrome X, cachexia, HIV wasting syndrome, long term critical illness, or sarcopenia, or for increasing muscle mass and/or muscle strength, or for maintenance of muscle strength and function in the elderly, or for reversal or prevention of fraility in the elderly, which comprises administering to a patient in need of treatment a therapeutically effective amount of a compound as defined in claim 1 in combination with estrogen, testosterone, a selective estrogen receptor modulator, or a selective androgen receptor modulator.

* * * * *